(12) United States Patent
Prien et al.

(10) Patent No.: US 7,750,000 B2
(45) Date of Patent: Jul. 6, 2010

(54) SUBSTITUTED IMIDAZO[1,2B]PYRIDAZINES AS KINASE INHIBITORS, THEIR PREPARATION AND USE AS MEDICAMENTS

(75) Inventors: Olaf Prien, Berlin (DE); Stuart James Ince, Berlin (DE); Knut Eis, Berlin (DE); Christoph Huwe, Berlin (DE); Ulrich Lücking, Berlin (DE); Rolf Jautelat, Berlin (DE); Ulrich Zügel, Berlin (DE); Judith Günther, Berlin (DE); Benjamin Bader, Berlin (DE); Manfred Husemann, Hohen Neuendorf (DE); Karina Schuck, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 162 days.

(21) Appl. No.: 11/514,308

(22) Filed: Sep. 1, 2006

(65) Prior Publication Data

US 2007/0093490 A1 Apr. 26, 2007

Related U.S. Application Data

(60) Provisional application No. 60/713,333, filed on Sep. 2, 2005.

(30) Foreign Application Priority Data

Sep. 2, 2005 (DE) .................. 10 2005 042 742

(51) Int. Cl.
| | |
|---|---|
| A61K 31/4985 | (2006.01) |
| A61K 31/5355 | (2006.01) |
| C07D 487/04 | (2006.01) |
| C07D 413/12 | (2006.01) |
| A61P 3/10 | (2006.01) |
| A61P 11/06 | (2006.01) |
| A61P 29/00 | (2006.01) |
| A61P 17/06 | (2006.01) |
| A61P 17/00 | (2006.01) |

(52) U.S. Cl. .................. 514/233.2; 514/248; 544/117; 544/236
(58) Field of Classification Search ................ 544/236, 544/117; 514/248, 233.2
See application file for complete search history.

(56) References Cited

U.S. PATENT DOCUMENTS 6,248,740 B1 6/2001 Kawano et al.

| | | |
|---|---|---|
| 2003/0203897 A1 | 10/2003 | Love et al. |
| 2004/0097506 A1 | 5/2004 | Thomas |
| 2005/0171108 A1* | 8/2005 | Tabuchi et al. ............ 514/248 |
| 2006/0014746 A1* | 1/2006 | Hutchison et al. .......... 514/248 |
| 2006/0211704 A1 | 9/2006 | Love et al. |

FOREIGN PATENT DOCUMENTS

| | | | |
|---|---|---|---|
| DE | 3542661 A1 | | 6/1987 |
| DE | 69827786 T2 | | 11/2005 |
| WO | WO 01/64674 | | 9/2001 |
| WO | WO 01/64674 A | | 9/2001 |
| WO | WO 02/066481 | | 8/2002 |
| WO | WO 02066481 A | | 8/2002 |
| WO | WO 2005/066177 | * | 7/2005 |
| WO | WO 2005/066177 A1 | | 7/2005 |
| WO | WO 2007/013673 | * | 2/2007 |
| WO | WO 2007/025090 | * | 3/2007 |

OTHER PUBLICATIONS

Koivunen, et al., Clin. Cancer Res. 14, 4275, Jul. 1, 2008.*
Martiny-Baron, et al., Pharmacolog. Res., vol. 55, #6, Jun. 2007, pp. 477-486.*
Bullock, A. N. et al., "Structural basis of inhibitor specificity of the human protooncogene proviral insertion site in Moloney Murine Leukemia Virus (PIM-1) kinase," Journal of Medical Chemistry, vol. 48 No. 24, 27 Oct. 2005, pp. 7604-7614.
Byth, Kate F. et al., "imidazo(1,2-b)pyridazines: a process and selective class of cyclin-dependent kinase inhibitors," Bioorganic and Medicinal Chemistry Letters, 2004, pp. 2249-2252, XP002420105.
Polanc, S. et al., "Pyridazines LIX: An unusual reaction of azidoazolopyridazines with diethylamine," Department of Chemistry, University of Ljubljana, Yugoslavia, vol. 10, Aug. 1973, pp. 565-567.
Gorup, A. et al., "Reactions of azidoazolopyridazines with 1,3-dicarbonyl compounds," Tetrahedron, vol. 30, 1974, Pergamon Press, GB, pp. 2251-2256.
Watanabe et al, "Peripheral conjugate system; part 2. Synthesis of diimidazo[1,2-b:2',1'-f]pyridazine," Synthesis, 1977, vol. 11, pp. 761-763. Abstract.
Kate F. Byth et al., "Imidazo (1,2-b)pyridazines: a potent and selective class of cyclin-dependent kinase inhibitors", Bioorganic & Medicinal Chemistry Letters, 2004, pp. 2249-2252.
Bullock et al., Structural basis of inhibitor specificity of the human protooncogene proviral insertion site in Moloney Murine Leukemia Virus (PIM-1) Kinase, Journal of Medicinal Chemistry, American Chemical Society, Oct. 2005, pp. 7604-7614.

* cited by examiner

*Primary Examiner*—James O Wilson
*Assistant Examiner*—Cecilia M Jaisle
(74) *Attorney, Agent, or Firm*—Millen, White, Zelano, Branigan, P.C.

(57) ABSTRACT

The invention relates to novel inhibitors of kinases, and pharmaceutical compositions comprising them. The inhibitors are substituted imidazo[1,2b]pyridazines.

2 Claims, No Drawings

SUBSTITUTED IMIDAZO[1,2B]PYRIDAZINES AS KINASE INHIBITORS, THEIR PREPARATION AND USE AS MEDICAMENTS

This application claims the benefit of the filing date of U.S. Provisional Application Ser. No. 60/713,333 filed Sep. 2, 2005.

The present invention relates to novel substituted imidazo[1,2b]pyridazines, their preparation and use as medicament for the treatment of various disorders.

The compounds described in this invention are suitable for inhibiting kinases, preferably kinases of the protein kinase (PK) family and, in this connection, especially for inhibiting kinases of the PKC subfamily, very particularly for inhibiting the PKC theta kinase. The present compounds are suitable as kinase inhibitors for the treatment of a large number of disorders which are attributable to a dysfunction is of a kinase, including immunological and general inflammatory processes, and oncological processes, but also disorders such as, for example, type II diabetes and asthma, and transplants; preferably inflammatory processes and immune responses which exhibit the clinical appearance of acute dermatitis, of contact dermatitis but also of psoriasis.

A single publication (*Bioorg. Med. Chem. Lett.* 2004, 14, 2249-2252.) discloses pyrimidine derivatives with an attached imidazo[1,2b]pyridazine residue as kinase inhibitors. These compounds differ from the compounds of the invention through their structure, in particular on the imidazo[1,2b]pyridazine ring. The patent application WO 02/066481 (AstraZeneca) describes pyridazine-substituted pyrimidines as antiproliferative substances. Further prior art is mentioned hereinafter.

There is a continuing great need for effective medicaments for the treatment of immunological and also cell-proliferative disorders, in particular in dermatological indications.

It has now been found that substituted imidazo[1,2b]pyridazines of the general formula I in which

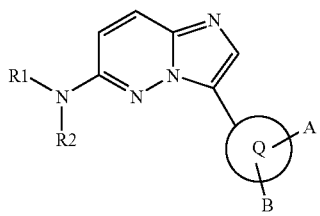

Formula I where

Q is aryl or heteroaryl—with the exception of pyrimidine;

A and B are identical or different and are selected from the group consisting of
i) H, Hal, —OH, —NR³R⁴, —CN, or —NO₂,
ii) optionally mono- or poly-Hal-, —OH—, C3-C6-heterocycloalkyl-, —NR³R⁴—, —SO₂NR³R⁴—, —SO₂R³— or —(CO)—NR³-L-substituted C1-C6-alkyl, C1-C6-haloalkyl, C1-C6-alkoxy, C1-C6-haloalkoxy, C3-C6-cycloalkyl or C3-C6-heterocycloalkyl, where the C3-C6-heterocycloalkyl may comprise in the ring optionally one or more nitrogen, oxygen and/or sulfur atoms and/or one or more —(CO)— or —(SO₂)— groups and/or one or more double bonds, and
iii) —NR³(CO)-L, —NR³(CO)—NR³-L, —(CO)—R⁶, —O—(CH₂)ₚ—R⁶, —(CO)—(NR³)-L, —NR³(CS)—NR³R⁴, —NR³(SO₂)-L, —(SO₂)—NR³R⁴, —NR³(CO)NR³R⁴, —(CO)NR³R⁴, —CO₂R⁷, —NR³(SO₂)R⁴ or —O—(CH₂)ₚ-aryl, where the substituents in the case of polysubstitution may be identical or different, A and B in addition to the aforementioned definition together form a Q-fused C5-C7-cycloalkyl or C5-C7-heterocycloalkyl ring, where the latter comprises at least one oxygen or one nitrogen atom in the ring, and may optionally comprise additionally in the ring one or more oxygen, nitrogen or sulfur atoms and/or one or more —(CO)— or —(SO₂)— groups and/or optionally one or more double bonds, p is 0 to 4, L is optionally mono- or poly-hydroxy-, C1-C6-alkyl-, C1-C6-haloalkyl-, C1-C6-haloalkyl-, C1-C6-hydroxyalkoxy-, C1-C6-alkoxy-, C1-C6-haloalkoxy-, C1-C6-alkoxyalkoxy-, C3-C6-heterocycloalkyl-, or —NR³R⁴-substituted C1-C6-alkyl, C1-C6-haloalkyl or C3-C6-cycloalkyl or C3-C6-heterocycloalkyl, where the C3-C6 heterocycloalkyl may comprise in the ring optionally one or more nitrogen, oxygen and/or sulfur atoms and/or one or more —(CO)— or —(SO₂)— groups and/or one or more double bonds;

R¹ and R² are identical or different and are selected from the group consisting of
j) —H and
jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6-heterocycloalkyl-, C2-C6-alkynyl-, aryl-, aryloxy-, heteroaryl-, —S—C1-C6-alkyl-, —(CO)—R⁶—, —NR³R⁴—, —NR³(CO)-L-, —NR³COOR⁷—, —COOR⁷—, —NR³CONR³R⁴—, —NR³SO₂R⁴—, —SO₂NR³R⁴—, —CONR³R⁴— or —SO₂R³-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl or
with —(CH₂)ᵣ—R⁸ radical, where r is a number 0-3, and R⁸ is a radical

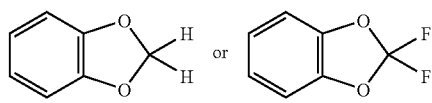

where aryl, heteroaryl, C3-C6-cycloalkyl or C3-C6-heterocycloalkyl groups optionally present in R¹ or R² may be substituted one or more times by -Hal, —CN, —OH, —C1-C6-alkyl, C1-C6-haloalkyl, —C1-C6-alkoxy, C1-C6-haloalkoxy, —C1-C6-hydroxyalkyl, —C3-C6-cycloalkyl, —NO₂, —NH₂, —C1-C6-haloalkyl, —NR³R⁴, —CONR³R⁴, —NR³COR⁴, NR³SO₂R⁴, —COR⁶, CO₂R⁷, —SO₂NR³R⁴, —SR³, SOR³, —SO₂R³, —OR³, —O(CH₂)ₚR⁶, where the substituents in the case of polysubstitution may be identical or different;

where two or more aryl or heteroaryl groups may not be substituents on the same carbon atom in R¹ or R²;

R¹ and R² in addition to the aforementioned definition may together form a C3-C6-heterocycloalkyl ring which comprises at least one nitrogen atom in the ring and may optionally comprise additionally in the ring one or more nitrogen, oxygen or sulfur atoms and/or one or more —(CO)— or —(SO₂)— groups and/or optionally one or more double bonds, where the ring formed by R¹ and R² may be optionally substituted one or more times by —CN, -Hal, —OH, C1-C6-alkyl, C1-C6-haloalkyl, C3-C6-cycloalkyl, C1-C6-hydroxyalkyl, C1-C6-alkoxyalkyl, C1-C6-haloalkoxy-, C1-C6-haloalkoxyalkyl, —NR³R⁴, —CONR⁶R⁷, —(CO)—R⁶ or —COOR⁷ and/or by optionally mono- or poly-Hal-, C1-C6-alkoxy-, C1-C6-haloalkoxy- or —(CO)—$R^6$-substituted aryl or heteroaryl, where the substituents in the case of polysubstitution may be identical or different;

$R^3$ and $R^4$ are identical or different and are selected from the group consisting of
j) —H, and jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —$NR^6R^7$—, —$CONR^6R^7$—, —(CO)—$R^6$— or —$COOR^7$-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may comprise in the ring optionally one or more nitrogen, oxygen and/or sulfur atoms and/or one or more —(CO)— or —$SO_2$— groups and/or one or more double bonds, and where the substituents in the case of polysubstitution may be identical or different;

$R^3$ and $R^4$ in addition to the aforementioned definition may together form a C3-C6-heterocycloalkyl ring which comprises at least one nitrogen atom in the ring and may optionally comprise additionally in the ring one or more nitrogen, oxygen or sulfur atoms and/or one or more —(CO)— or —($SO_2$)— groups and/or optionally one or more double bonds, where the ring formed by $R^3$ and $R^4$ may be optionally substituted one or more times by —CN, -Hal, —OH, C1-C6-alkyl, C1-C6-haloalkyl, C3-C6-cycloalkyl, C1-C6-hydroxyalkyl, C1-C6-haloalkoxy, C1-C6-haloalkoxyalkyl, C1-C6-alkoxyalkyl, or by —$NR^6R^7$, —$CONR^6R^7$, —(CO)—$R^6$ or —$COOR^7$ and/or by optionally mono- or poly-Hal-, C1-C6-alkoxy-, C1-C6-haloalkoxy- or —(CO)—$R^6$-substituted aryl or heteroaryl, where the substituents in the case of polysubstitution may be identical or different;

$R^6$ and $R^7$ are identical or different and are selected from the group consisting of
j) —H and jj) optionally mono- or poly-Hal-, —OH—, —CN— substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may comprise in the ring optionally one or more nitrogen, oxygen and/or sulfur atoms and/or one or more —(CO)— or —$SO_2$— groups and/or one or more double bonds, and where the substituents in the case of polysubstitution may be identical or different, and the isomers, diastereomers, enantiomers and salts thereof, represent effective compounds for inhibiting kinases (defined hereinafter) and therefore can be employed for a number of disorders (defined hereinafter).

Alkyl means in each case a straight-chain or branched alkyl radical such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy means in each case a straight-chain or branched alkoxy radical such as, for example, methyloxy, ethyloxy, propyloxy, isoproplyoxy, butyloxy, isobutyloxy, sec butyloxy, pentyloxy, isopentyloxy, hexyloxy, heptyloxy, octyloxy, nonyloxy or decyloxy.

The alkenyl substituents are in each case straight-chain or branched, with the following radicals being meant for example: vinyl, propen-1-yl, propen-2-yl, but-1-en-1-yl, but-1-en-2-yl, but-2-en-1-yl, but-2-en-2-yl, 2-methylprop-2-en-1-yl, 2-methylprop-1-en-1-yl, but-1-en-3-yl, but-3-en-1-yl, allyl.

Alkynyl means in each case a straight-chain or branched alkynyl radical which comprises 2-6, preferably 2-4, C atoms.

Examples of suitable radicals are the following: ethynyl, propyn-1-yl, propyn-3-yl (propargyl), but-1-yn-1-yl, but-1-yn-4-yl, but-2-yn-1-yl, but-1-yn-3-yl, 3-methylbut-1-yn-3-yl.

C1-C6-Haloalkyl stands for a straight-chain or branched alkyl radical in which at least one hydrogen atom is replaced by a halogen atom (fluorine, chlorine, bromine or iodine, preferably fluorine or chlorine), such as, for example fluoromethyl, trichloromethyl, 1,2-difluoroethyl, perfluoropropyl, 3,3,3-trifluoropropyl, 1-fluoroisopropyl, perfluorobutyl, etc. Perfluoromethyl and perfluoroethyl groups are very particularly preferred.

C1-C6-Haloalkoxy stands for a straight-chain or branched alkoxy radical in which at least one hydrogen atom is replaced by a halogen atom (fluorine, chlorine, bromine or iodine, preferably fluorine or chlorine), such as, for example, fluoromethoxy, trichloromethoxy, 1,2-difluoroethoxy, perfluoropropoxy, 3,3,3-trifluoropropoxy, 1-fluoroisopropoxy, perfluorobutoxy, etc. Perfluoromethoxy and perfluoroethoxy groups are very particularly preferred.

C3-C6-Heterocycloalkyl stands for an alkyl ring including 3-6 carbon atoms, where the heterocycloalkyl comprises in the ring at least one atom, identical or different, from the following group oxygen, sulfur or nitrogen, and may optionally be interrupted by one or more —(CO)—, —(CS)— or —$SO_2$— groups in the ring, and may optionally comprise one or more double bonds in the ring, and the ring itself may optionally be substituted one or more times, identically or differently.

Examples of heterocycloalkyl which may be mentioned are: oxiranyl, oxethanyl, dioxolanyl, dithianyl, dioxanyl, aziridinyl, azetidinyl, tetrahydrofuranyl, tetrahydropyranyl, dihydrooxazolyl, tetrahydrooxazolyl, tetrahydrothiazolyl, tetrahydroisoquinolinyl, octahydroisoquinolinyl, tetrahydroquinolinyl, octahydroquinolinyl, tetrahydroimidazolonyl, pyrazolidinyl, pyrrolidinyl, pyrrolidonyl, piperidinyl, piperidonyl, piperazinyl, piperazinonyl, N-methylpyrrolidinyl, 2-hydroxymethylpyrolidinyl, 3-hydroxypyrolidinyl, N-methylpiperazinyl, N-benzylpiperazinyl, N-acetylpiperazinyl, N-methylsulfonylpiperazinyl, 4-hydroxypiperidinyl, 4-aminocarbonylpiperidinyl, 2-hydroxyethylpiperidinyl, 4-hydroxymethylpiperidinyl, imidazolidinyl, tetrahydroimidazolonyl, morpholinyl, thiomorpholinyl, 1,1-dioxothiomorpholinyl, trithianyl, tetrahydrotriazinthionyl, triazinthionyl, quinuclidinyl, nortropinyl, pydridonyl.

Preferred heterocycloalkyl groups which may be mentioned are: tetrahydropyranyl, pyrrolidinyl, piperidinyl, N-methylpiperidinyl, piperazinonyl, N-methylpiperazinyl, morpholinyl, pyrridonyl.

Substituents on the heterocycloalkyl ring may be for example: cyano, halogen, hydroxy, C1-C6-alkyl, C1-C6-haloalkyl, C1-C6-alkoxy, C1-C6-haloalkoxy, $C_1$-$C_6$-alkoxyalkyl, $C_1$-$C_6$-hydroxyalkyl, $C_3$-$C_6$-cycloalkyl, aryl or optionally identically or differently mono- or poly-halogen-, hydroxyl- or $C_1$-$C_6$-alkylthio-substituted C1-C6-alkyl, C1-C6-haloalkyl or a substituent from the group —(CO)—$C_1$-$C_6$-alkyl, —(CO)—O—$C_1$-$C_6$-alkyl, —($SO_2$)—$C_1$-$C_6$-alkyl, —($SO_2$)-phenyl, —$NH_2$, —N($C_1$-$C_6$-alkyl)$_2$, —NH ($C_1$-$C_6$-alkyl) etc.

Cycloalkyl means monocyclic alkyl rings such as cyclopropyl, cyclobutyl, cyclopentyl, cyclohexyl or cycloheptyl, but also bicyclic rings or tricyclic rings such as, for example, adamantanyl. The cycloalkyl may also optionally be benzo-fused, such as, for example, (tetralin)yl etc.

Preferred cycloalkyl groups are cyclopropyl, cyclobutyl, cyclopentyl and cyclohexyl.

Halogen means in each case fluorine, chlorine, bromine or iodine.

The aryl radical in Q and the aryl radical optionally present in $R^1$ and $R^2$ includes in each case 3-12 carbon atoms and may in each case be benzo-fused. Examples which may be mentioned are: cyclopropenyl, cyclopentadienyl, phenyl, tropyl, cyclooctadienyl, indenyl, naphthyl, azulenyl, biphenyl, fluorenyl, anthracenyl, tetralinyl etc.

The heteroaryl radical Q includes in each case 5-16 ring atoms and may comprise in place of the carbon one or more identical or different heteroatoms such as oxygen, nitrogen or sulfur in the ring, and may be mono-, bi- or tricyclic, and may additionally be in each case benzo-fused. Pyrimidine is not included as group Q in the definition of heteroaryl.

Examples which may be mentioned are: thienyl, furanyl, pyrrolyl, oxazolyl, thiazolyl, imidazolyl, pyrazolyl, isoxazolyl, isothiazolyl, oxadiazolyl, triazolyl, thiadiazolyl, etc. and benzo derivatives thereof, such as, for example, benzofuranyl, benzothienyl, benzoxazolyl, benzimidazolyl, indazolyl, indolyl, isoindolyl, etc.; or pyridyl, pyridazinyl, pyrazinyl, triazinyl, etc. and benzo derivatives thereof, such as, for example, quinolyl, isoquinolyl, etc.; or oxepinyl, azocinyl, indolizinyl, indolyl, indolinyl, isoindolyl, indazolyl, benzimidazolyl, purinyl, etc. and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, tetralinyl, etc.

Preferred heteroaryl radicals are for example 5-membered heteroaromatic rings such as thienyl, furanyl, oxazolyl, thiazolyl, pyrazolyl, imidazolyl and benzo derivatives of the 5-membered heteroaromatic rings, and 6-membered heteroaromatic rings, such as pyridinyl, triazinyl, and benzo derivatives of the 5-membered heteroaromatic rings, such as quinolinyl, isoquinolinyl.

The heteroaryl radical optionally present in $R^1$ or $R^2$ includes in each case 5-16 ring atoms and may comprise instead of the carbon one or more identical or different heteroatoms such as oxygen, nitrogen or sulfur in the ring, and may be mono-, bi- or tricyclic, and may additionally in each case be benzo-fused.

Examples of the heteroaryl radical in $R^1$ or $R^2$ which may be mentioned are: thienyl, furanyl, pyrroidinylyl, oxazolyl, thiazolyl, imidazolyl, pyrazolyl, isoxazolyl, isothiazolyl, oxadiazolyl, triazolyl, thiadiazolyl, etc. and benzo derivatives thereof, such as, for example, benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc. and benzo derivatives thereof, such as, for example, quinolyl, isoquinolyl, etc.; or oxepinyl, azocinyl, indolizinyl, indolyl, indolinyl, isoindolyl, indazolyl, benzimidazolyl, purinyl, etc. and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, tetralinyl, etc.

Examples of preferred heteroaryl radicals in $R^1$ or $R^2$ are 5-membered heteroaromatic rings such as thienyl, pyrazolyl, furanyl, oxazolyl, thiazolyl, triazolyl, imidazolyl and benzo derivatives thereof and 6-membered heteroaromatic rings such as pyridinyl, pyrazinyl, triazinyl, quinolinyl, isoquinolinyl and benzo derivatives thereof.

Particularly preferred heteroaryl radicals in $R^1$ or $R^2$ are thienyl, pyrazolyl, furanyl, oxazolyl, thiazolyl, triazolyl, imidazolyl, pyridinyl, pyrazinyl, triazinyl, quinolinyl, isoquinolinyl.

If a plurality of aryl or heteroaryl groups are present in $R^1$ or $R^2$, two or more aryl or heteroaryl groups may not be substituents on the same carbon atom.

Thus, for example, a group

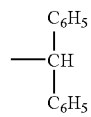

is precluded as group $R^1$ or $R^2$.

Should aryl, heteroaryl, C3-C6-cycloalkyl or C3-C6-heterocycloalkyl groups be present in $R^1$ or $R^2$, these may be substituted one or more times by -Hal, —CN, —OH, —C1-C6-alkyl, C1-C6-haloalkyl, —C1-C6-alkoxy, C1-C6-haloalkoxy, —C1-C6-hydroxyalkyl, —C3-C6-cycloalkyl, —NO$_2$, —NH$_2$, —C1-C6-haloalkyl, —NR$^3$R$^4$, —CONR$^3$R$^4$, —NR$^3$COR$^4$, NR$^3$SO$_2$R$^4$, —COR$^6$, CO$_2$R$^7$, —SO$_2$NR$^3$R$^4$, —SR$^3$, SOR$^3$, —SO$_2$R$^3$, —OR$^3$, —O(CH$_2$)$_p$ R$^6$, where the substituents in the case of polysubstitution may be identical or different. In a preferred embodiment, the aryl, heteroaryl, C3-C6-cycloalkyl or C3-C6-heterocycloalkyl groups present in $R^1$ or $R^2$ have not more than 3 of the above-mentioned substituents.

Isomers mean chemical compounds of the same molecular formula but different chemical structure. A distinction is made in general between constitutional isomers and stereoisomers.

Constitutional isomers have the same molecular formula but differ through the manner of attachment of their atoms or atomic groups. These include functional isomers, positional isomers, tautomers or valence isomers.

Stereoisomers have in principle the same structure (constitution)—and thus also the same molecular formula—but differ through the spatial arrangement of the atoms.

A distinction is made in general between configurational isomers and conformational isomers. Configurational isomers are stereoisomers which can be converted into one another only by breaking a bond. These include enantiomers, diastereomers and E/Z (cis/trans) isomers.

Enantiomers are stereoisomers which are related to one another as image and mirror image and have no plane of symmetry. All stereoisomers which are not enantiomers are referred to as diastereomers. E/Z (cis/trans) isomers at double bonds are a special case.

Conformational isomers are stereoisomers which can be converted into one another by rotation of single bonds.

See also the IUPAC rules section E (*Pure Appl. Chem.* 1976, 45, 11-30.) concerning the categorization of the type of isomerism.

The compounds of the invention of the general formula I also encompass the possible tautomeric forms and include the E or Z isomers or, if a chiral center is present, also the racemates and enantiomers. Double-bond isomers are also to be understood thereby.

The compounds of the invention may also exist in the form of solvates, in particular of hydrates, in which case the compounds according to the invention accordingly comprise polar solvents, in particular water, as structural element of the crystal lattice of the compounds according to the invention. The proportion of polar solvent, in particular water, may be in a stoichiometric or else non-stoichiometric ratio. Terms used in connection with stoichiometric solvates, hydrates are also hemi-, (semi-), mono-, sesqui-, di-, tri-, tetra-, penta-, etc. solvates or hydrates.

If an acidic function is present, suitable salts are the physiologically tolerated salts of organic and inorganic bases such as, for example, the readily soluble alkali metal and alkaline earth metal salts, and salts of N-methylglucamine, dimethylglucamine, ethylglucamine, lysine, 1,6-hexanediamine, ethanolamine, glucosamine, sarcosine, serinol, trishydroxymethylaminomethane, aminopropanediol, Sovak base, 1-amino-2,3,4-butanetriol.

If a basic function is present, the physiologically tolerated salts of organic and inorganic acids are suitable, such as hydrochloric acid, sulfuric acid, phosphoric acid, citric acid, tartaric acid, fumaric acid, maleic acid, malic acid and others.

Preferred compounds of the general formula I are those compounds in which $R^1$ and $R^2$ are identical or different and are selected from the group consisting of j) —H and jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—$R^6$—, —$NR^3R^4$—, —$NR^3$(CO)-L-, or —$NR^3COOR^7$-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, where the C3-C6-heterocycloalkyl may optionally comprise in the ring one or more nitrogen, oxygen and/or sulfur atoms and/or one or more —(CO)— or —$SO_2$— groups and/or one or more double bonds, and where the substituents in the case of polysubstitution may be identical or different. Q, A, B, $R^3$, $R^4$, $R^6$, $R^7$, p and L may in this case be varied as defined above.

Further preferred compounds of the general formula I are those in which $R^1$ and $R^2$ are identical or different and are selected from the group consisting of j) —H and jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryloxy-, —S—C1-C6-alkyl-, —(CO)—$R^6$—, —$NR^3R^4$—, —$NR^3$(CO)-L-, or —$NR^3COOR^7$-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —$SO_2$— groups and/or one or more double bonds, where the group aryl or heteroaryl defined in jj) may be substituted as long as alkyl is not involved, and where the substituents in the case of polysubstitution may be identical or different. Q, A, B, $R^3$, $R^4$, $R^6$, $R^7$, p and L may in this case be varied as defined above.

Further preferred compounds of the general formula I are those in which Q is: —OH—, -Hal-, —CN—, alkyl-, —$R^6$—, or —$NR^3R^4$-substituted phenyl, pyridyl, thiophenyl, furyl, imidazolyl or pyrazolyl, where $R^1$ and $R^2$ are identical or different and are selected from the group consisting of j) —H and jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryloxy-, —S—C1-C6-alkyl-, —(CO)—$R^6$—, —$NR^3R^4$—, —$NR^3$(CO)-L- or —$NR^3COOR^7$-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —$SO_2$— groups and/or one or more double bonds, where the group aryl or heteroaryl defined in jj) may be substituted as long as alkyl is not involved, and where the substituents in the case of polysubstitution may be identical or different. $R^3$, $R^4$, $R^6$, $R^7$, p and L may in this case be varied as defined above.

Further preferred compounds of the general formula I are those in which $R^1$ and $R^2$ are identical or different and are selected from the group consisting of —H, $NR^3R^4$-substituted C1-C4 alkyl, optionally additionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—$R^6$—, —$NR^3$(CO)-L- or —$NR^3COOR^7$-substituted, optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—$R^6$—, —$NR^3$(CO)-L-, —$NR^3R^4$— or —$NR^3COOR^7$-substituted C5-C6-cycloalkyl, C5-C6-heterocycloalkyl, where $R^3$ and $R^4$ may optionally be identically or differently C1-C6-alkyl, C1-C6-haloalkyl, where $R^3$ and $R^4$ may together form a C3-C6-heterocycloalkyl ring which comprises at least one nitrogen atom in the ring and may optionally additionally comprise in the ring one or more nitrogen, oxygen or sulfur atoms and/or one or more —(CO)— or —($SO_2$)— groups and/or optionally one or more double bonds, and where R6 and R7 is identically or differently —H, —OH, C1-C6-alkoxy, C1-C6-haloalkoxy, or C1-C3 alkyl.

Particularly preferred compounds of the general formula I are those in which $R^1$ is selected from the group consisting of —H and C1-C3-alkyl, where $R^2$ is selected from the group consisting of $NR^3R^4$-substituted C3-C4 alkyl, optionally additionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—$R^6$—, —$NR^3$(CO)-L- or —$NR^3COOR^7$-substituted, where $R^3$ and $R^4$ are identically or differently optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —$NR^6R^7$—, —$CONR^6R^7$—, —(CO)—$R^6$— or —$COOR^7$-substituted C1-C6-alkyl, C1-C6-haloalkyl, where $R^3$ and $R^4$ may together form a C3-C6-heterocycloalkyl ring which comprises at least one nitrogen atom in the ring and may optionally additionally comprise in the ring one or more nitrogen, oxygen or sulfur atoms and/or one or more —(CO)— or —($SO_2$)— groups and/or optionally one or more double bonds, and where R6 and R7 is identically or differently —H, —OH, C1-C6-alkoxy, C1-C6-haloalkoxy, or C1-C3 alkyl.

In a further preferred embodiment, $R^1$ or $R^2$ is a hydrogen atom.

The following compounds mentioned in the examples are particularly preferred:

2.0-2.21

3.0-3.80

4.0-4.11

5.0-5.389

6.0-6.2

7.0-7.1

8.0-8.1

A further aspect of the present invention is represented by a compound of the general formula IIa and the use thereof for preparing a compound according to formula I, in which

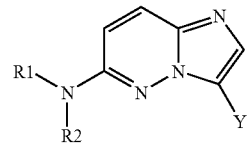

General Formula IIa

Y is a halogen atom (preferably chlorine or bromine), $R^1$ and $R^2$ are identical or different and selected from the group consisting of j) —H and jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—$R^6$—, —$NR^3R^4$—, —$NR^3$(CO)-L- or —$NR^3COOR^7$-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —$SO_2$— groups and/or one or more double bonds, and where the substituents in the case of polysubstitution may be identical or different;

$R^1$ and $R^2$ in addition to the preceding definition may together form a C3-C6-heterocycloalkyl ring which comprises at least one nitrogen atom in the ring and may optionally additionally comprise in the ring one or more nitrogen, oxygen or sulfur atoms and/or one or more —(CO)— or —($SO_2$)— groups and/or optionally one or more double bonds, where the ring formed via $R^1$ and $R^2$ may be optionally substituted one or more times by —CN, -Hal, —OH, C1-C6-alkyl, C1-C6-haloalkyl, C3-C6-cycloalkyl, C1-C6-hydroxyalkyl, C1-C6-haloalkoxyalkyl: C1-C6-haloalkoxy, C1-C6-alkoxyalkyl, —$NR^3R^4$, —$CONR^6R^7$, —(CO)—$R^6$ or —$COOR^7$ and/or by optionally mono- or poly-Hal-, C1-C6-alkoxy-, C1-C6-haloalkoxy- or —(CO)—$R^6$-substituted aryl or heteroaryl, where the substituents in the case of polysubstitution may be identical or different;

where three or more nitrogen atoms in the ring may not be linked directly to one another;

where aryl, heteroaryl, C3-C6-cycloalkyl or C3-C6-heterocycloalkyl groups optionally present in $R^1$ or $R^2$ may be substituted one or more times by -Hal, —CN, —OH, —C1-C6-alkyl, C1-C6-haloalkyl, —C1-C6-alkoxy, C1-C6-haloalkoxy, —C1-C6-hydroxyalkyl, —C3-C6-cycloalkyl, —$NO_2$, —$NH_2$, —C1-C6-haloalkyl, —$NR^3R^4$, —$CONR^3R^4$, —$NR^3COR^4$, $NR^3SO_2R^4$, —$COR^6$, $CO_2R^7$, —$SO_2NR^3R^4$, —$SR^3$, $SOR^3$, —$SO_2R^3$, —$OR^3$, —$O(CH_2)_pR^6$, where the substituents in the case of polysubstitution may be identical or different;

$R^3$ and $R^4$ are identical or different and selected from the group consisting of j) —H and jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —$NR^6R^7$—, —$CONR^6R^7$—, —(CO)—$R^6$— or —$COOR^7$-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —$SO_2$— groups and/or one or more double bonds, and where the substituents in the case of polysubstitution may be identical or different;

$R^3$ and $R^4$ in addition to the preceding definition may together form a C3-C6-heterocycloalkyl ring which comprises at least one nitrogen atom in the ring and may optionally additionally comprise in the ring one or more nitrogen, oxygen or sulfur atoms and/or one or more —(CO)— or —($SO_2$)— groups and/or optionally one or more double bonds, where the ring formed by R3 and R4 may optionally be substituted one or more times by —CN, -Hal, —OH, C1-C6-alkyl, C1-C6-haloalkyl, C3-C6-cycloalkyl, C1-C6-hydroxyalkyl, C1-C6-alkoxyalkyl C1-C6-haloalkoxyalkyl, C1-C6-haloalkyl, C1-C6-alkoxy, C1-C6-haloalkoxy, —$NR^6R^7$, —$CONR^6R^7$, —(CO)—$R^6$ or —$COOR^7$ and/or by optionally mono- or poly-Hal-, C1-C6-alkoxy-, C1-C6-haloalkoxy- or —(CO)—$R^6$-substituted aryl or heteroaryl, where the substituents in the case of polysubstitution may be identical or different;

$R^6$ and $R^7$ are identical or different and selected from the group consisting of j) —H and jj) optionally mono- or poly-Hal-, —OH—, —CN-substituted C1-C6-alkyl, C1-C6-haloalkyl, C1-C6-alkoxy, C1-C6-haloalkoxy, C2-C6-alkenyl, C2-C6

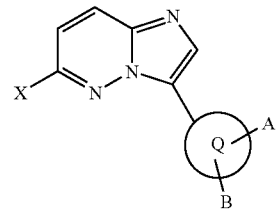

-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —$SO_2$— groups and/or one or more double bonds, and where the substituents in the case of polysubstitution may be identical or different, and the isomers, diastereomers, enantiomers and salts thereof.

A further aspect of the present invention is represented by a compound of the general formula IIb and the use thereof for preparing a compound according to formula I, in which general formula IIb X is chlorine, bromine, O—$SO_2$—$CF_3$ or O—$SO_2$—$C_4F_9$;

Q is aryl or heteroaryl—with the exception of pyrimidine;

A and B are identical or different and selected from the group consisting of i) H, Hal, —OH, —$NR^3R^4$, —CN or —$NO_2$, ii) optionally mono- or poly-Hal-, —OH—, C3-C6-heterocycloalkyl-, —$NR^3R^4$—, —$SO_2NR^3R^4$—, —$SO_2R^3$— or —(CO)—$NR^3$-L-substituted C1-C6-alkyl, C1-C6-haloalkyl, C1-C6-alkoxy, C1-C6-haloalkoxy, C3-C6-cycloalkyl or C3-C6-heterocycloalkyl, where the C3-C6-heterocycloalkyl may optionally comprise in the ring one or more nitrogen, oxygen and/or sulfur atoms and/or one or more —(CO)— or —($SO_2$)— groups and/or one or more double bonds, and iii) —$NR^3$(CO)-L, —$NR^3$(CO)—$NR^3$-L, —(CO)—$R^6$, —O—$(CH_2)_p$—$R^6$, —(CO)—($NR^3$)-L, —$NR^3$(CS)—$NR^3R^4$, —$NR^3(SO_2)$-L, —($SO_2$)—$NR^3R^4$, —$NR^3$(CO)$NR^3R^4$, —(CO)$NR^3R^4$, —$CO_2R^7$, —$NR^3(SO_2)$$NR^4$ or —O—$(CH_2)_p$-aryl, where the substituents in the case of polysubstitution may be identical or different, A and B in addition to the preceding definition together form a Q-fused C5-C7-cycloalkyl or C5-C7-heterocycloalkyl ring, where the latter comprises at least one oxygen or nitrogen atom in the ring and may optionally additionally comprise in the ring one or more oxygen, nitrogen or sulfur atoms and/or one or more —(CO)— or —($SO_2$)— groups and/or optionally one or more double bonds, p is 0 to 4, L is optionally mono- or poly-hydroxy-, C1-C6-alkyl-, C1-C6-haloalkyl-, C1-C6-hydroxyalkoxy-, C1-C6-alkoxy-, C1-C6-haloalkoxy-, C1-C6-alkoxyalkoxy-, C3-C6-heterocycloalkyl- or —$NR^3R^4$-substituted C1-C6-alkyl, C1-C6-haloalkyl or C3-C6-cycloalkyl or C3-C6-heterocycloalkyl, where the C3-C6 heterocycloalkyl may optionally comprise in the ring one or more nitrogen, oxygen and/or sulfur atoms and/or one or more —(CO)— or —(SO$_2$)— groups and/or one or more double bonds;

$R^3$ and $R^4$ are identical or different and selected from the group consisting of j) —H, and jj) optionally mono- or poly-Hal-, —OH—, —CN—, C1-C6-alkyl-, C1-C6-haloalkyl-, C1-C6-alkoxy-, C1-C6-haloalkoxy-, C1-C6-hydroxyalkyl-, C3-C6-cycloalkyl-, C3-C6 heterocycloalkyl-, C2-C6-alkynyl-, aryl-, aryloxy-, heteroaryl-, —NR$^6$R$^7$—, —CONR$^6$R$^7$—, —(CO)—R$^6$— or —COOR$^7$-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one more —(CO)— or —SO$_2$— groups and/or one or more double bonds, and where the substituents in the case of polysubstitution may be identical or different;

$R^3$ and $R^4$ may in addition to the preceding definition together form a C3-C6-heterocycloalkyl ring which comprises at least one nitrogen atom in the ring and may optionally additionally comprise in the ring one or more nitrogen, oxygen or sulfur atoms and/or one or more —(CO)— or —(SO$_2$)— groups and/or optionally one or more double bonds, where the ring formed via R3 and R4 may optionally be substituted one or more times by —CN, -Hal, —OH, C1-C6-alkyl, C1-C6-haloalkyl, C3-C6-cycloalkyl, C1-C6-hydroxyalkyl, C1-C6-alkoxyalkyl, C1-C6-haloalkoxyalkyl, C1-C6-haloalkoxy or by —NR$^6$R$^7$, —CONR$^6$R$^7$, —(CO)—R$^6$ or —COOR$^7$ and/or by optionally mono- or poly-Hal-, C1-C6-alkoxy-, C1-C6-haloalkoxy- or —(CO)—R$^6$-substituted aryl or heteroaryl, where the substituents may in the case of polysubstitution be identical or different;

$R^6$ and $R^7$ are identical or different and selected from the group consisting of j) —H and jj) optionally mono- or poly-Hal-, —OH—, —CN-substituted C1-C6-alkyl, C1-C6-haloalkyl, C1-C6-alkoxy, C1-C6-haloalkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —SO$_2$— groups and/or one or more double bonds, and where the substituents in the case of polysubstitution may be identical or different and the isomers, diastereomers, enantiomers and salts thereof.

These compounds of the general formulae IIa and IIb represent advantageous intermediates and can be employed in the synthesis of the abovementioned compounds of the general formula I.

The explanations made above for the compounds of the formula I, including the preferred embodiments of the radicals, apply in principle analogously to the compounds of the formulae IIa and IIb. It is particularly preferred for Q to be an optionally mono- or poly-OH—, -Hal-, —CN—, alkyl-, —OR$^6$— or —NR$^3$R$^4$-substituted phenyl, pyridyl, thiophenyl, furyl, imidazolyl or pyrazolyl. It is further preferred for X to be —Cl or —Br.

The following intermediates of the invention are particularly preferred: 3-bromo-6-chloroimidazo[1,2-b]pyridazines, imidazo[1,2-b]pyridazin-6-yl-(3-pyrrolidin-1-yl-propyl)amines, 6-chloro-3-phenylimidazo[1,2-b]pyridazines, 6-chloro-3-(3-chlorophenyl)imidazo[1,2-b]pyridazines, 6-chloro-3-(1-methyl-1H-pyrazol-4-yl)imidazo[1,2-b]pyridazines, 6-chloro-3-thiophen-3-ylimidazo[1,2-b]pyridazines.

The intermediates 1.0-1.28 described in the examples are very particularly preferred.

Synthesis scheme:

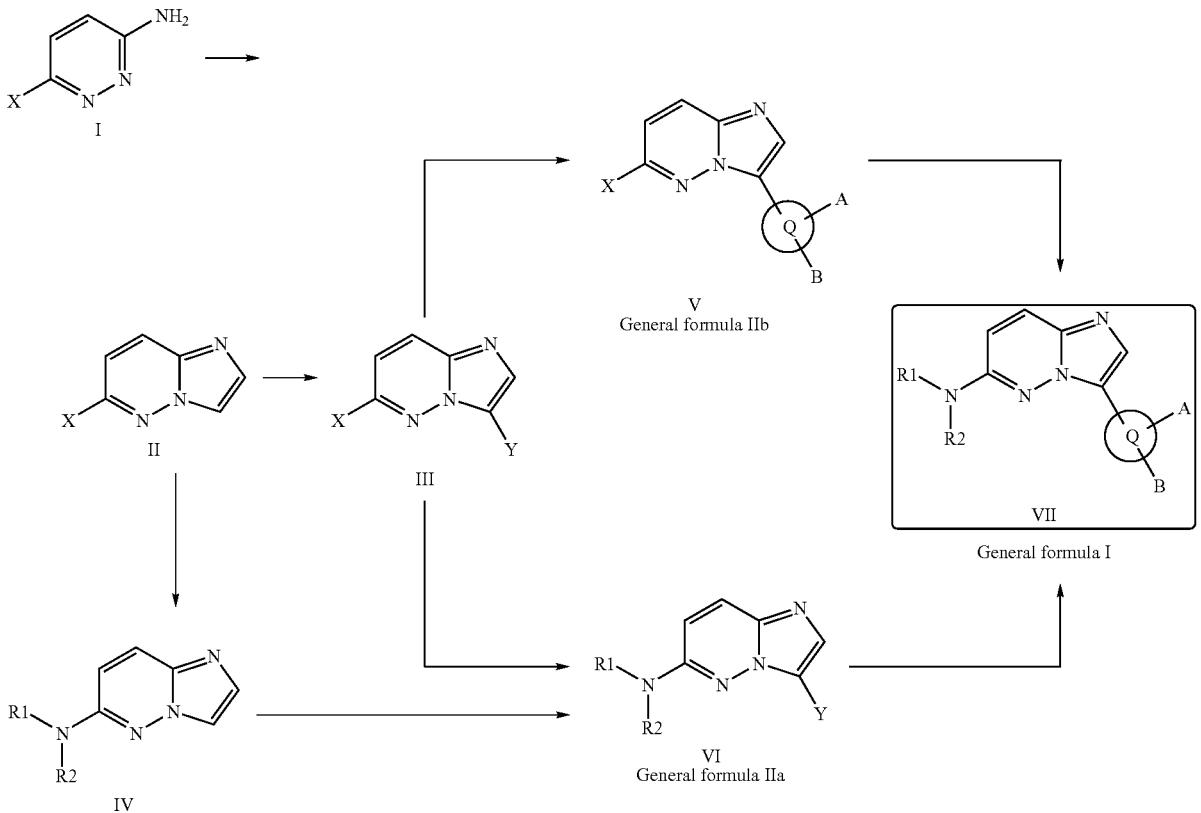

The invention accordingly also relates to a method for preparing a compound of the invention with the following stages of the method:

A1) 3-amino-6-halopyrazine is converted into 6-haloimidazo[1,2-b]pyridazine II,
A2) the product from stage A1 is converted into a 3-halo-6-haloimidazo[1,2-b]pyridazine III,
A3) the product from stage A2 is converted by reaction with a compound NHR$^1$R$^2$ into the compound according to the general formula IIa,
A4) the product from stage A3 is converted into the compound according to the general formula I, or B1) 3-amino-6-halopyrazine is converted into 6-haloimidazo[1,2-b]pyridazine II,
B2) the product from stage B1 is converted into a 3-halo-6-haloimidazo[1,2-b]pyridazine III,
B3) the product from stage B2 is converted into the compound according to the general formula IIb,
B4) the product from stage B3 is converted into the compound according to the general formula I, or C1) 3-amino-6-halopyrazine is converted into 6-haloimidazo[1,2-b]pyridazine II,
C2) the product from stage C1 is converted by reaction with a compound NHR$^1$R$^2$ into an imidazo[1,2-b]pyridazin-6-yl)-(R$^1$)—(R$^2$)-amine IV,
C3) the product from stage C2 is converted into the compound according to the general formula IIa,
C4) the product from stage C3 is converted into the compound according to the general formula I.

Said reactions are preferably carried out as follows:

A1) 3-amino-6-halopyrazine is reacted with chloractetaldehyde to give 6-haloimidazo[1,2-b]pyridazine,
A2) the product from stage A1 is reacted with N-bromosuccinimide to give a 3-bromo-6-haloimidazo[1,2-b]pyridazine,
A3) the product from stage A2 is converted by reaction with a compound NHR$^1$R$^2$ in a Buchwald-Hartwig cross-coupling reaction into a (3-bromoimidazo[1,2-b]pyridazin-6-yl)-(R$^1$)—(R$^2$)-amine,
A4) the product from stage A3 is reacted for example with a boronic acid which is optionally substituted by the radicals A and B to give the compound according to the general formula I, or B1) 3-amino-6-halopyrazine is reacted with chloractetaldehyde to give 6-haloimidazo[1,2-b]pyridazine,
B2) the product from stage B1 is reacted with N-bromosuccinimide to give a 3-bromo-6-haloimidazo[1,2-b]pyridazine,
B3) the product from stage B2 is reacted for example with a boronic acid which is optionally substituted by the radicals A and B to give the compound according to the general formula II,
B4) the product from stage B3 is converted by reacting with a compound NHR$^1$R$^2$ in a Buchwald-Hartwig cross-coupling reaction into the compound according to the general formula I, or C1) 3-amino-6-halopyrazine is reacted with chloractetaldehyde to give 6-haloimidazo[1,2-b]pyridazine,
C2) the product from stage C1 is converted by reacting with a compound NHR$^1$R$^2$ in a Buchwald-Hartwig cross-coupling reaction into an imidazo[1,2-b]pyridazin-6-yl)-(R$^1$)—(R$^2$)-amine,
C3) the product from stage C2 is reacted with N-bromosuccinimide to give a (3-bromoimidazo[1,2-b]pyridazin-6-yl)-(R$^1$)—(R$^2$)-amine,
C4) the product from stage C3 is reacted for example with a boronic acid which is optionally substituted by the radicals A and B to give the compound according to the general formula I.

The compounds of the invention are particularly preferably prepared by synthesis route A1-A4.

To protect sensitive side groups, said synthesis routes can also be prepared with use of protective groups. Such protective group techniques are known to the skilled worker, e.g. from T. W. Greene, P. G. M. Wuts "Protective Groups in Organic Synthesis", 2$^{nd}$ edition, John Wiley and Sons, 1991.

Stages A1, B1 and C1 can be carried out for example by heating with, for example, chloracetaldehyde at 60 to 130° C., in particular 100 to 130° C., in n-butanol as solvent and for a period of from 1 hour to 10 days, in particular 3 to 6 days.

The amination (stages A3, B4 and C2 respectively) can be carried out for example by heating with the appropriate amine at 90-180° C., in particular 90° C., for a period of from 1 hour to 24 hours, in particular 1 hour to 16 hours. The heating can take place by means of conventional heating or else by means of microwave radiation through a suitable apparatus. The use of an auxiliary base such as, for example, K$_2$CO$_3$ or Et$_3$N is not always necessary. The use of a solvent such as, for example, acetonitrile, EtOH, n-BuOH or NMP is not always necessary. It is possible to use for the amination for example the so-called Buchwald-Hartwig cross-coupling reaction. The Buchwald-Hartwig cross-coupling reaction can be carried out for example in accordance with one of the references D. Zim, S. L. Buchwald, *Org. Lett.*, 5:2413-2415 (2003) or S. Urgaonkar, M. Nagarajan, J. G. Verkade, *J. Org. Chem.*, 68:452-459 (2003).

The reaction to give the 3-bromo intermediate (stages A2, B2 and C3) can take place by introducing the precursor compound into chloroform and adding the N-bromosuccinimide at −5 to 30° C., in particular at 0 to 10° C., followed by reaction for 1 hour to 2 days, in particular 5 to 15 hours, at 0 to 30° C., in particular at 15 to 25° C. However, alternative synthesis routes for preparing the 3-halo intermediates of the invention are also known to the skilled worker.

Stages A4, B3 and C4 can be carried out for example by introducing the precursor compound into dimethoxyethane and adding a boronic acid in the presence of a palladium(0) source, for example bis(dibenzylidene-acetone)palladium (O), of a ligand, for example tri-o-tolylphosphine and of a base, for example sodium bicarbonate, and by heating under reflux for 5 to 40 hours, in particular 10 to 20 hours.

Where the preparation of the starting compounds is not described, they are known or can be prepared in analogy to known compounds or methods described herein.

The isomer mixtures can be fractionated by conventional methods such as, for example, crystallization, chromatography or salt formation into the isomers such as, for example, into the enantiomers, diastereomers or E/Z isomers, as long as the isomers are not in equilibrium with one another.

The salts are prepared in a conventional way by adding the equivalent amount or an excess of a base or acid, which is in solution where appropriate, to a solution of the compound of the formula I, and removing the precipitate or working up the solution in a conventional way.

Additional reference is made to the examples for merely exemplary details of the synthesis.

The invention further relates also to intermediates of the invention as defined in the claims.

Compounds of the invention are suitable as kinase inhibitors, in particular of tyrosine and serine/threonine kinases. The compounds of the invention of the general formula I are inter alia inhibitors of the protein kinase C family, such as, for example, PKC theta, delta, iota, alpha and zeta.

An inhibitor of a kinase can therefore be employed on the one hand for investigating the mechanisms of functioning of the kinase, in particular research into a disorder which derives from a dysfunction of the kinase. However, it is also possible for a disorder derived from the dysfunction of the kinase to be treated or prevented using the kinase inhibitor.

The invention therefore further relates to the use of a compound of the invention of the general formula I for producing a pharmaceutical composition, in particular for inhibiting a cellular kinase, preferably kinases of the protein kinase (PK) family and in this connection in particular for inhibiting kinases of the PKC subfamily, very especially for inhibiting the PKC theta kinase, and for the treatment or for the prophylaxis of a disorder which is associated with overexpression or mutation of a cellular kinase, in particular of such a cellular kinase.

It has additionally been found that, surprisingly, the compounds of the invention are also inhibitors of kinases of the ALK family. ALK means "activin receptor-like kinase" or "activin-like kinase". In this connection, the compounds of the invention act on ALK1, ALK2, ALK4 and ALK5, in particular on ALK1 and ALK5. The compounds of the invention are therefore also suitable for the treatment or prophylaxis of disorders which are associated with overexpression or mutation of a kinase of the ALK family, in particular ALK1 and ALK5.

In one embodiment of the invention, the disorder is a disorder from the group consisting of epidermal hyperproliferation such as psoriasis, Alzheimer's, autoinflammatory disorders, fibroses, impaired wound healing, diabetic retinopathy, nephropathy, age-related macular degeneration, Crohn's disease, exaggerated immune response, contact dermatitis, atopic dermatitis, multiple sclerosis, ALS, diabetes, asthma.

In another embodiment of the invention, the disorder is a disorder from the group consisting of benign tumors, malignant tumors, leukemia such as myeloblastic leukemia, lymphoma, sarcoma such as osteosarcoma or chondrosarcoma, neuroblastoma, Wilm's tumor, malignant neoplasms of the bladder, breast, lung, pancreas, prostate, kidney, neoplasms of epithelial origin such as carcinoma of the breast or metastases thereof.

In a further embodiment of the invention, compounds of the invention are used for modulating, in particular reducing, an immune response, for example after a transplantation has taken place to prevent rejection of an organ.

A pharmaceutical composition of the invention can be produced by mixing a physiologically effective dose of a compound of the invention with at least one pharmaceutical excipient and manufacturing a desired dosage form.

A suitable physiologically effective dose is for example an amount of from 1 to 1000 mg, in particular from 50 to 500 mg, per dose unit per day for a person weighing 75 kg, it being possible to give the dose as a single dose to be administered once or divided into 2 or more daily doses.

The pharmaceutical manufacture of a pharmaceutical composition of the invention can take place in a manner customary in the art. Examples of suitable counter ions for ionic compounds are $Na^+$, $K^+$, $Li^+$ or cyclohexylammonium, or $Cl^-$, $Br^-$, acetate, trifluoroacetate, propionate, lactate, oxalate, malonate, maleate, citrate, benzoate, salicylate etc. Examples of suitable solid or liquid pharmaceutical presentations are granules, powders, coated tablets, tablets, (micro) capsules, suppositories, syrups, solutions, ointments, suspensions, emulsions, drops or solutions for injection (i.v., i.p., i.m., s.c.) or atomization (aerosols), transdermal systems, and products with protracted release of active ingredient which are produced by using conventional aids such as carriers, disintegrants, binders, coating agents, swelling agents, glidants or lubricants, and preservatives, stabilizers, wetting agents or emulsifiers; salts to alter the osmotic pressure or buffers, flavorings, sweeteners and solubilizers. Carrier systems which can also be used are surface-active excipients such as salts of bile acids or animal or vegetable phospholipids, but also mixtures thereof, and liposomes or constituents thereof. Excipients which may be mentioned are magnesium carbonate, magnesium stearate, gum Arabic, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycols and solvents such as, for example, sterile water and monohydric or polyhydric alcohols, for example glycerol. Preferred dosage forms are for topical application (ointments, transdermal systems, patches, dressings), for oral administration (tablets, coated tablets, solutions, powders) or for parenteral use (suspension, injection).

A pharmaceutical composition of the invention can be produced by mixing at least one inhibitor used according to the invention in defined dose with a pharmaceutically suitable and physiologically tolerated carrier and, where appropriate, further suitable active ingredients, additives or excipients with a defined dose of inhibitor and manufacturing the desired dosage form. These pharmaceutical products are likewise an aspect of the present invention.

Finally, the invention also relates to a method for the treatment or prophylaxis of a disorder which is associated with overexpression of a cellulose kinase, where a pharmaceutical composition comprising a physiologically effective dose of a compound as claimed in any of claims 1 to 8 is administered to a person suffering from or under threat of suffering from the disorder.

The invention is explained in more detail below by means of examples which represent merely exemplary embodiments.

Preparation of the Starting Materials:

6-Chloroimidazo[1,2-b]pyridazine
(Example 1.0 OP 3055)

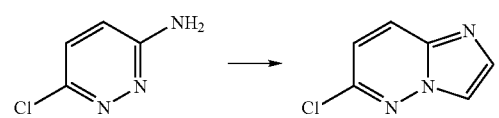

5.0 g (38.6 mmol) of 3-amino-6-chloropyridazine were heated together with 4.7 ml (40 mmol) of chloracetaldehyde (55% strength in water) in 15 ml of n-butanol at 120° C. for a period of 5 days. After the reaction was complete, the reaction mixture was added to saturated sodium bicarbonate solution and extracted three times with ethyl acetate. The combined organic phases were then washed with sat. sodium chloride solution and dried over sodium sulfate, and the solvent was removed in vacuo. In the final purification by chromatography on silica gel, 4.17 g (70%) of the desired product were isolated in the form of an amorphous white solid.

$^1$H-NMR (CDCl$_3$, stored over molecular sieves): δ=7.06 (d, 1H); 7.79 (d, 1H); 7.92, (d, 1H); 7.96 (d, 1H) ppm.

3-Bromo-6-chloroimidazo[1,2-b]pyridazine
(Example 1.1 OP 3056)

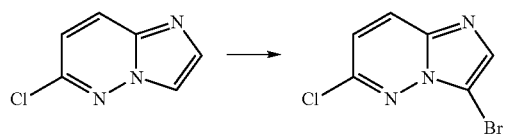

478 mg (3.11 mmol) of 6-chloroimidazo[1,2-b]pyridazine were introduced into 10 ml of chloroform under argon and, while cooling in ice, 664 mg (3.73 mmol) of N-bromosuccuinimide were added. After the addition was complete, the reaction mixture was stirred at room temperature overnight. The reaction mixture was then mixed with water and ethyl acetate and, after addition of saturated sodium bicarbonate solution, the phases were separated. The aqueous phase was extracted three more times with ethyl acetate. The combined organic phases were then washed with sat. sodium chloride solution and dried over sodium sulfate. In the final removal of the solvent in vacuo, the desired product was isolated in quantitative yield in the form of an amorphous white solid which was employed without further chromatographic purification in subsequent reactions.

$^1$H-NMR (CDCl$_3$, stored over molecular sieves): δ=7.12 (d, 1H); 7.79 (s, 1H); 7.90, (d, 1H) ppm.

6-Chloro-3-iodoimidazo[1,2-b]pyridazine
(Example 1.2)

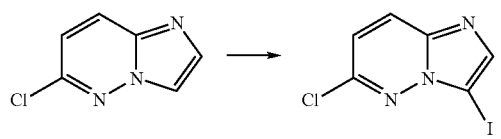

14 g of 6-chloroimidazo[1,2-b]pyridazine (Example 1.0) were suspended in 364 ml of acetonitrile, and 20.51 g of N-iodosuccinimide were added. The mixture was stirred at RT for 19 hours. A further 4.31 g of N-iodosuccinimide were added, and the mixture was stirred for 24 hours. The reaction was cooled and the precipitated solid was filtered off with suction, washed with acetonitrile and dried. 17.67 g of the desired product are obtained.

$^1$H-NMR (300 MHz, d$_6$-DMSO): δ=7.40 (d, 1H); 7.95 (s, 1H); 8.19 (d, 1H) ppm.

Preparation of the Intermediates of the Invention:

Imidazo[1,2-b]pyridazin-6-yl-(3-pyrrolidin-1-ylpropyl)amine (Example 1.3)

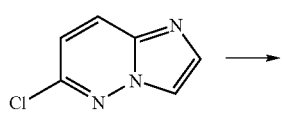

-continued

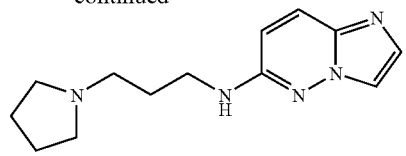

100 mg (0.65 mmol) of 6-chloroimidazo[1,2-b]pyridazine were introduced into 9 ml of tetrahydrofuran and 3 ml of dimethylformamide under argon. 83 mg (0.65 mmol, 1.0 eq.) of 1-(3-aminopropyl)pyrrolidine, 60 mg (0.065 mmol, 0.1 eq.) of (dibenzylideneacetone)palladium(0), 41 mg (0.065 mmol, 0.1 eq.) of rac. 2,2'-bis(diphenylphosphino)-1,1'binaphthyl and 125 mg (1.3 mmol, 2.0 eq) of sodium tert-butoxide were successively added, and the mixture was then heated at 80° C. for 4 h.

The reaction mixture was then mixed with water and ethyl acetate and, after addition of saturated sodium bicarbonate solution, the phases were separated. The aqueous phase was extracted three more times with ethyl acetate. The combined organic phases were then washed with sat. sodium chloride solution and dried over sodium sulfate. In the final purification by chromatography on silica gel, 53 mg (39%) of the desired product were isolated in the form of an amorphous white solid.

$^1$H-NMR (CDCl$_3$, stored over molecular sieves): δ=1.77-1.89 (m, 6H); 2.54 (m, 4H); 2.66 (m, 2H); 3.43 (m, 2H); 6.18 (s. br, 1H); 6.31 (d, 1H); 7.44 (d, 1 H); 7.57, (d, 1H); 7.61 (d, 1H) ppm.

LC-MS (ACN/H$_2$O 0.01% HCOOH; 33×4.6×1.5µ ODSII, Gradient: 100% H$_2$O→90% ACN in 4.5 min): t=0.41 min; m/z=246 [M+H]$^+$ 38%; 123 [M+H]$^{++}$ 100%;

6-Chloro-3-phenylimidazo[1,2-b]pyridazine
(Example 1.4)

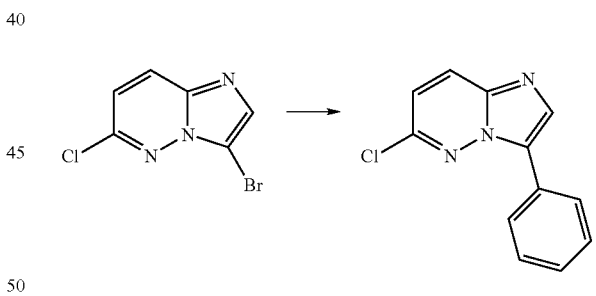

500 mg (2.15 mmol) of 3-bromo-6-chloroimidazo[1,2-b] pyridazine were introduced into 25 ml of dimethoxyethane under argon. 290 mg (2.4 mmol, 1.1 eq.) of phenyl boronic acid, 250 mg (0.43 mmol, 0.2 eq.) of bis(dibenzylideneacetone)palladium(0) and 130 mg (0.43 mmol, 0.2 eq.) of tritolylphosphine, 2.2 ml of saturated sodium bicarbonate solution, were successively added, and the reaction mixture was heated under reflux for 15 hours.

The reaction mixture was then mixed with ethyl acetate and, after addition of saturated sodium bicarbonate solution, the phases were separated. The aqueous phase was extracted three more times with ethyl acetate. The combined organic phases were then washed with sat. sodium chloride solution and dried over sodium sulfate. In the final purification by chromatography on silica gel, 239 mg (48%) of the desired product were isolated.

¹H-NMR (CDCl₃, stored over molecular sieves): δ=7.02 (d, 1H); 7.35 (m, 1H); 7.43 (m, 2H); 7.89 (d, 1H); 7.95-8.0 (m, 3H) ppm.

MS (ES+): m/z=230 (100%)([M+H]⁺; 232 (45%).

2-(3-Bromoimidazo[1,2-b]pyridazin-6-ylamino)ethanol (Example 1.5)

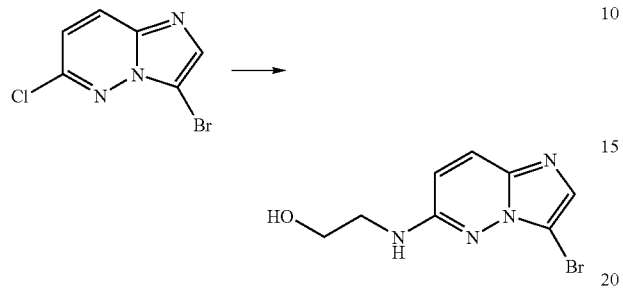

400 mg (1.72 mmol) of 3-bromo-6-chloroimidazo[1,2-b]pyridazine and 2.0 ml (33.4 mmol) of ethanolamine were stirred at 90° C. for 16 h. After cooling, the mixture was concentrated. The resulting residue was purified by chromatography (DCM/EtOH 9:1). 282 mg of the product were obtained.

¹H-NMR (300 MHz; d₆-DMSO): δ=3.28-3.34 (m, 2H, covered by solvent); 3.56-3.61 (m, 2H); 4.74 (t, 1H); 6.71 (d, 1H); 7.13 (t, 1H); 7.43 (s, 1H); 7.64 (d, 1H) ppm.

MS (EI+): m/z=256; 258 (M+H)⁺. [mol. weight=257.09].

2-(3-Iodoimidazo[1,2-b]pyridazin-6-ylamino)ethanol (Example 1.6)

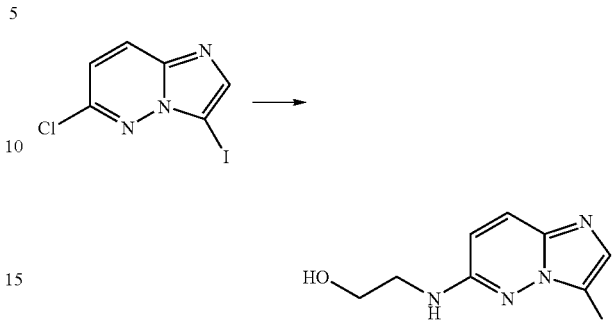

562 mg (2.0 mmol) of 6-chloro-3-iodoimidazo[1,2-b]pyridazine and 2.35 ml (39.2 mmol) of ethanolamine were stirred at 90° C. for 16 h. After cooling, the mixture was concentrated. The resulting residue was purified by chromatography (DCM/EtOH 9:1). 224 mg of the product were obtained.

¹H-NMR (300 MHz; d₆-DMSO): δ=3.27-3.35 (m, 2H, covered by solvent); 3.58-3.63 (m, 2H); 4.72 (t, 1H); 6.67 (d, 1H); 7.06 (t, 1H); 7.42 (s, 1H); 7.59 (d, 1H) ppm.

MS (ESI+): m/z=305 (M+H)⁺. [mol. weight=304.09].

The following are prepared in an analogous manner:

TABLE 1

| | Example No. | Structure and name of the main isomer | ¹H-NMR | Mol. weight/MS (ES+) |
|---|---|---|---|---|
| 358 846 | 1.7 | 6-Chloro-3-(3-chloro-phenyl)-imidazo[1,2-b]pyridazine | (CDCl₃, stored over molecular sieves): δ = 7.12(d, 1H); 7.38(m, 1H); 7.46(m, 1H); 7.94(m, 2H); 8.07(m, 1H); 8.09(s, 1H) ppm. | MW: 264.12 MS (ES+) [M + 1]+: 264 |
| 358 860 | 1.8 | 6-Chloro-3-(1-methyl-1H-pyrazol-4-yl)-imidazo[1,2-b]pyridazine | (CDCl₃, stored over molecular sieves): δ = 4.04(s, 3H); 7.04(d, 1H); 7.92(d, 2H); 7.96(s, 1H); 8.03(s, 1H); 8.25(s, 1H) ppm. | MW: 233.66 MS (ES+) [M + 1]+: 234 |
| 358 861 | 1.9 | 6-Chloro-3-thiophen-3-yl-imidazo[1,2-b]pyridazine | (CDCl₃, stored over molecular sieves); δ = 7.14(d, 1H); 7.48(m, 1H); 7.64(m, 1H); 8.02(d, 1H); 8.07(s, 1H); 8.34(m, 1H) ppm. | MW: 235.70 MS (ES+) [M + 1]+: 236 |

TABLE 1-continued

| Example No. | | Structure and name of the main isomer | ¹H-NMR | Mol. weight/MS (ES+) |
|---|---|---|---|---|
| 6013526 | 1.10 | 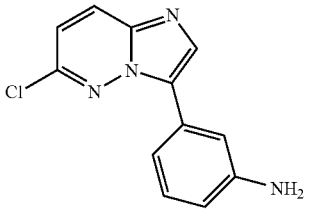<br>3-(6-Chloro-imidazo[1,2-b]pyridazin-3-yl)-phenylamine | | MW: 244.69<br>MS (Cl+) 245 |
| 6013731 | 1.11 | 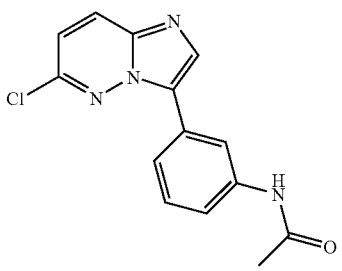<br>N-[3-(6-Chloro-imidazo[1,2-b]pyridazin-3-yl)-phenyl]-acetamide | | MW: 286.72<br>MS (Cl+) 287 |
| 6021472 | 1.12 | 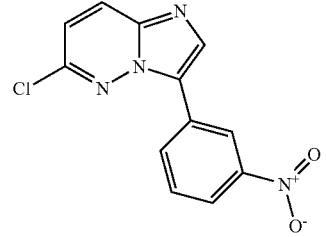<br>6-Chloro-3-(3-nitro-phenyl)-imidazo[1,2-b]pyridazine | | MW: 274.67<br>MS (Cl+) 275 |
| 6025642 | 1.13 | 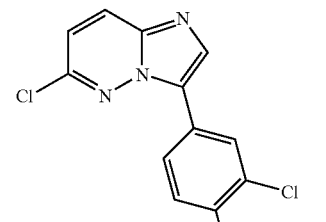<br>6-Chloro-3-(3-chloro-4-methyl-phenyl)-imidazo[1,2-b]pyridazine | | MW: 278.14<br>MS (Cl+) 279 |
| 6032621 | 1.14 | 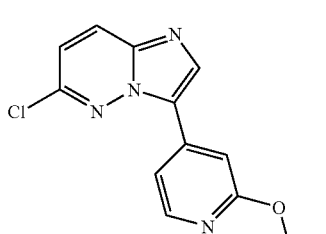<br>6-Chloro-3-(2-methoxy-pyridin-4-yl)-imidazo[1,2-b]pyridazine | (400 MHz, d₆-DMSO):<br>δ = 3.87(s, 3H); 7.49(d, 1H); 7.62(m, 1H); 7.66-7.67(m, 1H); 8.24-8.26(m, 1H); 8.32(d, 1H); 8.55(s, 1H) ppm. | MW: 260.68<br>MS (ES+) 261; 263(Cl Isotopes) |

TABLE 1-continued

| Example No. | | Structure and name of the main isomer | $^1$H-NMR | Mol. weight/MS (ES+) |
|---|---|---|---|---|
| 603 013 5 | 1.15 | 6-Chloro-3-(6-methoxy-pyridin-3-yl)-imidazo[1,2-b]pyridazine | (300 MHz, d$_6$-DMSO): δ = 3.89(s, 3H); 6.96-7.00(m, 1H); 7.38(d, 1H); 8.24-8.28(m, 2H); 8.28-8.32(m, 1H); 8.82-8.83(m, 1H) ppm. | MW: 260.68 MS (ES+) 261; 263(Cl Isotopes) |
| 602 976 8 | 1.16 | 6-Chloro-3-(3,5-dimethoxy-phenyl)-imidazo[1,2-b]pyridazine | (300 MHz, d$_6$-DMSO): δ = 3.84(s, 6H); 6.58(t, 1H); 7.32(d, 2H); 7.43(d, 1H); 8.30(d, 1H); 8.40(s, 1H) ppm. | MW: 289.72 MS (ES+) 290; 292 (Cl Isotopes) |
| 601 957 6 | 1.17 | 6-Chloro-3-(3,4,5-trimethoxy-phenyl)-imidazo[1,2-b]pyridazine | (300 MHz, d$_6$-DMSO): δ = 3.69(s, 3H); 3.83(s, 6H); 7.38(d, 1H); 7.40(s, 2H); 8.25(d, 1H); 8.33(s, 1H) ppm. | |
| 601 957 2 | 1.18 | 6-Chloro-3-(3-trifluoromethyl-phenyl)-imidazo[1,2-b]pyridazine | (400 MHz, d$_6$-DMSO): δ = 7.45(d, 1H); 7.73-7.78(m, 2H); 8.31(d, 1H); 8.36-8.39(m, 1H); 8.46(m, 2H) ppm. | |
| 601 957 0 | 1.19 | 3-Benzo[b]thiophen-2-yl-6-chloro-imidazo[1,2-b]pyridazine | (300 MHz, d$_6$-DMSO): δ = 7.36-7.40(m, 2H); 7.46(d, 1H); 7.90-7.93(m, 1H); 8.02-8.05(m, 1H); 8.18(s, 1H); 8.32(d, 1H); 8.43(s, 1H) ppm. | |

TABLE 1-continued

| Example No. | | Structure and name of the main isomer | ¹H-NMR | Mol. weight/MS (ES+) |
|---|---|---|---|---|
| 601 370 5 | 1.20 | 6-Chloro-3-(3-methoxy-phenyl)-imidazo[1,2-b]pyridazine | (300 MHz, $d_6$-DMSO): δ = 3.80(s, 3H); 6.94-6.98(m, 1H); 7.37-7.45(m, 2H); 7.63-7.66(m, 2H); 8.26(d, 1H); 8.32(s, 1H) ppm. | MW: 259.70 MS (ES+) 260; 262 (Cl Isotopes) |
| 601 979 6 | 1.21 | 6-Chloro-3-(3-trifluoromethoxy-phenyl)-imidazo[1,2-b]pyridazine | (400 MHz, $d_6$-DMSO): δ = 7.36-7.38(m, 1H); 7.43(d, 1H); 7.62-7.66(m, 1H); 8.09-8.11(m, 1H); 8.13(m, 1H); 8.29(d, 1H); 8.41(s, 1H) ppm. | |
| 602 059 5 | 1.22 | 6-Chloro-3-(3,4-dichloro-phenyl)-imidazo[1,2-b]pyridazine | (300 MHz, $d_6$-DMSO): δ = 7.45(d, 1H); 7.77(d, 1H); 8.09(dd, 1H); 8.29(d, 1H); 8.36(d, 1H); 8.43(s, 1H) ppm. | MW: 298.56 MS (ES+) 298; 300; 302 (Cl Isotopes) |
| 602 059 7 | 1.23 | 6-Chloro-3-(3-chloro-4-fluoro-phenyl)-imidazo[1,2-b]pyridazine | (300 MHz, $d_6$-DMSO): δ = 7.42(d, 1H); 7.55-7.61(m, 1H); 8.08-8.13(m, 1H); 8.27-8.31(m, 2H); 8.36(s, 1H) ppm. | |
| 602 059 6 | 1.24 | 3-(6-Chloro-imidazo[1,2-b]pyridazin-3-yl)-benzonitrile | (300 MHz, $d_6$-DMSO): δ = 7.45(d, 1H); 7.70-7.75(m, 1H); 7.82-7.85(m, 1H); 8.31(d, 1H); 8.41-8.45(m, 2H); 8.51(m, 1H) ppm. | |

TABLE 1-continued

| Example No. | Structure and name of the main isomer | $^1$H-NMR | Mol. weight/MS (ES+) |
|---|---|---|---|
| 603 336 3 | 1.25 4-(6-Chloro-imidazo[1,2-b]pyridazin-3-yl)-2-fluoro-phenol | (400 MHz, d$_6$-DMSO): δ = 7.05-7.10(m, 1H); 7.36(d, 1H); 7.72-7.74(m, 1H); 7.87-7.91(m, 1H); 8.22-8.25(m, 2H); 10.24(br s, 1H) ppm. | MW: 263.66 MS (ES+) 264; 266 (Cl Isotopes) |
| | 1.26 6-Chloro-3-(3-methanesulfonyl-phenyl)-imidazol[1,2-b]pyridazine | | MW: 307.76 MS (ES+) 308; 310 (Cl Isotopes) |
| 600 073 4 | 1.27 (3-Bromo-imidazo[1,2-b]pyridazin-6-yl)-(3-pyrrolidin-1-yl-propyl)-amine | | MW: 324.23 MS (EI+) 323/325 |

6-Chloro-3-naphthalen-2-ylimidazo[1,2-b]pyridazine (Example 1.28)

1.03 g of 6-chloro-3-naphthalen-2-ylimidazo[1,2-b]pyridazine were prepared from 5 3.5 g (12.52 mmol) of 6-chloro-3-iodoimidazo[1,2-b]pyridazine (Example 1.2) and 2.37 g (13.78 mmol) of 2-naphthylboronic acid (CAS No. 32316-92-0) in analogy to Example 1.4.

$^1$H-NMR (400 MHz, d$_6$-DMSO): δ=7.43 (d, 1H); 7.51-7.57 (m, 2H); 7.92-7.98 (m, 2H); 8.02-8.05 (m, 1H); 8.13-8.16 (m, 1H); 8.31 (d, 1H); 8.43 (s, 1H); 8.69 (s, 1H) ppm.

Preparation of the Final Products of the Invention:

Method A: (3-phenylimidazo[1,2-b]pyridazin-6-yl)-(3-pyrrolidin-1-ylpropyl)-amine (Example 2.0)

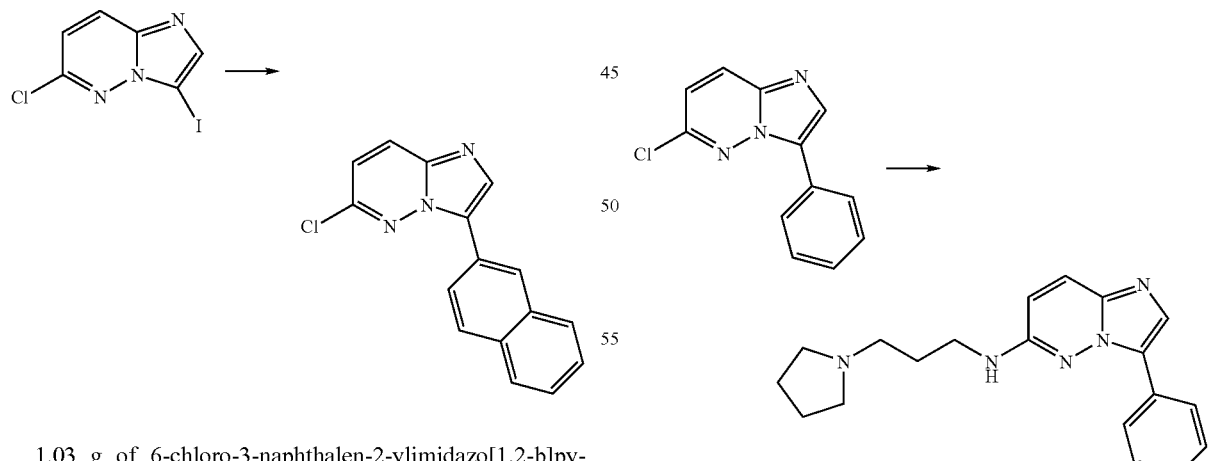

100 mg (0.435 mmol) of 6-chloro-3-phenylimidazo[1,2-b]pyridazine were dissolved in a mixture of 6 ml of tetrahydrofuran and 2 ml of dimethylformamide under argon. 56 mg (0.435 mmol, 1.0 eq.) of 1-(3-aminopropyl)pyrrolidine, 40 mg (0.07 mmol, 0.16 eq.) of bis(dibenzylideneacetone)palladium(0) (Pd$_2$dba$_3$), 27 mg (0.0435 mmol, 0.1 eq.) of rac. 2,2'-bis(diphenylphosphino)-1,1'-binaphthyl (rac-BINAP) and 84 mg (0.87 mmol, 2 eq.) of sodium tert-butoxide (NaOtBu) were successively added, and the reaction mixture was heated at 80° C. for 4 hours.

The reaction mixture was then mixed with ethyl acetate and, after addition of water, the phases were separated. The aqueous phase was extracted three more times with ethyl acetate. The combined organic phases were then washed with sat. sodium chloride solution and dried over sodium sulfate. After multiple purification on silica gel in the final chromatographic fractionation, 9 mg (6%) of the desired product were isolated in pure form.

$^1$H-NMR (CDCl$_3$, stored over molecular sieves): δ=1.8 (m, 4H); 1.88 (m, 2H); 2.55 (m, 4H); 2.68 (t, 2H); 3.51 (m, 2H); 6.19 (s, br. 1H); 6.38 (d, 1H); 7.33 (m, 1H); 7.46 (m, 2H); 7.63 (d, 1H); 7.79 (s, 1H); 8.12 (d, 2H) ppm.

MS (ES+): m/z=322 (100%)([M+H]$^+$.

The following are prepared in an analogous manner:

TABLE 2

| Example No. | Structure and name of the main isomer | $^1$H-NMR | Mol. weight/MS (ES+) [M + 1]$^+$ |
|---|---|---|---|
| 2.1 | 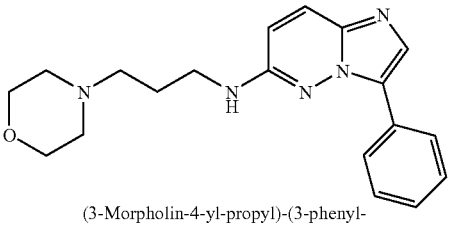<br>(3-Morpholin-4-yl-propyl)-(3-phenyl-imidazo[1,2-b]pyridazin-6-yl)-amine | (CDCl$_3$, stored over molecular sieves): δ = 1.86(m, 2H); 2.50(m, 4H); 2.54(m, 2H); 3.50(m, 2H); 3.75(m, 4H); 6.02(s, br. 1H); 6.41(d, 1H); 7.46(m, 2H); 7.67(d, 1H); 7.80(s, 1H); 8.12(d, 2H) ppm. | |
| 2.2 | 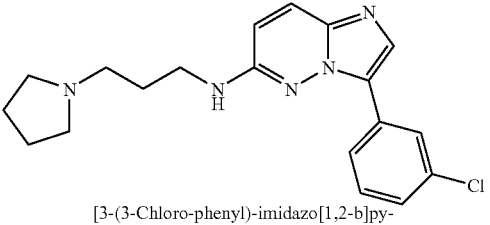<br>[3-(3-Chloro-phenyl)-imidazo[1,2-b]pyridazin-6-yl]-(3-pyrrolidin-1-yl-propyl)-amine | (CDCl$_3$, stored over molecular sieves): δ = 1.81(m, 4H); 1.89(m, 2H); 2.56(m, 4H); 2.68(m, 2H); 3.53(m, 2H); 6.34(s, br. 1H); 6.39(d, 1H); 7.29(m, 1H); 7.38(dd, 1H); 7.64(d, 1H); 7.81(s, 1H); 7.95(m, 1H); 8.30(s, 1H) ppm. | MW: 355.87<br>MS (ES+) [M + 1]$^+$: 356 |
| 2.3 | 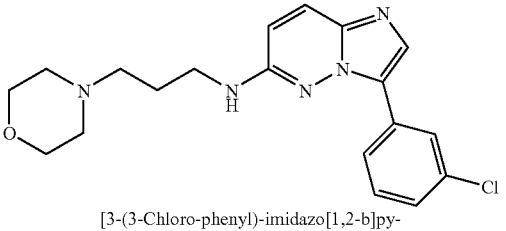<br>[3-(3-Chloro-phenyl)-imidazo[1,2-b]pyridazin-6-yl]-(3-morpholin-4-yl-propyl)-amine | (CDCl$_3$, stored over molecular sieves): δ = 1.88(m, 2H); 2.50(m, 4H); 2.57(m, 2H); 3.53(m, 2H); 3.75(m, 4H); 6.08(m, 1H); 6.45(d, 1H); 7.29(m, 1H); 7.38(dd, 1H); 7.67(d, 1H); 7.82(s, 1H); 7.94(dd, 1H); 8.32(d, 2H) ppm. | MW: 371.87<br>MS (ES+) [M + 1]$^+$: 372 |
| 2.4 | 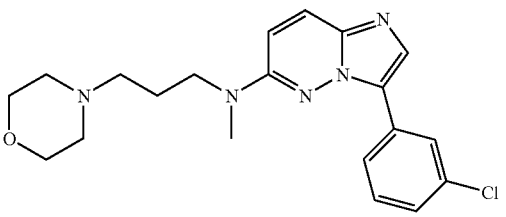<br>[3-(3-Chloro-phenyl)-imidazo[1,2-b]pyridazin-6-yl]-methyl-(3-morpholin-4-yl-propyl)-amine | | MW: 385.90<br>MS (Cl+) 386 |

TABLE 2-continued

| Example No. | Structure and name of the main isomer | $^1$H-NMR | Mol. weight/MS (ES+) [M + 1]$^+$ |
|---|---|---|---|
| 2.5 | 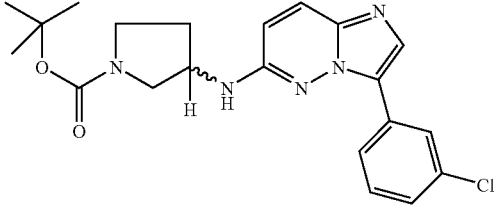<br>3-[3-(3-Chloro-phenyl)-imidazo[1,2-b]py-ridazin-6-ylamino]-pyrrolidine-1-carboxylic acid tert-butyl ester | (CDCl$_3$, stored over molecular sieves): δ = 1.45(s, 9H); 2.04(m, 1H); 2.34(m, 1H); 3.45-3.60(m, 3H); 3.77(m, 1H); 4.46(m, 1H); 4.65(m, 1H); 6.48(d, 1H); 7.28(m, 1H); 7.37(m, 1H); 7.70(m, 1H); 7.84(m, 2H); 8.32(m, 1H) ppm. | |
| 2.6 | 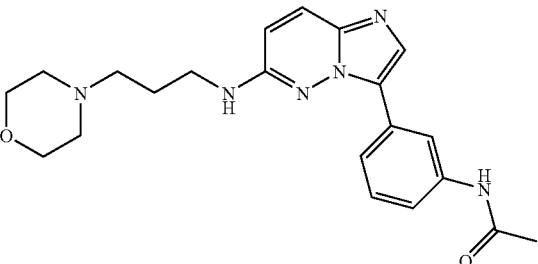<br>N-{3-[6-(3-Morpholin-4-yl-propylami-no)-imidazo[1,2-b]pyridazin-3-yl]-phe-nyl}-acetamide | | MW: 394.48<br>MS (ES+) 395 |
| 2.7 | 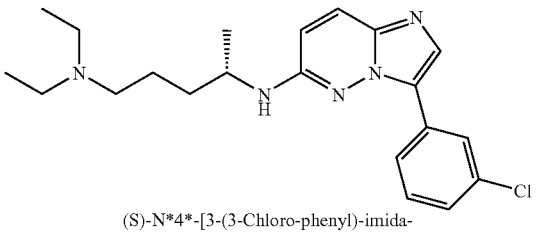<br>(S)-N*4*-[3-(3-Chloro-phenyl)-imida-zo[1,2-b]pyridazin-6-yl]-N*1*,N*1*-di-ethyl-pentane-1,4-diamine | | MW: 385.94<br>MS (ES+) 386 |
| 2.8 | 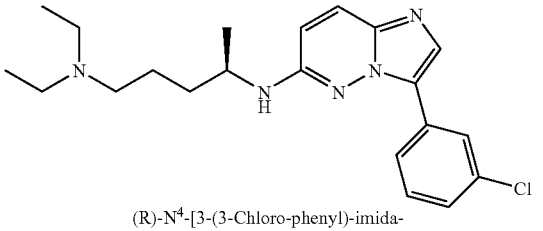<br>(R)-N$^4$-[3-(3-Chloro-phenyl)-imida-zo[1,2-b]pyridazin-6-yl]-N$^1$,N$^1$-di-ethyl-pentane-1,4-diamine | | MW: 385.94<br>MS (ES+) 386 |
| 2.9 | 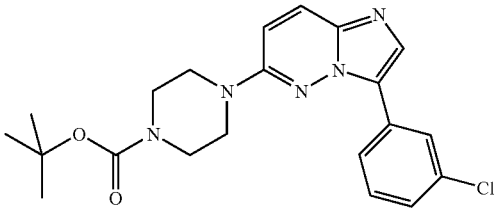<br>4-[3-(3-Chloro-phenyl)-imidazo[1,2-b]py-ridazin-6-yl]-piperazine-1-carb-oxylic acid tert-butyl ester | | MW: 413.91<br>MS (CI+) 414 |

TABLE 2-continued

| Example No. | Structure and name of the main isomer | $^1$H-NMR | Mol. weight/MS (ES+) [M + 1]$^+$ |
|---|---|---|---|
| 2.10 | 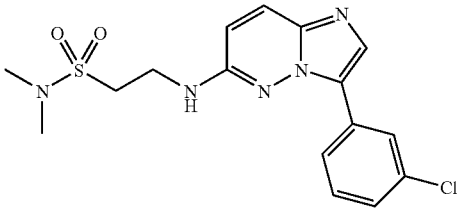<br>2-[3-(3-Chloro-phenyl)-imidazo[1,2-b]pyridazin-6-ylamino]-ethanesulfonic acid dimethylamide | | MW: 379.87<br>MS (CI+)<br>380 |
| 2.11 | 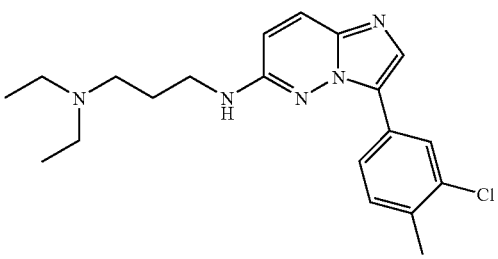<br>N'-[3-(3-Chloro-4-methyl-phenyl)-imidazo[1,2-b]pyridazin-6-yl]-N,N-diethyl-propane-1,3-diamine | (CDCl$_3$, stored over molecular sieves): δ = 1.09(t, 6H); 1.85(m, 2H); 2.43(s, 3H); 2.53-2.69(m, 6H); 3.49(m, 2H); 6.40(d, 1H); 6.76(m, 1H); 7.39(d, 1H); 7.62(d, 2H); 7.75(s, 1H); 7.93(m, 1H); 8.01(m, 1H) ppm. | |
| 2.12 | 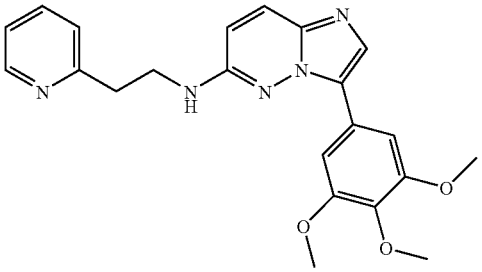<br>(2-Pyridin-2-yl-ethyl)-[3-(3,4,5-trimethoxy-phenyl)-imidazo[1,2-b]pyridazin-6-yl]-amine | (300 MHz, d$_6$-DMSO): δ = 3.03-3.08(m, 2H); 3.63-3.70(m, 5H); 3.73(s, 6H); 6.65(d, 1H); 7.15-7.26(m, 3H); 7.54(s, 2H); 7.64-7.71(m, 2H); 7.92(s, 1H); 8.46-8.48(m, 1H) ppm. | |
| 2.13 | 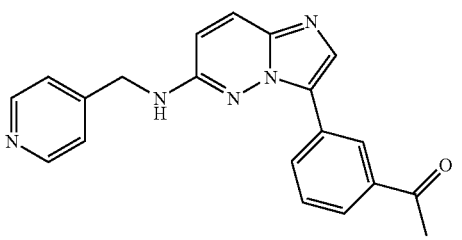<br>1-(3-{6-[(Pyridin-4-ylmethyl)-amino]-imidazo[1,2-b]pyridazin-3-yl}-phenyl)-ethanone | (400 MHz, d$_6$-DMSO): δ = 2.58(s, 3H); 4.58-4.60(m, 2H); 6.86(d, 1H); 7.39-7.40(m, 2H); 7.47-7.50(m, 1H); 7.79-7.86(m, 3H); 7.99(s, 1H); 8.09-8.12(m, 1H); 8.49-8.50(m, 2H); 8.67-8.68(m, 1H) ppm. | |
| 2.14 | 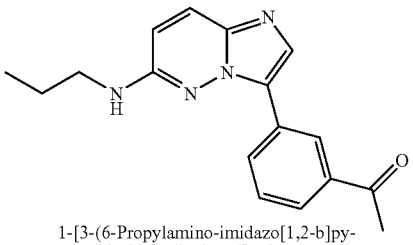<br>1-[3-(6-Propylamino-imidazo[1,2-b]pyridazin-3-yl)-phenyl]-ethanone | (400 MHz, d$_6$-DMSO): δ = 0.93(t, 3H); 1.58-1.67(m, 2H); (m, 2H, covered by solvent); 2.61(s, 3H); 6.70(d, 1H); 7.09-7.11(m, 1H); 7.55-7.59(m, 1H); 7.73(d, 1H); 7.83-7.86(m, 1H); 7.97(s, 1H); 8.28-8.31(m, 1H); 8.96-8.97(m, 1H) ppm. | |

TABLE 2-continued

| Example No. | Structure and name of the main isomer | ¹H-NMR | Mol. weight/MS (ES+) [M + 1]⁺ |
|---|---|---|---|
| 2.15 | 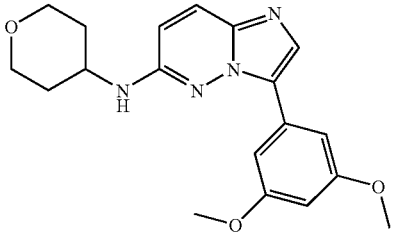<br>[3-(3,5-Dimethoxy-phenyl)-imidazo[1,2-b]pyridazin-6-yl]-(tetrahydro-pyran-4-yl)-amine | (300 MHz, d₆-DMSO): δ = 1.40-1.52(m, 2H); 1.98-2.03(m, 2H); 3.34-3.42(m, 2H); 3.78-3.90(m, 9H); 6.43(t, 1H); 6.65(d, 1H); 7.02-7.05(m, 1H); 7.36(d, 2H); 7.71(d, 1H); 7.90(s, 1H) ppm. | MW: 354.41 MS (ES+) 355 |
| 2.16 | 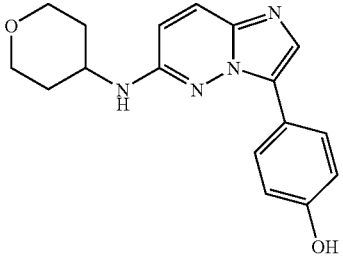<br>4-[6-(Tetrahydro-pyran-4-ylamino)-imidazo[1,2-b]pyridazin-3-yl]-phenol | (300 MHz, d₆-DMSO): δ = 1.38-1.52(m, 2H); 1.98-2.03(m, 2H); 3.38-3.46(m, 2H); 3.73-3.91(m, 3H); 6.60(d, 1H); 6.79-6.82(m, 2H); 6.95-6.97(m, 1H); 7.66-7.69(m, 2H); 7.91-7.94(m, 2H); 9.54(s, 1H) ppm. | MW: 310.36 MS (ES+) 311 |
| 2.17 | 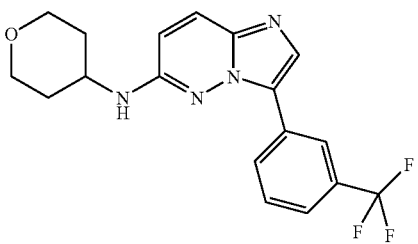<br>(Tetrahydro-pyran-4-yl)-[3-(3-trifluoromethyl-phenyl)-imidazo[1,2-b]pyridazin-6-yl]-amine | (400 MHz, d₆-DMSO): δ = 1.42-1.52(m, 2H); 1.96-2.01(m, 2H); 3.34-3.40(m, 2H); 3.78-3.90(m, 3H); 6.70(d, 1H); 7.13-7.15(m, 1H); 7.60-7.67(m, 2H); 7.77(d, 1H); 8.02(s, 1H); 8.24·48.27(m, 1H); 8.77(br s, 1H) ppm. | |
| 2.18 | 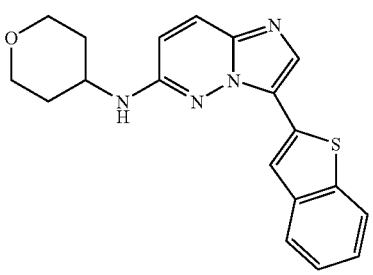<br>(3-Benzo[b]thiophen-2-yl-imidazo[1,2-b]pyridazin-6-yl)-(tetrahydro-pyran-4-yl)-amine | (300 MHz, d₆-DMSO): δ = 1.44-1.57(m, 2H); 2.10-2.16(m, 2H); 3.53-3.61(m, 2H); 3.92-4.05(m, 3H); 6.71(d, 1H); 7.23-7.25(m, 1H); 7.28-7.39(m, 2H); 7.76-7.81(m, 2H); 7.94-7.97(m, 1H); 8.00(s, 1H); 8.05(br s, 1H) ppm. | |

TABLE 2-continued

| Example No. | Structure and name of the main isomer | ¹H-NMR | Mol. weight/MS (ES+) [M + 1]⁺ |
|---|---|---|---|
| 2.19 | 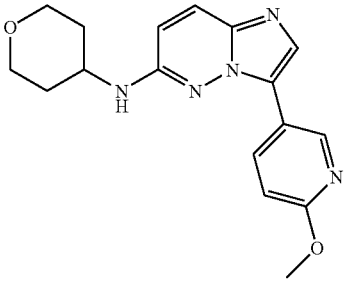<br>[3-(6-Methoxy-pyridin-3-yl)-imidazo[1,2-b]pyridazin-6-yl]-(tetrahydro-pyran-4-yl)-amine | (400 MHz, $d_6$-DMSO): δ = 1.40-1.50(m, 2H); 1.96-2.00(m, 2H); 3.39-3.45(m, 2H); 3.73-3.83(m, 1H); 3.85-3.89(m, 5H); 6.66(d, 1H); 6.90(d, 1H); 7.06-7.07(m, 1H); 7.73(d, 1H); 7.81(s, 1H); 8.37-8.39(dd, 1H) 8.86(m, 1H) ppm. | |
| 2.20 | 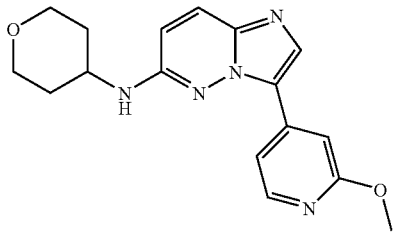<br>[3-(2-Methoxy-pyridin-4-yl)-imidazo[1,2-b]pyridazin-6-yl]-(tetrahydro-pyran-4-yl)-amine | (300 MHz, $d_6$-DMSO): δ = 1.41-1.53(m, 2H); 2.02-2.06(m, 2H); 3.41-3.49(m, 2H); 3.75-3.93(m, 6H); 6.73(d, 1H); 7.20-7.22(m, 1H); 7.61-7.63(m, 1H); 7.77(d, 1H); 7.82(s, 1H); 8.12-8.15(m, 2H) ppm. | MW: 325.37 MS (ES+) 326 |
| 2.21 | 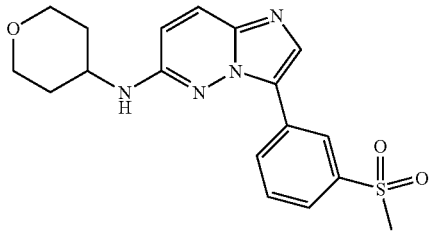<br>[3-(3-Methanesulfonyl-phenyl)-imidazo[1,2-b]pyridazin-6-yl]-(tetrahydro-pyran-4-yl)-amine | (400 MHz, $d_6$-DMSO): δ = 1.39-1.48(m, 2H); 1.97-1.99(m, 2H); 3.23(s, 3H); 3.48-3.53(m, 2H); 3.82-3.84(m, 2H); 3.96-4.01(m, 1H); 6.70(d, 1H); 7.10-7.11(m, 1H); 7.67-7.71(m, 1H); 7.76(d, 1H); 7.81-7.83(m, 1H); 8.02(s, 1H); 8.29-8.31(m, 1H); 9.00(m, 1H) ppm. | |

Method B: [3-(1-methyl-1H-pyrazol-4-yl)imidazo[1,2-b]pyridazin-6-yl]pyridin-3-ylmethylamine (Example 3.0)

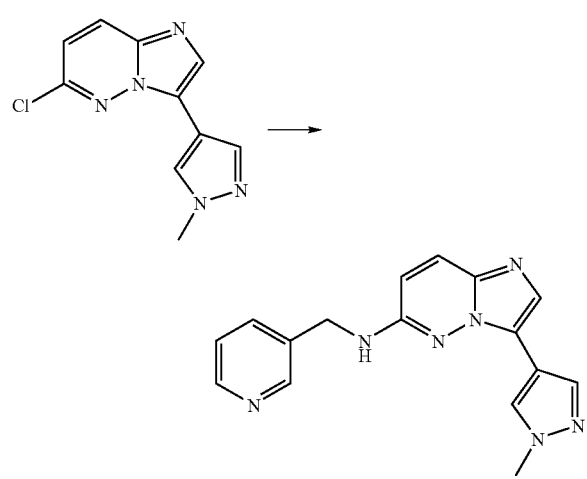

35 mg (0.15 mmol) of 6-chloro-3-(1-methyl-1H-pyrazol-4-yl)imidazo[1,2-b]pyridazine were introduced into a mixture of 0.67 ml of tetrahydrofuran and 0.33 ml of dimethylformamide under argon. Then 0.5 ml of a 0.45 M solution of pyridin-3-ylmethylamine (0.225 mmol) in toluene was added. Addition of solutions of 1.72 mg of Pd₂dba₃ (18.8 µmol) and 3.5 mg of rac-BINAP (56.3 µmol) in 0.91 ml of THF and 10 31.7 mg of NaOtBu (0.3 mmol) in 0.91 ml of THF was followed by shaking of the reaction mixture at 80° C. for 12 h.

The reaction mixture was then mixed with 1 ml of water and 3 ml of ethyl acetate. The organic phase was separated off and freed of solvent. The crude product obtained in this way was purified by HPLC. 8.7 mg (19%) of the desired product were isolated.

HPLC-MS (Analytical) of the Purified Product

Detection: UV=254 nm; column: Purospher STAR RP18e, 125×4 mm, 5 µm (Merck KGaA, Darmstadt); eluent: A: $H_2O$/0.1% TFA, B: $CH_3CN$/0.1% TFA, gradient: 5 to 95% B in 10 min; flow rate: 1 ml/min:

Retention time of the product 3.85 min; MS of the product: m/z=301 ([M+H]⁺)

The following are prepared in analogous manner:

TABLE 3

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| KE1322-001-a | 3.1 | 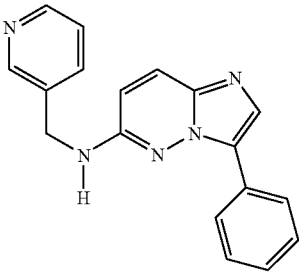<br>(3-Phenyl-imidazo[1,2-b]pyridazin-6-yl)-pyridin-3-ylmethyl-amine | A | 4.59 | 301/302 |
| KE1322-002-a | 3.2 | 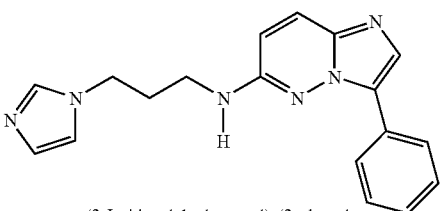<br>(3-Imidazol-1-yl-propyl)-(3-phenyl-imidazo[1,2-b]pyridazin-6-yl)-amine | A | 4.85 | 319/320 |
| KE1322-003-a | 3.3 | 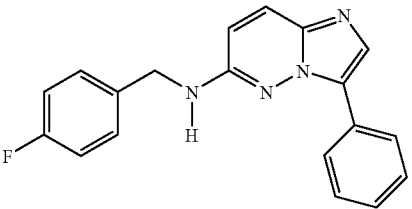<br>(4-Fluoro-benzyl)-(3-phenyl-imidazo[1,2-b]pyridazin-6-yl)-amine | A | 7.37 | 318/319 |
| KE1322-004-a | 3.4 | 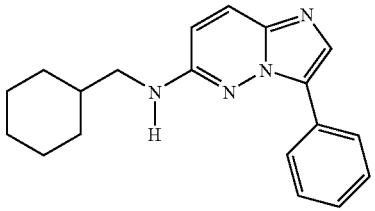<br>Cyclohexylmethyl-(3-phenyl-imidazo[1,2-b]pyridazin-6-yl)-amine | A | 8.36 | 306/307 |
| KE1322-005-a | 3.5 | 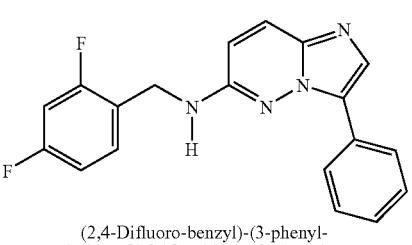<br>(2,4-Difluoro-benzyl)-(3-phenyl-imidazo[1,2-b]pyridazin-6-yl)-amine | A | 7.49 | 336/337 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| KE1322-006-a | 3.6 | 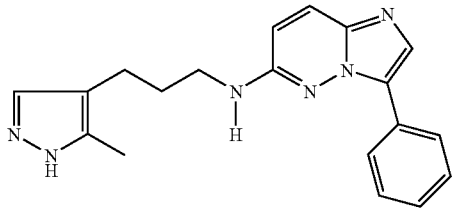<br>[3-(5-Methyl-1H-pyrazol-4-yl)-propyl]-(3-phenyl-imidazo[1,2-b]pyridazin-6-yl)-amine | A | 5.42 | 332/333 |
| KE1322-007-a | 3.7 | 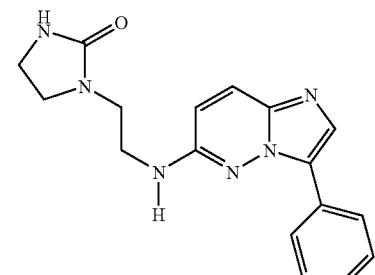<br>1-[2-(3-Phenyl-imidazo[1,2-b]pyridazin-6-ylamino)-ethyl]-imidazolidin-2-one | A | 4.84 | 322/323 |
| KE1322-009-a | 3.8 | 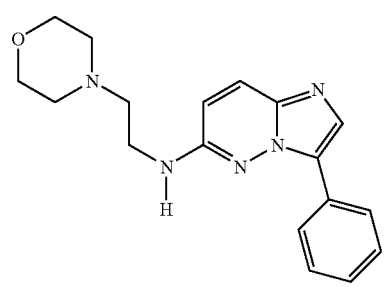<br>(2-Morpholin-4-yl-ethyl)-(3-phenyl-imidazo[1,2-b]pyridazin-6-yl)-amine | A | 4.71 | 323/324 |
| KE1322-010-a | 3.9 | 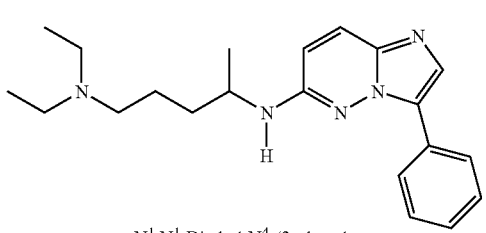<br>$N^1,N^1$-Diethyl-$N^4$-(3-phenyl-imidazo[1,2-b]pyridazin-6-yl)-pentane-1,4-diamine | A | 5.51 | 351/352 |
| KE1322-011-a | 3.10 | 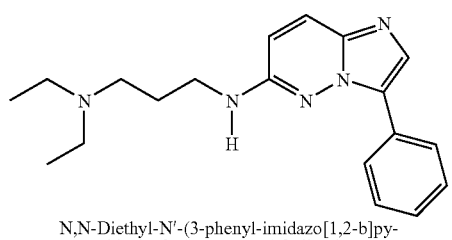<br>N,N-Diethyl-N'-(3-phenyl-imidazo[1,2-b]pyridazin-6-yl)-propane-1,3-diamine | A | 5 | 323/324 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| KE1322-012-a | 3.11 | 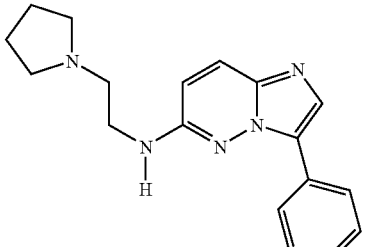<br>(3-Phenyl-imidazo[1,2-b]pyridazin-6-yl)-(2-pyrrolidin-1-yl-ethyl)-amine | A | 4.84 | 307/ 308 |
| KE1322-013-a | 3.12 | 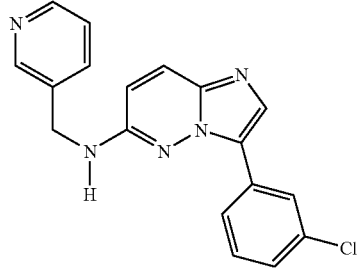<br>[3-(3-Chloro-phenyl)-imidazo[1,2-b]pyridazin-6-yl]-pyridin-3-ylmethyl-amine | A | 5.09 | 336/ 337 |
| KE1322-014-a | 3.13 | 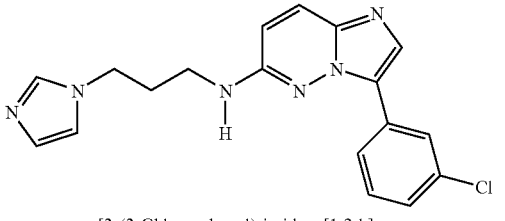<br>[3-(3-Chloro-phenyl)-imidazo[1,2-b]pyridazin-6-yl]-(3-imidazol-1-yl-propyl)-amine | A | 5.36 | 353/ 354 |
| KE1322-015-a | 3.14 | 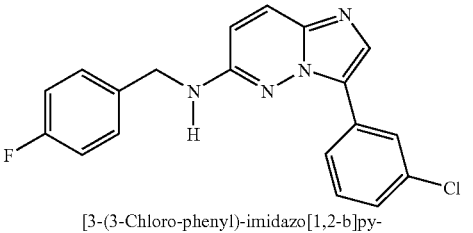<br>[3-(3-Chloro-phenyl)-imidazo[1,2-b]pyridazin-6-yl]-(4-fluoro-benzyl)-amine | A | 7.73 | 353/ 354 |
| KE1322-016-a | 3.15 | 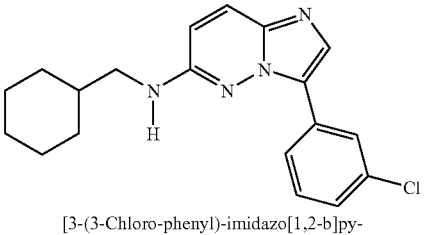<br>[3-(3-Chloro-phenyl)-imidazo[1,2-b]pyridazin-6-yl]-cyclohexylmethyl-amine | A | 8.87 | 341/ 342 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]⁺ |
|---|---|---|---|---|---|
| KE1322-017-a | 3.16 | 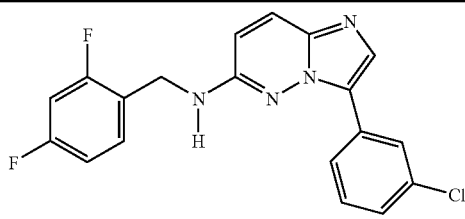<br>[3-(3-Chloro-phenyl)-imidazo[1,2-b]pyridazin-6-yl]-(2,4-difluoro-benzyl)-amine | A | 7.93 | 371/ 372 |
| KE1322-019-a | 3.17 | 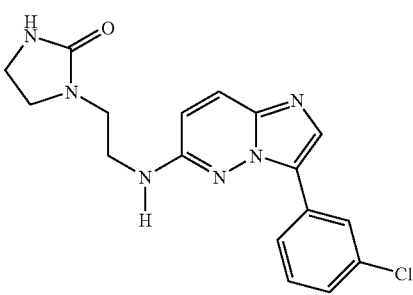<br>1-{2-[3-(3-Chloro-phenyl)-imidazo[1,2-b]pyridazin-6-ylamino]-ethyl}-imidazolidin-2-one | A | 5.25 | 357/ 358 |
| KE1322-022-a | 3.18 | 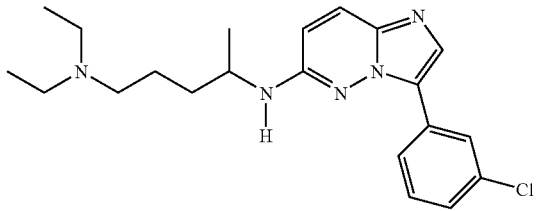<br>N*4*-[3-(3-Chloro-phenyl)-imidazo[1,2-b]pyridazin-6-yl]-N*1*,N*1*-diethyl-pentane-1,4-diamine | A | 5.87 | 386/ 387 |
| KE1322-023-a | 3.19 | 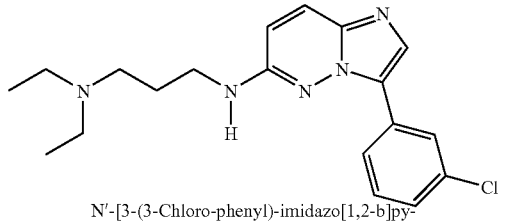<br>N'-[3-(3-Chloro-phenyl)-imidazo[1,2-b]pyridazin-6-yl]-N,N-diethyl-propane-1,3-diamine | A | 5.53 | 358/ 359 |
| KE1322-024-a | 3.20 | 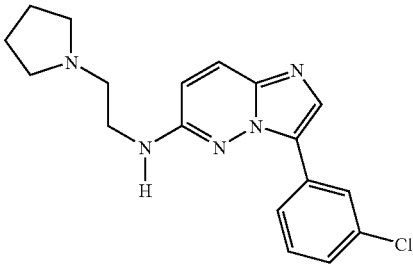<br>[3-(3-Chloro-phenyl)-imidazo[1,2-b]pyridazin-6-yl]-(2-pyrrolidin-1-yl-ethyl)-amine | A | 5.29 | 342/ 343 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| KE1322-026-a | 3.21 | 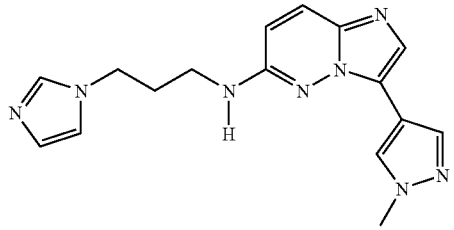<br>(3-Imidazol-1-yl-propyl)-[3-(1-methyl-1H-pyrazol-4-yl)-imidazo[1,2-b]pyridazin-6-yl]-amine | A | 4.21 | 322/ 323 |
| KE1322-027-a | 3.22 | 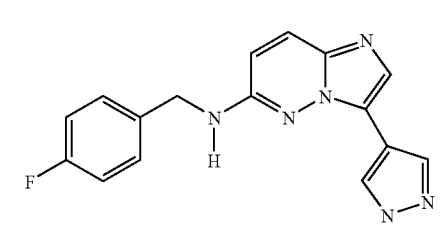<br>(4-Fluoro-benzyl)-[3-(1-methyl-1H-pyrazol-4-yl)-imidazo[1,2-b]-pyridazin-6-yl]-amine | A | 6.19 | 322/ 323 |
| KE1322-028-a | 3.23 | 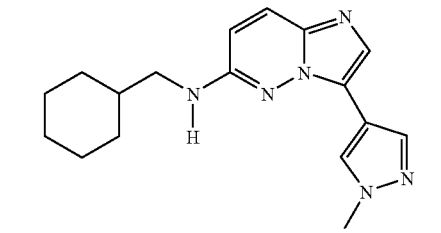<br>Cyclohexylmethyl-[3-(1-methyl-1H-pyrazol-4-yl)-imidazo[1,2-b]pyridazin-6-yl]-amine | A | 6.97 | 310/ 311 |
| KE1322-029-a | 3.24 | 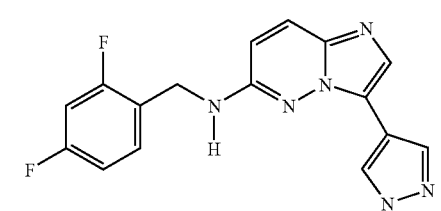<br>(2,4-Difluoro-benzyl)-[3-(1-methyl-1H-pyrazol-4-yl)-imidazo[1,2-b]-pyridazin-6-yl]-amine | A | 6.17 | 340/ 341 |
| KE1322-030-a | 3.25 | 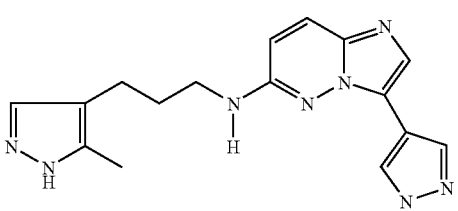<br>[3-(1-Methyl-1H-pyrazol-4-yl)-imidazo-[1,2-b]pyridazin-6-yl]-[3-(5-methyl-1H-pyrazol-4-yl)-propyl]-amine | A | 4.64 | 336/ 337 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
| --- | --- | --- | --- | --- | --- |
| KE1322-031-a | 3.26 | 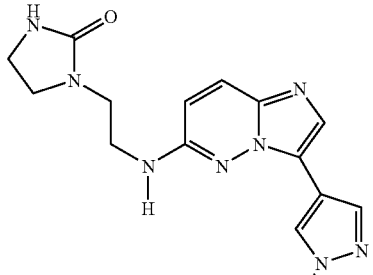<br>1-{2-[3-(1-Methyl-1H-pyrazol-4-yl)-imidazo[1,2-b]pyridazin-6-ylamino]-ethyl}-imidazolodin-2-one | A | 4.09 | 326/ 327 |
| KE1322-033-a | 3.27 | 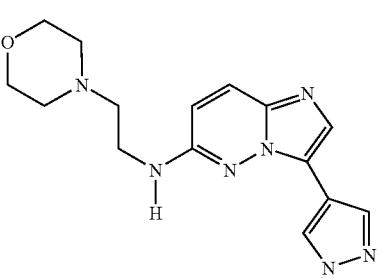<br>[3-(1-Methyl-1H-pyrazol-4-yl)-imidzo[1,2-b]pyridazin-6-yl]-(2-morpholin-4-yl-ethyl)-amine | A | 3.91 | 327/ 328 |
| KE1322-034-a | 3.28 | 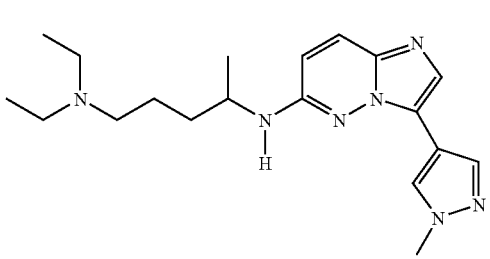<br>$N^1,N^1$-Diethyl-$N^4$-[3-(1-methyl-1H-pyrazol-4-yl)-imidazo[1,2-b]-pyridazin-6-yl]-pentane-1,4-diamine | A | 4.6 | 355/ 356 |
| KE1322-035-a | 3.29 | 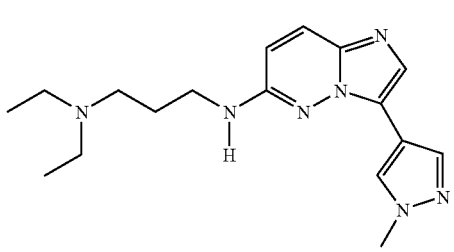<br>N,N-Diethyl-N'-[3-(1-methyl-1H-pyrazole-4-yl)-imidazo[1,2-b]pyridazin-6-yl]-propane-1,3-diamine | A | 4.29 | 327/ 328 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| KE1322-036-a | 3.30 | 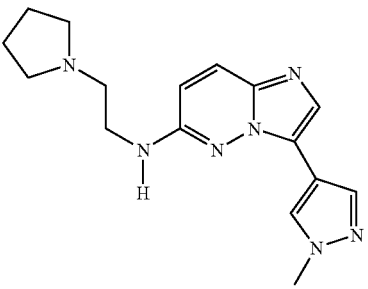<br>[3-(1-Methyl-1H-pyrazol-4-yl)-imidao[1,2-b]pyridazin-6-yl]-(2-pyrrolidin-1-yl-ethyl)-amine | A | 4.11 | 311/ 312 |
| KE1322-037-a | 3.31 | 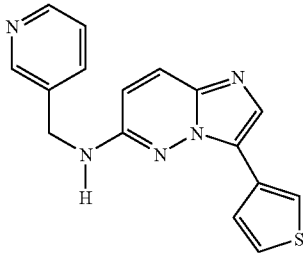<br>Pyridin-3-ylmethyl-(3-thiophen-3-yl-imidazo[1,2-b]pyridazin-6-yl)-amine | A | 4.55 | 307/ 308 |
| KE1322-038-a | 3.32 | 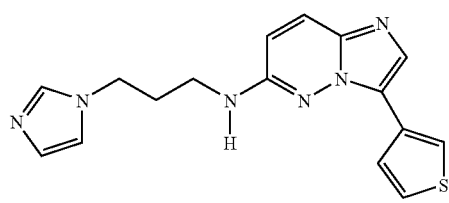<br>(3-Imidazol-1-yl-propyl)-(3-thiophen-3-yl-imidazo[1,2-b]pyridazin-6-yl)-amine | A | 4.8 | 324/ 325 |
| KE1322-039-a | 3.33 | 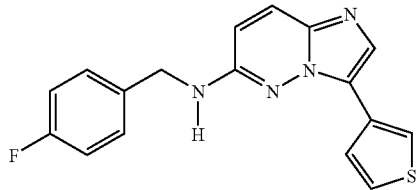<br>(4-Fluoro-benzyl)-(3-thiophen-3-yl-imidazo[1,2-b]pyridazin-6-yl)-amine | A | 7.29 | 324/ 325 |
| KE1322-040-a | 3.34 | 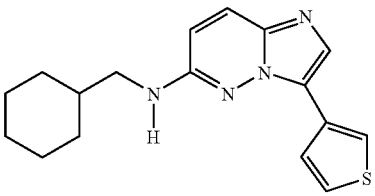<br>Cyclohexylmethyl-(3-thiophen-3-yl-imidazo[1,2-b]pyridazin-6-yl)-amine | A | 8.26 | 312/ 313 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| KE1322-041-a | 3.35 | 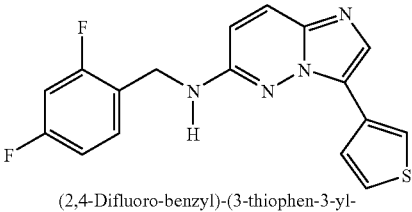 (2,4-Difluoro-benzyl)-(3-thiophen-3-yl-imidazo[1,2-b]pyridazin-6-yl)-amine | A | 7.37 | 342/ 343 |
| KE1322-042-a | 3.36 | 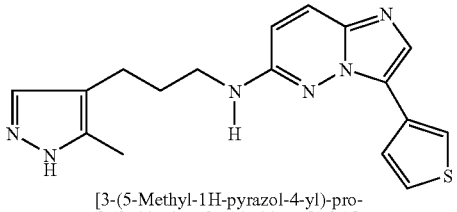 [3-(5-Methyl-1H-pyrazol-4-yl)-propyl]-(3-thiophen-3-yl-imidazo-[1,2-b]pyridazin-6-yl)-amine | A | 5.31 | 338/ 339 |
| KE1322-043-a | 3.37 | 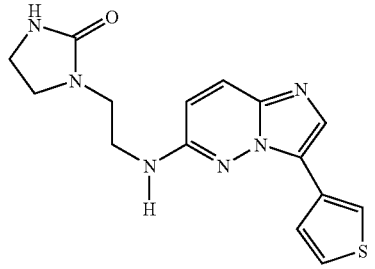 1-[2-(3-Thiophen-3-yl-imidazo-[1,2-b]pyridazin-6-ylamino)-ethyl]-imidazolidin-2-one | A | 4.71 | 328/ 329 |
| KE1322-045-a | 3.38 | 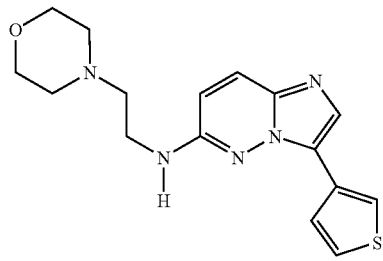 (2-Morpholin-4-yl-ethyl)-(3-thiophen-3-yl-imidazo[1,2-b]pyridazin-6-yl)-amine | A | 4.64 | 329/ 330 |
| KE1322-046-a | 3.39 | 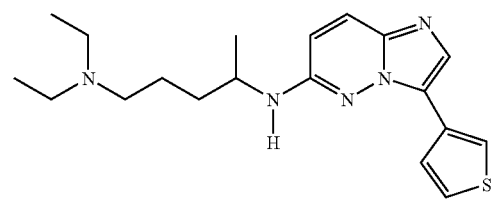 N1,N1-Diethyl-N4-(3-thiophen-3-yl-imidazo[1,2-b]pyridazin-6-yl)-penane-1,4-diamine | A | 5.42 | 358/ 359 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| KE1322-047-a | 3.40 | 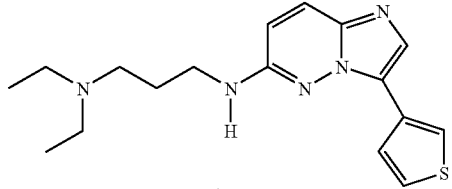<br>N,N-Diethyl-N'-(3-thiophen-3-yl-imidazo[1,2-b]pyridazin-6-yl)-propane-1,3-diamine | A | 4.92 | 329/ 330 |
| KE1322-048-a | 3.41 | 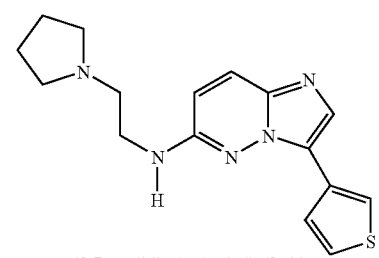<br>(2-Pyrrolidin-1-yl-ethyl)-(3-thiophen-3-yl-imidazo[1,2-b]-pyridazin-6-yl)-amine | A | 4.74 | 313/ 314 |
| HU6083-002 | 3.42 | 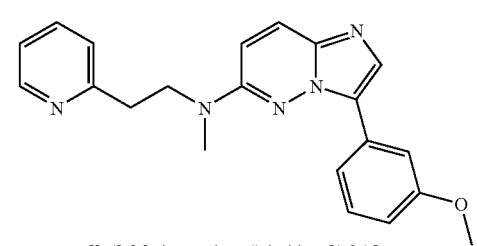<br>[3-(3-Methoxy-phenyl)-imidazo[1,2-b]pyridazin-6-yl]-methyl-(2-pyridin-2-yl-ethyl)-amine | B | 7.99 | 359.43/ 360.06/ |
| HU6083-003 | 3.43 | 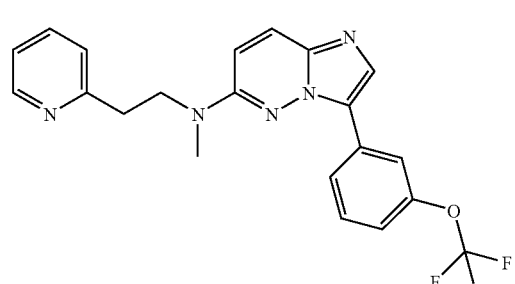<br>Methyl-(2-pyridin-2-yl-ethyl)-[3-(3-trifluoromethoxy-phenyl)-imidazo[1,2-b]pyridazin-6-yl]-amine | B | 9.42 | 413.40/ 413.99 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6083-004 | 3.44 | 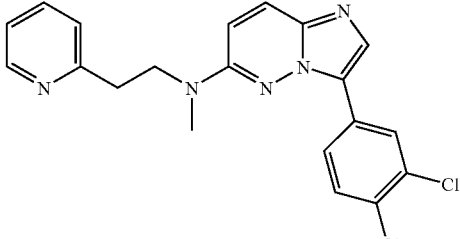<br>[3-(3,4-Dichloro-phenyl)-imidazo[1,2-b]pyridazin-6-yl]-methyl-(2-pyridin-2-yl-ethyl)-amine | B | 10.03 | 398.30/ 397.94 |
| HU6083-006 | 3.45 | 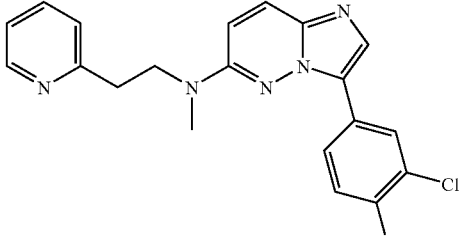<br>[3-(3-Chloro-4-fluoro-phenyl)-imidazo[1,2-b]pyridazin-6-yl]-methyl-(2-pyridin-2-yl-ethyl)-amine | B | 9.16 | 381.84/ 381.95 |
| HU6083-007 | 3.46 | 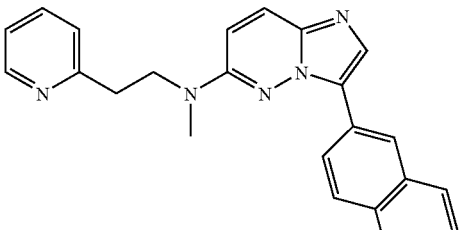<br>Methyl-(3-naphthalen-2-yl-imidazo[1,2-b]pyridazin-6-yl)-(2-pyridin-2-yl-ethyl)-amine | B | 9.32 | 379.46/ 380.02 |
| HU6083-010 | 3.47 | 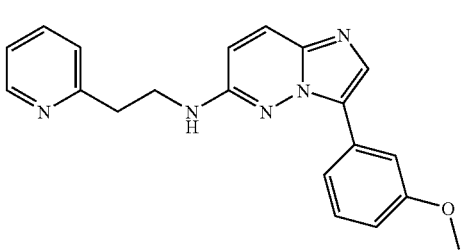<br>[3-(3-Methoxy-phenyl)-imidazo[1,2-b]pyridazin-6-yl]-(2-pyridin-2-yl-ethyl)-amine | B | 7.47 | 345.40/346. |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6083-012 | 3.48 | 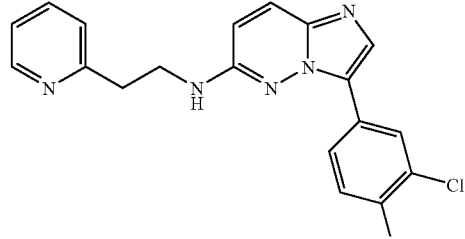<br>[3-(3,4-Dichloro-phenyl)-imidazo[1,2-b]pyridazin-6-yl]-(2-pyridin-2-yl-ethyl)-amine | B | 9.21 | 384.27/ 383.94 |
| HU6083-013 | 3.49 | 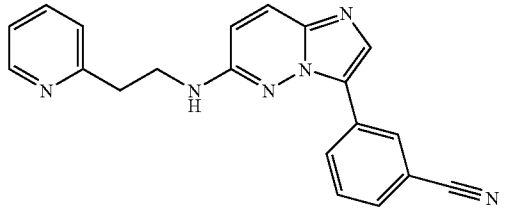<br>3-[6-(2-Pyridin-2-yl-ethylaminio)-imidazo[1,2-b]pyridazin-3-yl]-benzonitrile | B | 7.30 | 340.39/ 341.06 |
| HU6083-017 | 3.50 | 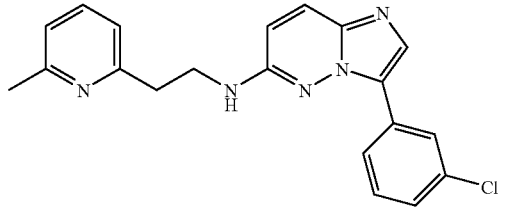<br>[3-(3-Chloro-phenyl)-imidazo[1,2-b]pyridazin-6-yl]-[2-(6-methyl-pyridin-2-yl)-ethyl]-amine | B | 8.84 | 363.85/ 363.97 |
| HU6083-019 | 3.51 | 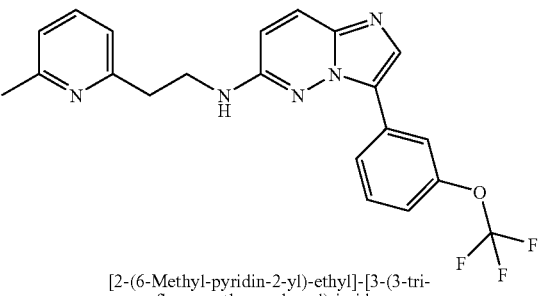<br>[2-(6-Methyl-pyridin-2-yl)-ethyl]-[3-(3-trifluoromethoxy-phenyl)-imidazo[1,2-b]pyridazin-6-yl]-amine | B | 9.24 | 413.40/ 413.99 |
| HU6083-023 | 3.52 | 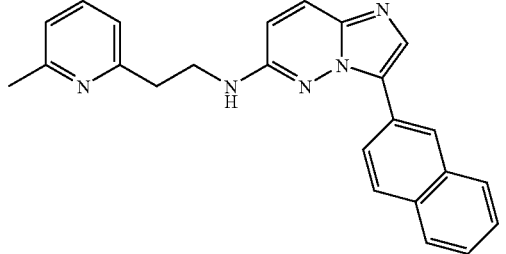<br>[2-(6-Methyl-pyridin-2-yl)-ethyl]-(3-naphthalen-2-yl-imidazo[1,2-b]pyridazin-6-yl)-amine | B | 9.15 | 379.46/ 380.02 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
| --- | --- | --- | --- | --- | --- |
| HU6083-036 | 3.53 | 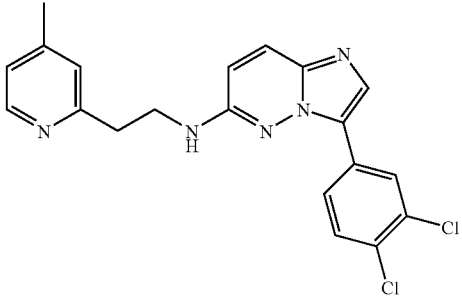<br>[3-(3,4-Dichloro-phenyl)-imidazo[1,2-b]py-ridazin-6-yl]-[2-(4-methyl-py-ridin-2-yl)-ethyl]-amine | B | 9.76 | 398.30/ 397.94 |
| HU6083-039 | 3.54 | 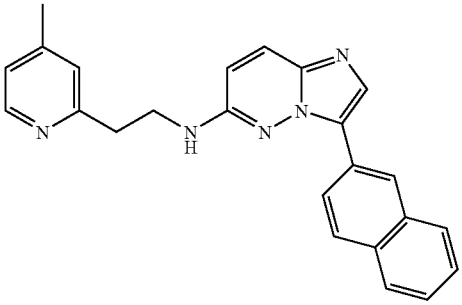<br>[2-(4-Methyl-pyridin-2-yl)-ethyl]-(3-naph-thalen-2-yl-imidazo[1,2-b]pyri-dazin-6-yl)-amine | B | 9.15 | 379.46/ 380.02 |
| HU6083-067 | 3.55 | 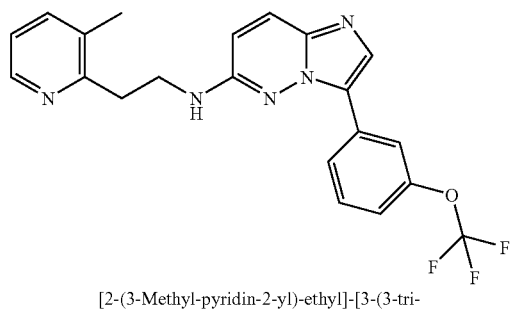<br>[2-(3-Methyl-pyridin-2-yl)-ethyl]-[3-(3-tri-fluoromethoxy-phenyl)-imida-zo[1,2-b]pyridazin-6-yl]-amine | B | 9.36 | 413.40/ 413.93 |
| HU6108-058 | 3.56 | 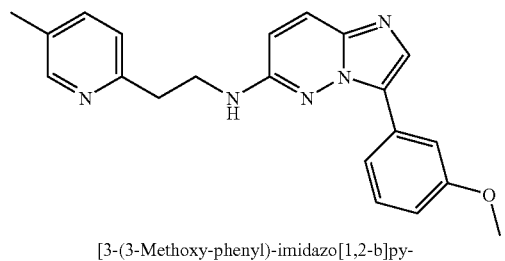<br>[3-(3-Methoxy-phenyl)-imidazo[1,2-b]py-ridazin-6-yl]-[2-(5-methyl-pyrid-in-2-yl)-ethyl]-amine | B | 8.13 | 359.43/ 359.17 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6108-059 | 3.57 | 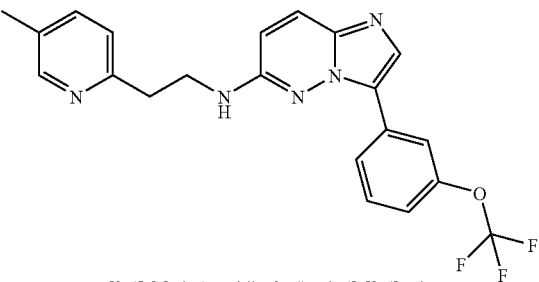<br>[2-(5-Methyl-pyridin-2-yl)-ethyl]-[3-(3-tri-fluoromethoxy-phenyl)-imida-zo[1,2-b]pyridazin-6-yl]-amine | B | 9.49 | 413.40/ 413.15 |
| HU6108-060 | 3.58 | 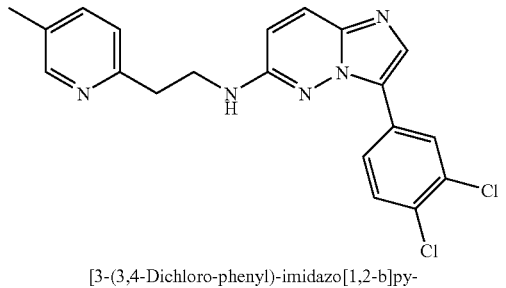<br>[3-(3,4-Dichloro-phenyl)-imidazo[1,2-b]py-ridazin-6-yl]-[2-(5-methyl-py-ridin-2-yl)-ethyl]-amine | B | 10.11 | 398.30/ 397.94 |
| HU6108-062 | 3.59 | 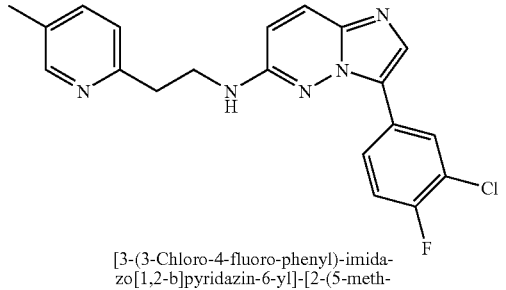<br>[3-(3-Chloro-4-fluoro-phenyl)-imida-zo[1,2-b]pyridazin-6-yl]-[2-(5-meth-yl-pyridin-2-yl)-ethyl]-amine | B | 9.24 | 381.84/ 381.12 |
| HU6108-068 | 3.60 | 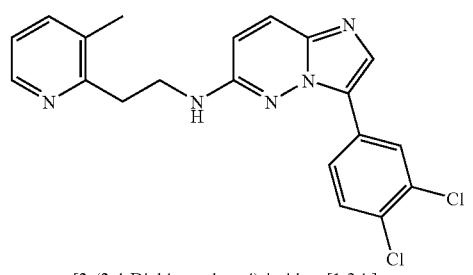<br>[3-(3,4-Dichloro-phenyl)-imidazo[1,2-b]py-ridazin-6-yl]-[2-(3-methyl-pyridin-2-yl)-ethyl]-amine | B | 10.16 | 398.30/ 397.09 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6083-020 | 3.61 | 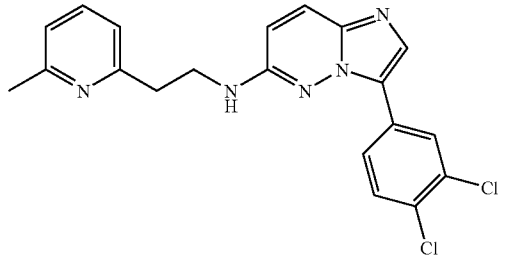<br>[3-(3,4-Dichloro-phenyl)-imidazo[1,2-b]pyridazin-6-yl]-[2-(6-methyl-pyridin-2-yl)-ethyl]-amine | B | 9.79 | 398.30/ 397.94 |
| HU6083-025 | 3.62 | 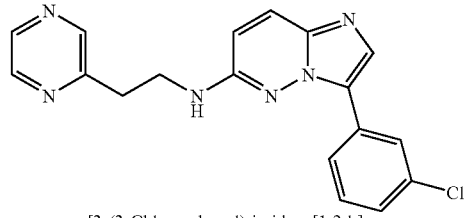<br>[3-(3-Chloro-phenyl)-imidazo[1,2-b]pyridazin-6-yl]-(2-pyrazin-2-yl-ethyl)-amine | B | 7.62 | 350.81/ 351.01 |
| HU6083-026 | 3.63 | 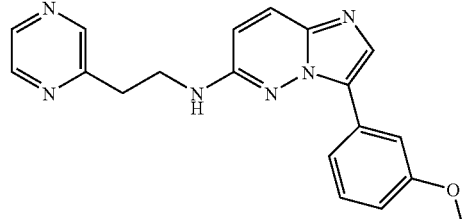<br>[3-(3-Methoxy-phenyl)-imidazo[1,2-b]pyridazin-6-yl]-(2-pyrazin-2-yl-ethyl)-amine | B | 6.88 | 346.39/ 347.03 |
| HU6083-030 | 3.64 | 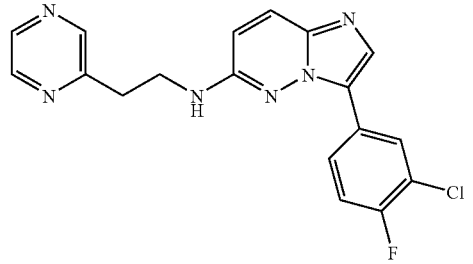<br>[3-(3-Chloro-4-fluoro-phenyl)-imidazo[1,2-b]pyridazin-6-yl]-(2-pyrazin-2-yl-ethyl)-amine | B | 7.79 | 368.80/ 368.92 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6083-031 | 3.65 | 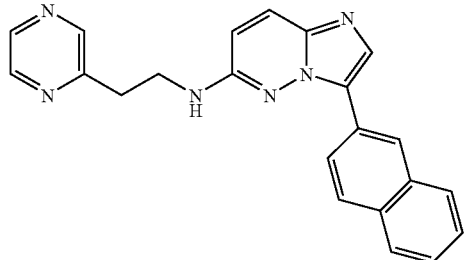<br>(3-Naphthalen-2-yl-imidazo[1,2-b]py-ridazin-6-yl)-(2-pyrazin-2-yl-ethyl)-amine | B | 8.01 | 366.43/ 366.99 |
| HU6083-033 | 3.66 | 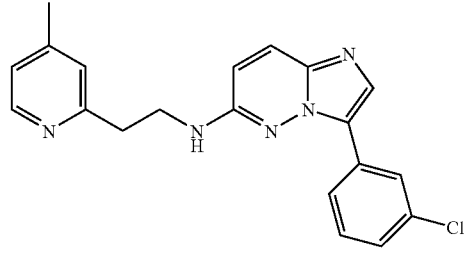<br>[3-(3-Chloro-phenyl)-imidazo[1,2-b]py-ridazin-6-yl]-[2-(4-methyl-pyridin-2-yl)-eth-yl]-amine | B | 8.78 | 363.85/ 363.97 |
| HU6083-035 | 3.67 | 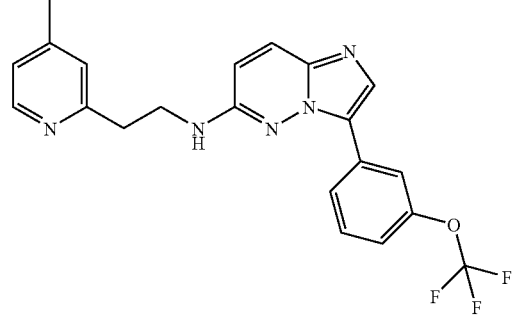<br>[2-(4-Methyl-pyridin-2-yl)-ethyl]-[3-(3-tri-fluoromethoxy-phenyl)-imida-zo[1,2-b]pyridazin-6-yl]-amine | B | 9.19 | 413.40/ 413.99 |
| HU6083-038 | 3.68 | 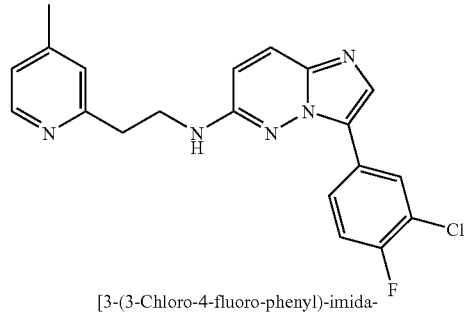<br>[3-(3-Chloro-4-fluoro-phenyl)-imida-zo[1,2-b]pyridazin-6-yl]-[2-(4-meth-yl-pyridin-2-yl)-ethyl]-amine | B | 8.92 | 381.84/ 381.95 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6083-049 | 3.69 | 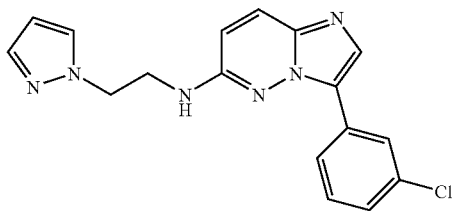<br>[3-(3-Chloro-phenyl)-imidazo[1,2-b]pyridazin-6-yl]-(2-pyrazol-1-yl-ethyl)-amine | B | 7.90 | 338.80/ 339.00 |
| HU6083-050 | 3.70 | 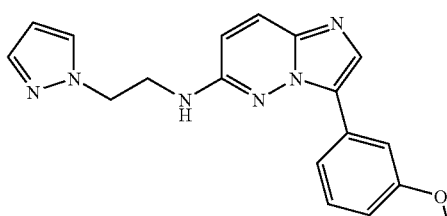<br>[3-(3-Methoxy-phenyl)-imidazo[1,2-b]pyridazin-6-yl]-(2-pyrazol-1-yl-ethyl)-amine | B | 7.15 | 334.38/ 335.02 |
| HU6083-051 | 3.71 | 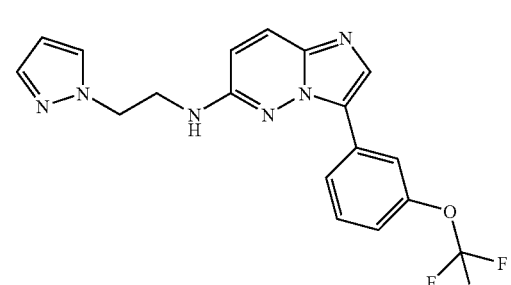<br>(2-Pyrazol-1-yl-ethyl)-[3-(3-trifluoromethoxy-phenyl)-imidazo[1,2-b]pyridazin-6-yl]-amine | B | 8.37 | 388.35/ 338.95 |
| HU6083-052 | 3.72 | 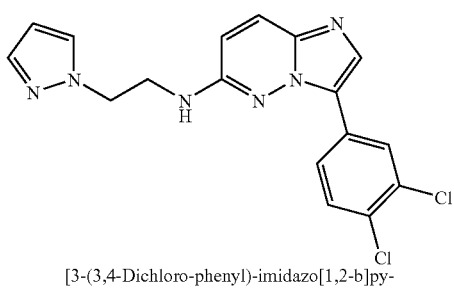<br>[3-(3,4-Dichloro-phenyl)-imidazo[1,2-b]pyridazin-6-yl]-(2-pyrazol-2-yl-ethyl)-amine | B | 8.66 | 373.25/ 372.90 |
| HU6083-053 | 3.73 | 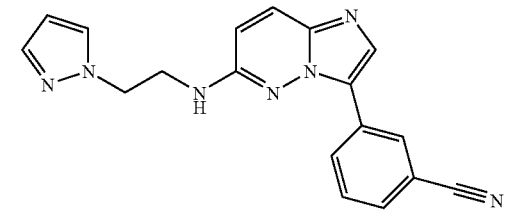<br>3-[6-(2-Pyrazol-1-yl-ethylamino)-imidazo[1,2-b]pyridazin-3-yl]-benzonitrile | B | 6.86 | 329.37/ 330.02 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6083-054 | 3.74 | 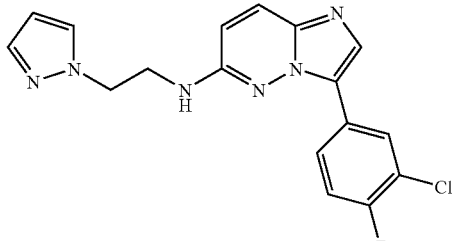<br>[3-(3-Chloro-4-fluoro-phenyl)-imidazo[1,2-b]pyridazin-6-yl]-(2-pyrazol-1-yl-ethyl)-amine | B | 8.04 | 356.79/ 356.98 |
| HU6083-055 | 3.75 | 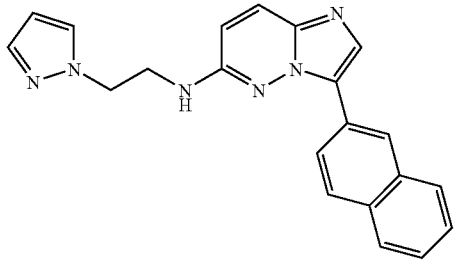<br>(3-Naphthalen-2-yl-imidazo[1,2-b]pyridazin-6-yl)-(2-pyrazol-1-yl-ethyl)-amine | B | 8.22 | 354.42/ 335.05 |
| HU6108-075 | 3.76 | 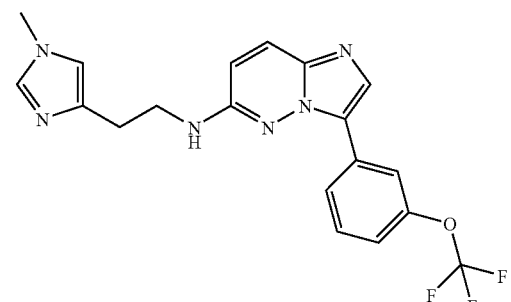<br>[2-(1-Methyl-1H-imidazol-4-yl)-ethyl]-[3-(3-trifluoromethoxy-phenyl)-imidazo[1,2-b]pyridazin-6-yl]-amine | B | 7.98 | 402.38/ 402.14 |
| HU6108-077 | 3.77 | 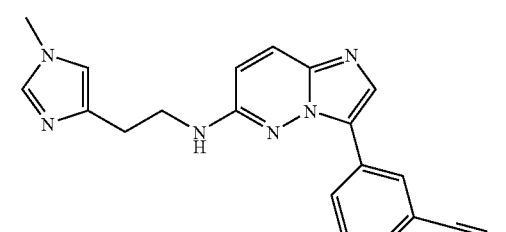<br>3-{6-[2-(1-Methyl-1H-imidazol-4-yl)-ethylamino]-imidazo[1,2-b]pyridazin-3-yl}-benzonitrile | B | 6.65 | 343.39/ 343.15 |

TABLE 3-continued

| Prot. No. | Example No. | Structure and Name of the main isomer | HPLC-MS method (see below) | Retention time (HPLC, UV 254 nm) [min] | Mol. weight/ MS (HPLC-MS) [M + 1]+ |
|---|---|---|---|---|---|
| HU6108-079 | 3.78 | 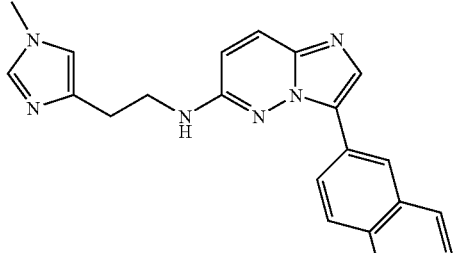<br>[2-(1-Methyl-1H-imidazol-4-yl)-ethyl]-(3-naphthalen-2-yl-imidazo[1,2-b]pyridazin-6-yl)-amine | B | 7.75 | 368.44/ 368.18 |
| SG26724-51-A | 3.79 | 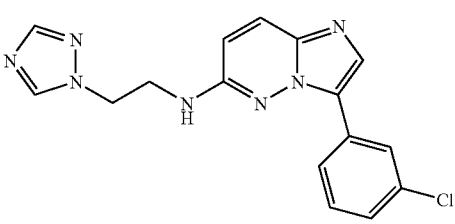<br>[3-(3-Chloro-phenyl)-imidazo[1,2-b]pyridazin-6-yl]-(2-[1,2,4]triazol-1-yl-ethyl)-amine | B | 6.89 | 339.79/ 339.10 |
| SG26724-53-A | 3.80 | 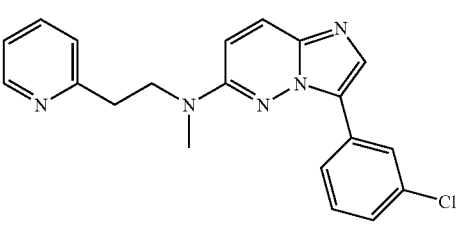<br>[3-(3-Chloro-phenyl)-imidazo[1,2-b]pyridazin-6-yl]-methyl-(2-pyridin-2-yl-ethyl)-amine | B | 9.38 | 363.85/ 363.13 |

Description of the HPLC-MS analysis conditions for the examples listed in Table 3:

HPLC-MS method A: detection: UV=254 nm; column: Purospher STAR RP18e, 125×4 mm, 5 μm (Merck KGaA, Darmstadt); eluent: A: H₂O/0.1% TFA, B: CH₃CN/0.1% TFA, gradient: 5 to 95% B in 10 min; flow rate: 1 ml/min:

HPLC-MS method B: detection: UV=254 nm; column XBridge C18, RP18e, 150×4.8 mm, 5 μm (Waters); gradient 5-95% acetonitrile (0.1% NH₄OH) in water (0.1% NH₄OH/ NH₄HCO₃) (10 min.); flow rate 1.0 ml/min.

Method C: (4-[6-(2-hydroxyethylamino)imidazo[1, 2-b]pyridazin-3-yl]phenol (Example 4.0)

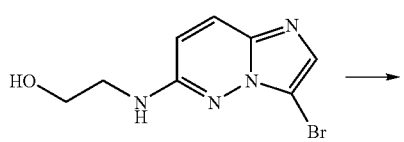

-continued

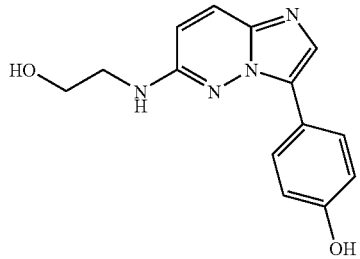

85 mg (0.33 mmol) of 2-(3-bromoimidazo[1,2-b]pyridazin-6-ylamino)ethanol (Example 1.5), 69 mg (0.5 mmol) of 4-hydroxybenzene boronic acid and 76 mg (0.066 mmol) of tetrakis(triphenylphosphine)palladium(0) were mixed under argon with 3.4 ml of dimethyl glycol and 2 ml of an aqueous NaOH solution (a stock solution of 190 mg of NaOH in 10 ml of water). The mixture was stirred at 90° C. for 19 hours. After cooling, the mixture was diluted with sat. NaCl solution and extracted 2× with ethyl acetate. The combined organic phases were washed with sat. NaCl solution, filtered through a silicone filter (from Whatman) and concentrated.

The resulting crude product was recrystallized from methanol. 40 mg of the desired product are obtained.

$^1$H-NMR (400 MHz; d$_6$-DMSO): δ=3.30-3.31 (m, 2H, covered by solvent); 3.61-3.62 (m, 2H); 4.74 (m, 1H); 6.66 (d, 1H); 6.81 (d, 2H); 6.94-6.96 (m, 1H); 7.64-7.67 (m, 2H); 7.93 (d, 2H); 9.57 (br s, 1H) ppm.

MS (ESI+): m/z=271 ([M+H]$^+$). [mol. weight=270.29].

The following are prepared in an analogous manner:

TABLE 4

| Example No. | Structure and Name of the main isomers | $^1$H-NMR | Mol. weight/ MS (ES+) |
|---|---|---|---|
| 4.1 | 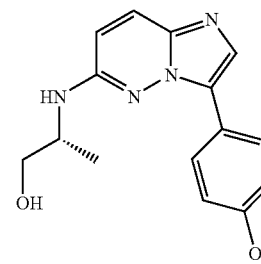<br>4-[6-((R)-2-Hydroxy-1-methyl-ethylamino)imidazo[1,2-b]pyridazin-3-yl]-phenol | | MW 284.32<br>MS (ES+):<br>[M + 1]$^+$<br>285 |
| 4.2 | 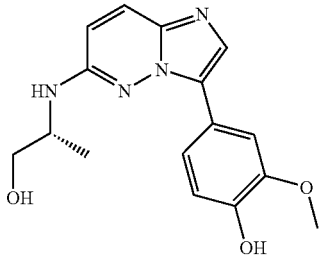<br>4-[6-((R)-2-Hydroxy-1-methyl-ethylamino)-imidazo[1,2-b]pyridazin-3-yl]-2-methoxy-phenol | | MW 314.35<br>MS (ES+):<br>[M + 1]$^+$<br>315 |
| 4.3 | 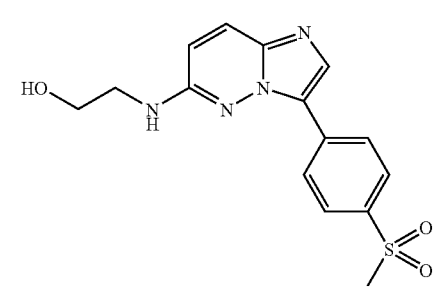<br>2-[3-(4-Methanesulfonyl-phenyl)-imidazo[1,2-b]pyridazin-6-ylamino]-ethanol | | MW: 332.38<br>MS (ES+)<br>333 |
| 4.4 | 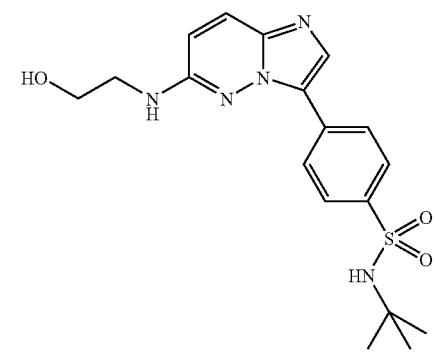<br>N-tert-Butyl-4-[6-(2-hydroxy-ethylamino)imidazo[1,2-b]pyridazin-3-yl]-benzenesulfonamide | | MW: 389.48<br>MS (ES+)<br>390 |

TABLE 4-continued

| Example No. | Structure and Name of the main isomers | ¹H-NMR | Mol. weight/ MS (ES+) |
|---|---|---|---|
| 4.5 | 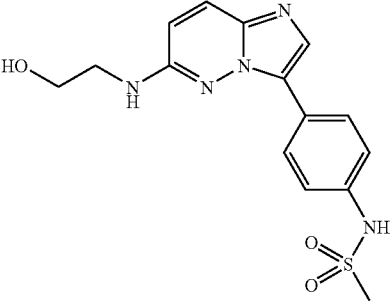<br>N-{4-[6-(2-Hydroxy-ethylamino)-imidazo[1,2-b]pyridazin-3-yl]-phenyl}-methanesulfonamide | | MW: 347.40<br>MS (ES+)<br>348 |
| 4.6 | 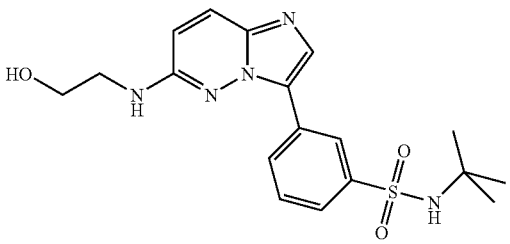<br>N-tert-Butyl-3-[6-(2-hydroxy-ethylamino)-imidazo[1,2-b]pyridazin-3-yl]-benzenesulfonamide | | MW: 389.48<br>MS (ES+)<br>390 |
| 4.7 | 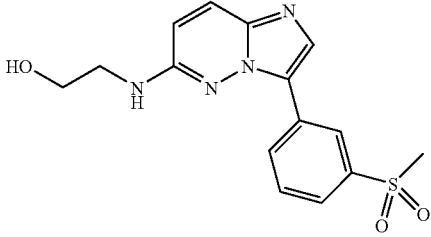<br>2-[3-(3-Methanesulfonyl-phenyl)-imidazo[1,2-b]pyridazin-6-ylamino]-ethanol | | MW: 332.38<br>MS (ESI+)<br>333 |
| 4.8 | 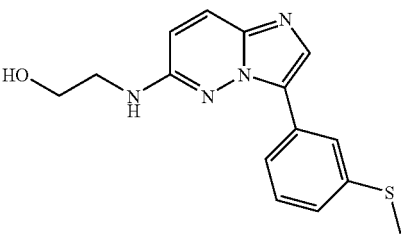<br>2-[3-(3-Methylsulfanyl-phenyl)-imidazo[1,2-b]pyridazin-6-ylamino]-ethanol | | MW: 300.38<br>MS (ESI+)<br>301 |
| 4.9 | 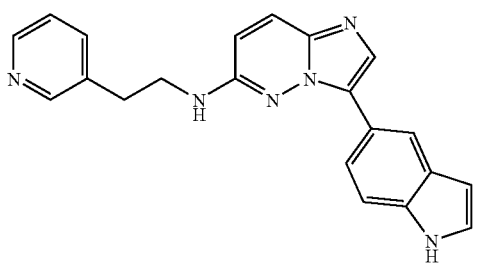<br>[3-(1H-Indol-5-yl)-imidazo[1,2-b]pyridazin-6-yl]-(2-pyridin-3-yl-ethyl)-amine | (300 MHz; d₆-DMSO): δ = 2.93-2.98 (m, 2H); 3.49-3.56 (m, 2H); 6.39-6.40 (m, 1H); 6.61 (d, 1H); 7.15-7.19 (m, 1H); 7.24-7.28 (m, 1H); 7.34-7.36 (m, 1H); 7.43 (d, 1H); 7.64-7.68 (m, 1H); 7.70 (d, 1H); 7.74 (s, 1H); 7.76-7.79 (m, 1H); 8.39-8.41 (m, 2H); 8.50-8.51 (m, 1H); 11.16 (s, 1H) ppm. | MW: 354.42 |

TABLE 4-continued

| Example No. | Structure and Name of the main isomers | ¹H-NMR | Mol. weight/ MS (ES+) |
|---|---|---|---|
| 4.10 | 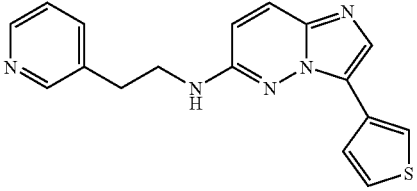<br>(2-Pyridin-3-yl-ethyl)-(3-thiophen-3-yl-imidazo[1,2-b]pyridazin-6-yl)-amine | (400 MHz; $d_6$-DMSO): δ = 2.94-2.98 (m, 2H); 3.55-3.60 (m, 2H); 6.65 (d, 1H); 7.19-7.22 (m, 1H); 7.28-7.31 (m, 1H); 7.63-7.65 (m, 1H); 7.67-7.68 (m, 1H); 7.70-7.74 (m, 2H); 7.85 (s, 1H); 8.32-8.33 (m, 1H); 8.39-8.40 (m, 1H); 8.48-8.49 (m, 1H) ppm. | MW: 321.41 |
| 4.11 | 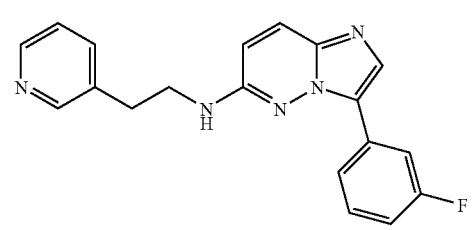<br>[3-(3-Fluoro-phenyl)-imidazo[1,2-b]pyridazin-6-yl]-(2-pyridin-3-yl-ethyl)-amine | (400 MHz; $d_6$-DMSO): δ = 2.92-2.96 (m, 2H); 3.50-3.55 (m, 2H); 6.69 (d, 1H); 7.09-7.13 (m, 1H); 7.27-7.30 (m, 2H); 7.42-7.48 (m, 1H); 7.65-7.68 (m, 1H); 7.75 (d, 1H); 7.96 (s, 1H); 7.97-7.99 (m, 1H); 8.09-8.13 (m, 1H); 8.38-8.40 (m, 1H); 8.47-8.48 (m, 1H) ppm. | MW: 333.37 |

The following are prepared in an analogous manner:

TABLE 5

| Char No. | Example No. | Structure and Name of the main isomer | Retention time (HPLC, UV 254 nm) [min]. | Mol. weight/ MS (HPLC-MS) |
|---|---|---|---|---|
| 229_0 115_0 057 | 5.0 | 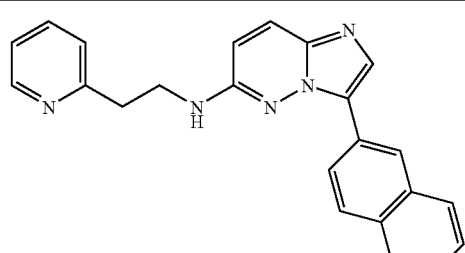<br>(3-Naphthalen-2-yl-imidazo[1,2-b]pyridazin-6-yl)-(2-pyridin-2-yl-ethyl)-amine | | 365.44 |
| 229_0 115_0 160 | 5.1 | 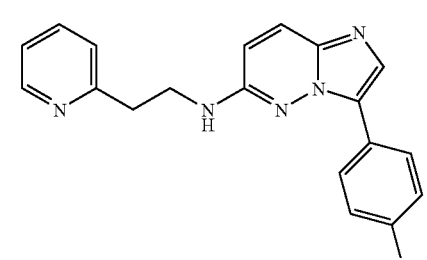<br>[3-(4-Chloro-phenyl)-imidazo[1,2-b]pyridazin-6-yl]-(2-pyridin-2-yl-ethyl)-amine | | 349.82 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 115_0 167 | 5.2 | 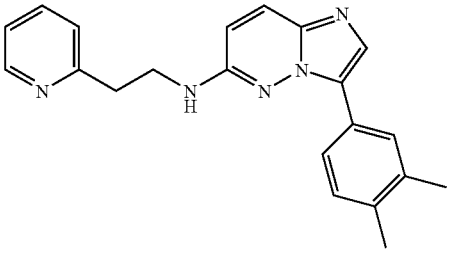<br>[3-(3,4-Dimethyl-phenyl)-imidazo[1,2-b]pyridazin-6-yl]-(2-pyridin-2-yl-ethyl)-amine | | 343.43 |
| 229_0 115_0 168 | 5.3 | 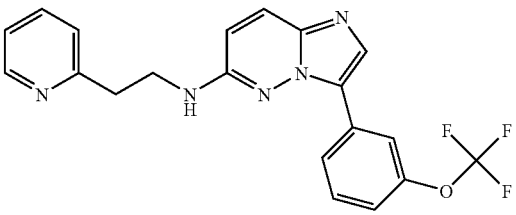<br>(2-Pyridin-2-yl-ethyl)-[3-(3-trifluoromethoxy-phenyl)-imidazo[1,2-b]pyridazin-6-yl]-amine | | 399.37 |
| 229_0 231_0 164 | 5.4 | 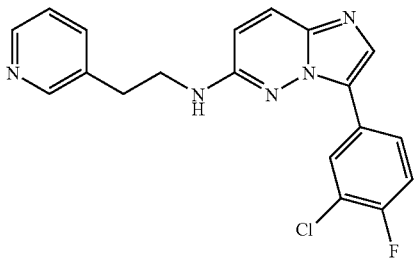<br>[3-(3-Chloro-4-fluoro-phenyl)-imidazo[1,2-b]pyridazin-6-yl]-(2-pyridin-3-yl-ethyl)-amine | | 367.81 |
| 229_0 115_0 279 | 5.5 | 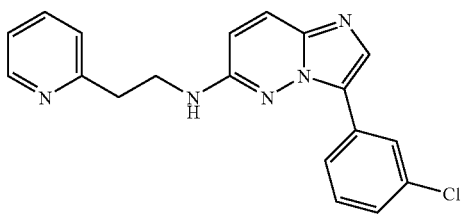<br>[3-(3-Chloro-phenyl)-imidazo[1,2-b]pyridazin-6-yl]-(2-pyridin-2-yl-ethyl)-amine | | 349.82 |
| 229_0 231_0 279 | 5.6 | 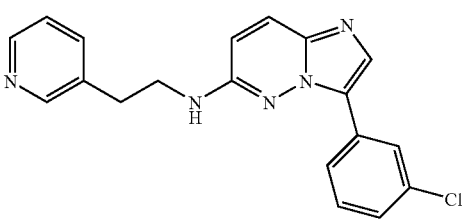<br>[3-(3-Chloro-phenyl)-imidazo[1,2-b]pyridazin-6-yl]-(2-pyridin-3-yl-ethyl)-amine | | 349.82 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 115_0 312 | 5.7 | 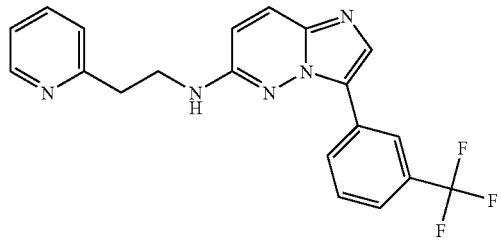<br>(2-Pyridin-2-yl-ethyl)-[3-(3-trifluoromethyl-phenyl)-imidazo[1,2-b]pyridazin-6-yl]-amine | | 383.38 |
| 229_0 115_0 313 | 5.8 | 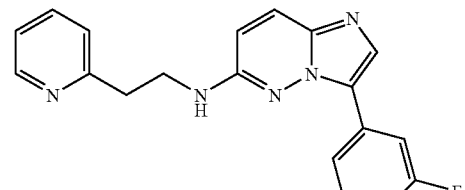<br>[3-(3-Fluoro-phenyl)-imidazo[1,2-b]pyridazin-6-yl]-(2-pyridin-2-yl-ethyl)-amine | | 333.37 |
| 229_0 115_0 339 | 5.9 | 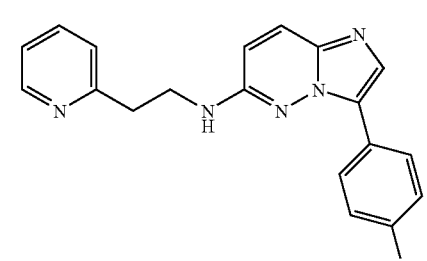<br>[3-(4-Fluoro-phenyl)-imidazo[1,2-b]pyridazin-6-yl]-(2-pyridin-2-yl-ethyl)-amine | | 333.37 |
| 229_0 115_0 345 | 5.10 | 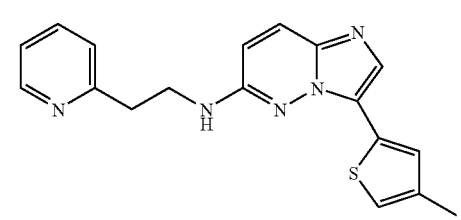<br>[3-(4-Methyl-thiophen-2-yl)-imidazo[1,2-b]pyridazin-6-yl]-(2-pyridin-2-yl-ethyl)-amine | | 335.43 |
| 229_0 240_0 164 | 5.11 | 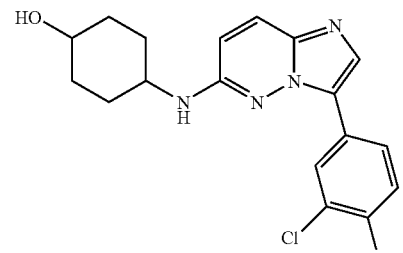<br>4-[3-(3-Chloro-4-fluoro-phenyl)-imidazo[1,2-b]pyridazin-6-ylamino]-cyclohexanol | | 360.82 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 115_4 145 | 5.12 | 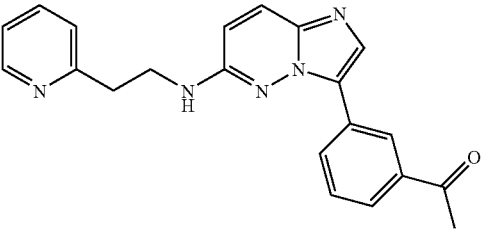<br>1-{3-[6-(2-Pyridin-2-yl-ethylamino)-imidazo[1,2-b]pyridazin-3-yl]-phenyl}-ethanone | | 357.42 |
| 229_0 115_6 488 | 5.13 | 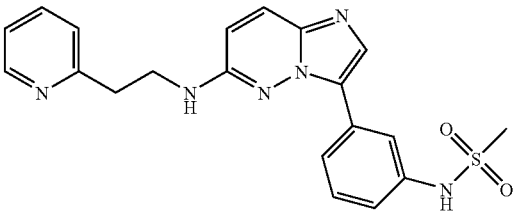<br>N-{3-(6-(2-Pyridin-2-yl-ethylamino)-imidazo[1,2-b]pyridazin-3-yl]-phenyl}-methanesulfonamide | | 408.48 |
| 229_0 115_0 086 | 5.14 | 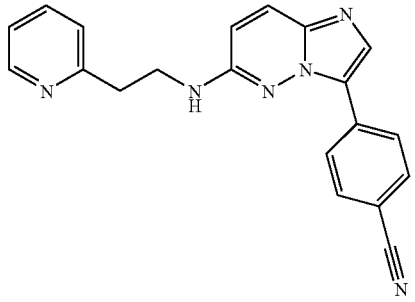<br>4-[6-(2-Pyridin-2-yl-ethylamino)-imidazo[1,2-b]pyridazin-3-yl]-benzonitrile | | 340.39 |
| 229_0 115_4 139 | 5.15 | 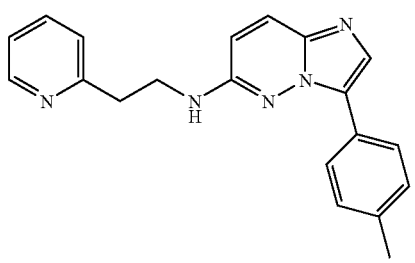<br>(2-Pyridin-2-yl-ethyl)-(3-p-tolyl-imidazol[1,2-b]pyridazin-6-yl)-amine | | 329.41 |
| 229_0 115_0 061 | 5.16 | 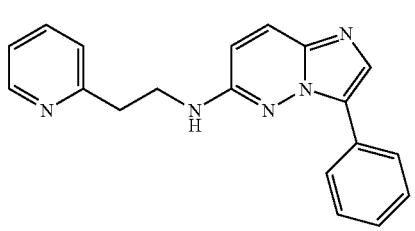<br>(3-Phenyl-imidazo[1,2-b]pyridazin-6-yl)-(2-pyridin-2-yl-ethyl)-amine | | 315.38 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 115_0 062 | 5.17 | 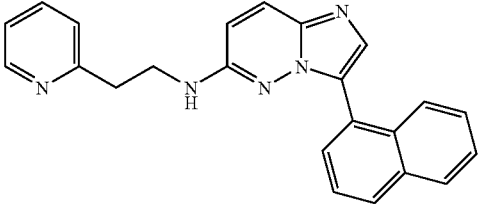<br>(3-Naphthalen-1-yl-imidazo[1,2-b]pyridazin-6-yl)-(2-pyridin-2-yl-ethyl)-amine | | 365.44 |
| 229_0 115_0 073 | 5.18 | 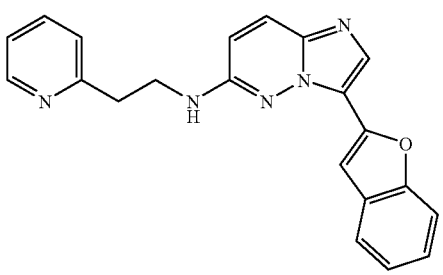<br>(3-Benzofuran-2-yl-imidazo[1,2-b]pyridazin-6-yl)-(2-pyridin-2-yl-ethyl)-amine | | 355.40 |
| 229_0 115_0 164 | 5.19 | 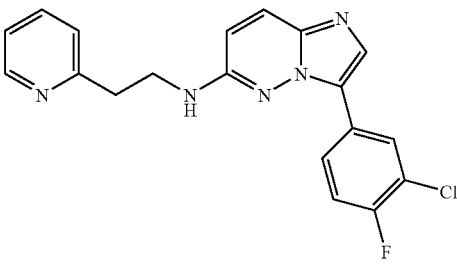<br>[3-(3-Chloro-4-fluoro-phenyl)-imidazo[1,2-b]pyridazin-6-yl]-(2-pyridin-2-yl-ethyl)-amine | | 367.81 |
| 229_0 115_0 076 | 5.20 | 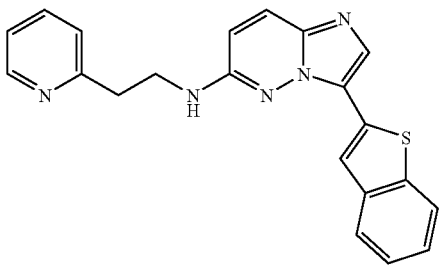<br>(3-Benzo[b]thiophen-2-yl-imidazo[1,2-b]pyridazin-6-yl)-(2-pyridin-2-yl-ethyl)-amine | | 371.47 |
| 229_0 115_0 068 | 5.21 | 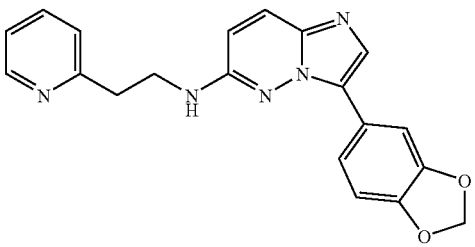<br>(3-Benzo[1,3]dioxol-5-yl-imidazo[1,2-b]pyridazin-6-yl)-(2-pyridin-2-yl-ethyl)-amine | | 359.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 115_0 280 | 5.22 | 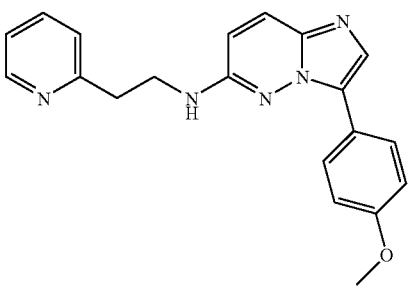<br>[3-(4-Methoxy-phenyl)-imidazo[1,2-b]pyridazin-6-yl]-<br>(2-pyridin-2-yl-ethyl)-amine | | 345.40 |
| 229_0 231_0 087 | 5.23 | 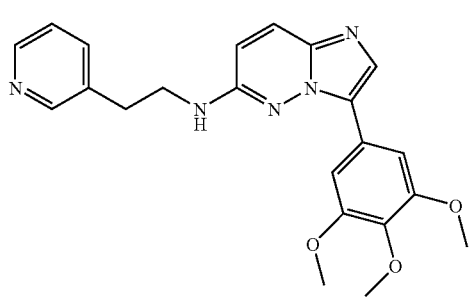<br>(2-Pyridin-3-yl-ethyl)-[3-(3,4,5-trimethoxy-phenyl)-<br>imidazo[1,2-b]pyridazin-6-yl]-amine | | 405.46 |
| 229_0 231_0 339 | 5.24 | 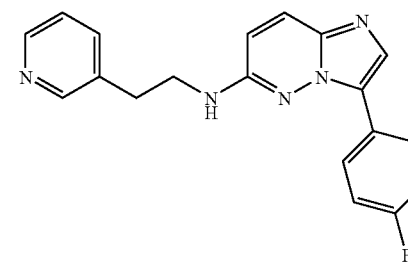<br>[3-(4-Fluoro-phenyl)-imidazo[1,2-b]pyridazin-6-yl]-(2-<br>pyridin-3-yl-ethyl)-amine | | 333.37 |
| 229_0 231_0 068 | 5.25 | 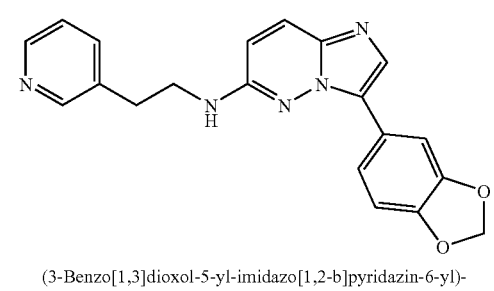<br>(3-Benzo[1,3]dioxol-5-yl-imidazo[1,2-b]pyridazin-6-yl)-<br>(2-pyridin-3-yl-ethyl)-amine | | 359.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 231_0 280 | 5.26 | 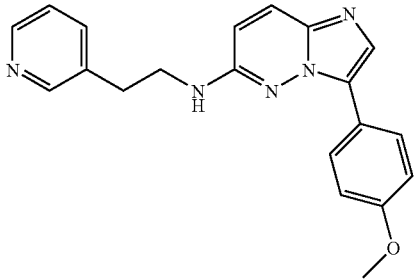<br>[3-(4-Methoxy-phenyl)-imidazo[1,2-b]pyridazin-6-yl]-(2-pyridin-3-yl-ethyl)-amine | | 345.40 |
| 229_0 231_0 345 | 5.27 | 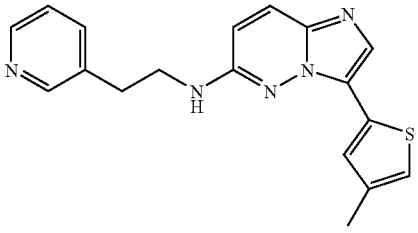<br>[3-(4-Methyl-thiophen-2-yl)-imidazo[1,2-b]pyridazin-6-yl]-(2-pyridin-3-yl-ethyl)-amine | | 335.43 |
| 229_0 231_0 073 | 5.28 | 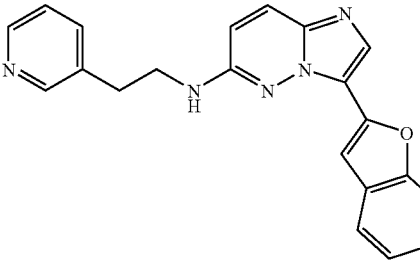<br>(3-Benzofuran-2-yl-imidazo[1,2-b]pyridazin-6-yl)-(2-pyridin-3-yl-ethyl)-amine | | 355.40 |
| 229_0 231_0 057 | 5.29 | 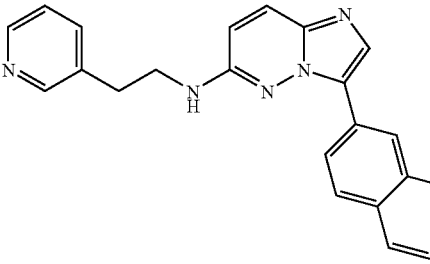<br>(3-Naphthalen-2-yl-imidazo[1,2-b]pyridazin-6-yl)-(2-pyridin-3-yl-ethyl)-amine | | 365.44 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 231_0 076 | 5.30 | 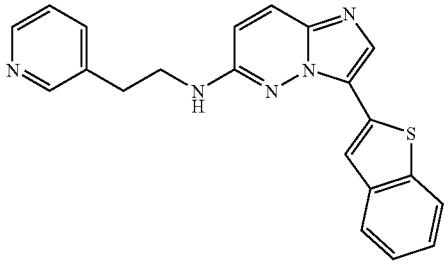<br>(3-Benzo[b]thiophen-2-yl-imidazo[1,2-b]pyridazin-6-yl)-(2-pyridin-3-yl-ethyl)-amine | | 371.47 |
| 229_0 231_0 061 | 5.31 | 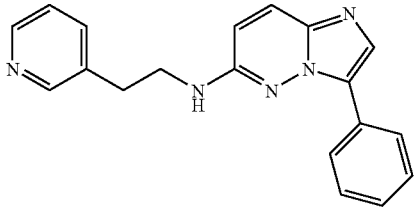<br>(3-Phenyl-imidazo[1,2-b]pyridazin-6-yl)-(2-pyridin-3-yl-ethyl)-amine | | 315.38 |
| 229_0 231_0 160 | 5.32 | 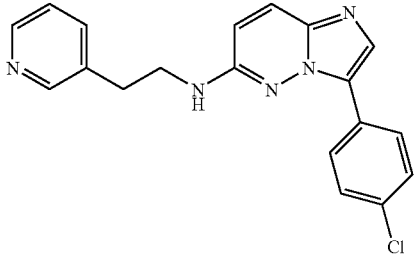<br>[3-(4-Chloro-phenyl)-imidazo[1,2-b]pyridazin-6-yl]-(2-pyridin-3-yl-ethyl)-amine | | 349.82 |
| 229_0 231_0 086 | 5.33 | 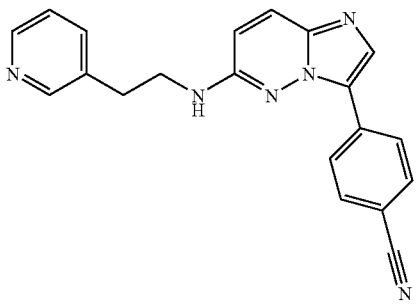<br>4-[6-(2-Pyridin-3-yl-ethylamino)-imidazo[1,2-b]pyridazin-3-yl]-benzonitrile | | 340.39 |
| 229_0 231_0 312 | 5.34 | 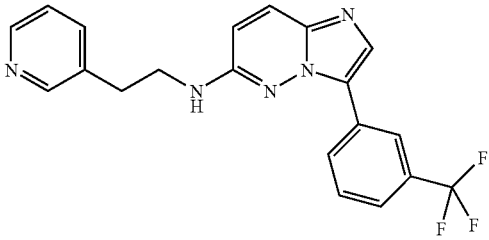<br>(2-Pyridin-3-yl-ethyl)-[3-(3-trifluoromethyl-phenyl)-imidazo[1,2-b]pyridazin-6-yl]-amine | | 383.38 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 231_7 468 | 5.35 | 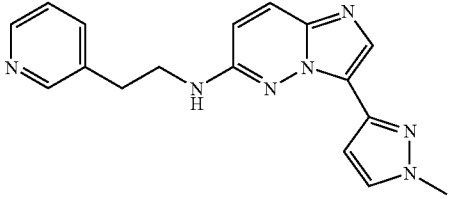<br>[3-(1-Methyl-1H-pyrazol-3-yl)-imidazo[1,2-b]pyridazin-6-yl]-(2-pyridin-3-yl-ethyl)-amine | | 319.37 |
| 229_0 231_4 147 | 5.36 | 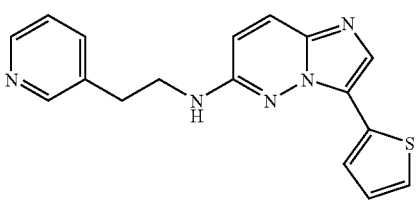<br>(2-Pyridin-3-yl-ethyl)-(3-thiophen-2-yl-imidazo[1,2-b]pyridazin-6-yl)-amine | 0.67 | 321.41/320 (negative mode |
| 229_0 231_6 488 | 5.37 | 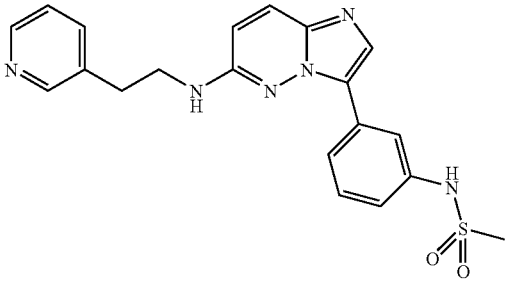<br>N-{3-[6-(2-Pyridin-3-yl-ethylamino)-imidazo[1,2-b]pyridazin-3-yl]-phenyl}-methanesulfonamide | | 408.48 |
| 229_0 144_0 339 | 5.38 | 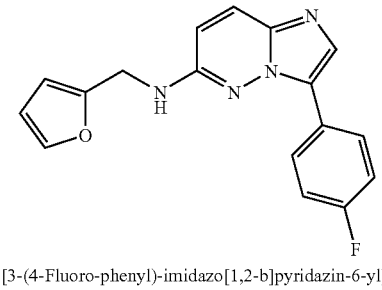<br>[3-(4-Fluoro-phenyl)-imidazo[1,2-b]pyridazin-6-yl]-furan-2-ylmethyl-amine | | 308.32 |
| 229_0 144_0 061 | 5.39 | 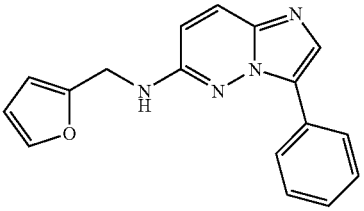<br>Furan-2-ylmethyl-(3-phenyl-imidazo[1,2-b]pyridazin-6-yl)-amine | | 290.33 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 144_0 280 | 5.40 | Furan-2-ylmethyl-[3-(4-methoxy-phenyl)-imidazo[1,2-b]pyridazin-6-yl]-amine | | 320.35 |
| 229_0 144_0 204 | 5.41 | Furan-2-ylmethyl-[3-(1H-indol-5-yl)-imidazo[1,2-b]pyridazin-6-yl]-amine | | 329.36 |
| 229_0 144_0 135 | 5.42 | [3-(3-Dimethylamino-phenyl)-imidazo[1,2-b]pyridazin-6-yl]-furan-2-ylmethyl-amine | | 333.39 |
| 229_0 144_4 140 | 5.43 | Furan-2-ylmethyl-[3-(3-methoxy-phenyl)-imidazo[1,2-b]pyridazin-6-yl]-amine | | 320.35 |
| 229_0 144_0 081 | 5.44 | N-(3-{6-[(Furan-2-ylmethyl)-amino]-imidazo[1,2-b]pyridazin-3-yl}-phenyl)-acetamide | | 347.38 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0144_0291 | 5.45 | 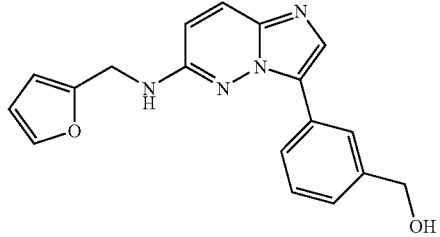<br>(3-{6-[(Furan-2-ylmethyl)-amino]-imidazo[1,2-b]pyridazin-3-yl}-phenyl)-methanol | | 320.35 |
| 229_0144_0080 | 5.46 | 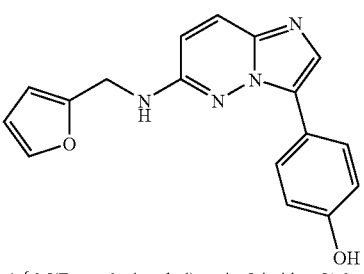<br>4-{6-[(Furan-2-ylmethyl)-amino]-imidazo[1,2-b]pyridazin-3-yl}-phenol | | 306.32 |
| 229_0144_0284 | 5.47 | 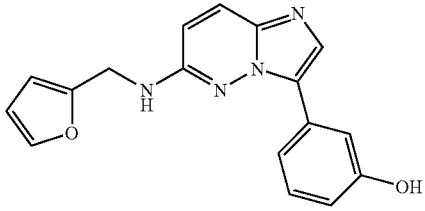<br>3-{6-[(Furan-2-ylmethyl)-amino]-imidazo[1,2-b]pyridazin-3-yl}-phenol | | 306.32 |
| 229_0144_0347 | 5.48 | 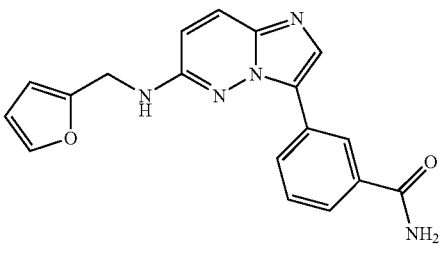<br>3-{6-[(Furan-2-ylmethyl)-amino]-imidazo[1,2-b]pyridazin-3-yl}-benzamide | | 333.35 |
| 229_0144_6488 | 5.49 | 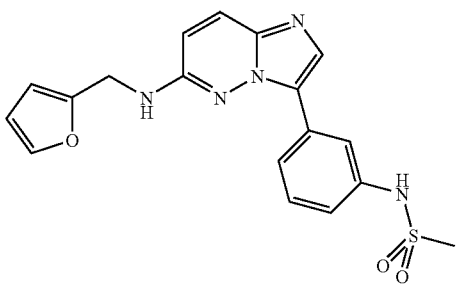<br>N-(3-{6-[(Furan-2-ylmethyl)-amino]-imidazo[1,2-b]pyridazin-3-yl}-phenyl)-methanesulfonamide | | 383.43 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 144_0 314 | 5.50 | 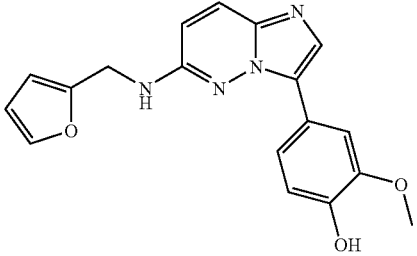<br>4-{6-[(Furan-2-ylmethyl)-amino]-imidazo[1,2-b]pyridazin-3-yl}-2-methoxy-phenol | | 336.35 |
| 229_0 144_4 145 | 5.51 | 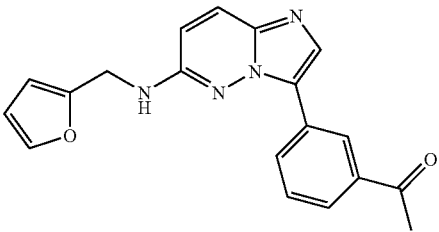<br>1-(3-{6-[(Furan-2-ylmethyl)-amino]-imidazo[1,2-b]pyridazin-3-yl}-phenyl)-ethanone | | 332.36 |
| 229_0 144_0 311 | 5.52 | 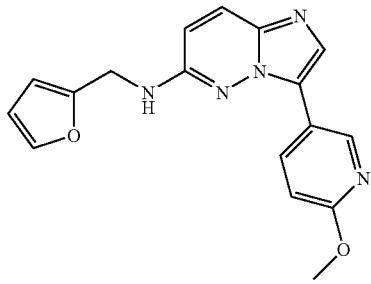<br>Furan-2-ylmethyl-[3-(6-methoxy-pyridin-3-yl)-imidazo[1,2-b]pyridazin-6-yl]-amine | | 321.34 |
| 229_0 144_0 071 | 5.53 | 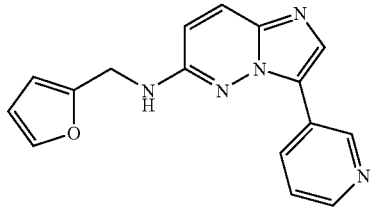<br>Furan-2-ylmethyl-(3-pyridin-3-yl-imidazo[1,2-b]pyridazin-6-yl)-amine | | 291.31 |
| 229_0 144_0 196 | 5.54 | 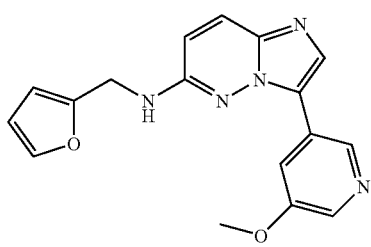<br>Furan-2-ylmethyl-[3-(5-methoxy-pyridin-3-yl)-imidazo[1,2-b]pyridazin-6-yl]-amine | | 321.34 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 144_0 069 | 5.55 | 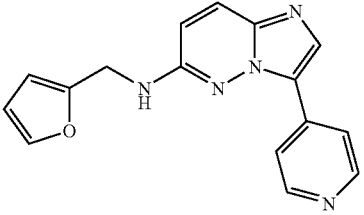<br>Furan-2-ylmethyl-(3-pyridin-4-yl-imidazo[1,2-b]pyridazin-6-yl)-amine | | 291.31 |
| 229_0 146_0 079 | 5.56 | 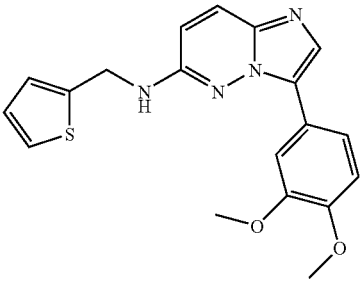<br>[3-(3,4-Dimethoxy-phenyl)-imidazo[1,2-b]pyridazin-6-yl]-thiophen-2-ylmethyl-amine | | 366.44 |
| 229_0 146_0 087 | 5.57 | 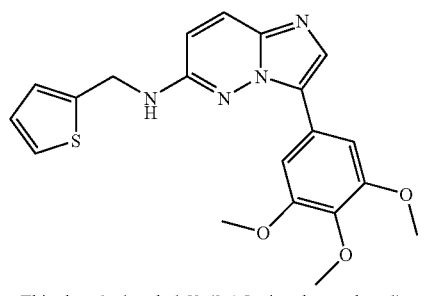<br>Thiophen-2-ylmethyl-[3-(3,4,5-trimethoxy-phenyl)-imidazo[1,2-b]pyridazin-6-yl]-amine | | 396.47 |
| 229_0 146_4 145 | 5.58 | 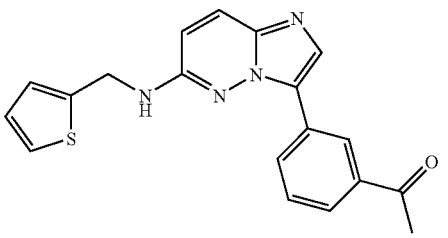<br>1-(3-{6-[(Thiophen-2-ylmethyl)-amino]-imidazo[1,2-b]pyridazin-3-yl}-phenyl)-ethanone | | 348.43 |
| 229_0 146_0 284 | 5.59 | 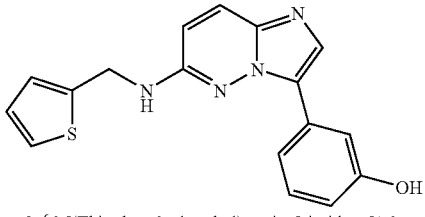<br>3-{6-[(Thiophen-2-ylmethyl)-amino]-imidazo[1,2-b]pyridazin-3-yl}-phenol | | 322.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 146_0 196 | 5.60 | 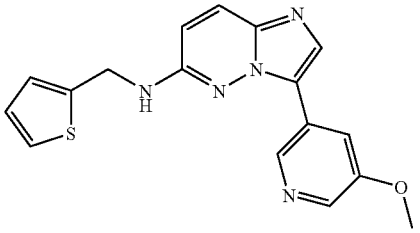<br>[3-(5-Methoxy-pyridin-3-yl)-imidazo[1,2-b]pyridazin-6-yl]-thiophen-2-ylmethyl-amine | | 337.41 |
| 229_0 146_0 285 | 5.61 | 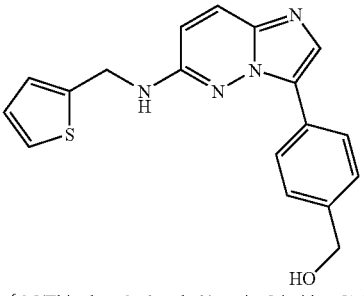<br>(4-{6-[(Thiophen-2-ylmethyl )-amino]-imidazo[1,2-b]pyridazin-3-yl}-phenyl)-methanol | | 336.42 |
| 229_0 146_0 192 | 5.62 | 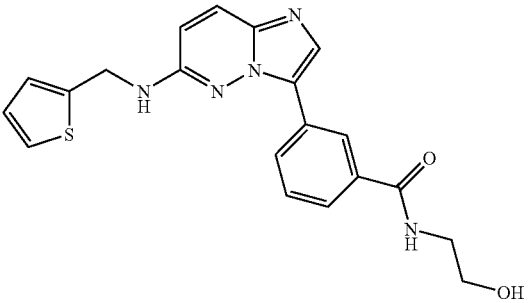<br>N-(2-Hydroxy-ethyl)-3-{6-[(thiophen-2-ylmethyl)-amino]-imidazo[1,2-b]pyridazin-3-yl}-benzamide | | 393.47 |
| 229_0 146_0 345 | 5.63 | 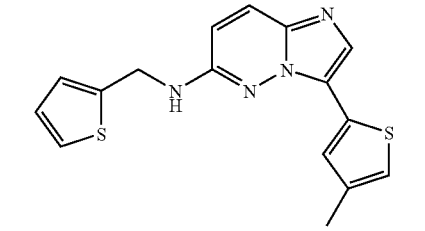<br>[3-(4-Methyl-thiophen-2-yl)-imidazo[1,2-b]pyridazin-6-yl]-thiophen-2-ylmethyl-amine | | 326.45 |
| 229_0 146_4 147 | 5.64 | 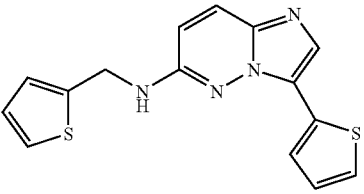<br>(3-Thiophen-2-yl-imidazo[1,2-b]pyridazin-6-yl)-thiophen-2-ylmethyl-amine | 1.02 | 312.42/314 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 146_0 074 | 5.65 | 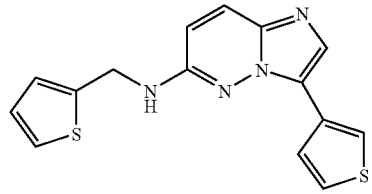<br>(3-Thiophen-3-yl-imidazo[1,2-b]pyridazin-6-yl)-thiophen-2-ylmethyl-amine | | 312.42 |
| 229_0 146_0 311 | 5.66 | 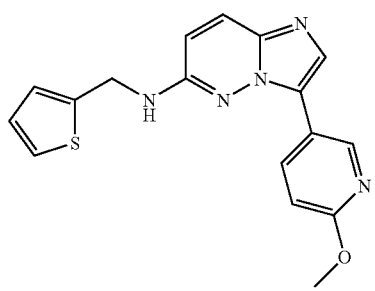<br>[3-(6-Methoxy-pyridin-3-yl)-imidazo[1,2-b]pyridazin-6-yl]-thiophen-2-ylmethyl-amine | | 337.41 |
| 229_0 146_0 204 | 5.67 | 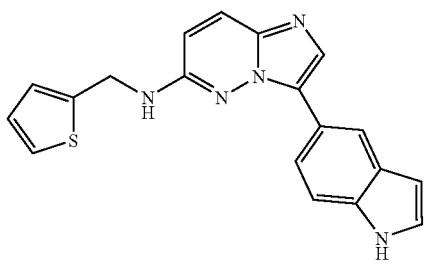<br>[3-(1 H-Indol-5-yl)-imidazo[1,2-b]pyridazin-6-yl]-thiophen-2-ylmethyl-amine | | 345.43 |
| 229_0 146_0 135 | 5.68 | 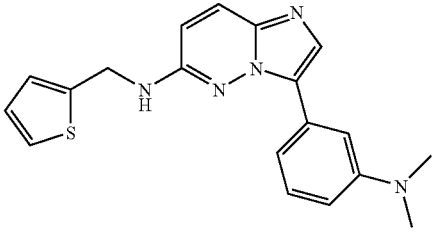<br>[3-(3-Dimethylamino-phenyl)-imidazo[1,2-b]pyridazin-6-yl]-thiophen-2-ylmethyl-amine | | 349.46 |
| 229_0 146_0 339 | 5.69 | 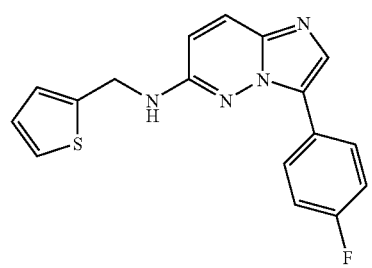<br>[3-(4-Fluoro-phenyl)-imidazo[1,2-b]pyridazin-6-yl]-thiophen-2-ylmethyl-amine | | 324.38 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 146_7 468 | 5.70 | 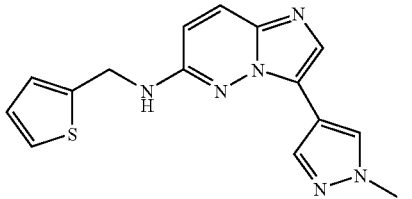<br>[3-(1-Methyl-1H-pyrazol-4-yl)-imidazo[1,2-b]pyridazin-6-yl]-thiophen-2-ylmethyl-amine | | 310.38 |
| 229_0 146_0 071 | 5.71 | 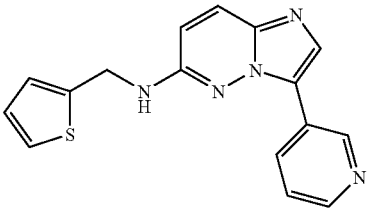<br>(3-Pyridin-3-yl-imidazo[1,2-b]pyridazin-6-yl)-thiophen-2-ylmethyl-amine | | 307.38 |
| 229_0 146_0 081 | 5.72 | 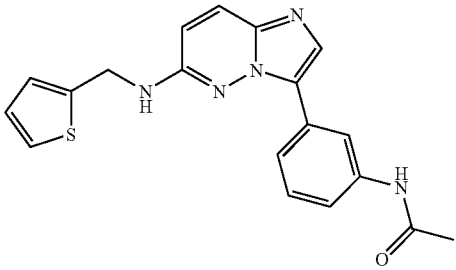<br>N-(3-{6-[(Thiophen-2-ylmethyl)-amino]-imidazo[1,2-b]pyridazin-3-yl}-phenyl)-acetamide | | 363.44 |
| 229_0 146_4 140 | 5.73 | 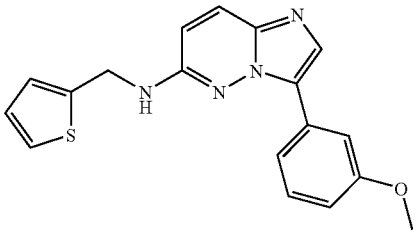<br>[3-(3-Methoxy-phenyl)-imidazo[1,2-b]pyridazin-6-yl]-thiophen-2-ylmethyl-amine | 1.01 | 336.42/338 |
| 229_0 146_0 080 | 5.74 | 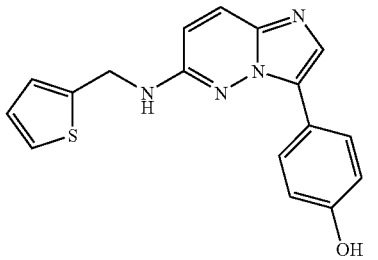<br>4-{6-[(Thiophen-2-ylmethyl)-amino]-imidazo[1,2-b]pyridazin-3-yl}-phenol | | 322.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 146_0 069 | 5.75 | 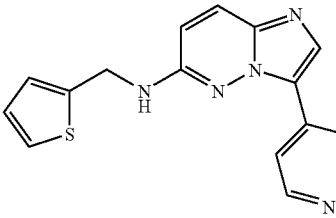<br>(3-Pyridin-4-yl-imidazo[1,2-b]pyridazin-6-yl)-thiophen-2-ylmethyl-amine | | 307.38 |
| 229_0 146_0 314 | 5.76 | 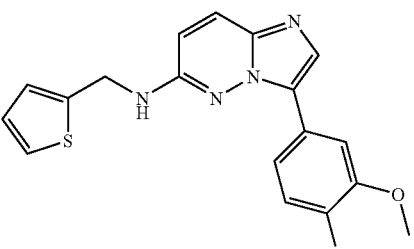<br>2-Methoxy-4-{6-[(thiophen-2-ylmethyl)-amino]-imidazo[1,2-b]pyridazin-3-yl}-phenol | | 352.42 |
| 229_0 146_0 347 | 5.77 | 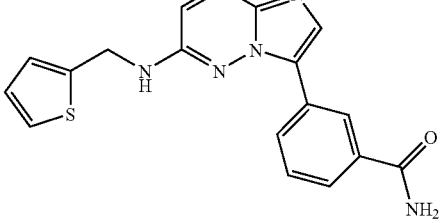<br>3-{6-[(Thiophen-2-ylmethyl)-amino]-imidazo[1,2-b]pyridazin-3-yl}-benzamide | | 349.42 |
| 229_0 146_6 488 | 5.78 | 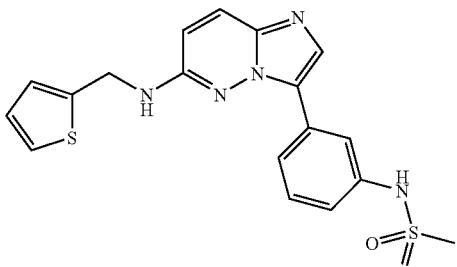<br>N-(3-{6-[(Thiophen-2-ylmethyl)-amino]-imidazo[1,2-b]pyridazin-3-yl}-phenyl)-methanesulfonamide | | 399.50 |
| 229_0 146_0 140 | 5.79 | 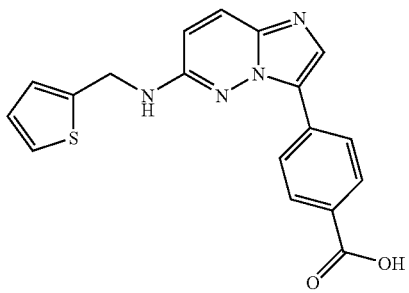<br>4-{6-[(Thiophen-2-ylmethyl)-amino]-imidazo[1,2-b]pyridazin-3-yl}-benzoic acid | | 350.40 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 237_4 140 | 5.80 | 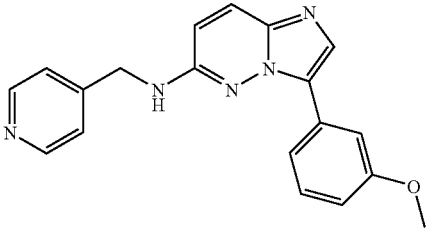<br>[3-(3-Methoxy-phenyl)-imidazo[1,2-b]pyridazin-6-yl]-pyridin-4-ylmethyl-amine | 0.62 | 331.38/332 |
| 229_0 237_0 168 | 5.81 | 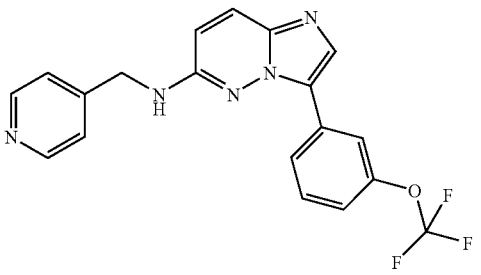<br>Pyridin-4-ylmethyl-[3-(3-trifluoromethoxy-phenyl)-imidazo[1,2-b]pyridazin-6-yl]-amine | | 385.35 |
| 229_0 237_0 279 | 5.82 | 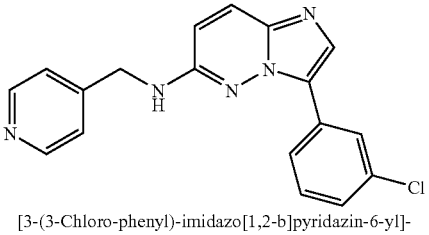<br>[3-(3-Chloro-phenyl)-imidazo[1,2-b]pyridazin-6-yl]-pyridin-4-ylmethyl-amine | | 335.80 |
| 229_0 237_0 312 | 5.83 | 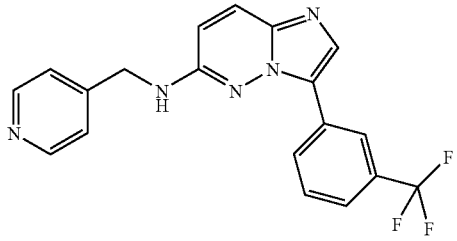<br>Pyridin-4-ylmethyl-[3-(3-trifluoromethyl-phenyl)-imidazo[1,2-b]pyridazin-6-yl]-amine | | 369.35 |
| 229_0 237_0 164 | 5.84 | 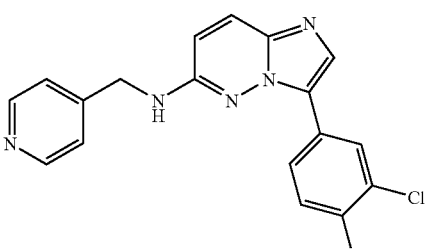<br>[3-(3-Chloro-4-fluoro-phenyl)-imidazo[1,2-b]pyridazin-6-yl]-pyridin-4-ylmethyl-amine | | 353.79 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 237_0 073 | 5.85 | 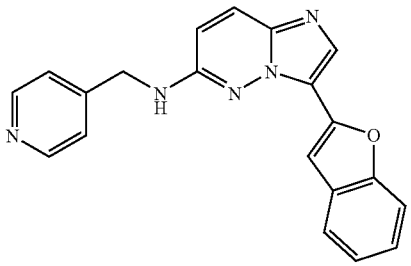<br>(3-Benzofuran-2-yl-imidazo[1,2-b]pyridazin-6-yl)-pyridin-4-ylmethyl-amine | | 341.37 |
| 229_0 237_0 167 | 5.86 | 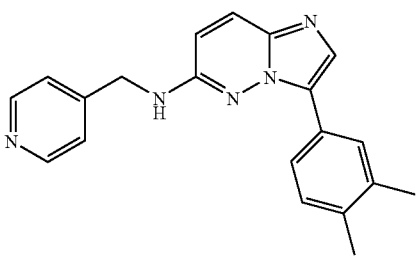<br>[3-(3,4-Dimethyl-phenyl)-imidazo[1,2-b]pyridazin-6-yl]-pyridin-4-ylmethyl-amine | | 329.41 |
| 229_0 237_4 139 | 5.87 | 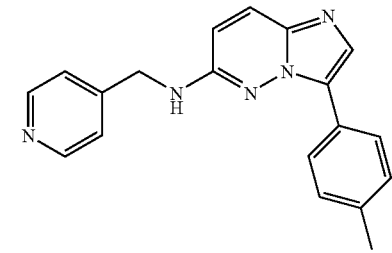<br>Pyridin-4-ylmethyl-(3-p-tolyl-imidazo[1,2-b]pyridazin-6-yl)-amine | 0.66 | 315.38/316 |
| 229_0 237_4 147 | 5.88 | 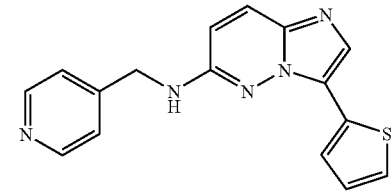<br>Pyridin-4-ylmethyl-(3-thiophen-2-yl-imidazo[1,2-b]pyridazin-6-yl)-amine | 0.61 | 307.38/308 |
| 229_0 237_0 061 | 5.89 | 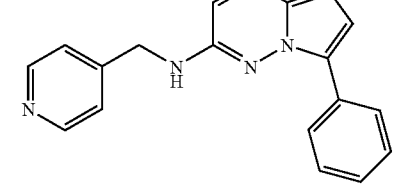<br>(3-Phenyl-imidazo[1,2-b]pyridazin-6-yl)-pyridin-4-ylmethyl-amine | | 301.35 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 237_0 068 | 5.90 | 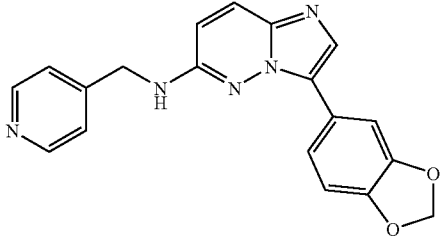<br>(3-Benzo[1,3]dioxol-5-yl-imidazo[1,2-b]pyridazin-6-yl)-pyridin-4-ylmethyl-amine | | 345.36 |
| 229_0 237_0 057 | 5.91 | 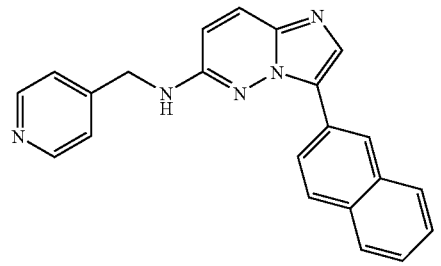<br>(3-Naphthalen-2-yl-imidazo[1,2-b]pyridazin-6-yl)-pyridin-4-ylmethyl-amine | | 351.41 |
| 229_0 237_0 076 | 5.92 | 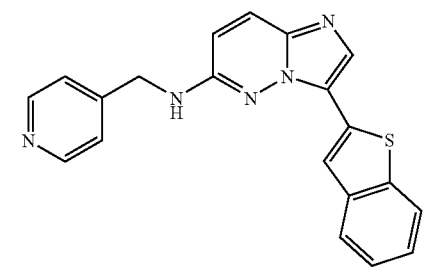<br>(3-Benzo[b]thiophen-2-yl-imidazo[1,2-b]pyridazin-6-yl)-pyridin-4-ylmethyl-amine | | 357.44 |
| 229_0 237_0 160 | 5.93 | 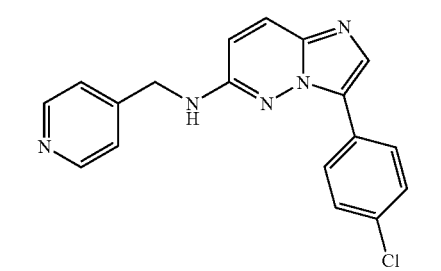<br>[3-(4-Chloro-phenyl)-imidazo[1,2-b]pyridazin-6-yl]-pyridin-4-ylmethyl-amine | | 335.80 |
| 229_0 237_0 277 | 5.94 | 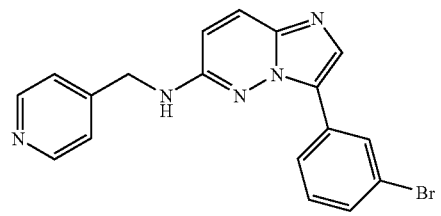<br>[3-(3-Bromo-phenyl)-imidazo[1,2-b]pyridazin-6-yl]-pyridin-4-ylmethyl-amine | | 380.25 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 237_6 488 | 5.95 | N-(3-{6-[(Pyridin-4-ylmethyl)-amino]-imidazo[1,2-b]pyridazin-3-yl}-phenyl)-methanesulfonamide | | 394.46 |
| 229_0 237_4 038 | 5.96 | [3-(2-Fluoro-phenyl)-imidazo[1,2-b]pyridazin-6-yl]-pyridin-4-ylmethyl-amine | | 319.34 |
| 229_4 007_0 087 | 5.97 | Pyridin-2-ylmethyl-[3-(3,4,5-trimethoxy-phenyl)-imidazo[1,2-b]pyridazin-6-yl]-amine | | 391.43 |
| 229_4 007_0 339 | 5.98 | [3-(4-Fluoro-phenyl)-imidazo[1,2-b]pyridazin-6-yl]-pyridin-2-ylmethyl-amine | | 319.34 |
| 229_4 007_0 073 | 5.99 | (3-Benzofuran-2-yl-imidazo[1,2-b]pyridazin-6-yl)-pyridin-2-ylmethyl-amine | | 341.37 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4 007_0 057 | 5.100 | 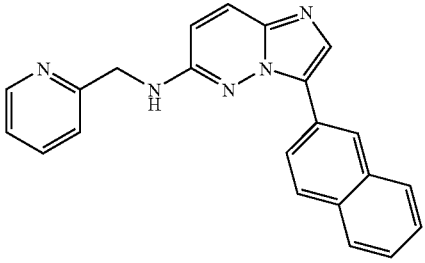<br>(3-Naphthalen-2-yl-imidazo[1,2-b]pyridazin-6-yl)-pyridin-2-ylmethyl-amine | | 351.41 |
| 229_4 007_0 311 | 5.101 | 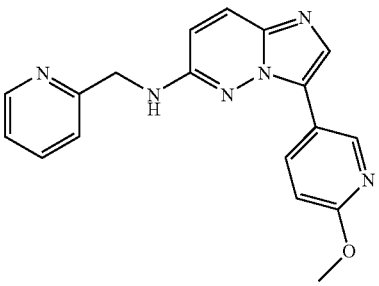<br>[3-(6-Methoxy-pyridin-3-yl)-imidazo[1,2-b]pyridazin-6-yl]-pyridin-2-ylmethyl-amine | | 332.37 |
| 229_4 007_0 076 | 5.102 | 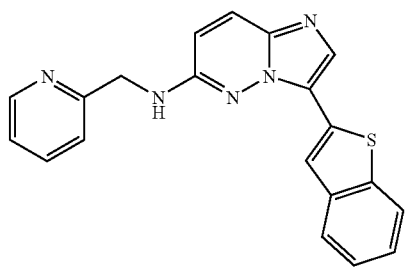<br>(3-Benzo[b]thiophen-2-yl-imidazo[1,2-b]pyridazin-6-yl)-pyridin-2-ylmethyl-amine | | 357.44 |
| 229_4 007_0 168 | 5.103 | 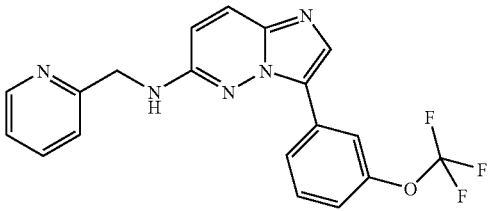<br>Pyridin-2-ylmethyl-[3-(3-trifluoromethoxy-phenyl)-imidazo[1,2-b]pyridazin-6-yl]-amine | | 385.35 |
| 229_4 007_0 074 | 5.104 | 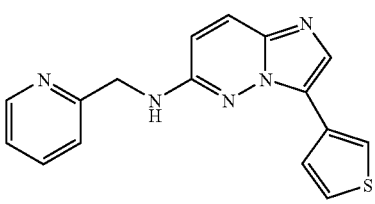<br>Pyridin-2-ylmethyl-(3-thiophen-3-yl-imidazo[1,2-b]pyridazin-6-yl)-amine | | 307.38 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4007_0312 | 5.105 | 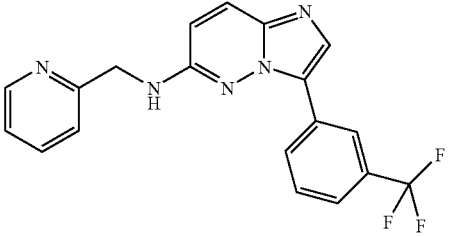<br>Pyridin-2-ylmethyl-[3-(3-trifluoromethyl-phenyl)-imidazo[1,2-b]pyridazin-6-yl]-amine | | 369.35 |
| 229_4007_0135 | 5.106 | 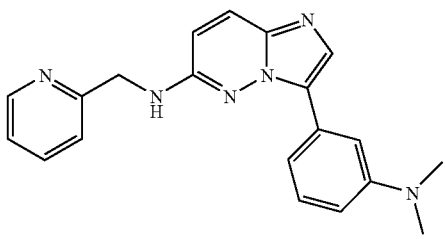<br>[3-(3-Dimethylamino-phenyl)-imidazo[1,2-b]pyridazin-6-yl]-pyridin-2-ylmethyl-amine | | 344.42 |
| 229_4007_0164 | 5.107 | 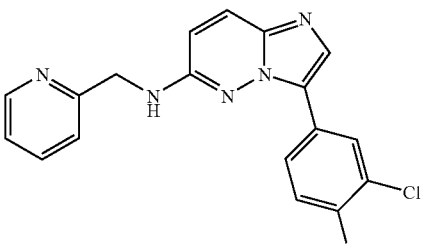<br>[3-(3-Chloro-4-fluoro-phenyl)-imidazo[1,2-b]pyridazin-6-yl]-pyridin-2-ylmethyl-amine | | 353.79 |
| 229_4007_0280 | 5.108 | 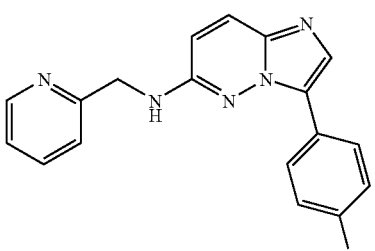<br>[3-(4-Methoxy-phenyl)-imidazo[1,2-b]pyridazin-6-yl]-pyridin-2-ylmethyl-amine | | 331.38 |
| 229_4007_0079 | 5.109 | 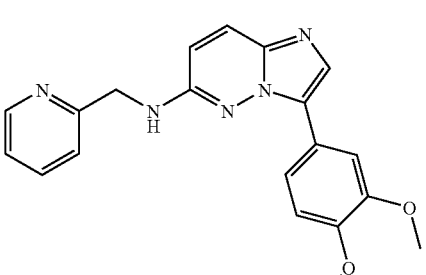<br>[3-(3,4-Dimethoxy-phenyl)-imidazol[1,2-b]pyridazin-6-yl]-pyridin-2-ylmethyl-amine | | 361.40 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 223_0 314 | 5.110 | 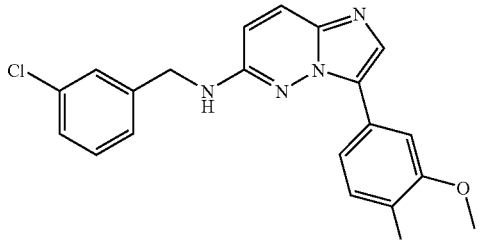 4-[6-(3-Chloro-benzylamino)-imidazo[1,2-b]pyridazin-3-yl]-2-methoxy-phenol | 0.93 | 380.83/380 (negative mode) |
| 229_0 223_0 285 | 5.111 | 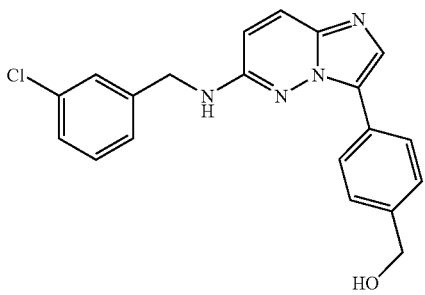 {4-[6-(3-Chloro-benzylamino)-imidazo[1,2-b]pyridazin-3-yl]-phenyl}-methanol | | 364.83 |
| 229_0 223_0 196 | 5.112 | 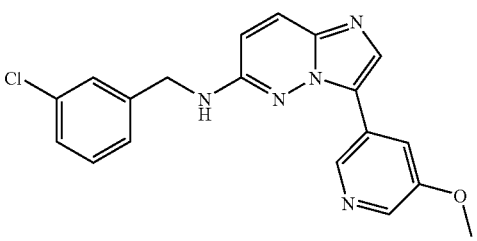 (3-Chloro-benzyl)-[3-(5-methoxy-pyridin-3-yl)-imidazo[1,2-b]pyridazin-6-yl]-amine | | 365.82 |
| 229_0 223_0 284 | 5.113 | 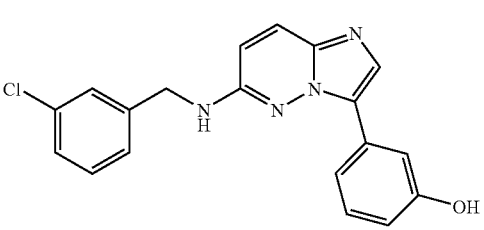 3-[6-(3-Chloro-benzylamino)-imidazo[1,2-b]pyridazin-3-yl]-phenol | | 350.81 |
| 229_0 223_0 071 | 5.114 | 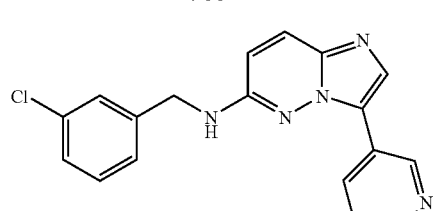 (3-Chloro-benzyl)-(3-pyridin-3-yl-imidazo[1,2-b]pyridazin-6-yl)-amine | | 335.80 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0223_0005 | 5.115 | 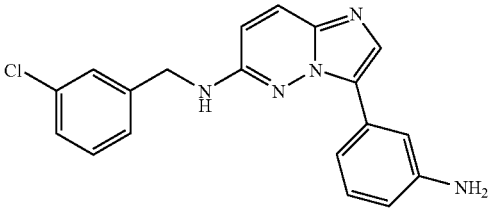<br>[3-(3-Amino-phenyl)-imidazo[1,2-b]pyridazin-6-yl]-(3-chloro-benzyl)-amine | 0.92 | 349.82/349 (negative mode) |
| 229_0223_0311 | 5.116 | 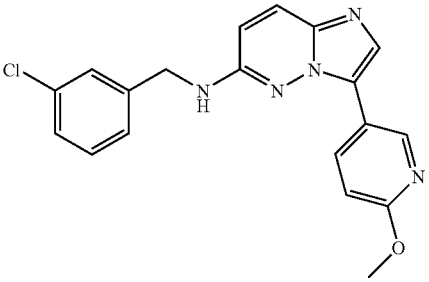<br>(3-Chloro-benzyl)-[3-(6-methoxy-pyridin-3-yl)-imidazo[1,2-b]pyridazin-6-yl]-amine | | 365.82 |
| 229_0223_0080 | 5.117 | 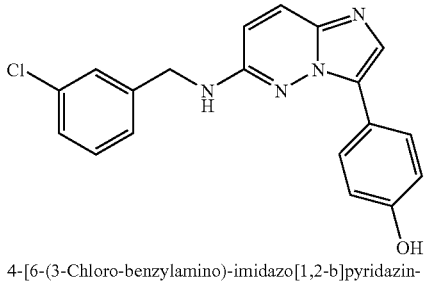<br>4-[6-(3-Chloro-benzylamino)-imidazo[1,2-b]pyridazin-3-yl]-phenol | 0.89 | 350.81/350 (negative mode) |
| 229_0223_0069 | 5.118 | 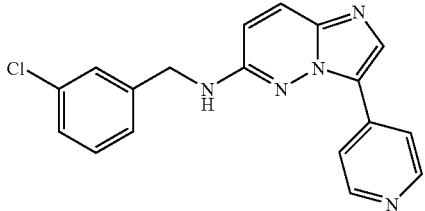<br>(3-Chloro-benzyl)-(3-pyridin-4-yl-imidazo[1,2-b]pyridazin-6-yl)-amine | | 335.80 |
| 229_0223_0347 | 5.119 | 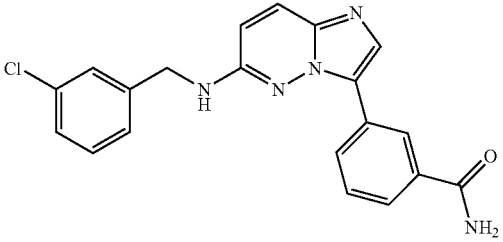<br>3-[6-(3-Chloro-benzylamino)-imidazo[1,2-b]pyridazin-3-yl]-benzamide | | 377.83 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 223_0 140 | 5.120 | 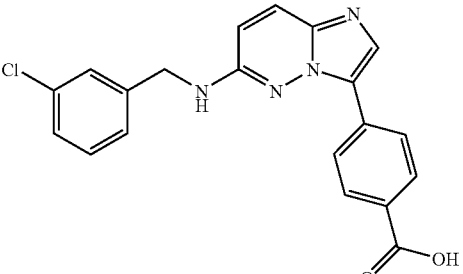<br>4-[6-(3-Chloro-benzylamino)-imidazo[1,2-b]pyridazin-3-yl]-benzoic acid | | 378.82 |
| 229_0 224_0 069 | 5.121 | 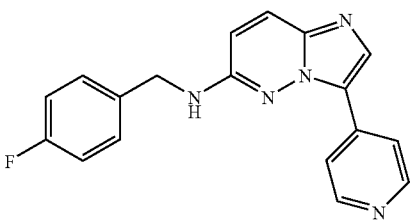<br>(4-Fluoro-benzyl)-(3-pyridin-4-yl-imidazo[1,2-b]pyridazin-6-yl)-amine | 0.77 | 319.34/320 |
| 229_0 224_0 080 | 5.122 | 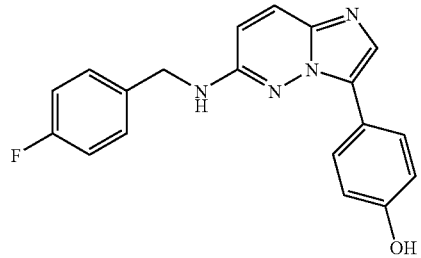<br>4-[6-(4-Fluoro-benzylamino)-imidazo[1,2-b]pyridazin-3-yl]-phenol | 0.86 | 334.35/335 |
| 229_0 224_0 196 | 5.123 | 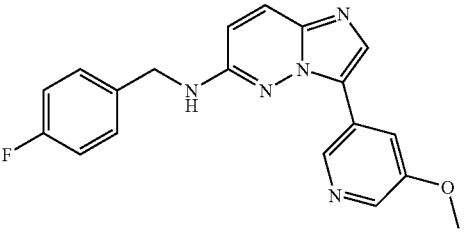<br>(4-Fluoro-benzyl)-[3-(5-methoxy-pyridin-3-yl)-imidazo[1,2-b]pyridazin-6-yl]-amine | 0.92 | 349.37/350 |
| 229_0 224_0 284 | 5.124 | 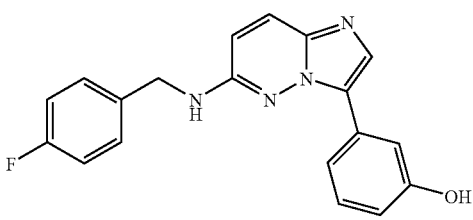<br>3-[6-(4-Fluoro-benzylamino)-imidazo[1,2-b]pyridazin-3-yl]-phenol | | 334.35 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 224_0 345 | 5.125 | 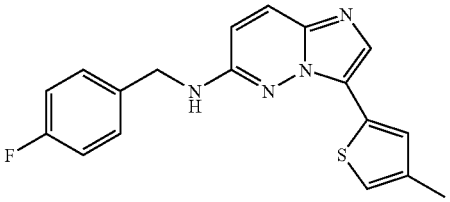<br>(4-Fluoro-benzyl)-[3-(4-methyl-thiophen-2-yl)-imidazo[1,2-b]pyridazin-6-yl]-amine | 1.14 | 338.41/340 |
| 229_0 224_0 068 | 5.126 | 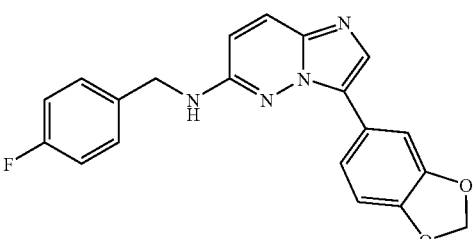<br>(3-Benzo[1,3]dioxol-5-yl-imidazo[1,2-b]pyridazin-6-yl)-(4-fluoro-benzyl)-amine | 1.02 | 362.36/363 |
| 229_0 224_0 204 | 5.127 | 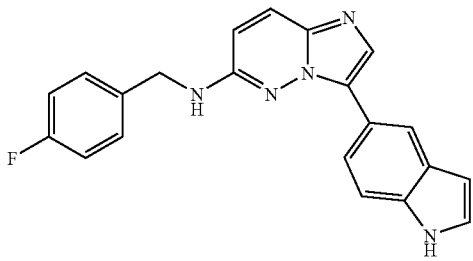<br>(4-Fluoro-benzyl)-[3-(1H-indol-5-yl)-imidazo[1,2-b]pyridazin-6-yl]-amine | 0.96 | 357.39/358 |
| 229_0 224_0 280 | 5.128 | 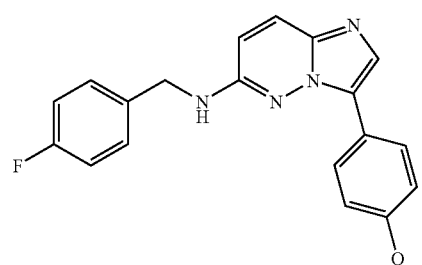<br>(4-Fluoro-benzyl)-[3-(4-methoxy-phenyl)-imidazo[1,2-b]pyridazin-6-yl]-amine | 1.04 | 348.38/349 |
| 229_0 224_0 311 | 5.129 | 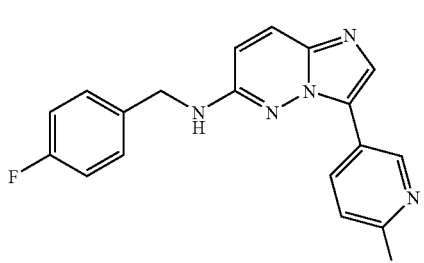<br>(4-Fluoro-benzyl)-[3-(6-methoxy-pyridin-3-yl)-imidazo[1,2-b]pyridazin-6-yl]-amine | 1.00 | 349.37/350 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 224_0 081 | 5.130 | N-{3-[6-(4-Fluoro-benzylamino)-imidazo[1,2-b]pyridazin-3-yl]-phenyl}-acetamide | 0.89 | 375.41/376 |
| 229_0 224_0 071 | 5.131 | (4-Fluoro-benzyl)-(3-pyridin-3-yl-imidazo[1,2-b]pyridazin-6-yl)-amine | 0.83 | 319.34/320 |
| 229_0 224_0 285 | 5.132 | {4-[6-(4-Fluoro-benzylamino)-imidazo[1,2-b]pyridazin-3-yl]-phenyl}-methanol | 0.85 | 348.38/349 |
| 229_0 224_0 347 | 5.133 | 3-[6-(4-Fluoro-benzylamino)-imidazo[1,2-b]pyridazin-3-yl]-benzamide | | 361.38 |
| 229_0 224_0 140 | 5.134 | 4-[6-(4-Fluoro-benzylamino)-imidazo[1,2-b]pyridazin-3-yl]-benzoic acid | | 362.36 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 244_4 139 | 5.135 | 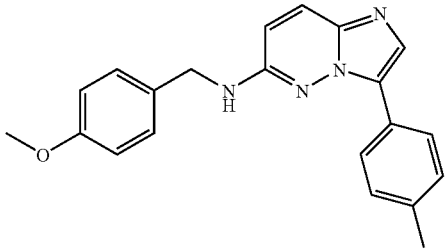<br>(4-Methoxy-benzyl)-(3-p-tolyl-imidazo[1,2-b]pyridazin-6-yl)-amine | 1.06 | 344.42/345 |
| 229_0 244_0 160 | 5.136 | 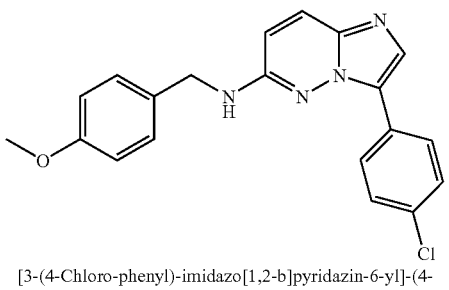<br>[3-(4-Chloro-phenyl)-imidazo[1,2-b]pyridazin-6-yl]-(4-methoxy-benzyl)-amine | 1.13 | 364.83/364 (negative mode) |
| 229_0 244_0 345 | 5.137 | 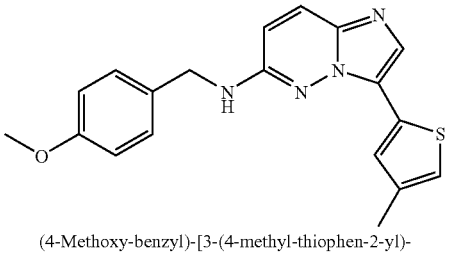<br>(4-Methoxy-benzyl)-[3-(4-methyl-thiophen-2-yl)-imidazo[1,2-b]pyridazin-6-yl]-amine | 1.09 | 350.44/349 (negative mode) |
| 229_0 244_0 204 | 5.138 | 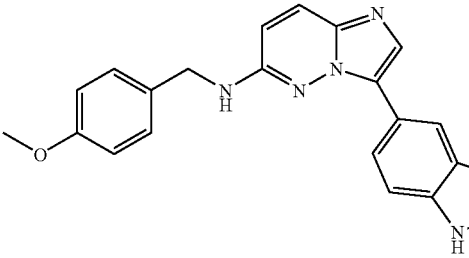<br>[3-(1H-Indol-5-yl)-imidazo[1,2-b]pyridazin-6-yl]-(4-methoxy-benzyl)-amine | 0.93 | 369.43/370 |
| 229_0 244_0 280 | 5.139 | 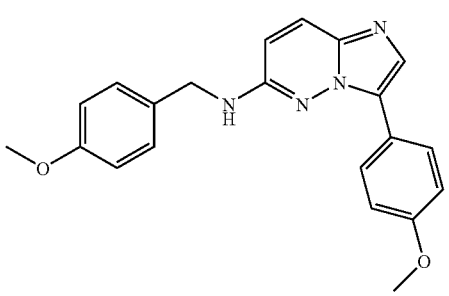<br>(4-Methoxy-benzyl)-[3-(4-methoxy-phenyl)-imidazo[1,2-b]pyridazin-6-yl]-amine | | 360.42 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 244_0 339 | 5.140 | 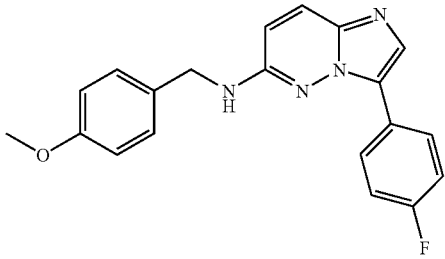<br>[3-(4-Fluoro-phenyl)-imidazo[1,2-b]pyridazin-6-yl]-(4-methoxy-benzyl)-amine | 1.04 | 348.38/349 |
| 229_0 244_0 080 | 5.141 | 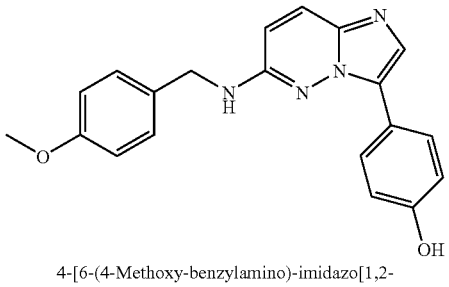<br>4-[6-(4-Methoxy-benzylamino)-imidazo[1,2-b]pyridazin-3-yl]-phenol | 0.85 | 346.39/347 |
| 229_0 244_7 467 | 5.142 | 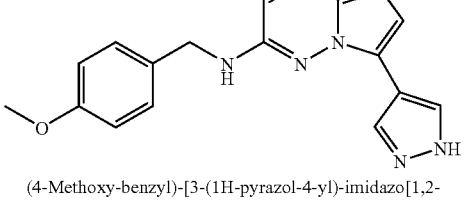<br>(4-Methoxy-benzyl)-[3-(1H-pyrazol-4-yl)-imidazo[1,2-b]pyridazin-6-yl]-amine | 0.72 | 320.35/321 |
| 229_0 244_7 468 | 5.143 | 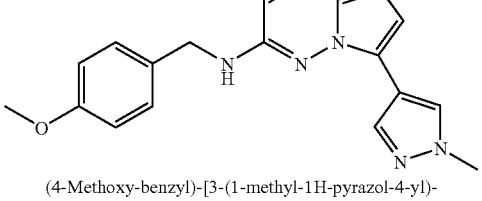<br>(4-Methoxy-benzyl)-[3-(1-methyl-1H-pyrazol-4-yl)-imidazo[1,2-b]pyridazin-6-yl]-amine | 0.82 | 334.38/335 |
| 229_0 244_0 140 | 5.144 | 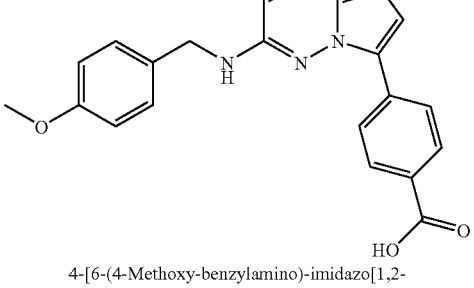<br>4-[6-(4-Methoxy-benzylamino)-imidazo[1,2-b]pyridazin-3-yl]-benzoic acid | | 374.40 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_6 307_0 087 | 5.145 | 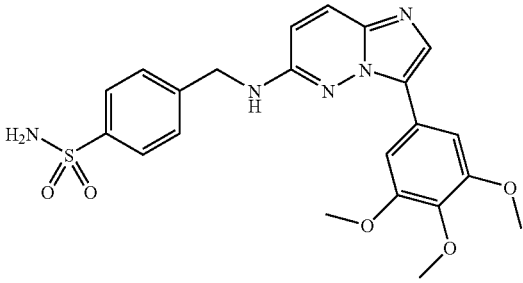 4-{[3-(3,4,5-Trimethoxy-phenyl)-imidazo[1,2-b]pyridazin-6-ylamino]-methyl}-benzenesulfonamide | | 469.52 |
| 229_6 307_0 314 | 5.146 | 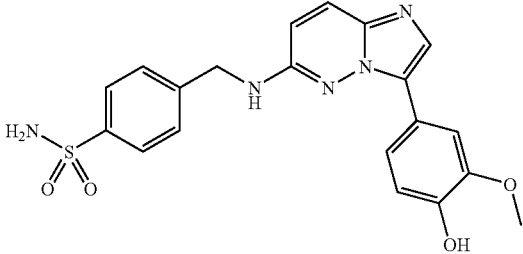 4-{[3-(4-Hydroxy-3-methoxy-phenyl)-imidazo[1,2-b]pyridazin-6-ylamino]-methyl}-benzenesulfonamide | | 425.47 |
| 229_6 307_0 284 | 5.147 | 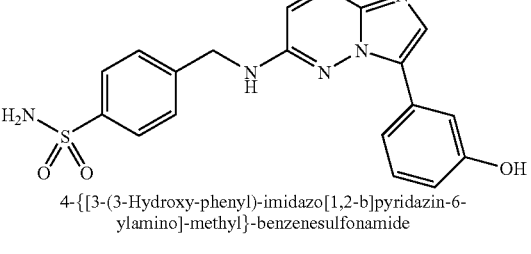 4-{[3-(3-Hydroxy-phenyl)-imidazo[1,2-b]pyridazin-6-ylamino]-methyl}-benzenesulfonamide | | 395.44 |
| 229_6 307_0 057 | 5.148 | 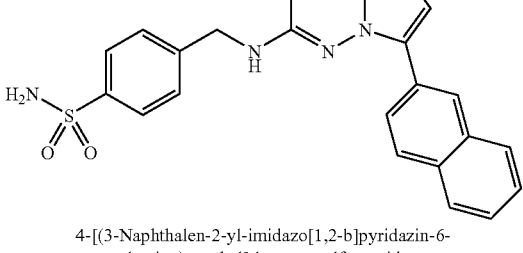 4-[(3-Naphthalen-2-yl-imidazo[1,2-b]pyridazin-6-ylamino)-methyl]-benzenesulfonamide | | 429.50 |
| 229_6 307_4 139 | 5.149 | 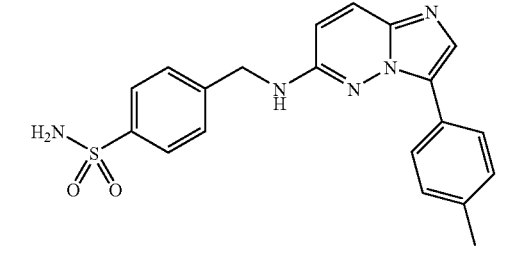 4-[(3-p-Tolyl-imidazo[1,2-b]pyridazin-6-ylamino)-methyl]-benzenesulfonamide | | 393.47 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_6 307_0 167 | 5.150 | 4-{[3-(3,4-Dimethyl-phenyl)-imidazo[1,2-b]pyridazin-6-ylamino]-methyl}-benzenesulfonamide | | 407.50 |
| 229_6 307_0 086 | 5.151 | 4-{[3-(4-Cyano-phenyl)-imidazo[1,2-b]pyridazin-6-ylamino]-methyl}-benzenesulfonamide | | 404.45 |
| 229_6 307_0 312 | 5.152 | 4-{[3-(3-Trifluoromethyl-phenyl)-imidazo[1,2-b]pyridazin-6-ylamino]-methyl}-benzenesulfonamide | | 447.44 |
| 229_6 307_0 204 | 5.153 | 4-{[3-(1H-Indol-5-yl)-imidazo[1,2-b]pyridazin-6-ylamino]-methyl}-benzenesulfonamide | | 418.48 |
| 229_6 307_0 068 | 5.154 | 4-[(3-Benzo[1,3]dioxol-5-yl-imidazo[1,2-b]pyridazin-6-ylamino)-methyl]-benzenesulfonamide | | 423.45 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_6 307_0 164 | 5.155 | 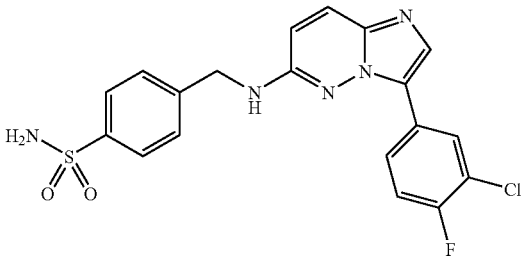<br>4-{[3-(3-Chloro-4-fluoro-phenyl)-imidazo[1,2-b]pyridazin-6-ylamino]-methyl}-benzenesulfonamide | | 431.88 |
| 229_6 307_0 168 | 5.156 | 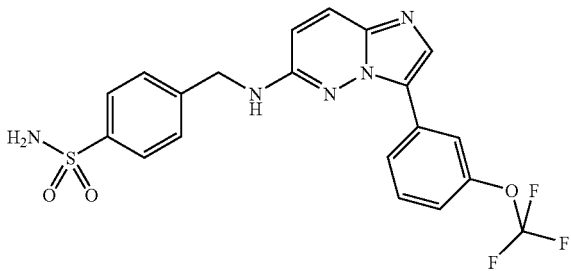<br>4-{[3-(3-Trifluoromethoxy-phenyl)-imidazo[1,2-b]pyridazin-6-ylamino]-methyl}-benzenesulfonamide | | 463.44 |
| 229_6 307_0 280 | 5.157 | 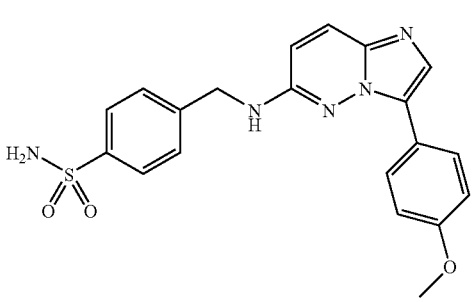<br>4-{[3-(4-Methoxy-phenyl)-imidazo[1,2-b]pyridazin-6-ylamino]-methyl}-benzenesulfonamide | | 409.47 |
| 229_6 307_0 080 | 5.158 | 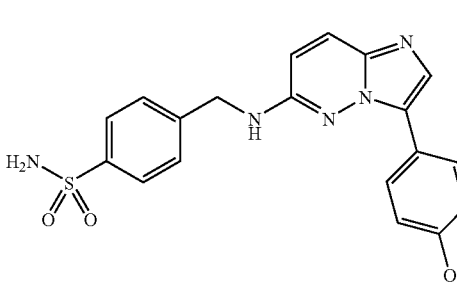<br>4-{[3-(4-Hydroxy-phenyl)-imidazo[1,2-b]pyridazin-6-ylamino]-methyl}-benzenesulfonamide | | 395.44 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_6 307_0 291 | 5.159 | 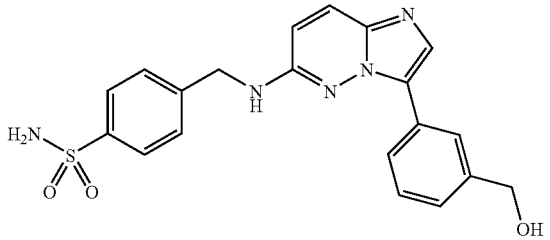  4-{[3-(3-Hydroxymethyl-phenyl)-imidazo[1,2-b]pyridazin-6-ylamino]-methyl}-benzenesulfonamide | | 409.47 |
| 229_6 307_0 145 | 5.160 | 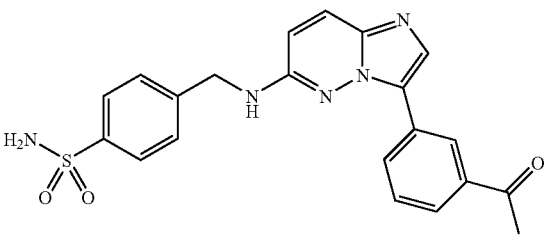  4-{[3-(3-Acetyl-phenyl)-imidazo[1,2-b]pyridazin-6-ylamino]-methyl}-benzenesulfonamide | | 421.48 |
| 229_6 307_7 468 | 5.161 | 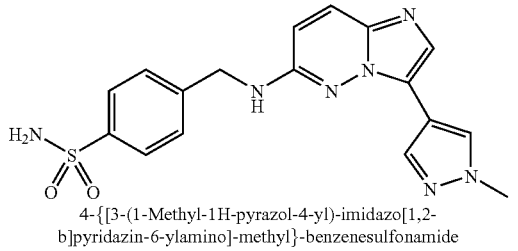  4-{[3-(1-Methyl-1H-pyrazol-4-yl)-imidazo[1,2-b]pyridazin-6-ylamino]-methyl}-benzenesulfonamide | | 383.43 |
| 229_0 227_0 087 | 5.162 | 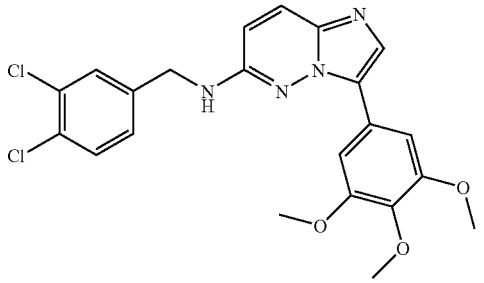  (3,4-Dichloro-benzyl)-[3-(3,4,5-trimethoxy-phenyl)-imidazo[1,2-b]pyridazin-6-yl]-amine | 1.14 | 459.33/461 |
| 229_0 227_0 080 | 5.163 | 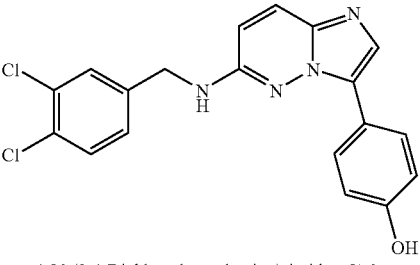  4-[6-(3,4-Dichloro-benzylamino)-imidazo[1,2-b]pyridazin-3-yl]-phenol | | 385.25 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 227_0 280 | 5.164 | 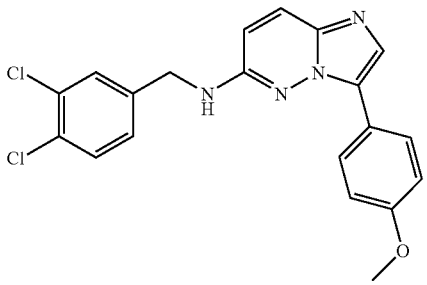<br>(3,4-Dichloro-benzyl)-[3-(4-methoxy-phenyl)-imidazo[1,2-b]pyridazin-6-yl]-amine | | 399.28 |
| 229_0 227_0 311 | 5.165 | 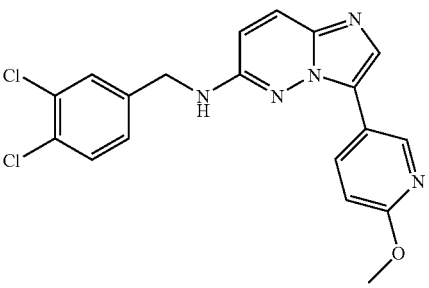<br>(3,4-Dichloro-benzyl)-[3-(6-methoxy-pyridin-3-yl)-imidazo[1,2-b]pyridazin-6-yl]-amine | | 400.27 |
| 229_0 227_0 204 | 5.166 | 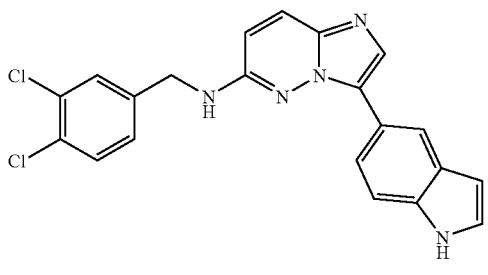<br>(3,4-Dichloro-benzyl)-[3-(1H-indol-5-yl)-imidazo[1,2-b]pyridazin-6-yl]-amine | | 408.29 |
| 229_0 227_0 140 | 5.167 | 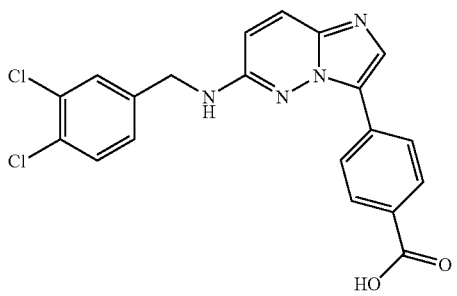<br>4-[6-(3,4-Dichloro-benzylamino)-imidazo[1,2-b]pyridazin-3-yl]-benzoic acid | | 413.26 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 236_0 069 | 5.168 | 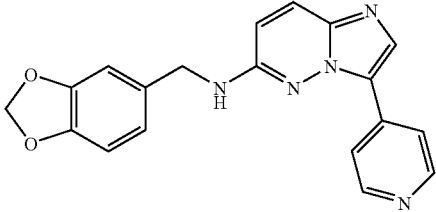 Benzo[1,3]dioxol-5-ylmethyl-(3-pyridin-4-yl-imidazo[1,2-b]pyridazin-6-yl)-amine | 0.74 | 345.36/346 |
| 229_0 236_0 314 | 5.169 | 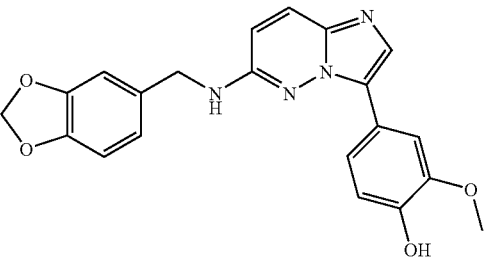 4-{6-[(Benzo[1,3]dioxol-5-ylmethyl)-amino]-imidazo[1,2-b]pyridazin-3-yl}-2-methoxy-phenol | | 390.40 |
| 229_0 236_0 280 | 5.170 | 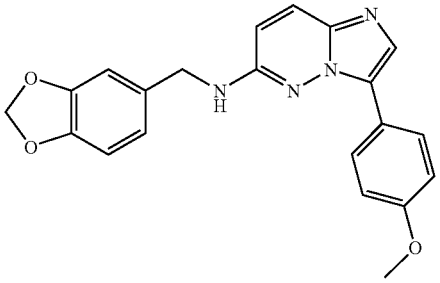 Benzo[1,3]dioxol-5-ylmethyl-[3-(4-methoxy-phenyl)-imidazo[1,2-b]pyridazin-6-yl]-amine | 0.97 | 374.40/375 |
| 229_0 236_0 311 | 5.171 | 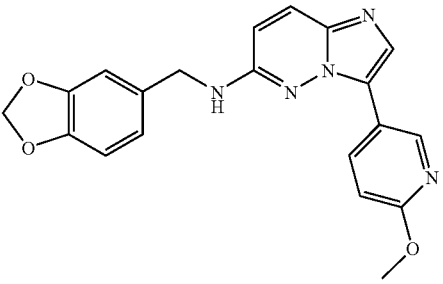 Benzo[1,3]dioxol-5-ylmethyl-[3-(6-methoxy-pyridin-3-yl)-imidazo[1,2-b]pyridazin-6-yl]-amine | 0.95 | 375.39/376 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 236_0 080 | 5.172 | 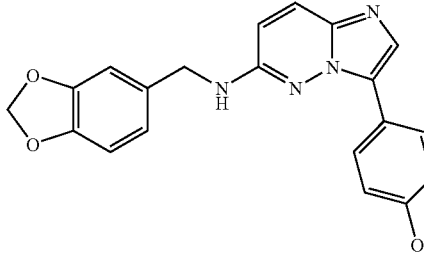<br>4-{6-[(Benzo[1,3]dioxol-5-ylmethyl)-amino]-imidazo[1,2-b]pyridazin-3-yl}-phenol | 0.83 | 360.37/361 |
| 229_0 236_0 284 | 5.173 | 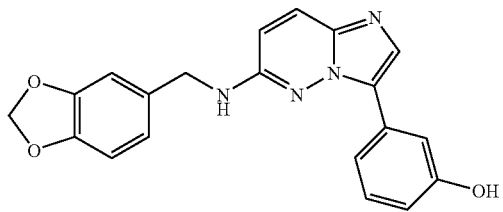<br>3-{6-[(Benzo[1,3]dioxol-5-ylmethyl)-amino]-imidazo[1,2-b]pyridazin-3-yl}-phenol | 0.87 | 360.37/361 |
| 229_0 236_7 468 | 5.174 | 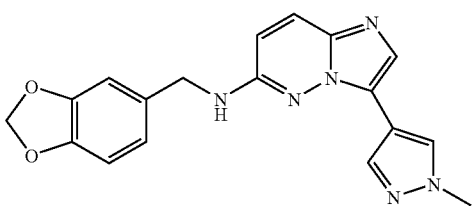<br>Benzo[1,3]dioxol-5-ylmethyl-[3-(1-methyl-1H-pyrazol-4-yl)-imidazo[1,2-b]pyridazin-6-yl]-amine | 0.79 | 348.36/349 |
| 229_0 236_0 140 | 5.175 | 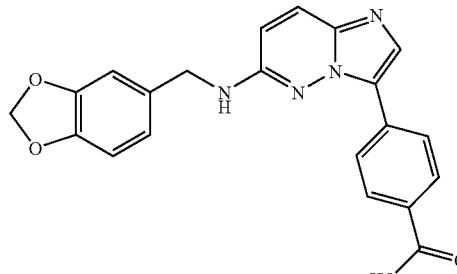<br>4-{6-[(Benzo[1,3]dioxol-5-ylmethyl)-amino]-imidazo[1,2-b]pyridazin-3-yl}-benzoic acid | | 388.38 |
| 229_0 236_6 488 | 5.176 | 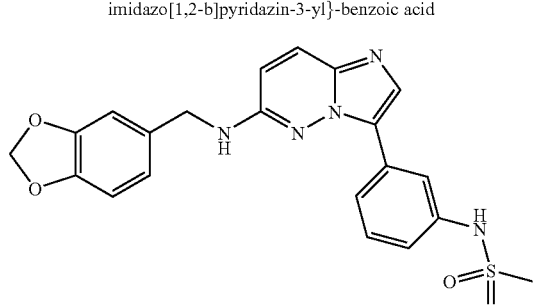<br>N-(3-{6-[(Benzo[1,3]dioxol-5-ylmethyl)-amino]-imidazo[1,2-b]pyridazin-3-yl}-phenyl)-methanesulfonamide | | 437.48 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 236_0 347 | 5.177 | 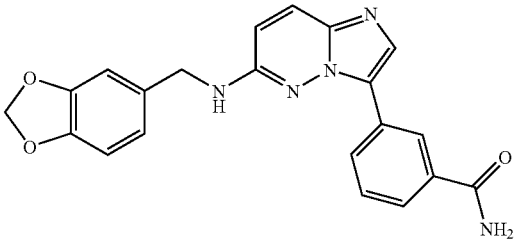<br>3-{6-[(Benzo[1,3]dioxol-5-ylmethyl)-amino]-imidazo[1,2-b]pyridazin-3-yl}-benzamide | | 387.40 |
| 229_0 033_0 087 | 5.178 | 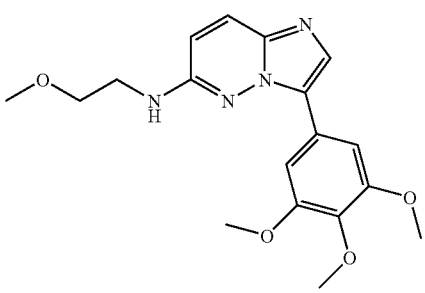<br>(2-Methoxy-ethyl)-[3-(3,4,5-trimethoxy-phenyl)-imidazo[1,2-b]pyridazin-6-yl]-amine | 0.84 | 358.40/359 |
| 229_0 033_0 284 | 5.179 | 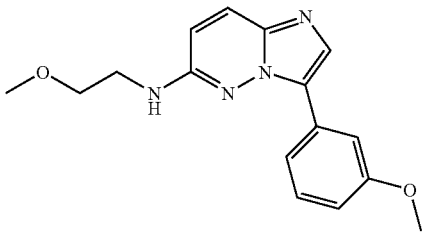<br>(2-Methoxy-ethyl)-[3-(3-methoxy-phenyl)-imidazo[1,2-b]pyridazin-6-yl]-amine | | 284.32 |
| 229_0 033_0 314 | 5.180 | 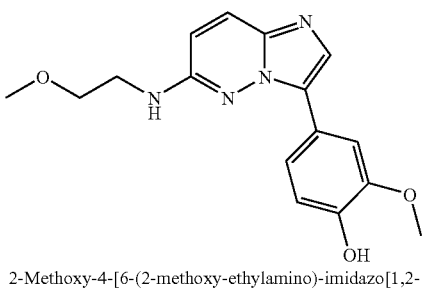<br>2-Methoxy-4-[6-(2-methoxy-ethylamino)-imidazo[1,2-b]pyridazin-3-yl]-phenol | | 314.34 |
| 229_0 033_0 196 | 5.181 | 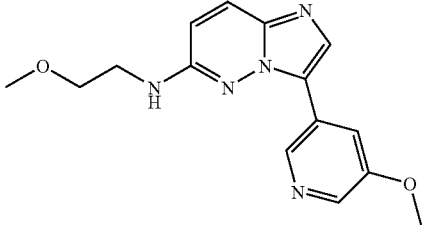<br>(2-Methoxy-ethyl)-[3-(5-methoxy-pyridin-3-yl)-imidazo[1,2-b]pyridazin-6-yl]-amine | | 299.33 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 033_0 057 | 5.182 | 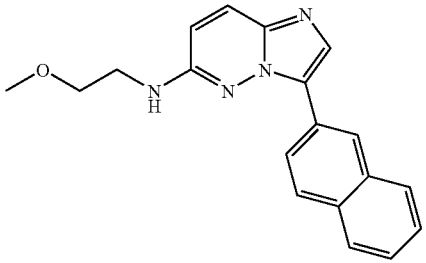<br>(2-Methoxy-ethyl)-(3-naphthalen-2-yl-imidazo[1,2-b]pyridazin-6-yl)-amine | 1.00 | 318.38/319 |
| 229_0 033_0 311 | 5.183 | 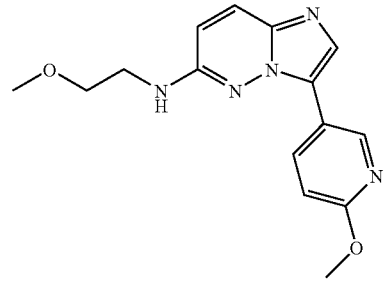<br>(2-Methoxy-ethyl)-[3-(6-methoxy-pyridin-3-yl)-imidazo[1,2-b]pyridazin-6-yl]-amine | | 299.33 |
| 229_0 033_0 076 | 5.184 | 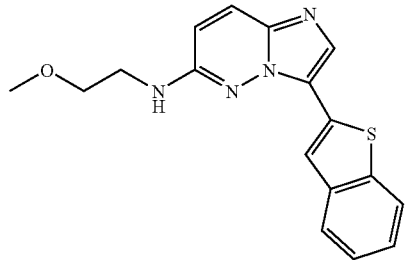<br>(3-Benzo[b]thiophen-2-yl-imidazo[1,2-b]pyridazin-6-yl)-(2-methoxy-ethyl)-amine | 1.07 | 324.41/323 (negative mode) |
| 229_0 033_0 160 | 5.185 | 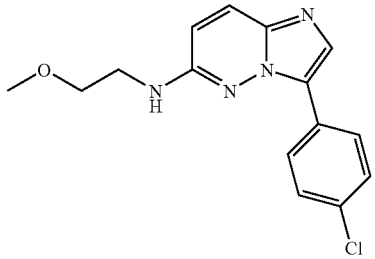<br>[3-(4-Chloro-phenyl)-imidazo[1,2-b]pyridazin-6-yl]-(2-methoxy-ethyl)-amine | | 302.76 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 033_0 280 | 5.186 | 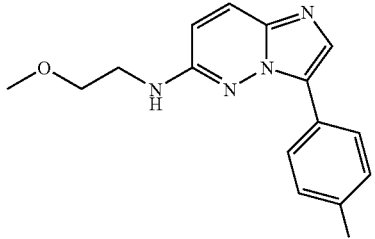<br>(2-Methoxy-ethyl)-[3-(4-methoxy-phenyl)-imidazo[1,2-b]pyridazin-6-yl]-amine | 0.84 | 298.34/299 |
| 229_0 033_0 068 | 5.187 | 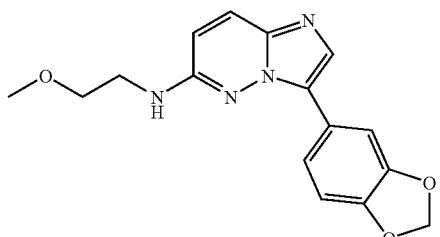<br>(3-Benzo[1,3]dioxol-5-yl-imidazo[1,2-b]pyridazin-6-yl)-(2-methoxy-ethyl)-amine | | 312.33 |
| 229_0 033_0 312 | 5.188 | 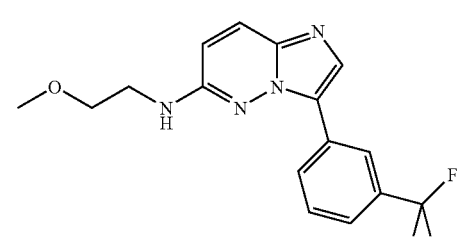<br>(2-Methoxy-ethyl)-[3-(3-trifluoromethyl-phenyl)-imidazo[1,2-b]pyridazin-6-yl]-amine | 1.02 | 336.32/337 |
| 229_0 033_0 081 | 5.189 | 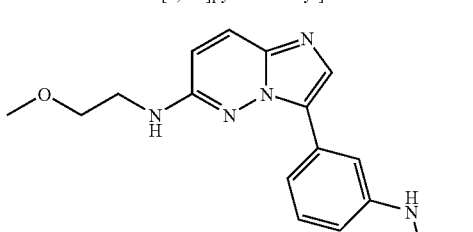<br>N-{3-[6-(2-Methoxy-ethylamino)-imidazo[1,2-b]pyridazin-3-yl]-phenyl}-acetamide | 0.71 | 325.37/326 |
| 229_0 033_0 168 | 5.190 | 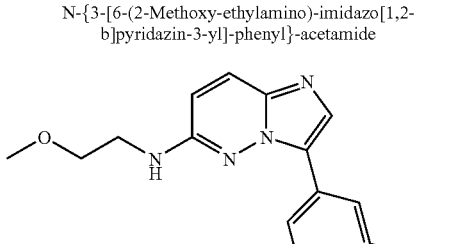<br>(2-Methoxy-ethyl)-[3-(3-trifluoromethoxy-phenyl)-imidazo[1,2-b]pyridazin-6-yl]-amine | 1.05 | 352.32/353 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 033_0 204 | 5.191 | 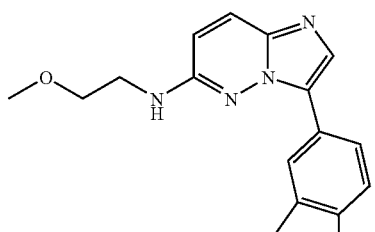<br>[3-(1H-Indol-5-yl)-imidazo[1,2-b]pyridazin-6-yl]-(2-methoxy-ethyl)-amine | 0.78 | 307.36/308 |
| 229_0 033_0 279 | 5.192 | 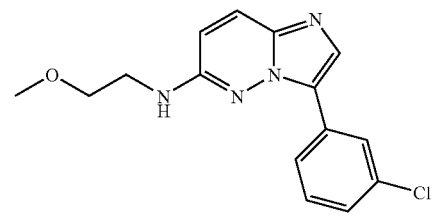<br>[3-(3-Chloro-phenyl)-imidazo[1,2-b]pyridazin-6-yl]-(2-methoxy-ethyl)-amine | | 302.76 |
| 229_0 033_0 345 | 5.193 | 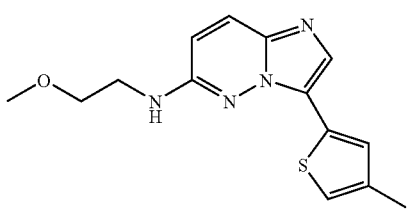<br>(2-Methoxy-ethyl)-[3-(4-methyl-thiophen-2-yl)-imidazo[1,2-b]pyridazin-6-yl]-amine | 0.92 | 288.37/289 |
| 229_0 033_0 080 | 5.194 | 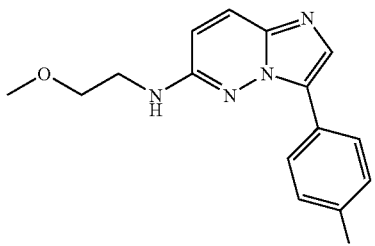<br>4-[6-(2-Methoxy-ethylamino)-imidazo[1,2-b]pyridazin-3-yl]-phenol | 0.68 | 284.32/285 |
| 229_0 033_0 285 | 5.195 | 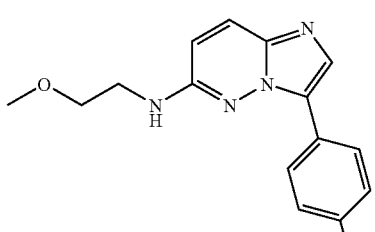<br>{4-[6-(2-Methoxy-ethylamino)-imidazo[1,2-b]pyridazin-3-yl]-phenyl}-methanol | 0.67 | 298.34/299 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0033_4140 | 5.196 | 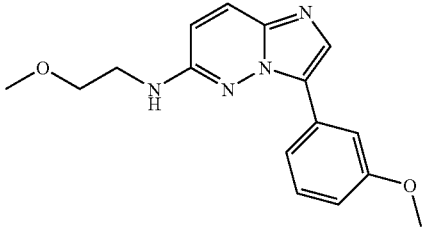<br>(2-Methoxy-ethyl)-[3-(3-methoxy-phenyl)-imidazo[1,2-b]pyridazin-6-yl]-amine | 0.86 | 298.34/299 |
| 229_0033_0277 | 5.197 | 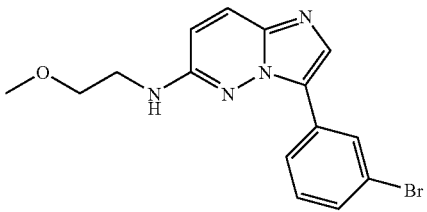<br>[3-(3-Bromo-phenyl)-imidazo[1,2-b]pyridazin-6-yl]-(2-methoxy-ethyl)-amine | | 347.22 |
| 229_0033_0140 | 5.198 | 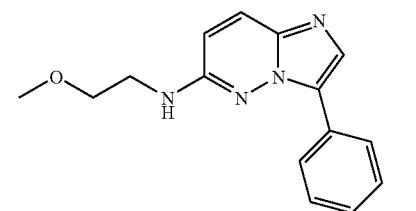<br>4-[6-(2-Methoxy-ethylamino)-imidazo[1,2-b]pyridazin-3-yl]-benzoic acid | | 312.33 |
| 229_0033_0347 | 5.199 | 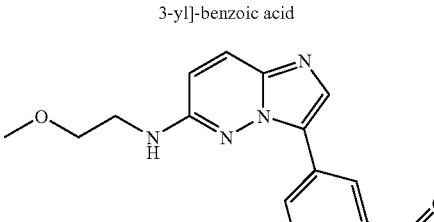<br>3-[6-(2-Methoxy-ethylamino)-imidazo[1,2-b]pyridazin-3-yl]-benzamide | | 311.34 |
| 229_0033_6488 | 5.200 | 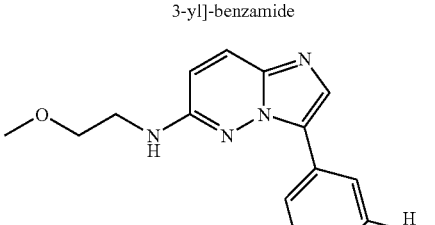<br>N-{3-[6-(2-Methoxy-ethylamino)-imidazo[1,2-b]pyridazin-3-yl]-phenyl}-methanesulfonamide | | 361.42 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 033_7 469 | 5.201 | 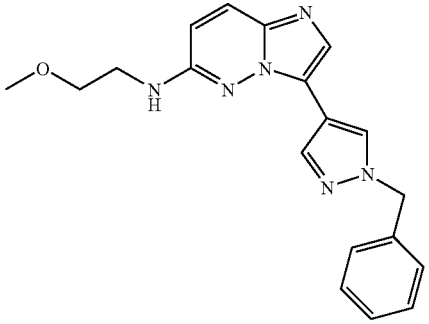 [3-(1-Benzyl-1H-pyrazol-4-yl)-imidazo[1,2-b]pyridazin-6-yl]-(2-methoxy-ethyl)-amine | | 348.41 |
| 229_0 033_0 079 | 5.202 | 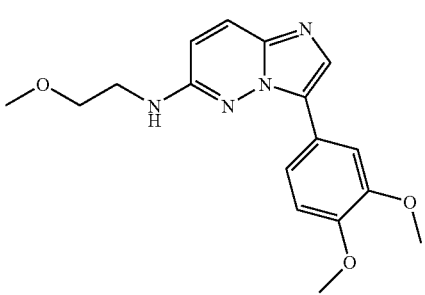 [3-(3,4-Dimethoxy-phenyl)-imidazo[1,2-b]pyridazin-6-yl]-(2-methoxy-ethyl)-amine | | 328.37 |
| 229_0 033_4 145 | 5.203 | 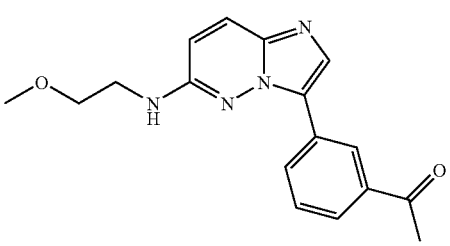 1-{3-[6-(2-Methoxy-ethylamino)-imidazo[1,2-b]pyridazin-3-yl]-phenyl}-ethanone | | 310.36 |
| 229_0 248_0 087 | 5.204 | 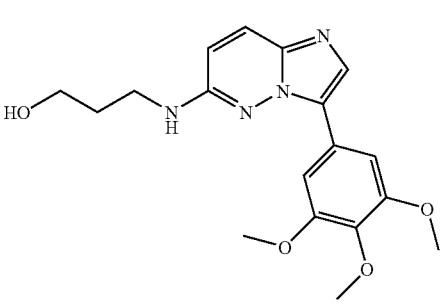 3-[3-(3,4,5-Trimethoxy-phenyl)-imidazo[1,2-b]pyridazin-6-ylamino]-propan-1-ol | 0.76 | 358.40/359 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 248_0 314 | 5.205 | 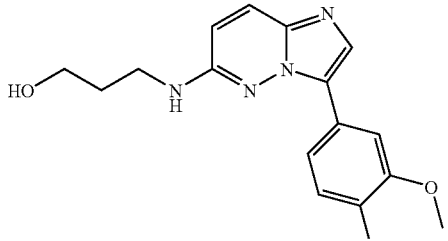　4-[6-(3-Hydroxy-propylamino)-imidazo[1,2-b]pyridazin-3-yl]-2-methoxy-phenol | | 314.34 |
| 229_0 248_0 277 | 5.206 | 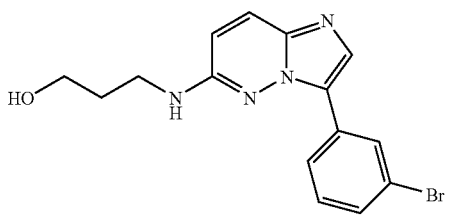　3-[3-(3-Bromo-phenyl)-imidazo[1,2-b]pyridazin-6-ylamino]-propan-1-ol | | 347.22 |
| 229_0 248_0 079 | 5.207 | 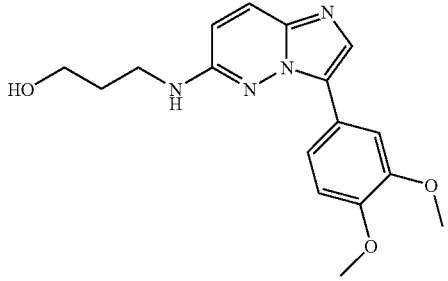　3-[3-(3,4-Dimethoxy-phenyl)-imidazo[1,2-b]pyridazin-6-ylamino]-propan-1-ol | 0.73 | 328.37/329 |
| 229_0 248_0 312 | 5.208 | 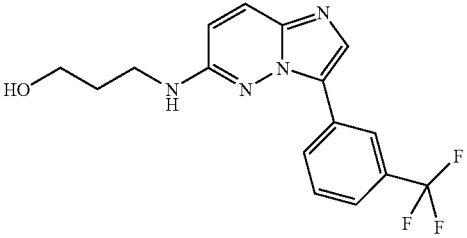　3-[3-(3-Trifluoromethyl-phenyl)-imidazo[1,2-b]pyridazin-6-ylamino]-propan-1-ol | | 336.32 |
| 229_0 248_7 468 | 5.209 | 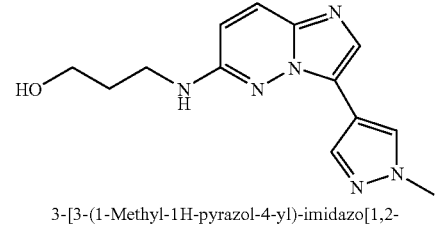　3-[3-(1-Methyl-1H-pyrazol-4-yl)-imidazo[1,2-b]pyridazin-6-ylamino]-propan-1-ol | | 272.31 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 248_0 168 | 5.210 | 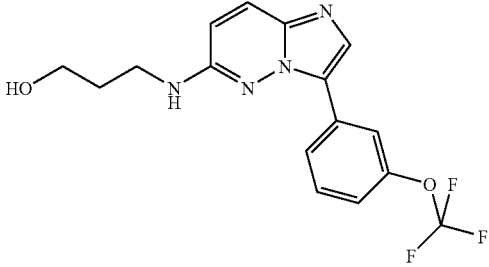<br>3-[3-(3-Trifluoromethoxy-phenyl)-imidazo[1,2-b]pyridazin-6-ylamino]-propan-1-ol | | 352.32 |
| 229_0 248_0 345 | 5.211 | 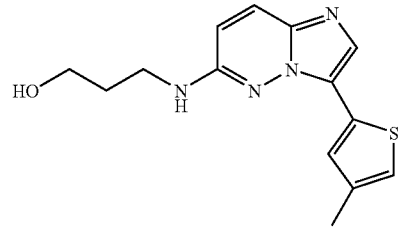<br>3-[3-(4-Methyl-thiophen-2-yl)-imidazo[1,2-b]pyridazin-6-ylamino]-propan-1-ol | | 288.37 |
| 229_0 248_0 057 | 5.212 | 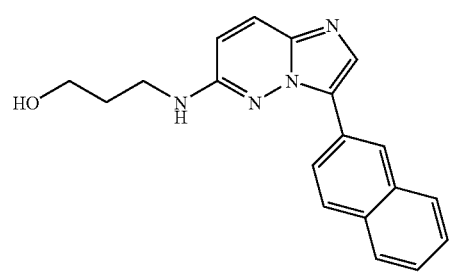<br>3-(3-Naphthalen-2-yl-imidazo[1,2-b]pyridazin-6-ylamino)-propan-1-ol | 0.90 | 318.38/319 |
| 229_0 248_4 139 | 5.213 | 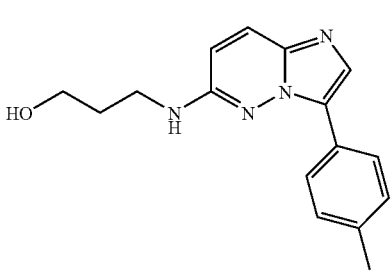<br>3-(3-p-Tolyl-imidazo[1,2-b]pyridazin-6-ylamino)-propan-1-ol | 0.79 | 282.35/283 |
| 229_0 248_0 074 | 5.214 | 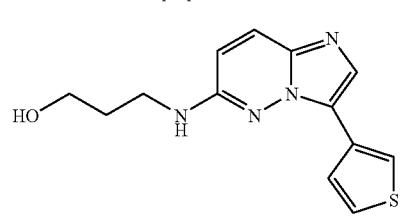<br>3-(3-Thiophen-3-yl-imidazo[1,2-b]pyridazin-6-ylamino)-propan-1-ol | 0.72 | 274.35/275 |

TABLE 5-continued
| Char No. | Example No. | Structure and Name of the main isomer | Retention time (HPLC, UV 254 nm) [min]. | Mol. weight/ MS (HPLC-MS) |
|---|---|---|---|---|
| 229_0 248_0 076 | 5.215 | 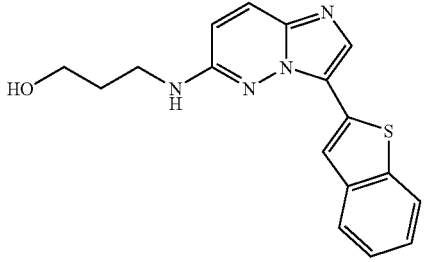<br>3-(3-Benzo[b]thiophen-2-yl-imidazo[1,2-b]pyridazin-6-ylamino)-propan-1-ol | 0.94 | 324.41/325 |
| 229_0 248_0 311 | 5.216 | 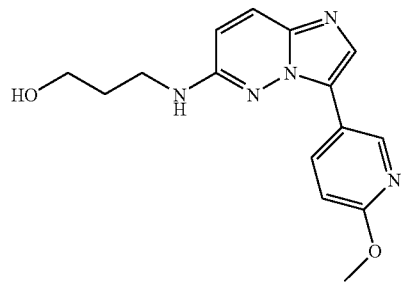<br>3-[3-(6-Methoxy-pyridin-3-yl)-imidazo[1,2-b]pyridazin-6-ylamino]-propan-1-ol | 0.69 | 299.33/300 |
| 229_0 248_0 204 | 5.217 | 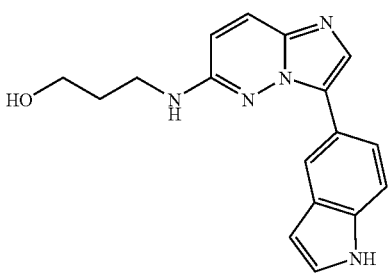<br>3-[3-(1H-Indol-5-yl)-imidazo[1,2-b]pyridazin-6-ylamino]-propan-1-ol | 0.71 | 307.36/308 |
| 229_0 248_0 280 | 5.218 | 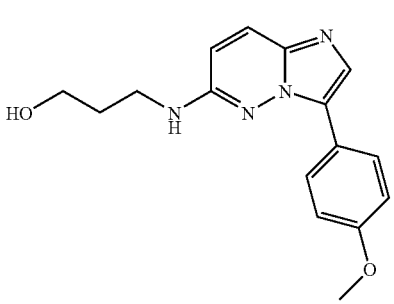<br>3-[3-(4-Methoxy-phenyl)-imidazo[1,2-b]pyridazin-6-ylamino]-propan-1-ol | 0.75 | 298.34/299 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 248_0 164 | 5.219 | 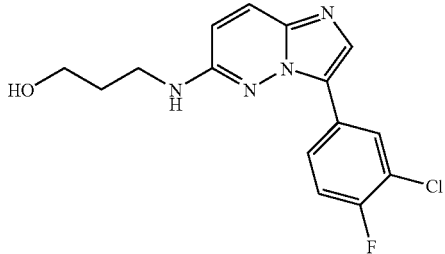<br>3-[3-(3-Chloro-4-fluoro-phenyl)-imidazo[1,2-b]pyridazin-6-ylamino]-propan-1-ol | | 320.75 |
| 229_0 248_0 279 | 5.220 | 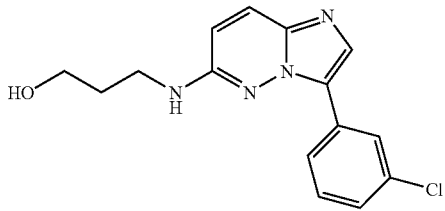<br>3-[3-(3-Chloro-phenyl)-imidazo[1,2-b]pyridazin-6-ylamino]-propan-1-ol | | 302.76 |
| 229_0 248_6 488 | 5.221 | 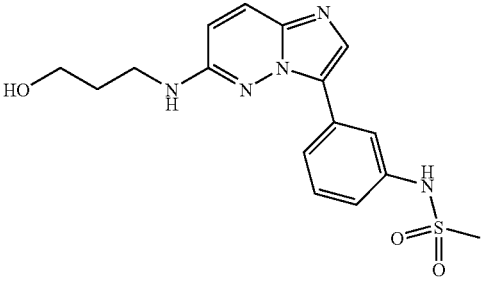<br>N-{3-[6-(3-Hydroxy-propylamino)-imidazo[1,2-b]pyridazin-3-yl]-phenyl}-methanesulfonamide | | 361.42 |
| 229_0 248_7 469 | 5.222 | 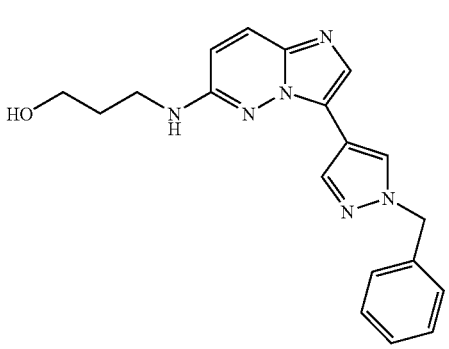<br>3-[3-(1-Benzyl-1H-pyrazol-4-yl)-imidazo[1,2-b]pyridazin-6-ylamino]-propan-1-ol | | 348.41 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 248_0 135 | 5.223 | 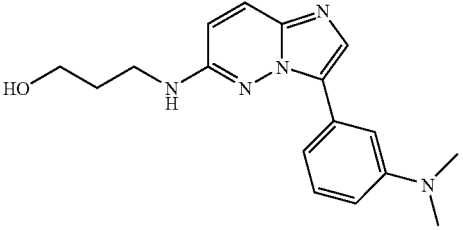<br>3-[3-(3-Dimethylamino-phenyl)-imidazo[1,2-b]pyridazin-6-ylamino]-propan-1-ol | | 311.39 |
| 229_0 248_0 062 | 5.224 | 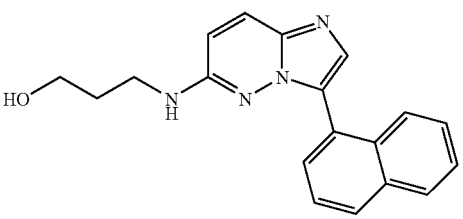<br>3-(3-Naphthalen-1-yl-imidazo[1,2-b]pyridazin-6-ylamino)-propan-1-ol | | 318.38 |
| 229_0 226_0 087 | 5.225 | 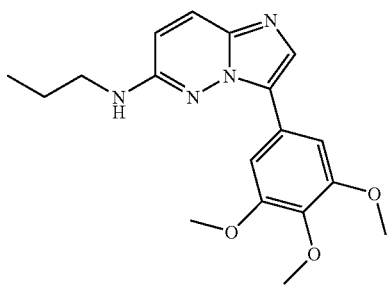<br>Propyl-[3-(3,4,5-trimethoxy-phenyl)-imidazo[1,2-b]pyridazin-6-yl]-amine | 0.94 | 342.40/343 |
| 229_0 226_0 314 | 5.226 | 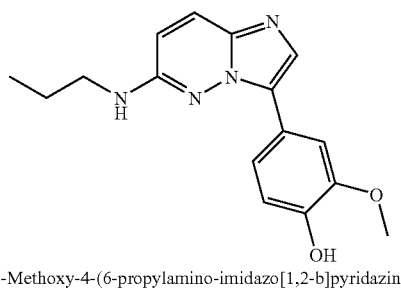<br>2-Methoxy-4-(6-propylamino-imidazo[1,2-b]pyridazin-3-yl)-phenol | 0.81 | 298.34/299 |
| 229_0 226_0 079 | 5.227 | 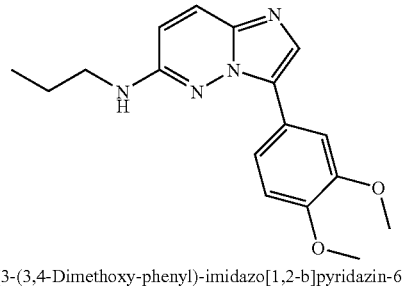<br>[3-(3,4-Dimethoxy-phenyl)-imidazo[1,2-b]pyridazin-6-yl]-propyl-amine | 0.91 | 312.37/313 |

TABLE 5-continued
| Char No. | Example No. | Structure and Name of the main isomer | Retention time (HPLC, UV 254 nm) [min]. | Mol. weight/ MS (HPLC-MS) |
|---|---|---|---|---|
| 229_0 226_0 204 | 5.228 | 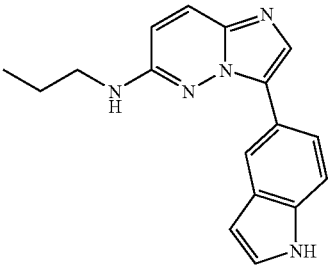 [3-(1H-Indol-5-yl)-imidazo[1,2-b]pyridazin-6-yl]-propyl-amine | | 291.36 |
| 229_0 226_4 140 | 5.229 | 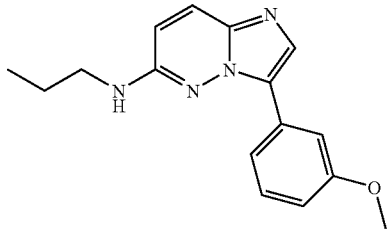 [3-(3-Methoxy-phenyl)-imidazo[1,2-b]pyridazin-6-yl]-propyl-amine | | 282.35 |
| 229_0 226_0 081 | 5.230 | 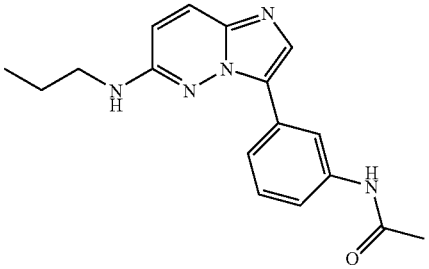 N-[3-(6-Propylamino-imidazo[1,2-b]pyridazin-3-yl)-phenyl]-acetamide | 0.80 | 309.37/310 |
| 229_0 226_0 168 | 5.231 | 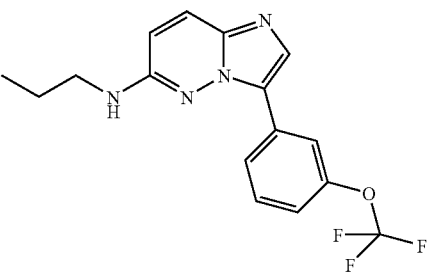 Propyl-[3-(3-trifluoromethoxy-phenyl)-imidazo[1,2-b]pyridazin-6-yl]-amine | 1.18 | 336.32/337 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 226_0 280 | 5.232 | [3-(4-Methoxy-phenyl)-imidazo[1,2-b]pyridazin-6-yl]-propyl-amine | 0.96 | 282.35/283 |
| 229_0 226_0 074 | 5.233 | Propyl-(3-thiophen-3-yl-imidazo[1,2-b]pyridazin-6-yl)-amine | 0.95 | 258.35/259 |
| 229_0 226_0 345 | 5.234 | [3-(4-Methyl-thiophen-2-yl)-imidazo[1,2-b]pyridazin-6-yl]-propyl-amine | 1.06 | 272.37/273 |
| 229_0 226_0 071 | 5.235 | Propyl-(3-pyridin-3-yl-imidazo[1,2-b]pyridazin-6-yl)-amine | 0.73 | 253.31/254 |
| 229_0 226_0 311 | 5.236 | [3-(6-Methoxy-pyridin-3-yl)-imidazo[1,2-b]pyridazin-6-yl]-propyl-amine | 0.91 | 283.33/284 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 226_0 080 | 5.237 | 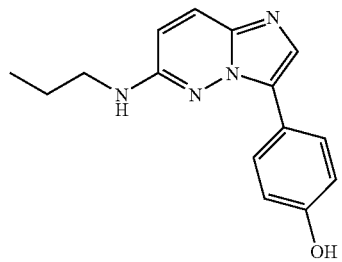<br>4-(6-Propylamino-imidazo[1,2-b]pyridazin-3-yl)-phenol | 0.78 | 268.32/269 |
| 229_0 226_0 068 | 5.238 | 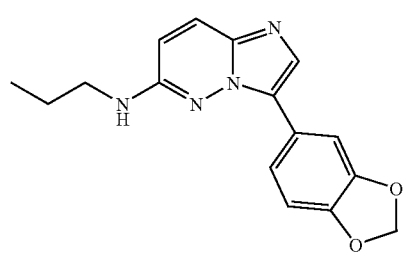<br>(3-Benzo[1,3]dioxol-5-yl-imidazo[1,2-b]pyridazin-6-yl)-propyl-amine | 0.94 | 296.33/297 |
| 229_0 226_0 291 | 5.239 | 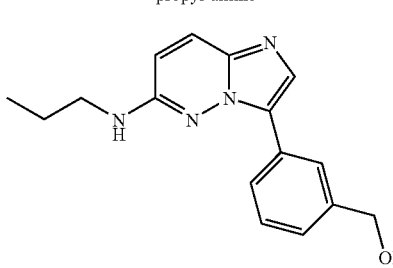<br>[3-(6-Propylamino-imidazo[1,2-b]pyridazin-3-yl)-phenyl]-methanol | 0.81 | 282.35/283 |
| 229_0 226_0 140 | 5.240 | 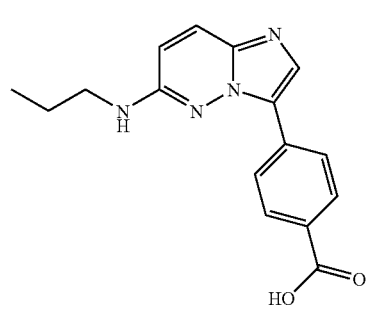<br>4-(6-Propylamino-imidazo[1,2-b]pyridazin-3-yl)-benzoic acid | | 296.33 |
| 229_0 226_0 347 | 5.241 | 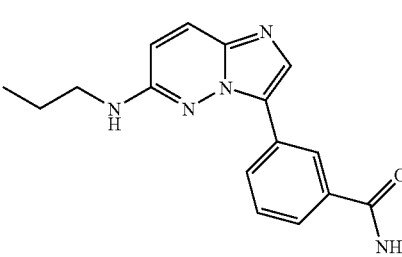<br>3-(6-Propylamino-imidazo[1,2-b]pyridazin-3-yl)-benzamide | | 295.34 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 226_0 135 | 5.242 | 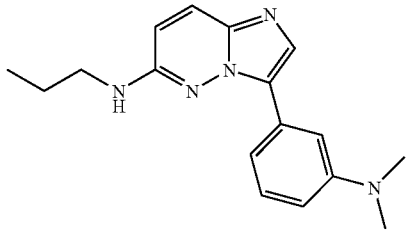<br>[3-(3-Dimethylamino-phenyl)-imidazo[1,2-b]pyridazin-6-yl]-propyl-amine | | 295.39 |
| 229_0 226_0 284 | 5.243 | 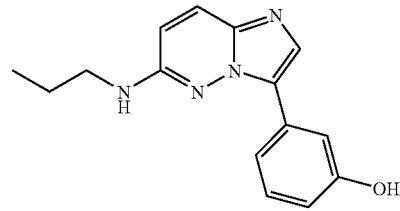<br>3-(6-Propylamino-imidazo[1,2-b]pyridazin-3-yl)-phenol | | 268.32 |
| 229_0 226_0 005 | 5.244 | 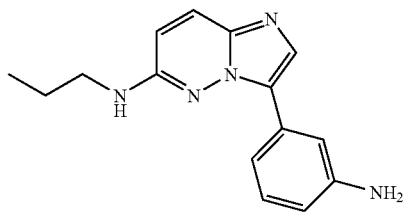<br>[3-(3-Amino-phenyl)-imidazo[1,2-b]pyridazin-6-yl]-propyl-amine | | 267.33 |
| 229_0 226_0 333 | 5.245 | 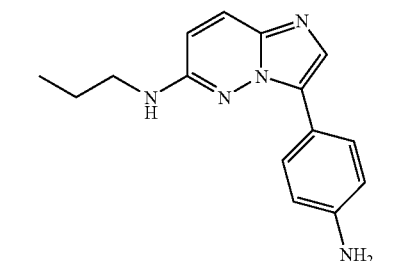<br>[3-(4-Amino-phenyl)-imidazo[1,2-b]pyridazin-6-yl]-propyl-amine | | 267.33 |
| 229_0 226_0 004 | 5.246 | 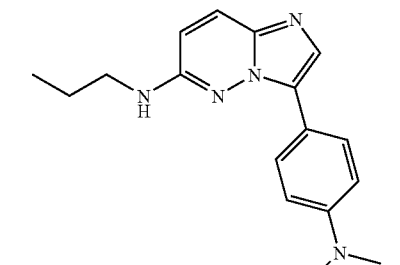<br>[3-(4-Dimethylamino-phenyl)-imidazo[1,2-b]pyridazin-6-yl]-propyl-amine | | 295.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 226_0 285 | 5.247 | 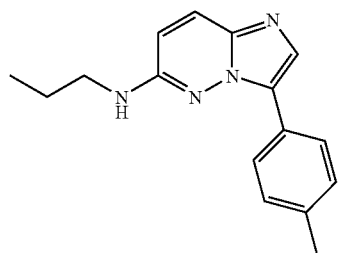<br>[4-(6-Propylamino-imidazo[1,2-b]pyridazin-3-yl)-phenyl]-methanol | | 282.35 |
| 229_0 226_0 196 | 5.248 | 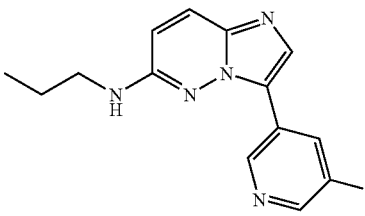<br>[3-(5-Methoxy-pyridin-3-yl)-imidazo[1,2-b]pyridazin-6-yl]-propyl-amine | | 283.33 |
| 229_4 016_4 139 | 5.249 | 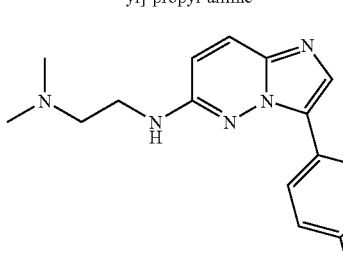<br>N,N-Dimethyl-N'-(3-p-tolyl-imidazo[1,2-b]pyridazin-6-yl)-ethane-1,2-diamine | | 295.39 |
| 229_4 016_0 073 | 5.250 | 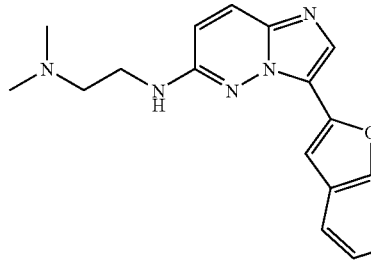<br>N'-(3-Benzofuran-2-yl-imidazo[1,2-b]pyridazin-6-yl)-N,N-dimethyl-ethane-1,2-diamine | 0.78 | 321.38/322 |
| 229_4 016_0 074 | 5.251 | 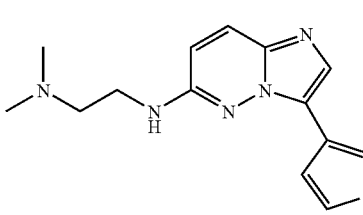<br>N,N-Dimethyl-N'-(3-thiophen-3-yl-imidazo[1,2-b]pyridazin-6-yl)-ethane-1,2-diamine | | 287.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4 016_0 057 | 5.252 | 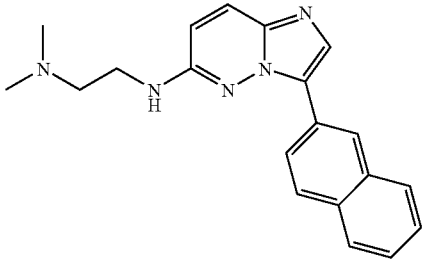<br>N,N-Dimethyl-N'-(3-naphthalen-2-yl-imidazo[1,2-b]pyridazin-6-yl)-ethane-1,2-diamine | | 331.42 |
| 229_4 016_0 076 | 5.253 | 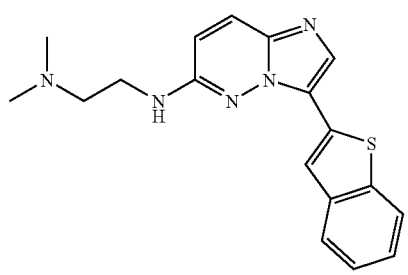<br>N'-(3-Benzo[b]thiophen-2-yl-imidazo[1,2-b]pyridazin-6-yl)-N,N-dimethyl-ethane-1,2-diamine | | 337.45 |
| 229_4 016_0 079 | 5.254 | 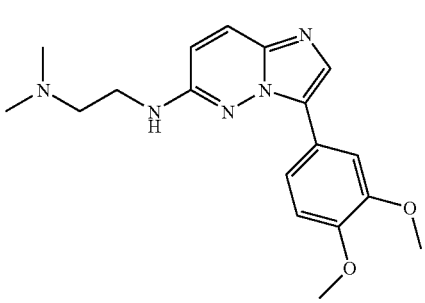<br>N'-[3-(3,4-Dimethoxy-phenyl)-imidazo[1,2-b]pyridazin-6-yl]-N,N-dimethyl-ethane-1,2-diamine | | 341.41 |
| 229_4 016_0 339 | 5.255 | 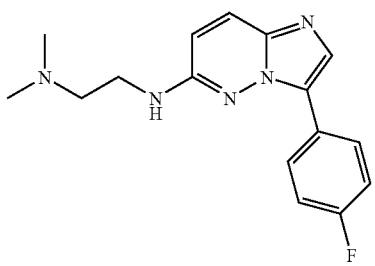<br>N'-[3-(4-Fluoro-phenyl)-imidazo[1,2-b]pyridazin-6-yl]-N,N-dimethyl-ethane-1,2-diamine | | 299.35 |
| 229_4 016_0 279 | 5.256 | <br>N'-[3-(3-Chloro-phenyl)-imidazo[1,2-b]pyridazin-6-yl]-N,N-dimethyl-ethane-1,2-diamine | | 315.81 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 254_0 087 | 5.257 | 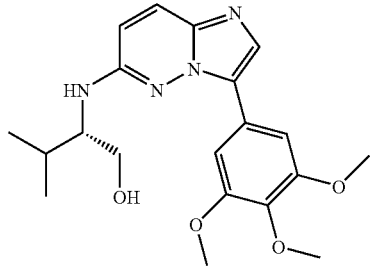<br>(S)-3-Methyl-2-[3-(3,4,5-trimethoxy-phenyl)-imidazo[1,2-b]pyridazin-6-ylamino]-butan-1-ol | | 386.45 |
| 229_0 254_0 314 | 5.258 | 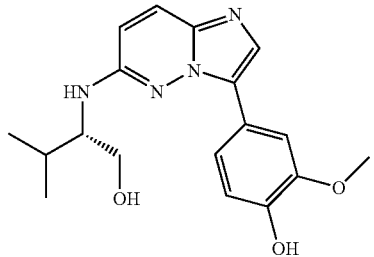<br>4-[6-((S)-1-Hydroxymethyl-2-methyl-propylamino)-imidazo[1,2-b]pyridazin-3-yl]-2-methoxy-phenol | | 342.40 |
| 229_0 254_0 079 | 5.259 | 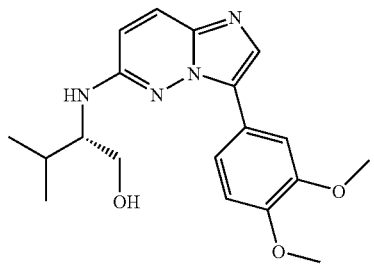<br>(S)-2-[3-(3,4-Dimethoxy-phenyl)-imidazo[1,2-b]pyridazin-6-ylamino]-3-methyl-butan-1-ol | | 356.42 |
| 229_0 254_0 284 | 5.260 | 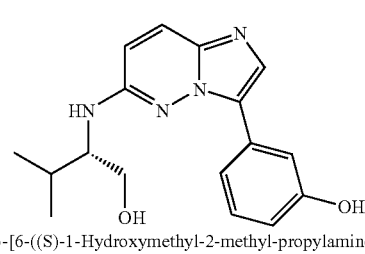<br>3-[6-((S)-1-Hydroxymethyl-2-methyl-propylamino)-imidazo[1,2-b]pyridazin-3-yl]-phenol | | 312.37 |
| 229_0 254_0 080 | 5.261 | 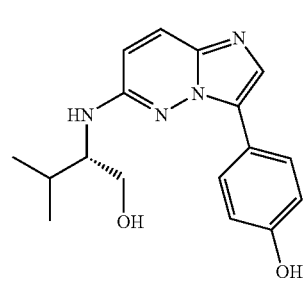<br>4-[6-((S)-1-Hydroxymethyl-2-methyl-propylamino)-imidazo[1,2-b]pyridazin-3-yl]-phenol | | 312.37 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 254_0 285 | 5.262 | 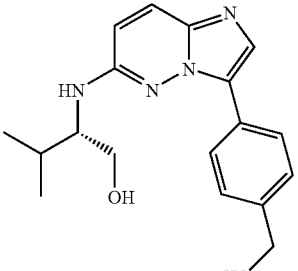<br>(S)-2-[3-(4-Hydroxymethyl-phenyl)-imidazo[1,2-b]pyridazin-6-ylamino]-3-methyl-butan-1-ol | | 326.40 |
| 229_0 254_0 135 | 5.263 | 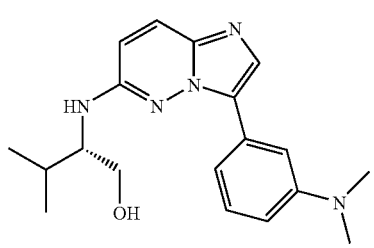<br>(S)-2-[3-(3-Dimethylamino-phenyl)-imidazo[1,2-b]pyridazin-6-ylamino]-3-methyl-butan-1-ol | | 339.44 |
| 229_0 254_0 057 | 5.264 | 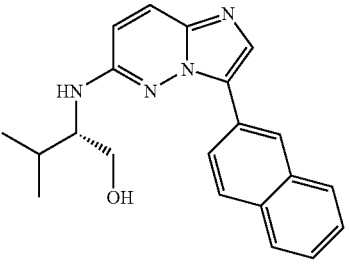<br>(S)-3-Methyl-2-(3-naphthalen-2-yl-imidazo[1,2-b]pyridazin-6-ylamino)-butan-1-ol | | 346.43 |
| 229_0 254_0 312 | 5.265 | 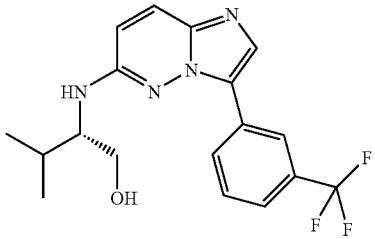<br>(S)-3-Methyl-2-[3-(3-trifluoromethyl-phenyl)-imidazo[1,2-b]pyridazin-6-ylamino]-butan-1-ol | | 364.37 |
| 229_0 254_0 068 | 5.266 | 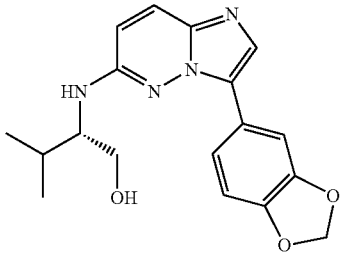<br>(S)-2-(3-Benzo[1,3]dioxol-5-yl-imidazo[1,2-b]pyridazin-6-ylamino)-3-methyl-butan-1-ol | | 364.37 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 254_0 345 | 5.267 | 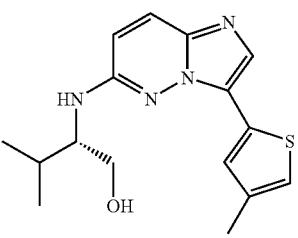<br>(S)-3-Methyl-2-[3-(4-methyl-thiophen-2-yl)-imidazo[1,2-b]pyridazin-6-ylamino]-butan-1-ol | | 316.43 |
| 229_0 254_0 074 | 5.268 | 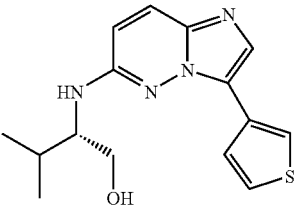<br>(S)-3-Methyl-2-(3-thiophen-3-yl-imidazo[1,2-b]pyridazin-6-ylamino)-butan-1-ol | | 302.40 |
| 229_0 254_0 168 | 5.269 | 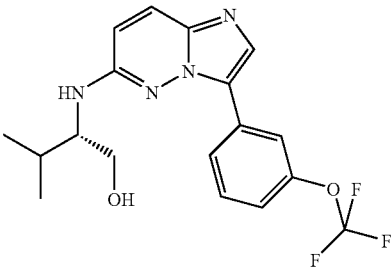<br>(S)-3-Methyl-2-[3-(3-trifluoromethoxy-phenyl)-imidazo[1,2-b]pyridazin-6-ylamino]-butan-1-ol | | 380.37 |
| 229_0 254_0 279 | 5.270 | 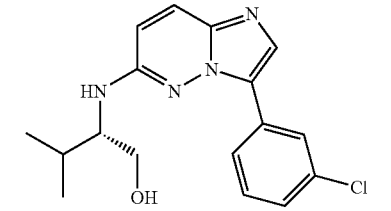<br>(S)-2-[3-(3-Chloro-phenyl)-imidazo[1,2-b]pyridazin-6-ylamino]-3-methyl-butan-1-ol | | 330.82 |
| 229_0 254_0 339 | 5.271 | 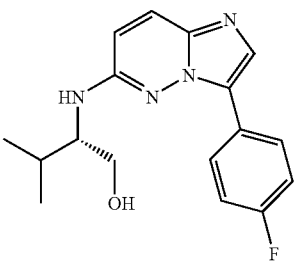<br>(S)-2-[3-(4-Fluoro-phenyl)-imidazo[1,2-b]pyridazin-6-ylamino]-3-methyl-butan-1-ol | | 314.36 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 254_0 204 | 5.272 | 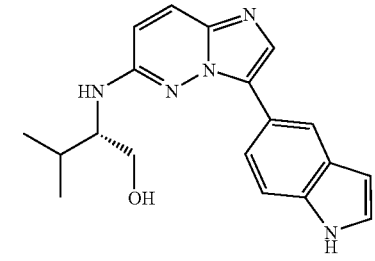<br>(S)-2-[3-(1H-Indol-5-yl)-imidazo[1,2-b]pyridazin-6-ylamino]-3-methyl-butan-1-ol | | 335.41 |
| 229_0 254_0 347 | 5.273 | 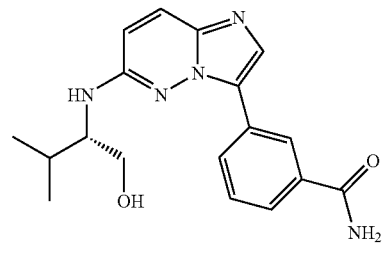<br>3-[6-((S)-1-Hydroxymethyl-2-methyl-propylamino)-imidazo[1,2-b]pyridazin-3-yl]-benzamide | | 339.40 |
| 229_0 254_4 145 | 5.274 | 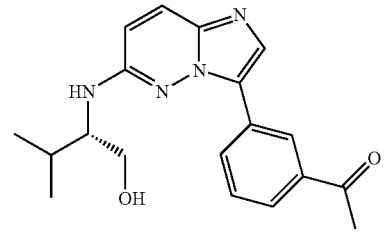<br>1-{3-[6-((S)-1-Hydroxymethyl-2-methyl-propylamino)-imidazo[1,2-b]pyridazin-3-yl]-phenyl}-ethanone | | 338.41 |
| 229_0 254_0 196 | 5.275 | 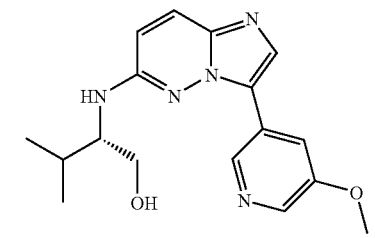<br>(S)-2-[3-(5-Methoxy-pyridin-3-yl)-imidazo[1,2-b]pyridazin-6-ylamino]-3-methyl-butan-1-ol | | 327.39 |
| 229_0 153_0 087 | 5.276 | 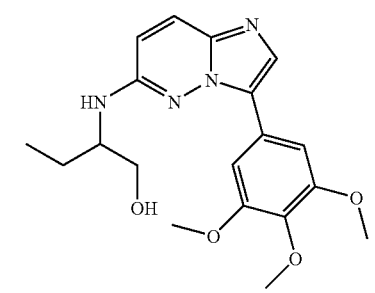<br>2-[3-(3,4,5-Trimethoxy-phenyl)-imidazo[1,2-b]pyridazin-6-ylamino]-butan-1-ol | | 372.42 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 153_0 164 | 5.277 | 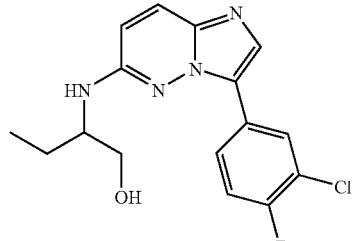<br>2-[3-(3-Chloro-4-fluoro-phenyl)-imidazo[1,2-b]pyridazin-6-ylamino]-butan-1-ol | | 334.78 |
| 229_0 153_0 057 | 5.278 | 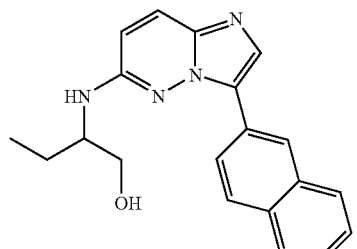<br>2-(3-Naphthalen-2-yl-imidazo[1,2-b]pyridazin-6-ylamino)-butan-1-ol | 0.99 | 332.41/333 |
| 229_0 153_0 168 | 5.279 | 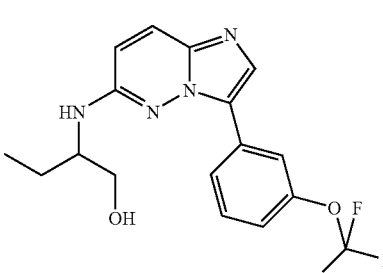<br>2-[3-(3-Trifluoromethoxy-phenyl)-imidazo[1,2-b]pyridazin-6-ylamino]-butan-1-ol | 1.02 | 366.34/367 |
| 229_0 153_0 074 | 5.280 | 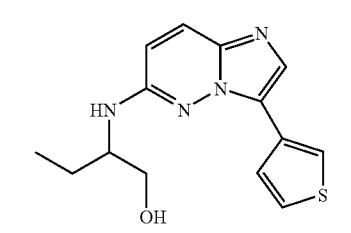<br>2-(3-Thiophen-3-yl-imidazo[1,2-b]pyridazin-6-ylamino)-butan-1-ol | 0.82 | 288.37/289 |
| 229_0 153_0 280 | 5.281 | 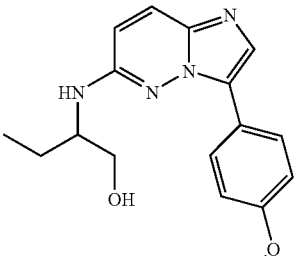<br>2-[3-(4-Methoxy-phenyl)-imidazo[1,2-b]pyridazin-6-ylamino]-butan-1-ol | 0.86 | 312.37/313 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 153_0 345 | 5.282 | 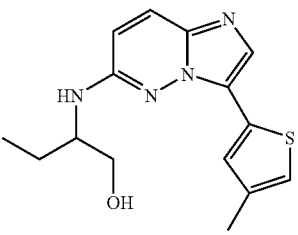<br>2-[3-(4-Methyl-thiophen-2-yl)-imidazo[1,2-b]pyridazin-6-ylamino]-butan-1-ol | 0.90 | 302.40/303 |
| 229_0 153_0 279 | 5.283 | 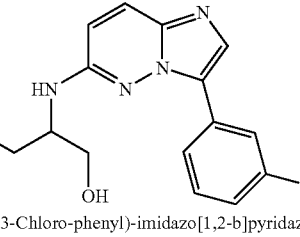<br>2-[3-(3-Chloro-phenyl)-imidazo[1,2-b]pyridazin-6-ylamino]-butan-1-ol | | 316.79 |
| 229_0 153_0 311 | 5.284 | 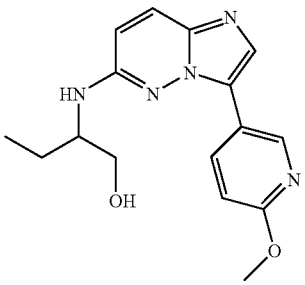<br>2-[3-(6-Methoxy-pyridin-3-yl)-imidazo[1,2-b]pyridazin-6-ylamino]-butan-1-ol | 0.79 | 313.36/314 |
| 229_0 153_7 468 | 5.285 | 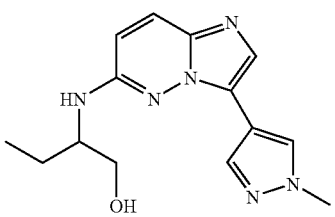<br>2-[3-(1-Methyl-1H-pyrazol-4-yl)-imidazo[1,2-b]pyridazin-6-ylamino]-butan-1-ol | 0.67 | 286.34/287 |
| 229_0 153_0 277 | 5.286 | 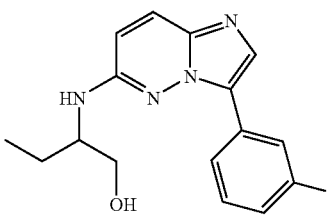<br>2-[3-(3-Bromo-phenyl)-imidazo[1,2-b]pyridazin-6-ylamino]-butan-1-ol | | 361.24 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 153_0 312 | 5.287 | 2-[3-(3-Trifluoromethyl-phenyl)-imidazo[1,2-b]pyridazin-6-ylamino]-butan-1-ol | 1.00 | 350.34/351 |
| 229_0 153_4 140 | 5.288 | 2-[3-(3-Methoxy-phenyl)-imidazo[1,2-b]pyridazin-6-ylamino]-butan-1-ol | 0.86 | 312.37/313 |
| 229_0 153_0 347 | 5.289 | 3-[6-(1-Hydroxymethyl-propylamino)-imidazo[1,2-b]pyridazin-3-yl]-benzamide | | 325.37 |
| 229_0 153_0 140 | 5.290 | 4-[6-(1-Hydroxymethyl-propylamino)-imidazo[1,2-b]pyridazin-3-yl]-benzoic acid | | 326.35 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 153_7 469 | 5.291 | 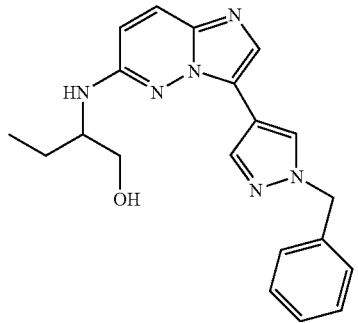<br>2-[3-(1-Benzyl-1H-pyrazol-4-yl)-imidazo[1,2-b]pyridazin-6-ylamino]-butan-1-ol | | 362.44 |
| 229_0 153_6 488 | 5.292 | 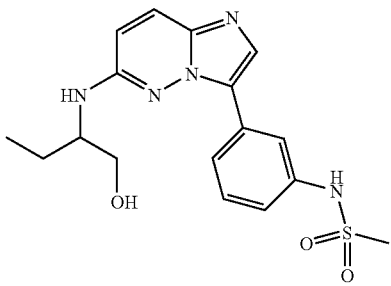<br>N-{3-[6-(1-Hydroxymethyl-propylamino)-imidazo[1,2-b]pyridazin-3-yl]-phenyl}-methanesulfonamide | | 375.45 |
| 229_0 153_0 145 | 5.293 | 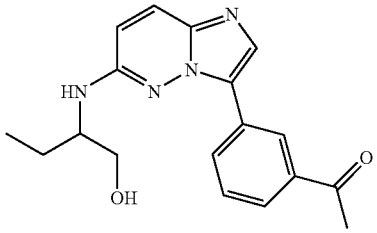<br>1-{3-[6-(1-Hydroxymethyl-propylamino)-imidazo[1,2-b]pyridazin-3-yl]-phenyl}-ethanone | | 324.38 |
| 229_0 153_0 079 | 5.294 | 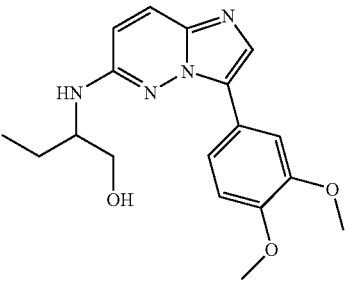<br>2-[3-(3,4-Dimethoxy-phenyl)-imidazo[1,2-b]pyridazin-6-ylamino]-butan-1-ol | | 342.40 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 153_0 196 | 5.295 | 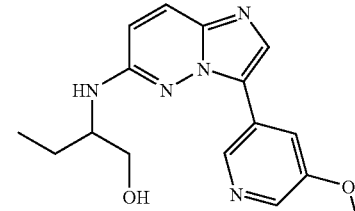<br>2-[3-(5-Methoxy-pyridin-3-yl)-imidazo[1,2-b]pyridazin-6-ylamino]-butan-1-ol | | 313.36 |
| 229_0 242_0 087 | 5.296 | 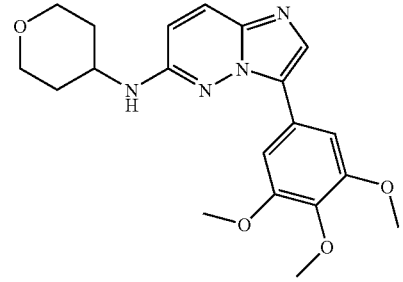<br>(Tetrahydro-pyran-4-yl)-[3-(3,4,5-trimethoxy-phenyl)-imidazo[1,2-b]pyridazin-6-yl]-amine | | 384.43 |
| 229_0 242_4 140 | 5.297 | 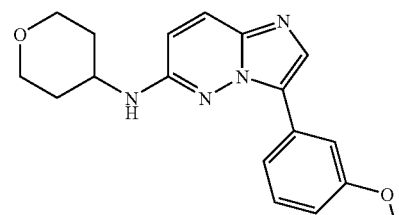<br>[3-(3-Methoxy-phenyl)-imidazo[1,2-b]pyridazin-6-yl]-(tetrahydro-pyran-4-yl)-amine | | 324.38 |
| 229_0 242_0 312 | 5.298 | 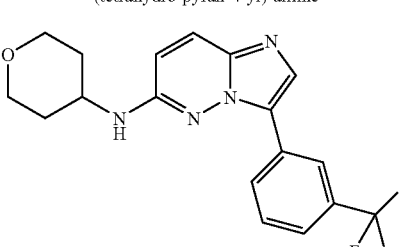<br>(Tetrahydro-pyran-4-yl)-[3-(3-trifluoromethyl-phenyl)-imidazo[1,2-b]pyridazin-6-yl]-amine | | 362.35 |
| 229_0 242_0 285 | 5.299 | 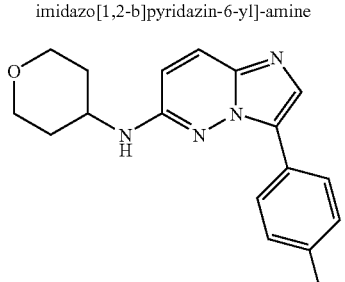<br>{4-[6-(Tetrahydro-pyran-4-ylamino)-imidazo[1,2-b]pyridazin-3-yl]-phenyl}-methanol | | 324.38 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 345 | 5.300 | 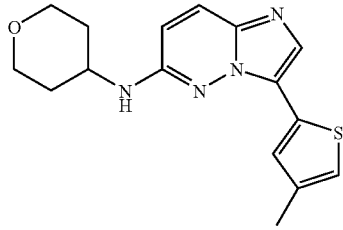<br>[3-(4-Methyl-thiophen-2-yl)-imidazo[1,2-b]pyridazin-6-yl]-(tetrahydro-pyran-4-yl)-amine | | 314.41 |
| 229_0 242_0 164 | 5.301 | 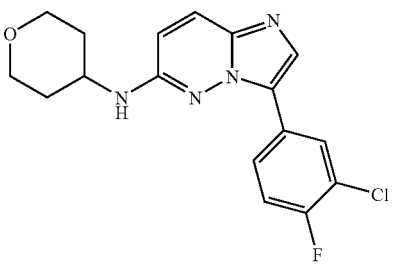<br>[3-(3-Chloro-4-fluoro-phenyl)-imidazo[1,2-b]pyridazin-6-yl]-(tetrahydro-pyran-4-yl)-amine | | 346.79 |
| 229_0 242_0 277 | 5.302 | 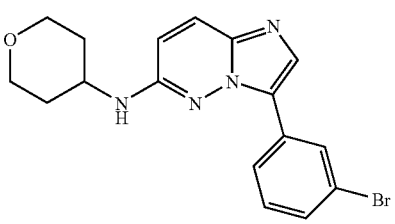<br>[3-(3-Bromo-phenyl)-imidazo[1,2-b]pyridazin-6-yl]-(tetrahydro-pyran-4-yl)-amine | | 373.25 |
| 229_0 242_7 468 | 5.303 | 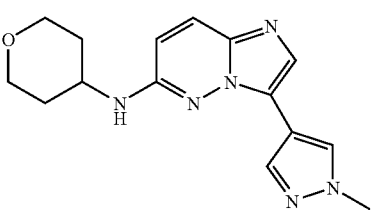<br>[3-(1-Methyl-1H-pyrazol-4-yl)-imidazo[1,2-b]pyridazin-6-yl]-(tetrahydro-pyran-4-yl)-amine | | 298.35 |
| 229_0 242_0 291 | 5.304 | 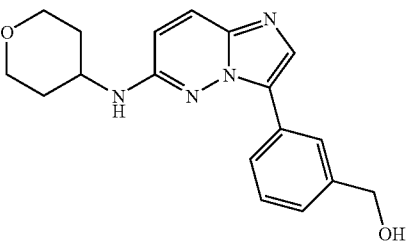<br>{3-[6-(Tetrahydro-pyran-4-ylamino)-imidazo[1,2-b]pyridazin-3-yl]-phenyl}-methanol | | 324.38 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 196 | 5.305 | 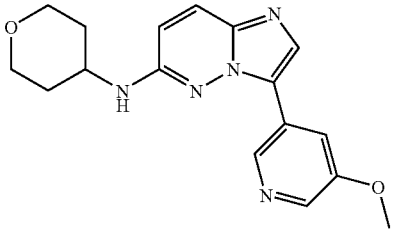<br>[3-(5-Methoxy-pyridin-3-yl)-imidazo[1,2-b]pyridazin-6-yl]-(tetrahydro-pyran-4-yl)-amine | | 325.37 |
| 229_0 242_0 280 | 5.306 | 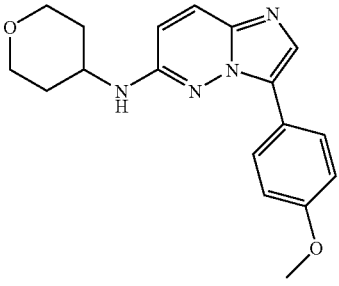<br>[3-(4-Methoxy-phenyl)-imidazo[1,2-b]pyridazin-6-yl]-(tetrahydro-pyran-4-yl)-amine | | 324.38 |
| 229_0 242_0 339 | 5.307 | 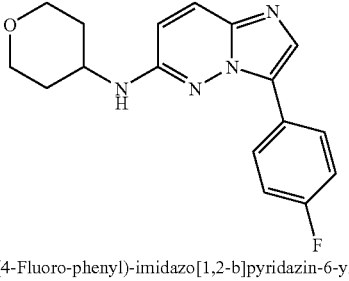<br>[3-(4-Fluoro-phenyl)-imidazo[1,2-b]pyridazin-6-yl]-(tetrahydro-pyran-4-yl)-amine | | 312.35 |
| 229_0 242_0 204 | 5.308 | 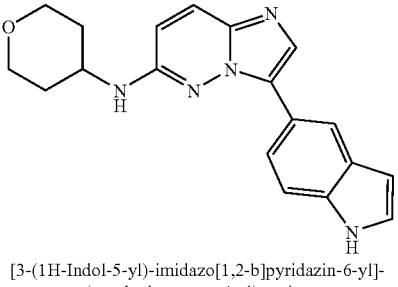<br>[3-(1H-Indol-5-yl)-imidazo[1,2-b]pyridazin-6-yl]-(tetrahydro-pyran-4-yl)-amine | | 333.39 |
| 229_0 242_0 135 | 5.309 | 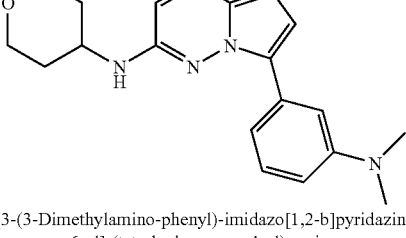<br>[3-(3-Dimethylamino-phenyl)-imidazo[1,2-b]pyridazin-6-yl]-(tetrahydro-pyran-4-yl)-amine | | 337.43 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 057 | 5.310 | 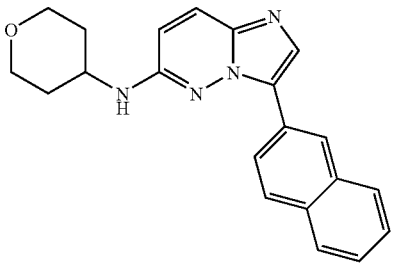<br>(3-Naphthalen-2-yl-imidazo[1,2-b]pyridazin-6-yl)-(tetrahydro-pyran-4-yl)-amine | 1.01 | 344.42/345 |
| 229_0 242_0 167 | 5.311 | 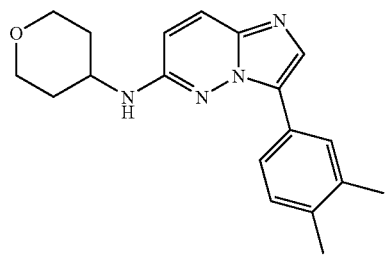<br>[3-(3,4-Dimethyl-phenyl)-imidazo[1,2-b]pyridazin-6-yl]-(tetrahydro-pyran-4-yl)-amine | 0.95 | 322.41/323 |
| 229_0 242_0 142 | 5.312 | 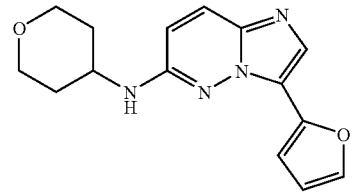<br>(3-Furan-2-yl-imidazo[1,2-b]pyridazin-6-yl)-(tetrahydro-pyran-4-yl)-amine | 0.81 | 284.32/285 |
| 229_0 242_0 192 | 5.313 | 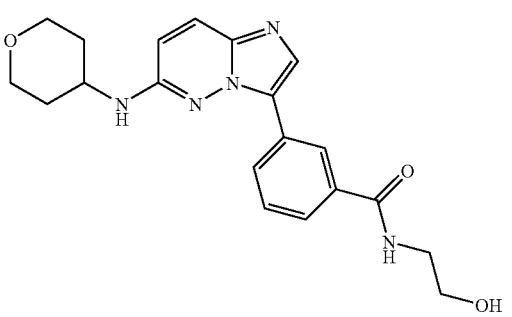<br>N-(2-Hydroxy-ethyl)-3-[6-(tetrahydro-pyran-4-ylamino)-imidazo[1,2-b]pyridazin-3-yl]-benzamide | 0.67 | 381.43/382 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_2 175 | 5.314 | 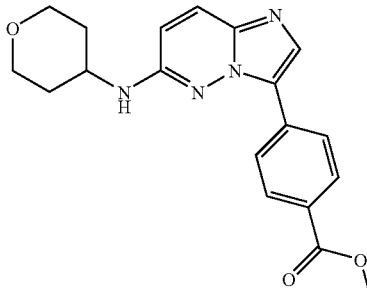<br>4-[6-(Tetrahydro-pyran-4-ylamino)-imidazo[1,2-b]pyridazin-3-yl]-benzoic aold methyl ester | 0.90 | 352.39/353 |
| 229_0 242_4 139 | 5.315 | 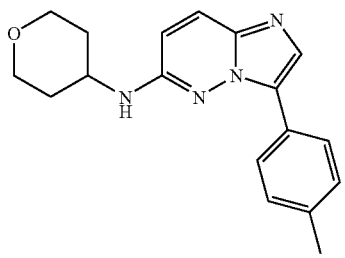<br>(Tetrahydro-pyran-4-yl)-(3-p-tolyl-imidazo[1,2-b]pyridazin-6-yl)-amine | 0.90 | 308.38/309 |
| 229_0 242_0 333 | 5.316 | 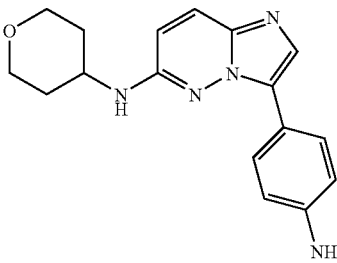<br>[3-(4-Amino-phenyl)-imidazo[1,2-b]pyridazin-6-yl]-(tetrahydro-pyran-4-yl)-amine | 0.68 | 309.37/310 |
| 229_0 242_0 004 | 5.317 | 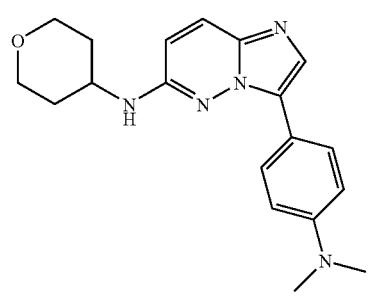<br>[3-(4-Dimethylamino-phenyl)-imidazo[1,2-b]pyridazin-6-yl]-(tetrahydro-pyran-4-yl)-amine | | 337.43 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 081 | 5.318 | 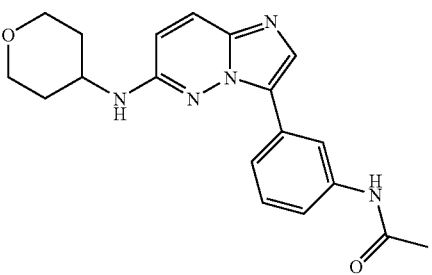<br>N-{3-[6-(Tetrahydro-pyran-4-ylamino)-imidazo[1,2-b]pyridazin-3-yl]-phenyl}-acetamide | 0.73 | 351.41/352 |
| 229_0 242_0 005 | 5.319 | 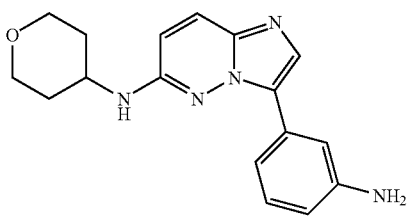<br>[3-(3-Amino-phenyl)-imidazo[1,2-b]pyridazin-6-yl]-(tetrahydro-pyran-4-yl)-amine | | 309.37 |
| 229_0 242_4 038 | 5.320 | 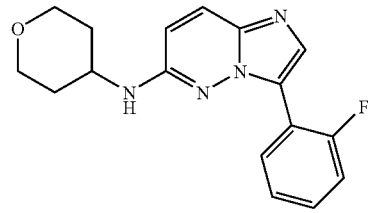<br>[3-(2-Fluoro-phenyl)-imidazo[1,2-b]pyridazin-6-yl]-(tetrahydro-pyran-4-yl)-amine | 0.85 | 312.35/313 |
| 229_0 242_0 062 | 5.321 | 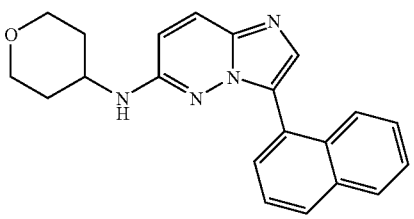<br>(3-Naphthalen-1-yl-imidazo[1,2-b]pyridazin-6-yl)-(tetrahydro-pyran-4-yl)-amine | | 344.42 |
| 229_0 242_0 071 | 5.322 | 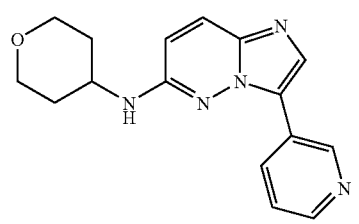<br>(3-Pyridin-3-yl-imidazo[1,2-b]pyridazin-6-yl)-(tetrahydro-pyran-4-yl)-amine | 0.65 | 295.34/296 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 160 | 5.323 | 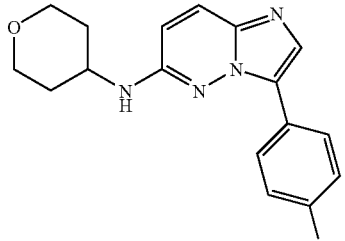<br>[3-(4-Chloro-phenyl)-imidazo[1,2-b]pyridazin-6-yl]-(tetrahydro-pyran-4-yl)-amine | | 328.80 |
| 229_0 242_0 068 | 5.324 | 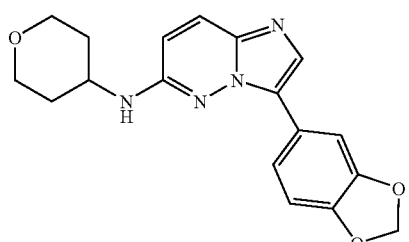<br>(3-Benzo[1,3]dioxol-5-yl-imidazo[1,2-b]pyridazin-6-yl)-(tetrahydro-pyran-4-yl)-amine | | 338.37 |
| 229_0 242_0 284 | 5.325 | 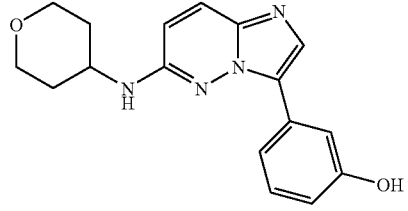<br>3-[6-(Tetrahydro-pyran-4-ylamino)-imidazo[1,2-b]pyridazin-3-yl]-phenol | 0.74 | 310.36/311 |
| 229_0 242_0 074 | 5.326 | 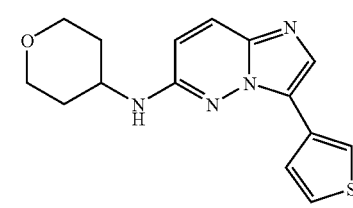<br>(Tetrahydro-pyran-4-yl)-(3-thiophen-3-yl-imidazo[1,2-b]pyridazin-6-yl)-amine | 0.84 | 300.38/301 |
| 229_0 242_0 079 | 5.327 | 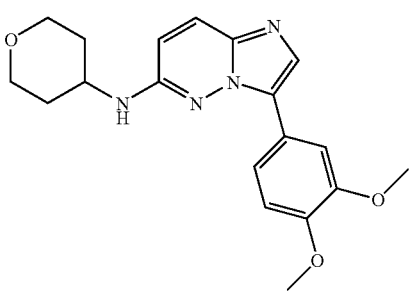<br>[3-(3,4-Dimethoxy-phenyl)-imidazo[1,2-b]pyridazin-6-yl]-(tetrahydro-pyran-4-yl)-amine | 0.81 | 354.41/355 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 168 | 5.328 | 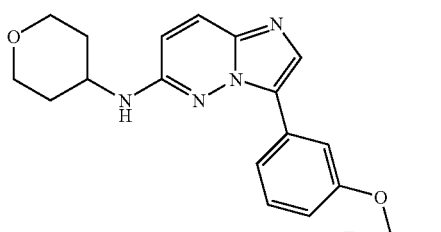<br>(Tetrahydro-pyran-4-yl)-[3-(3-trifluoromethoxy-phenyl)-imidazo[1,2-b]pyridazin-6-yl]-amine | 1.06 | 378.35/379 |
| 229_0 242_0 313 | 5.329 | 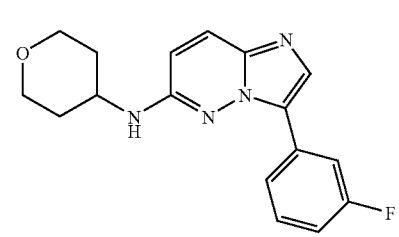<br>[3-(3-Fluoro-phenyl)-imidazo[1,2-b]pyridazin-6-yl]-(tetrahydro-pyran-4-yl)-amine | | 312.35 |
| 229_0 242_0 314 | 5.330 | 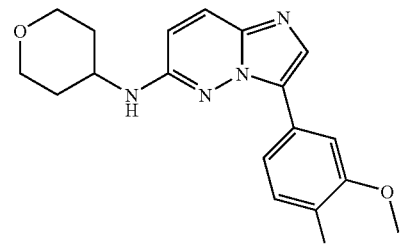<br>2-Methoxy-4-[6-(tetrahydro-pyran-4-ylamino)-imidazo[1,2-b]pyridazin-3-yl]-phenol | | 340.38 |
| 229_0 242_4 147 | 5.331 | 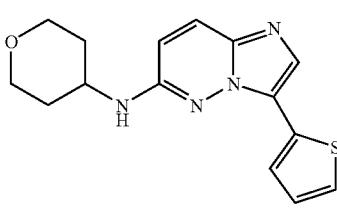<br>(Tetrahydro-pyran-4-yl)-(3-thiophen-2-yl-imidazo[1,2-b]pyridazin-6-yl)-amine | 0.83 | 300.38/301 |
| 229_0 242_7 467 | 5.332 | 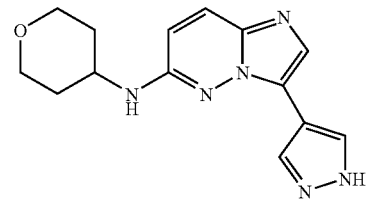<br>[3-(1H-Pyrazol-4-yl)-imidazo[1,2-b]pyridazin-6-yl]-(tetrahydro-pyran-4-yl)-amine | 0.59 | 284.32/285 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 347 | 5.333 | 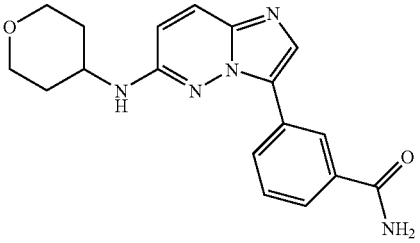<br>3-[6-(Tetrahydro-pyran-4-ylamino)-imidazo[1,2-b]pyridazin-3-yl]-benzamide | | 337.38 |
| 229_0 242_7 469 | 5.334 | 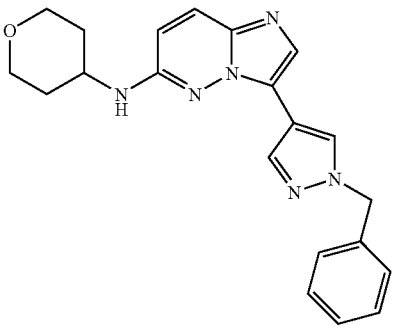<br>[3-(1-Benzyl-1H-pyrazol-4-yl)-imidazo[1,2-b]pyridazin-6-yl]-(tetrahydro-pyran-4-yl)-amine | | 374.45 |
| 229_0 242_0 140 | 5.335 | 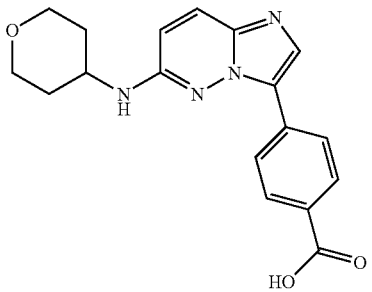<br>4-[6-(Tetrahydro-pyran-4-ylamino)-imidazo[1,2-b]pyridazin-3-yl]-benzoic acid | | 338.37 |
| 229_0 242_6 488 | 5.336 | 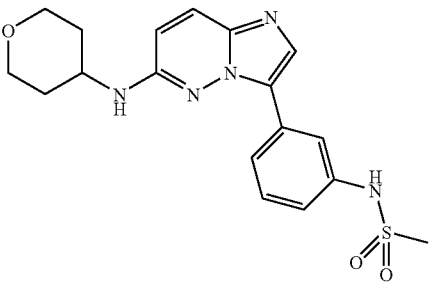<br>N-{3-[6-(Tetrahydro-pyran-4-ylamino)-imidazo[1,2-b]pyridazin-3-yl]-phenyl}-methanesulfonamide | | 387.46 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 242_0 279 | 5.337 | 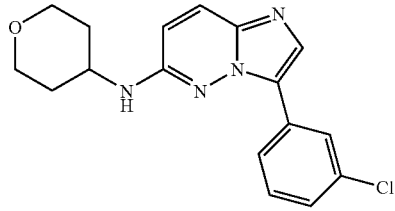<br>[3-(3-Chloro-phenyl)-imidazo[1,2-b]pyridazin-6-yl]-(tetrahydro-pyran-4-yl)-amine | | 328.80 |
| 229_0 240_0 314 | 5.338 | 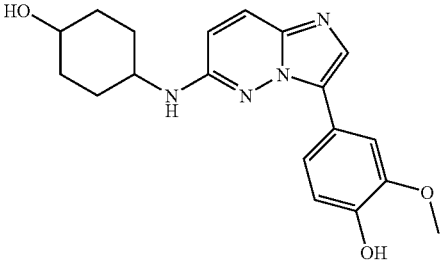<br>4-[6-(4-Hydroxy-cyclohexylamino)-imidazo[1,2-b]pyridazin-3-yl]-2-methoxy-phenol | 0.70 | 354.41/353 (negative mode) |
| 229_0 240_0 168 | 5.339 | 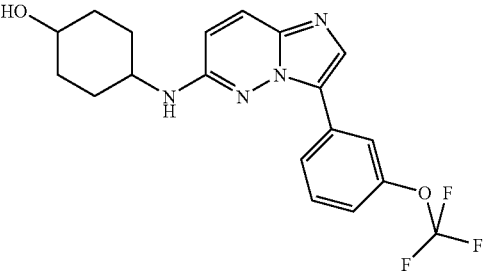<br>4-[3-(3-Trifluoromethoxy-phenyl)-imidazo[1,2-b]pyridazin-6-ylamino]-cyclohexanol | | 392.38 |
| 229_0 240_4 140 | 5.340 | 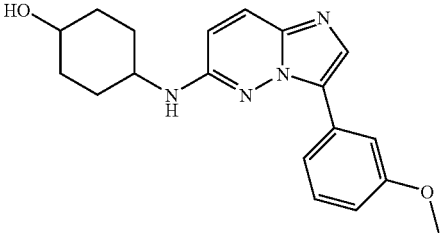<br>4-[3-(3-Methoxy-phenyl)-imidazo[1,2-b]pyridazin-6-ylamino]-cyclohexanol | 0.79 | 338.41/339 |
| 229_0 240_0 074 | 5.341 | 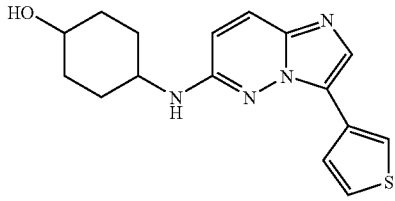<br>4-(3-Thiophen-3-yl-imidazo[1,2-b]pyridazin-6-ylamino)-cyclohexanol | | 314.41 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 240_0 076 | 5.342 | 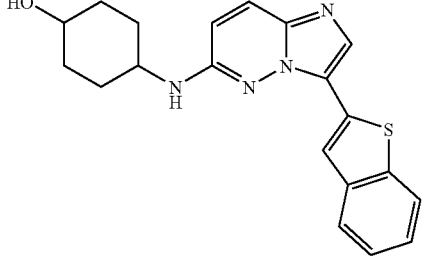 4-(3-Benzo[b]thiophen-2-yl-imidazo[1,2-b]pyridazin-6-ylamino)-cyclohexanol | | 364.47 |
| 229_0 240_0 135 | 5.343 | 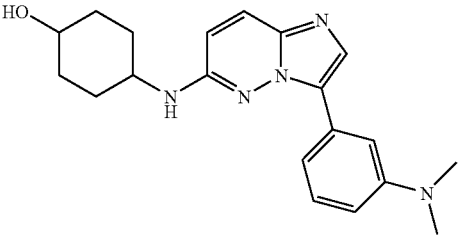 4-[3-(3-Dimethylamino-phenyl)-imidazo[1,2-b]pyridazin-6-ylamino]-cyclohexanol | | 351.45 |
| 229_0 240_0 313 | 5.344 | 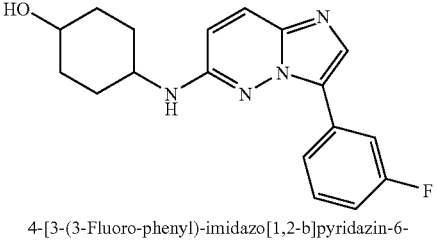 4-[3-(3-Fluoro-phenyl)-imidazo[1,2-b]pyridazin-6-ylamino]-cyclohexanol | | 326.37 |
| 229_0 240_0 062 | 5.345 | 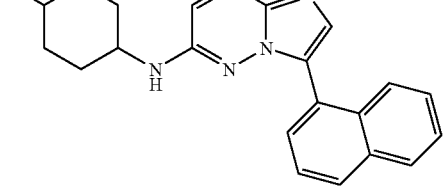 4-(3-Naphthalen-1-yl-imidazo[1,2-b]pyridazin-6-ylamino)-cyclohexanol | 0.83 | 358.44/359 |
| 229_0 240_0 081 | 5.346 | 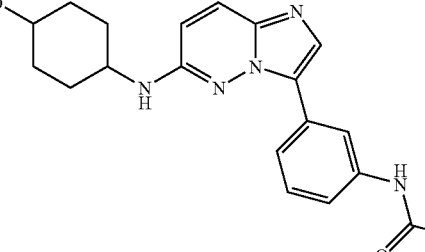 N-{3-[6-(4-Hydroxy-cyclohexylamino)-imidazo[1,2-b]pyridazin-3-yl]-phenyl}-acetamide | | 365.44 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 240_0 080 | 5.347 | 4-[6-(4-Hydroxy-cyclohexylamino)-imidazo[1,2-b]pyridazin-3-yl]-phenol | | 324.38 |
| 229_0 240_0 057 | 5.348 | 4-(3-Naphthalen-2-yl-imidazo[1,2-b]pyridazin-6-ylamino)-cyclohexanol | | 358.44 |
| 229_0 240_0 061 | 5.349 | 4-(3-Phenyl-imidazo[1,2-b]pyridazin-6-ylamino)-cyclohexanol | | 308.38 |
| 229_0 240_0 204 | 5.350 | 4-[3-(1H-Indol-5-yl)-imidazo[1,2-b]pyridazin-6-ylamino]-cyclohexanol | | 347.42 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 240_0 004 | 5.351 | 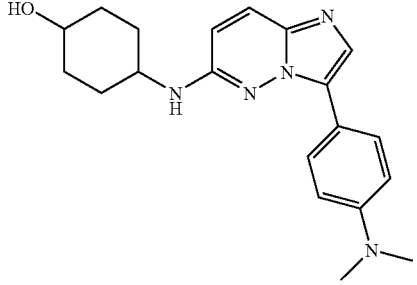<br>4-[3-(4-Dimethylamino-phenyl)-imidazo[1,2-b]pyridazin-6-ylamino]-cyclohexanol | | 351.45 |
| 229_0 240_0 280 | 5.352 | 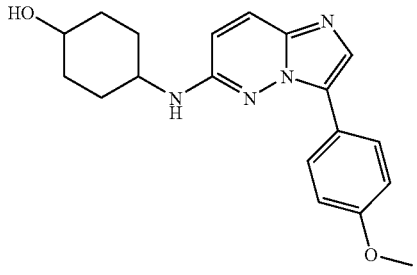<br>4-[3-(4-Methoxy-phenyl)-imidazo[1,2-b]pyridazin-6-ylamino]-cyclohexanol | | 338.41 |
| 229_0 240_0 078 | 5.353 | 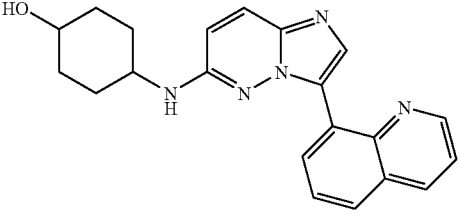<br>4-(3-Quinolin-8-yl-imidazo[1,2-b]pyridazin-6-ylamino)-cyclohexanol | | 359.43 |
| 229_0 240_0 142 | 5.354 | 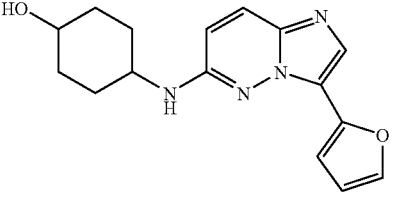<br>4-(3-Furan-2-yl-imidazo[1,2-b]pyridazin-6-ylamino)-cyclohexanol | | 298.34 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 240_2 175 | 5.355 | 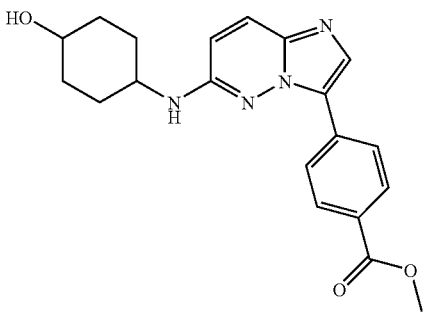<br>4-[6-(4-Hydroxy-cyclohexylamino)-imidazo[1,2-b]pyridazin-3-yl]-benzoic acid methyl ester | 0.82 | 366.42/365 (negative mode) |
| 229_0 240_0 085 | 5.356 | 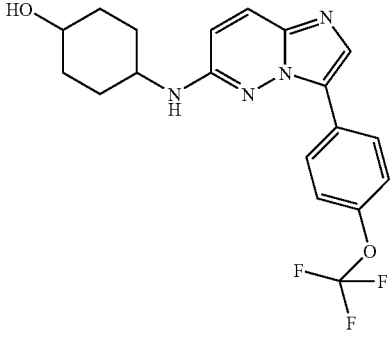<br>4-[3-(4-Trifluoromethoxy-phenyl)-imidazo[1,2-b]pyridazin-6-ylamino]-cyclohexanol | | 392.38 |
| 229_0 240_0 167 | 5.357 | 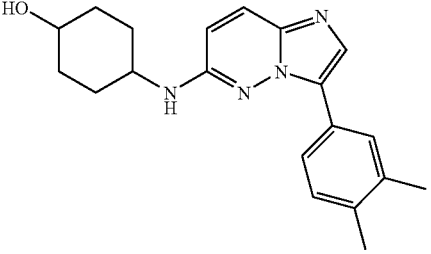<br>4-[3-(3,4-Dimethyl-phenyl)-imidazo[1,2-b]pyridazin-6-ylamino]-cyclohexanol | | 336.44 |
| 229_0 240_0 285 | 5.358 | 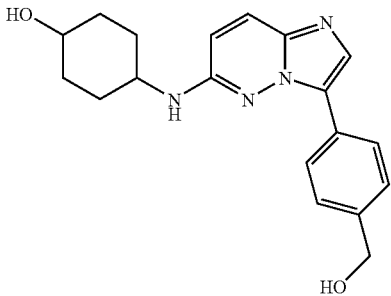<br>4-[3-(4-Hydroxymethyl-phenyl)-imidazo[1,2-b]pyridazin-6-ylamino]-cyclohexanol | | 338.41 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_0 240_0 160 | 5.359 | 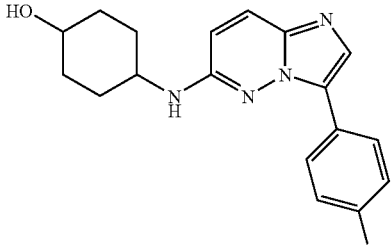<br>4-[3-(4-Chloro-phenyl)-imidazo[1,2-b]pyridazin-6-ylamino]-cyclohexanol | | 342.83 |
| 229_0 240_0 311 | 5.360 | 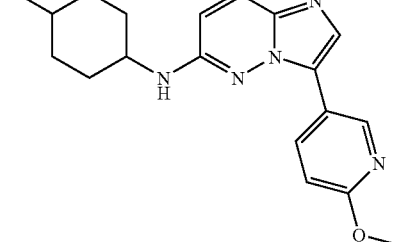<br>4-[3-(6-Methoxy-pyridin-3-yl)-imidazo[1,2-b]pyridazin-6-ylamino]cyclohexanol | | 339.40 |
| 229_0 240_0 196 | 5.361 | 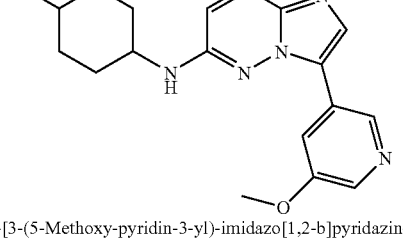<br>4-[3-(5-Methoxy-pyridin-3-yl)-imidazo[1,2-b]pyridazin-6-ylamino]-cyclohexanol | | 339.40 |
| 229_0 240_0 284 | 5.362 | 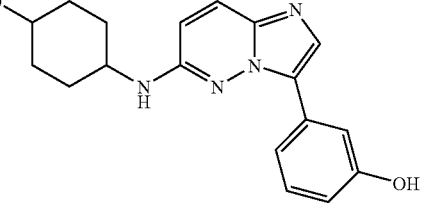<br>3-[6-(4-Hydroxy-cyclohexylamino)-imidazo[1,2-b]pyridazin-3-yl]-phenol | | 324.38 |
| 229_0 240_0 140 | 5.363 | 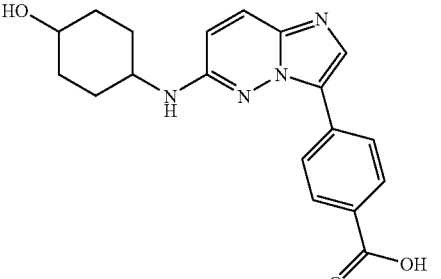<br>4-[6-(4-Hydroxy-cyclohexylamino)-imidazo[1,2-b]pyridazin-3-yl]-benzoic acid | | 352.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4 051_0 087 | 5.364 | 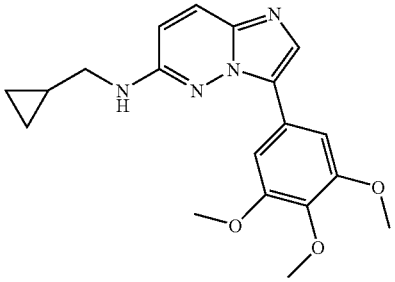<br>Cyclopropylmethyl-[3-(3,4,5-trimethoxy-phenyl)-imidazo[1,2-b]pyridazin-6-yl]-amine | | 354.41 |
| 229_4 051_0 314 | 5.365 | 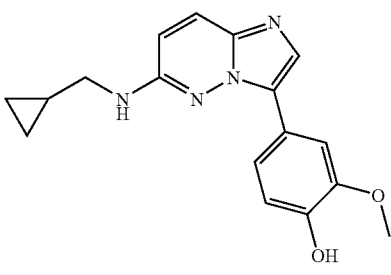<br>4-[6-(Cyclopropylmethyl-amino)-imidazo[1,2-b]pyridazin-3-yl]-2-methoxy-phenol | | 310.36 |
| 229_4 051_0 079 | 5.366 | 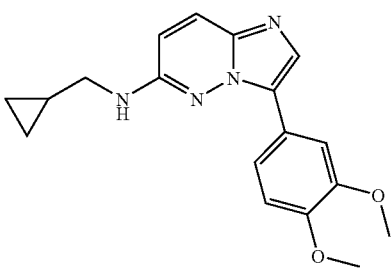<br>Cyclopropylmethyl-[3-(3,4-dimethoxy-phenyl)-imidazo[1,2-b]pyridazin-6-yl]-amine | | 324.38 |
| 229_4 051_0 135 | 5.367 | 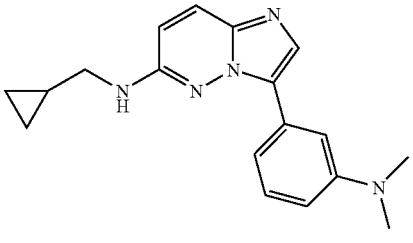<br>Cyclopropylmethyl-[3-(3-dimethylamino-phenyl) imidazo[1,2-b]pyridazin-6-yl]-amine | | 307.40 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4051_0069 | 5.368 | 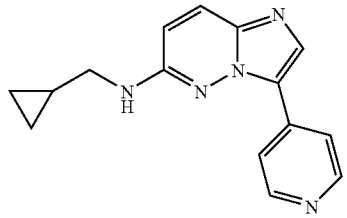<br>Cyclopropylmethyl-(3-pyridin-4-yl-imidazo[1,2-b]pyridazin-6-yl)-amine | | 265.32 |
| 229_4051_0291 | 5.369 | 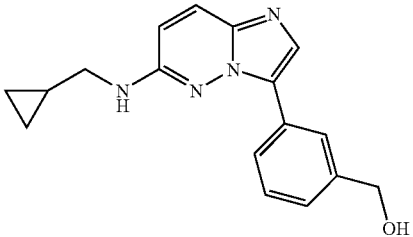<br>{3-[6-(Cyclopropylmethyl-amino)-imidazo[1,2-b]pyridazin-3-yl]-phenyl}-methanol | | 294.36 |
| 229_4051_4140 | 5.370 | 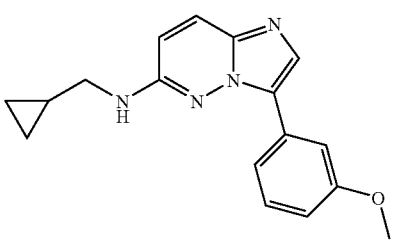<br>Cyclopropylmethyl-[3-(3-methoxy-phenyl)-imidazo[1,2-b]pyridazin-6-yl]-amine | | 294.36 |
| 229_4051_7468 | 5.371 | 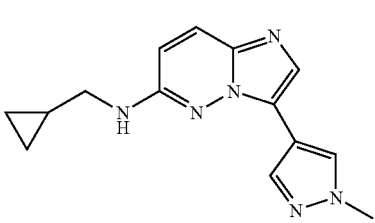<br>Cyclopropylmethyl-[3-(1-methyl-1H-pyrazol-4-yl)-imidazo[1,2-b]pyridazin-6-yl]-amine | | 268.32 |
| 229_4051_7467 | 5.372 | 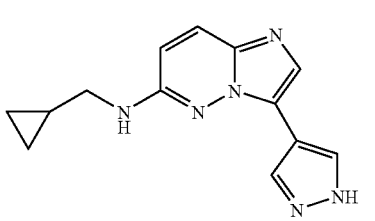<br>Cyclopropylmethyl-[3-(1H-pyrazol-4-yl)-imidazo[1,2-b]pyridazin-6-yl]-amine | | 254.30 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4 051_0 068 | 5.373 | 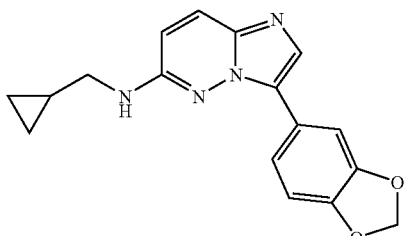<br>(3-Benzo[1,3]dioxol-5-yl-imidazo[1,2-b]pyridazin-6-yl)-cyclopropylmethyl-amine | | 308.34 |
| 229_4 051_0 280 | 5.374 | 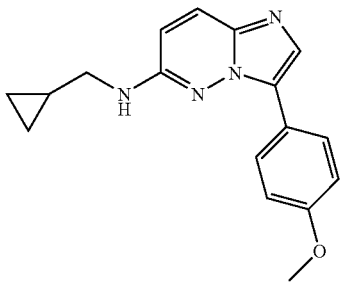<br>Cyclopropylmethyl-[3-(4-methoxy-phenyl)-imidazo[1,2-b]pyridazin-6-yl]-amine | | 294.36 |
| 229_4 051_0 074 | 5.375 | 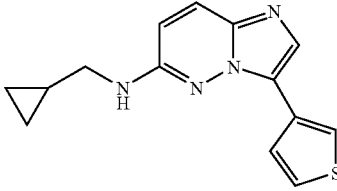<br>Cyclopropylmethyl-(3-thiophen-3-yl-imidazo[1,2-b]pyridazin-6-yl)-amine | | 270.36 |
| 229_4 051_0 311 | 5.376 | 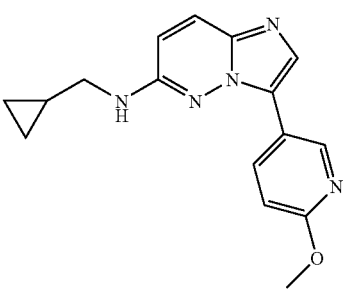<br>Cyclopropylmethyl-[3-(6-methoxy-pyridin-3-yl)-imidazo[1,2-b]pyridazin-6-yl]-amine | | 295.34 |
| 229_4 051_0 345 | 5.377 | 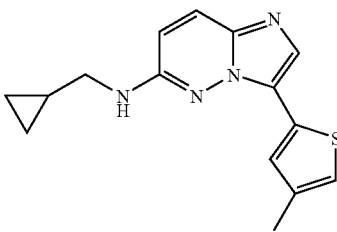<br>Cyclopropylmethyl-[3-(4-methyl-thiophen-2-yl)-imidazo[1,2-b]pyridazin-6-yl]-amine | | 284.39 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4051_0081 | 5.378 | N-{3-[6-(Cyclopropylmethyl-amino)-imidazo[1,2-b]pyridazin-3-yl]-phenyl}-acetamide | | 321.38 |
| 229_4051_0192 | 5.379 | 3-[6-(Cyclopropylmethyl-amino)-imidazo[1,2-b]pyridazin-3-yl]-N-(2-hydroxy-ethyl)-benzamide | | 351.41 |
| 229_4051_0285 | 5.380 | {4-[6-(Cyclopropylmethyl-amino)-imidazo[1,2-b]pyridazin-3-yl]-phenyl}-methanol | | 294.36 |
| 229_4051_0080 | 5.381 | 4-[6-(Cyclopropylmethyl-amino)-imidazo[1,2-b]pyridazin-3-yl]-phenol | | 280.33 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4 051_0 284 | 5.382 | 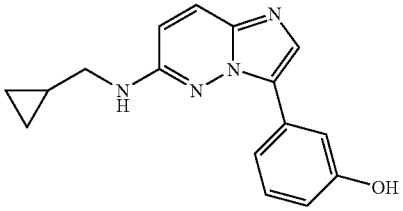<br>3-[6-(Cyclopropylmethyl-amino)-imidazo[1,2-b]pyridazin-3-yl]-phenol | | 280.33 |
| 229_4 051_6 488 | 5.383 | 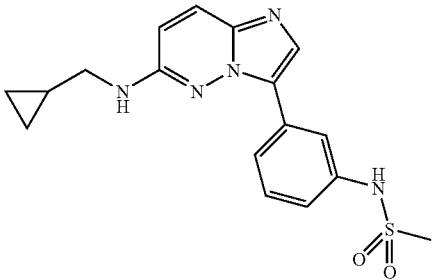<br>N-{3-[6-(Cyclopropylmethyl-amino)-imidazo[1,2-b]pyridazin-3-yl]-phenyl}-methanesulfonamide | | 357.44 |
| 229_4 051_0 139 | 5.384 | 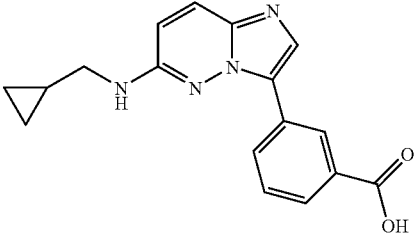<br>3-[6-(Cyclopropylmethyl-amino)-imidazo[1,2-b]pyridazin-3-yl]-benzoic acid | | 308.34 |
| 229_4 051_7 469 | 5.385 | 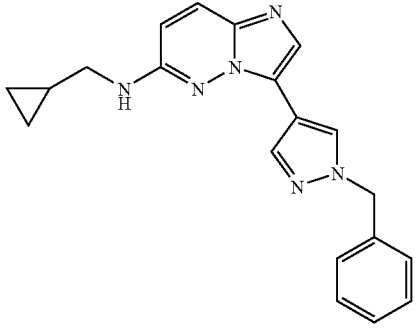<br>[3-(1-Benzyl-1H-pyrazol-4-yl)-imidazo[1,2-b]pyridazin-6-yl]-cyclopropylmethyl-amine | | 344.42 |

TABLE 5-continued

| Char No. | Example No. | Structure and Name of the main isomer | Retention time (HPLC, UV 254 nm) [min]. | Mol. weight/ MS (HPLC-MS) |
|---|---|---|---|---|
| 229_4 051_0 140 | 5.386 | 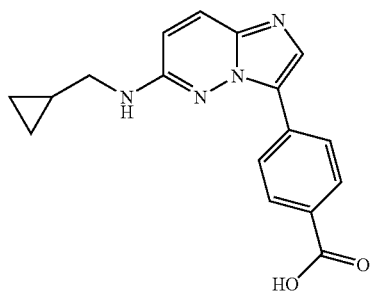<br>4-[6-(Cyclopropylmethyl-amino)-imidazo[1,2-b]pyridazin-3-yl]-benzoic acid | | 308.34 |
| 229_4 051_0 347 | 5.387 | 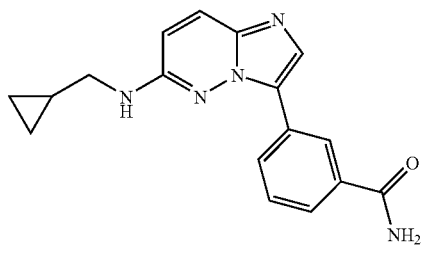<br>3-[6-(Cyclopropylmethyl-amino)-imidazo[1,2-b]pyridazin-3-yl]-benzamide | | 307.36 |
| 229_4 051_4 145 | 5.388 | 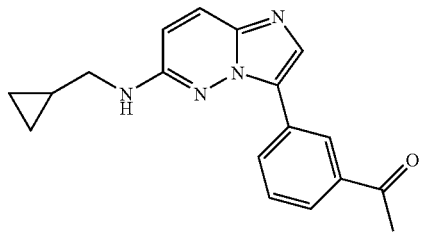<br>1-{3-[6-(Cyclopropylmethyl-amino)-imidazo[1,2-b]pyridazin-3-yl]-phenyl}-ethanone | | 306.37 |
| 229_4 051_4 147 | 5.389 | 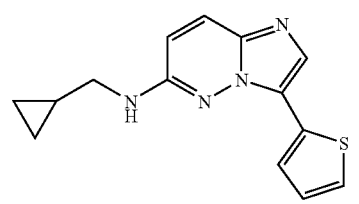<br>Cyclopropylmethyl-(3-thiophen-2-yl-imidazo[1,2-b]pyridazin-6-yl)-amine | | 270.36 |

Description of the HPLC-MS analysis conditions for the examples listed in Table 5:

Detection: UV=200-350 nm (Waters Acquity HPLC)/MS 100-800 Daltons; 20 V (Micromass/Waters ZQ 4000); column: X Bridge (Waters), 2.1×50 mm, BEH 1.7 µm; eluent: A: $H_2O$/0.05% HCOOH, B: $CH_3CN$/0.05% HCOOH.

Gradient: 10-90% B in 1.7 min, 90% B for 0.2 min, 98-2% B in 0.6 min; flow rate: 1.3 ml/min.

[3-(2-Methoxypyridin-4-yl)imidazo[1,2-b]pyridazin-6-yl]piperidin-4-ylamine (Example 6.0)

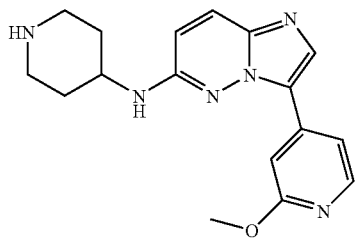

Stage A: 4-[3-(2-methoxypyridin-4-yl)imidazo[1,2-b]pyridazin-6-ylamino]piperidine-1-carboxylic acid tert-butyl ester (Example 6.1)

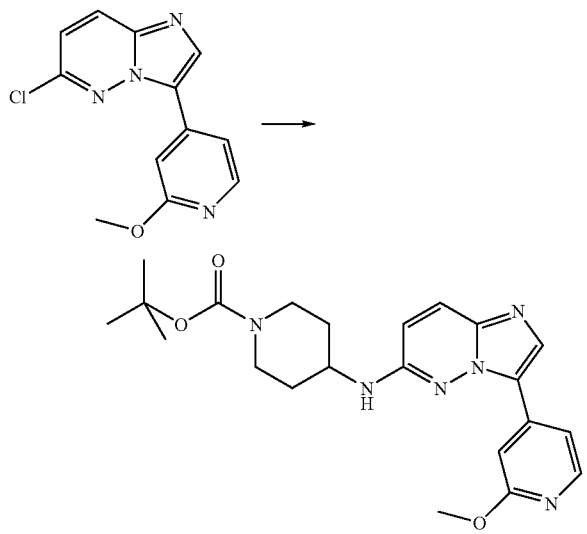

292 mg of 4-[3-(2-methoxypyridin-4-yl)imidazo[1,2-b]pyridazin-6-ylamino]piperidine-1-carboxylic acid tert-butyl ester were prepared from 300 mg (1.15 mmol) of 6-chloro-3-(2-methoxypyridin-4-yl)imidazo[1,2-b]pyridazine (Example 1.14) and 230 mg (1.15 mmol) of 4-aminopiperidine-1-carboxylic acid tert-butyl ester (CAS No. 87120-72-7) by method A.

1H-NMR (300 MHz, $d_6$-DMSO): δ=1.32-1.38 (m, 11H); 2.02-2.08 (m, 2H); 2.92-3.00 (m, 2H); 3.72-3.92 (m, 6H); 6.73 (d, 1H); 7.17-7.19 (m, 1H); 7.64-7.66 (m, 1H); 7.76-7.79 (m, 2H); 8.11-8.16 (m, 2H) ppm.

MS (ES+): m/z=425 (M+H)$^+$ [mol. weight=424.51].

Stage B: [3-(2-methoxypyridin-4-yl)imidazo[1,2-b]pyridazin-6-yl]piperidin-4-ylamine (Example 6.0)

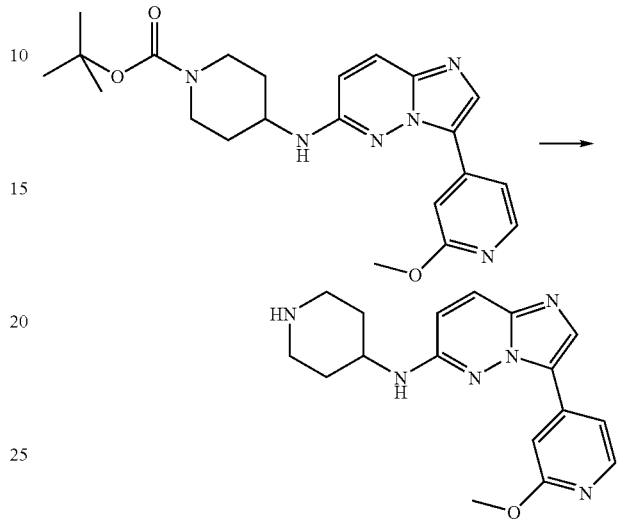

280 mg (0.66 mmol) of 4-[3-(2-methoxypyridin-4-yl)imidazo[1,2-b]pyridazin-6-ylamino]piperidine-1-carboxylic acid tert-butyl ester were introduced into 3 ml of THF and, after addition of 0.8 ml of HCl in dioxane (4M), stirred at RT overnight. HCl (conc.) was added, and the mixture was heated at 70° C. for 4 hours. The reaction was diluted with water, adjusted to pH 11 with $Et_3N$ and extracted three times with ethyl acetate. The combined organic phases were filtered through a silicone filter (from Whatman) and concentrated. In the final fractionation by chromatography on silica gel, 92 mg of the desired product were isolated.

1H-NMR (300 MHz, $d_6$-DMSO): δ=1.30-1.43 (m, 2H); 2.03-2.08 (m, 2H); 2.59-2.67 (m, 2H); 2.99-3.06 (m, 2H); 3.66-3.75 (m, 1H), 3.89 (s, 3H); 6.77 (d, 1H); 7.15-7.18 (m, 1H); 7.66-7.69 (m, 1H); 7.80 (d, 1H); 8.87 (s, 1H); 8.15-8.19 (m, 2H) ppm.

MS (ES+): m/z=325 (M+H)$^+$ [mol. weight=324.39].

The following example was prepared analogously:

| Example No. | Structure and name of the main isomer | 1H-NMR | Mol. weight/MS (ES+) [M + 1]$^+$ |
|---|---|---|---|
| 6.2 | [3-(6-Methoxy-pyridin-3-yl)-imidazo[1,2-b]pyridazin-6-yl]-piperidin-4-yl-amine | (300 MHz, $d_6$-DMSO): δ = 1.22-1.35(m, 2H); 1.92-1.97(m, 2H); 2.49-2.57(m, 2H, partly covered by solvent); 2.90-2.97(m, 2H); 3.55-3.67(m, 1H); 3.86(s, 3H); 6.64(d, 1H); 6.96-6.98(m, 1H); 7.70(d, 1H); 7.80(s, 1H); 8.38(dd, 1H) ppm. | 324.39/325 |

3-[6-(2-Hydroxyethylamino)imidazo[1,2-b]pyridazin-3-yl]benzenesulfonamide (Example 7.0)

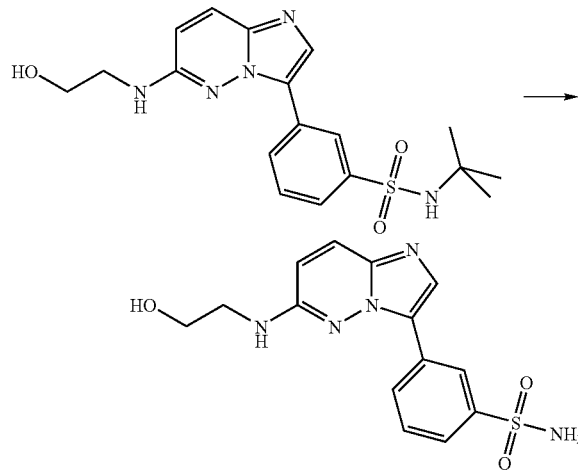

82 mg (0.21 mmol) of N-tert-butyl-3-[6-(2-hydroxyethylamino)imidazo[1,2-b]pyridazin-3-yl]benzenesulfonamide were mixed under argon with 1.7 ml of trifluoroacetic acid and stirred at 50° C. for 5 hours. After cooling, the mixture was concentrated in vacuo, and the residue was taken up in ethyl acetate. The organic phase was washed with saturated NaHCO$_3$ solution and saturated NaCl solution, filtered through a Whatman filter and concentrated. The resulting residue was purified by chromatography (DCM/EtOH 6:4). 47 mg of the product were obtained.

1H-NMR (400 MHz, d$_6$-DMSO): δ=3.36-3.40 (m, 2H); 3.61-3.65 (m, 2H); 4.77 (t, 1H); 6.78 (d, 1H); 7.17 (t, 1H); 7.35 (s, 2H); 7.59-7.63 (m, 1H); 7.70-7.76 (m, 2H); 7.95 (s, 1H); 8.25 (d, 1H); 8.87 (m, 1H) ppm.

The following example was prepared analogously:

| Example No. | Structure and name of the main isomer | 1H-NMR | Mol. weight/ MS (ESI) [M + 1]+ |
|---|---|---|---|
| 7.1 | 4-[6-(2-Hydroxy-ethylamino)-imidazo[1,2-b]pyridazin-3-yl]-benzenesulfonamide | | MW: 333.37 MS (ESI+): 334 |

The following examples were prepared from 4-(6-chloroimidazo[1,2-b]pyridazin-3-yl)phenol and the appropriate amine in analogy to Example 1.5:

| Example No. | Structure and name of the main isomer | 1H-NMR | Mol. weight/ MS (ES+) [M + 1]+ |
|---|---|---|---|
| 8.0 | 4-[6-(3-Dimethylamino-propylamino)-imidazo[1,2-b]pyridazin-3-yl]-phenol | | MW 311.39 MS (ES+): [M + 1]+ 312 |
| 8.1 | 4-[6-(2-Morpholin-4-yl-ethylamino)-imidazo[1,2-b]pyridazin-3-yl]-phenol | (DMSO-d$_6$, stored over molecular sieves): δ = 2.40(m, 4H); 2.54(m, 2H); 3.37(m, 2H); 3.56(m, 4H); 6.63(d, 1H); 6.80(d, 1H); 6.92(m, 1H); 7.66(m, 2H); 7.94(d, 1H) ppm. | |

Biological Effects

The following examples describe the biological effect of the compounds of the invention:

It is clear to the skilled worker that there is a number of disorders in which the cause of the disorder derives from a dysfunction of one or more kinases. Dysfunctions of kinases can be induced by a large number of mechanisms, e.g. a kinase may be overexpressed, leading to a faulty cellular activity, or a mutated kinase may be overexpressed, likewise leading to a faulty cellular activity. The faulty cellular activity may be for example a faulty cellular proliferation, especially an increased cellular proliferation (cellular hyperproliferation). The result of such dysfunctions may be for example a disorder which is characterized by overexpression or mutation of the kinase.

Appropriate assays for testing the efficacy of the compounds of the invention for the ability to modulate kinase activity are known. Also known are assays in order to investigate the efficacy of the compounds of the invention in modulating cellular proliferation.

The following biological examples therefore serve merely to describe by way of example the uses according to the invention of the claimed compounds and are therefore not to be understood as limiting in any way.

Significance of IL-2 in the T Cell Immune Response

The extent to which test substance influence antibody-induced interleukin 2 (IL-2) secretion was investigated in the following test system. IL-2 represents a central cytokine which is produced and released by activated T cells. IL-2 synthesis in the T cells is regulated by a plurality of kinases. An inhibitory effect of substances on kinases leads inter alia to inhibition of IL-2 synthesis and inhibition of the T cell immune response. The cytokine determinations were carried out using an ELISA kit.

Description of the Test System

Peripheral blood mononuclear cells (PBMC) were isolated from heparinized human whole blood by gradient centrifugation using Histopaque 1077 (Sigma) at room temperature, and the erythrocytes were lyzed hypotonically and, after washing twice in PBS, taken up in cell culture medium (10% fetal inactivated calf serum in RPMI-1640+Glutamax-I [Gibco]).

The 96 well culture plates (Costar) were previously incubated with 100 µl of antibody solution in PBS 0.1 µg/ml in PBS [Gibco]) per well at 4° C. for 18 hours. The antibodies used were anti-CD3 and anti-CD28 monoclonal antibodies (PharMingen). After washing with PBS three times, the plates were charged with 200 µl of the cell suspension (40 000 cells/well). In addition, the test substances were added in concentrations such that they were present in concentrations of $1 \times 10^{-6}$-$1 \times 10^{-12}$ M.

The cultures were incubated in an incubator at 37° C. for 20 hours. After this incubation, the plates were briefly shaken and centrifuged, and 250 µl of supernatant were removed, and the supernatants were then frozen at −20° C.

Interleukin-2 was determined using an ELISA kit (Bioscience), and the absorption of the color change was analyzed in a SpectraMax 340 PC (wavelength 450 nm). Active substances brought about a reduction in the absorption.

TABLE 1

| Example No. | Structure | Inhibition of PKC theta IC50 [mol/l] | IC50 [mol/l] (concentration for 50% inhibition of IL-2) inhibition at 10 µM |
|---|---|---|---|
| OP 3070 | 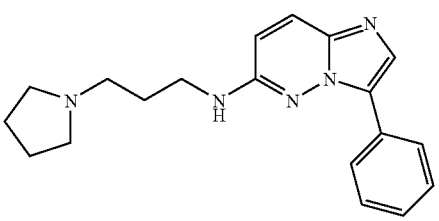 (3-Phenyl-imidazo[1,2-b]pyridazin-6-yl)-(3-pyrrolidin-1-yl-propyl)-amine | $6.1 \times 10^{-6}$ | $1.4 \times 10^{-6}$, >95% inhibition at 10 µM |
| OP 3071 | 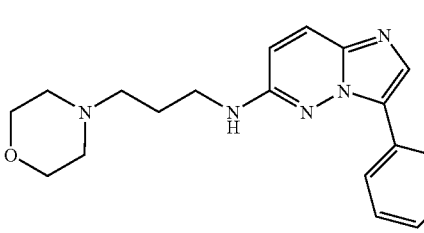 (3-Morpholin-4-yl-propyl)-(3-phenyl-imidazo[1,2-b]pyridazin-6-yl)-amine | $1.7 \times 10^{-5}$ | $2.5 \times 10^{-6}$, >95% inhibition at 10 µM |

TABLE 1-continued

Assay data

| Example No. | Structure | Inhibition of PKC theta IC50 [mol/l] | IC50 [mol/l] (concentration for 50% inhibition of IL-2) inhibition at 10 μM |
|---|---|---|---|
| OP 3073 | [3-(3-Chloro-phenyl)-imidazo[1,2-b]pyridazin-6-yl]-(3-pyrrolidin-1-yl-propyl)-amine | $2.5 \times 10^{-7}$ | $2.1 \times 10^{-7}$, >95% inhibition at 10 μM |
| OP 3074 | [3-(3-Chloro-phenyl)-imidazo[1,2-b]pyridazin-6-yl]-(3-morpholin-4-yl-propyl)-amine | $4.1 \times 10^{-7}$ | $9.2 \times 10^{-7}$, >95% inhibition at 10 μM |
| KE1322-002-a | (3-Imidazol-1-yl-propyl)-(3-phenyl-imidazo[1,2-b]pyridazin-6-yl)-amine | $1.29 \times 10^{-5}$ | $1.7 \times 10^{-6}$ |
| KE1322-006-a | [3-(5-Methyl-1H-pyrazol-4-yl)-propyl](3-phenyl-imidazo[1,2-b]pyridazin-6-yl-amine | $1.13 \times 10^{-5}$ | $2.0 \times 10^{-6}$ |
| KE1322-010-a | N*1,N*1*-Diethyl-N*4*-(3-phenyl-imidazo[1,2-b]pyridazin-6-yl)-pentane-1,4-diamine | $5.4 \times 10^{-6}$ | $1.1 \times 10^{-6}$ |

TABLE 1-continued

Assay data

| Example No. | Structure | Inhibition of PKC theta IC50 [mol/l] | IC50 [mol/l] (concentration for 50% inhibition of IL-2) inhibition at 10 μM |
|---|---|---|---|
| KE1322-011-a | 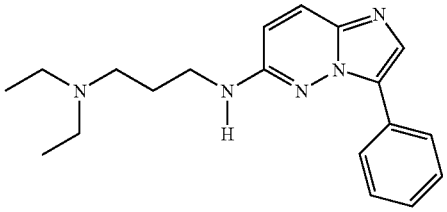<br>N,N-Diethyl-N'-(3-phenyl-imidazo[1,2-b]pyridazin-6-yl)-propane-1,3-diamine | $5.5 \times 10^{-6}$ | $2.6 \times 10^{-6}$ |
| KE1322-014-a | 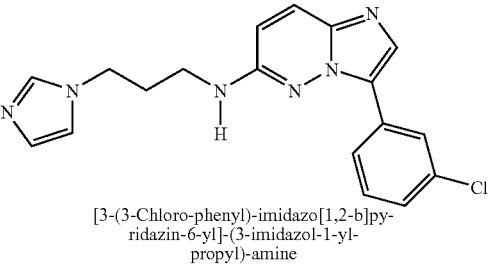<br>[3-(3-Chloro-phenyl)-imidazo[1,2-b]pyridazin-6-yl]-(3-imidazol-1-yl-propyl)-amine | $7.2 \times 10^{-6}$ | $1.1 \times 10^{-6}$ |
| KE1322-022-a | 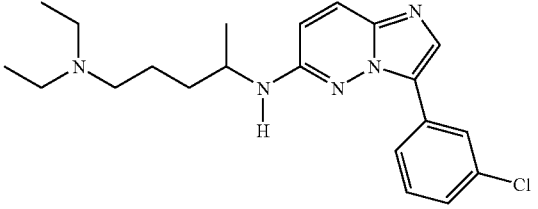<br>N*4*-[3-(3-Chloro-phenyl)-imidazo[1,2-b]pyridazin-6-yl]-N*1,N*1*-diethyl-pentane-1,4-diamine | $2.2 \times 10^{-7}$ | $2.9 \times 10^{-7}$ |
| KE1322-023-a | 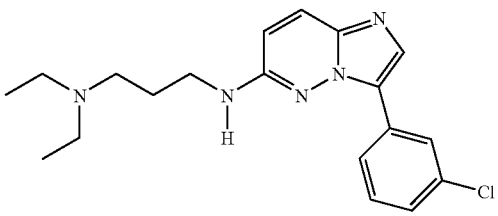<br>N'-[3-(3-Chloro-phenyl)-imidazo[1,2-b]pyridazin-6-yl]-N,N-diethyl-propane-1,3-diamine | $2.5 \times 10^{-7}$ | $2.1 \times 10^{-7}$ |
| KE1322-024-a | 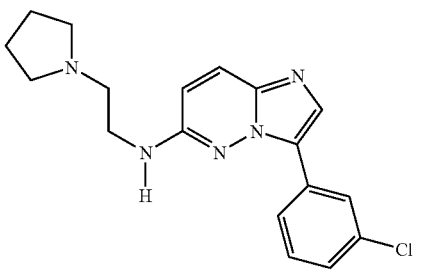<br>[3-(3-Chloro-phenyl)-imidazo[1,2-b]pyridazin-6-yl]-(2-pyrrolidin-1-yl-ethyl)-amine | $1.7 \times 10^{-6}$ | $1.0 \times 10^{-6}$ |

TABLE 1-continued

Assay data

| Example No. | Structure | Inhibition of PKC theta IC50 [mol/l] | IC50 [mol/l] (concentration for 50% inhibition of IL-2) inhibition at 10 μM |
|---|---|---|---|
| KE1322-028-a | Cyclohexylmethyl-[3-(1-methyl-1H-pyrazol-4-yl)-imidazo[1,2-b]pyridazin-6-yl]-amine | $7.0 \times 10^{-6}$ | |
| KE1322-030-a | [3-(1-Methyl-1H-pyrazol-4-yl)-imidazo[1,2-b]pyridazin-6-yl]-[3-(5-methyl-1H-pyrazol-4-yl)-propyl]-amine | $7.2 \times 10^{-6}$ | $0.7 \times 10^{-6}$ |
| KE1322-042-a | [3-(5-Methyl-1H-pyrazol-4-yl)-propyl]-(3-thiophen-3-yl-imidazo-[1,2-b]pyridazin-6-yl)-amine | $1.3 \times 10^{-5}$ | $0.4 \times 10^{-6}$ |

ALK1 Kinase Flashplate Assay

In order to examine the activity of compounds, an ALK1 kinase flashplate assay was established and used.

ALK1 phosphorylates serine/threonine residues of the biotinylated substrate bovine α-casein in the presence of [γ-$^{33}$P]ATP. The radiolabeled product is detected through binding to streptavidin-coated flashplates. The biotin residues of the biotinylated casein bind with high affinity to the streptavidin. Radiolabeled biotinylated casein resulting from the ALK1 kinase reaction causes a chemiluminescence signal after the streptavidin-mediated binding to the scintillator-containing surface of the flashplate has taken place. This signal derives from the closeness of the radioactive label to the scintillator in the surface of the well of the flashplate. Unphosphorylated substrate causes no signal because it contains no radiolabeled phosphate groups. Free [γ-$^{33}$P]ATP remaining unbound in the solution (supernatant) is washed out of the wells of the flashplates and therefore makes no significant contribution to a background signal. The measured signals are therefore a measure of the ALK1 kinase activity. Measurement takes place in a Perkin-Elmer top count apparatus or a Perkin-Elmer ViewLux instrument.

Material:

Enzyme: purified human recombinant ALK1 kinase (GST fused to the intracellular domain of ALK1 [His142-Gln503]); self-prepared; aliquots are stored at −80° C.; diluted enzyme working solution: 2.5 ng/μl ALK1 (in assay buffer) is freshly prepared and stored on ice until used.

Substrate: biotinylated bovine α-casein. Unbiotinylated casein from Sigma is biotinylated by standard methods using a biotin-N-hydroxysuccinimide (NHS) ester. Substrate working solution: 0.83 μM ATP, 1.67 μM biotinylated α-casein, 7.4 nCi of [γ-$^{33}$P]ATP/μl in assay buffer Assay plates: 384-well plates, small volume, white, Greiner (# 784075)

Flashplates: streptavidin-coated flashplates, Perkin Elmer (384-Well # SPM410A)

Assay buffer: 50 mM Tris/HCl pH 8.0, 1 mM MnCl$_2$, 1 mM DTT, 0.01% NP40, 0.5× complete EDTA-free Stop solution: 33.3 μM ATP, 33.3 mM EDTA, 0.07% Triton X-100 in PBS Saturation solution for flashplates: 100 μM ATP, 0.2% Triton X-100 in PBS Adhesive film for plates: Greiner (# 676080)

Description of Assay

Protocol for a 5 μl assay (all steps are carried out at 20° C.; a CyBi-well pipettor and a multidrop microdispensor is used for pipetting):

1. 50 nl or 250 nl of substance in 100% DMSO 2. addition of 3 µl of substrate working solution using a CyBi-Well pipettor 3. addition of 2 µl of enzyme working solution using a multidrop microdispensor Incubation at room temperature (20° C.) for 60 min 4. addition of 15 µl of stop solution using a CyBi-Well pipettor 5. transfer of 18 µl of assay mixture into flashplates** using a CyBi-Well pipettor Incubation at room temperature for at least 3 h or at 4° C. overnight in order to allow binding to the streptavidin-coated flashplates.

6. washing of the flashplates three times with 50 µl of PBS without $Ca^{++}$ and $Mg^{++}$ each time 7. sealing of the plates with adhesive film 8. measurement in the top count (60 sec/well)

**Saturation of the flashplates: the flashplates are preincubated with 50 µl of saturation solution for at least 1 h. 18 µl of this solution are discarded before 18 µl of assay mixture are transferred into the flashplates Final concentrations calculated for a reaction volume of 5 µl: 5 ng of ALK1/well; 1 µM biotinylated α-casein; 0.5 µM ATP; 22 nCi/well [γ-$^{33}$P]ATP; 1 mM $MnCl_2$; 1 mM DTT; 50 mM Tris-HCl, pH 8.0; 0.01% NP40; 0.5× complete EDTA-free; 1% or 5% DMSO.

The data are normalized (enzyme reaction without inhibitor=0% inhibition, enzyme reaction in the presence of 10 mM EDTA=100% inhibition) and $IC_{50}$ values are calculated using a 4-parameter fit with the aid of an in-house software.

ALK4 Kinase Flashplate Assay

In order to examine the activity of compounds, an ALK4 kinase flashplate assay was established and used.

ALK4 phosphorylates serine/threonine residues of the biotinylated substrate bovine α-casein in the presence of [γ-$^{33}$P]ATP. The radiolabeled product is detected through binding to streptavidin-coated flashplates. The biotin residues of the biotinylated casein bind with high affinity to the streptavidin. Radiolabeled biotinylated casein resulting from the ALK4 kinase reaction causes a chemiluminescence signal after the streptavidin-mediated binding to the scintillator-containing surface of the flashplate has taken place. This signal derives from the closeness of the radioactive label to the scintillator in the surface of the well of the flashplate. Unphosphorylated substrate causes no signal because it contains no radiolabeled phosphate groups. Free [γ-$^{33}$P]ATP remaining unbound in the solution (supernatant) is washed out of the wells of the flashplates and therefore makes no significant contribution to a background signal. The measured signals are therefore a measure of the ALK1 kinase activity. Measurement takes place in a Perkin-Elmer is top count apparatus or a Perkin-Elmer ViewLux instrument.

Material:

Enzyme: commercially available recombinant human ALK4 kinase (amino acids, 150-505), fused to GST at the N terminus, expressed by recombinant baculoviruses in Sf21 insect cells (Upstate Biotechnology, Dundee, Scotland; Cat#14-614MG), Lot#28232U; aliquots are stored at −80° C.; diluted enzyme working solution, 2.5 ng/µl ALK1 (in assay buffer) is freshly prepared and stored on ice until used.

Substrate: biotinylated bovine α-casein. Unbiotinylated casein from Sigma is biotinylated by standard methods using a biotin-N-hydroxysuccinimide (NHS) ester. Substrate working solution: 0.83 µM ATP, 1.67 µM biotinylated α-casein, 7.4 nCi of [γ-$^{33}$P]ATP/µl in assay buffer Assay plates: 384-well plates, small volume, white, Greiner (# 784075)

Flashplates: streptavidin-coated flashplates, Perkin Elmer (384-Well # SPM410A)

Assay buffer: 50 mM Tris/HCl pH 8.0, 1 mM $MnCl_2$, 1 mM DTT, 0.01% NP40, 0.5× complete EDTA-free Stop solution: 33.3 µM ATP, 33.3 mM EDTA, 0.07% Triton X-100 in PBS Saturation solution for flashplates: 100 µM ATP, 0.2% Triton X-100 in PBS Adhesive film for plates: Greiner (# 676080)

Description of Assay

Protocol for a 5 µl assay (all steps are carried out at 20° C.; a CyBi-well pipettor and a multidrop microdispensor is used for pipetting):

1. 50 nl or 250 nl of substance in 100% DMSO 2. addition of 3 µl of substrate working solution using a CyBi-Well pipettor 3. addition of 2 µl of enzyme working solution using a multidrop microdispensor Incubation at room temperature (20° C.) for 45 min 4. addition of 15 µl of stop solution using a CyBi-Well pipettor 5. transfer of 18 µl of assay mixture into flashplates** using a CyBi-Well pipettor Incubation at room temperature for at least 3 h or at 4° C. overnight in order to allow binding to the streptavidin-coated flashplates.

6. washing of the flashplates three times with 50 µl of PBS without $Ca^{++}$ and $Mg^{++}$ each time 7. sealing of the plates with adhesive film 8. measurement in the top count (60 sec/well)

**Saturation of the flashplates: the flashplates are preincubated with 50 µl of saturation solution for at least 1 h. 18 µl of this solution are discarded before 18 µl of assay mixture are transferred into the flashplates Final concentrations calculated for a reaction volume of 5 µl: 1 ng of ALK1/well; 1 µM biotinylated α-casein; 0.5 µM ATP; 22 nCi/well [γ-$^{33}$P]ATP; 1 mM $MnCl_2$; 1 mM DTT; 50 mM Tris-HCl, pH 8.0; 0.01% NP40; 0.5× complete EDTA-free; 1% or 5% DMSO.

The data are normalized (enzyme reaction without inhibitor 0% inhibition, enzyme reaction in the presence of 10 mM EDTA=100% inhibition) and $IC_{50}$ values are calculated using a 4-parameter fit with the aid of an in-house software.

ALK1 Transactivation Assay

In this case, HepG2 cell cultures are transiently transfected with an ALK1 plasmid (expression vector for the human ALK1 receptor) by known techniques. At the same time, an ID1 reporter plasmid which 1.3 kB (−1370 to +86) of the ID1 promoter upstream of the luciferase gene is cotransfected. ID1 is a known target gene of ALK1 and is therefore transactivated by cotransfection with the ALK1 receptor. The specific transactivation is quantified by ("relative light units", RLU) which are detected depending on the luciferase. A commercially available kit for detecting luciferase, comprising the substrate luciferin, is used for this.

Material:

HepG2 cells (hepatocellular carcinoma), ATCC HB-8065

96 well culture plates 96 white (Packard # 6005680)

96 well plate polypropylene for compound dilution in DMSO

PBS−; PBS++, DMSO

DMEM Ham's F12 (Biochrom #F4815) with 10% FCS after dialysis, 1% PenStrep and 200 mM Glutamine OPTI MEM (Gibco #51985-026)

Fugene (Roche #1814443 1 mL)

steadyliteHTS (Perkin Elmer# 6016981)

Experimental Procedure:

Day 1: Seeding of the Cells on 96-Well Plates

HepG2 cells are seeded on 96-well plates at a density of 7000 cell/well in DMEM/HamsF12+5% FCS (+1% P/S, +1% Gln).

Day 2: Transfection of the Cells

Per Well:

200 ng DNA: 100 ng ID1-luc (in pGL3basic, Promega)+5 ng ALK1wt (in pcDNA3.1)+95 ng pcDNA3.1 (empty vector, Invitogen)

0.4 µl of fugene

6 µl of OptiMEM

Fugene and OptiMEM are incubated at RT for 5 min. This mixture is incubated with the DNA at RT for 15 minutes.

The plate is then incubated under shaking conditions at RT for 1 hour. After 4 hours at 37° C., the supernatant is aspirated off, and medium (100 µl/well) which contains a little serum (0.2% FCS) and test substance is added to the wells. The plates are incubated at 37° C. for a further 18 hours.

Day 3: RLU Measurement

100 µl of luciferase substrate (steadyliteHTS, Packard) is added per well, and the plates are measured after 10 minutes in a luminometer (e.g. Viktor luminometer, Perkin Elmer). The luciferase activity is quantified by relative light units (RLU).

Calculation of the IC50:

ALK1wt−DMSO control (without ALK1)=100%

Substance (+ALK1wt)−DMSO control (without ALK1)=x %

IC50=50% inhibition of ALK1 transactivation

DU-145 Proliferation Assay

Firstly, DU-145 cells were seeded in a concentration of 200 cells per well in a 96-well microtiter plate (CulturPlate-96, flat bottom transparent) (volume of the culture medium: 100 µl; negative control in starvation medium) and grown under culturing conditions for 18 h. Then 100 µl of the culture medium were removed, and 100 µl of substance solution (dilution in culture medium) were added. The cells are incubated under culturing conditions for 72 h. After the end of the substance treatment, 5 µl of an Alamar Blue labeling solution (Biosource cat # DAL 1100, Lot# 143152SA; dissolved in culture medium) were added (in order to produce a 1:20 dilution) and the cells were grown under culturing conditions for a further 3 h. The proliferation rate was then analyzed by measurement in an FLx800 (fluorescence measuring instrument from BIO-TEK) at 528 nm and 590 nm in each case.

Cell Lines and Cell Culture

Human cell culture lines were used: DU-145 (prostate cell line ATCC No. HTB-81). All cell lines were grown in 175 cm$^2$ culture bottles at 37° C., 5% $CO_2$ and 95% humidity and split 1:5 to 1:65 at 80% confluence in accordance with the respective rates of division. For this purpose, the cells were initially washed with 10 ml of PBS and wetted with 2 ml of trypsin (Gibco). Excess trypsin was removed, and the cells were incubated at room temperature for 10 min. Complete detachment of the treated cells was checked under the microscope. The cells were then taken up in culture medium and transferred in the appropriate volumetric ratio into new cell culture bottles.

DU-145 Culture Medium:

DMEM HAM's F-12 (from Biochrom AG, cat# F4815)+1% P/S+1% glutamine+10% FCS (from Biochrom AG, Lot'0218G)

DU-145 Starvation Medium:

DMEM HAM's F-12 (from Biochrom AG, cat# F4815)+1% P/S+1% glutamine

Further Proliferation Assays

DNA-replicating cells can be labeled using bromodeoxyuiridine (BrdU) and used as measure of the proliferation of eukaryotic cells. In this method, cells which are in the synthesis phase (S phase) incorporate the thymidine analog BrdU instead of thymidine into the growing DNA chain. The replicated DNA is thus labeled with the modified nucleotide BrdU and can subsequently be detected with the aid of a fluorophore-labeled anti-BrdU antibody. The method was used in order to investigate the effect of substances on cellular proliferation.

Firstly, HeLa cells were seeded in a 96-well microtiter plate in a concentration of 7500 cells per well (volume: 200 µl) and grown under culturing conditions for 18 h. Then 100 µl of the culture medium were removed, and 100 µl of substance solution (dilution in culture medium) were added. The cells were incubated under culturing conditions for 6 h, 18 h or 48 h. After the end of the substance treatment, the BrdU-labeling solution (dissolved in culture medium) was added (final concentration of BrdU 10 µM), and the cells were grown under culturing conditions for a further 3 h. The BrdU-containing supernatant was then removed, and the cells were washed with PBS. The cells were subsequently fixed with 4% strength formalin solution (dissolved in PBS, 0.1% Triton-X-100) at 4° C. for 18 h and washed three times with 200 µl of PBS. In order to make the incorporated BrdU accessible for antibody labeling, the DNA of the cells was digested with nuclease (GE/Amersham). BrdU was subsequently detected with the aid of a monoclonal anti-BrdU antibody (GE/Amersham). For this purpose, the fixed cells were incubated with an antibody/nuclease solution (50 µl/well) at 37° C. for 45 min and then washed three times with 200 µl of PBS. The fluorescence labeling took place with a fluorophore-labeled second antibody which binds to the anti-BrdU antibody. The chromatin of the cell nuclei was stained with Hoechst 33342.

In each case 9 image sections per well were recorded in the various fluorescence channels using an automated microscope (Discovery-1, Molecular Devices), and the BrdU incorporation and the proliferation rate were analyzed by means of a high-content analysis (HCA) method.

Cell Lines and Cell Culture

Human cell culture lines were used: HeLa (from cervical carcinoma), PC3 (from prostatic carcinoma) and MCF-7 (from carcinoma of the breast). In addition, CHO cells (from Chinese hamster ovaries) were cultured.

All cell lines were grown in 175 cm² culture bottles at 37° C., 5% $CO_2$ and 95% humidity and split 1:5 to 1:65 at 80% confluence in accordance with the respective rates of division. For this purpose, the cells were initially washed with 10 ml of PBS and wetted with 2 ml of trypsin (Gibco). Excess trypsin was removed, and the cells were incubated at room temperature for 10 min. Complete detachment of the treated cells was checked under the microscope. The cells were then taken up in culture medium and transferred in the appropriate volumetric ratio into new cell culture bottles.

HeLa Culture Medium:

Dulbecco's medium (Gibco), 2 mM glutamine (Gibco), 100 U/ml penicillin (Gibco), 100 µg/ml streptomycin (Gibco) and 10% (v/v) fetal calf serum (PAA)

PC3 Culture Medium:

RPMI 1640 medium (Gibco), 2 mM glutamine (Gibco), 100 U/ml penicillin (Gibco), 100 µg/ml streptomycin (Gibco) and 10% (v/v) fetal calf serum (PAA)

MCF-7 Culture Medium:

RPMI 1640 medium (Gibco), 2 mM glutamine (Gibco), 100 U/ml penicillin (Gibco), 100 µg/ml streptomycin (Gibco) and 10% (v/v) fetal calf serum (PAA), 0.1 nM estradiol (Sigma) and 0.2 U/ml insulin (Sigma)

CHO Culture Medium:

Ham's F12 medium (PAA), 2 mM glutamine (Gibco), 100 U/ml penicillin (Gibco), 100 µg/ml streptomycin (Gibco) and 3% (v/v) fetal calf serum (PAA)

Further Prior Art

Further prior art is formed by the following publications and the literature cited in these publications:

| | |
|---|---|
| DE 3542661 | EP 1040818 |
| EP 979231 B1 | EP 1040817 |
| WO 02/066481 | EP 998908 |
| WO 2005/066177 | EP 966951 |
| WO 2004/087153 | EP 926149 |
| WO 98/03510 | WO 99/66894 |
| WO 99/38868 | WO 99/66893 |
| WO 2003/041670 | WO 99/66892 |
| WO 2004/085409 | WO 99/11230 |
| WO 2004/058755 | WO 99/66891 |
| WO 2004/111056 | WO 97/49378 |
| WO 2005/003101 | WO 98/54093 |
| WO 03/091256 | WO 2004/052315 |
| WO 2004/087707 | WO 2004/089416 |
| WO 96/35690 | WO 2004/089471 |
| WO 2004/085409 | US 2005/0282827 |
| WO 2003/006471 | US 2004/0209878 |
| WO 2005/085252 | US 2002/0041880 |
| WO 2005/003101 | Byth et al. Bioorganic & Medicinal Chemistry Letters 14 (2004) 2249-2252 |
| Gorup et al., Tetrahedron 30 (1974), 2251-2256 | |
| Polanc et al., J. Heterocyclic Chemistry 10 (1973), 565-567 | Watanabe et al, Synthesis 11 (1977), 761-763 |
| Bioorganic & Medicinal Chemistry Letters 2006, 1353 | Bioorganic & Medicinal Chemistry Letters 2005, 1943 |
| Bioorganic & Medicinal Chemistry Letters 2004, 6095 | Journal of Medicinal Chemistry 2005, 7604 |

Priorities of the Present Application:

The present patent application claims the priority of German patent application DE 10 2005 042 742.1 (date of filing: Sep. 2, 2005), and it also claims all the advantages of filing of the U.S. patent application No. 60/713,333 (date of filing: Sep. 2, 2005, provisional application).

1. A compound of the formula I

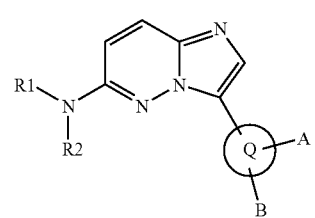

Formel I where

Q is aryl or heteroaryl;

A and B are identical or different and are selected from the group consisting of i) H, Hal, —OH, —$NR^3R^4$, —CN, or —$NO_2$, ii) optionally mono- or poly-Hal-, —OH—, C3-C6-heterocycloalkyl-, —$NR^3R^4$—, or —(CO)—$NR^3$-L-substituted C1-C6-alkyl, C1-C6-alkoxy, C3-C6-cycloalkyl or C3-C6-heterocycloalkyl, where the C3-C6-heterocycloalkyl may comprise in the ring optionally one or more nitrogen, oxygen and/or sulfur atoms and/or one or more —(CO)— or —($SO_2$)— groups and/or one or more double bonds, and iii) —$NR^3$(CO)-L, —$NR^3$(CO)—$NR^3$-L, —(CO)—$R^6$, —O($CH_2$)$_p$—$R^6$, —(CO)—($NR^3$)-L, —$NR^3$(CS)—$NR^3R^4$ or —O—($CH_2$)$_p$-aryl, where the substituents in the case of polysubstitution may be identical or different, A and B in addition or alternatively to the aforementioned definition together form a Q-fused C5-C7-cycloalkyl or C5-C7-heterocycloalkyl ring, where the latter comprises at least one oxygen or one nitrogen atom in the ring, and may optionally comprise additionally in the ring one or more oxygen, nitrogen or sulfur atoms and/or one or more —(CO)— or —($SO_2$)— groups and/or optionally one or more double bonds, p is 0 to 4, L is optionally mono- or poly-C1-C6-alkyl-, C1-C6-hydroxyalkoxy-, C1-C6-alkoxyalkoxy, C3-C6-heterocycloalkyl-, or —$NR^3R^4$-substituted C1-C6-alkyl, or C3-C6-cycloalkyl or C3-C6-heterocycloalkyl, where the C3-C6 heterocycloalkyl may comprise in the ring optionally one or more nitrogen, oxygen and/or sulfur atoms and/or one or more —(CO)— or —($SO_2$)— groups and/or one or more double bonds;

$R^1$ and $R^2$ are identical or different and are selected from the group consisting of j) —H and jj) optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—$R^6$—, —$NR^3R^4$—, —$NR^3$(CO)-L- or —$NR^3COOR^7$-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —SO₂— groups and/or one or more double bonds, and where the substituents in the case of polysubstitution may be identical or different;

$R^1$ and $R^2$ in addition or alternatively to the aforementioned definition may together form a C3-C6-heterocycloalkyl ring which comprises at least one nitrogen atom in the ring and may optionally comprise additionally in the ring one or more nitrogen, oxygen or sulfur atoms and/or one or more —(CO)— or —(SO₂)— groups and/or optionally one or more double bonds, where the ring formed by $R^1$ and $R^2$ may be optionally substituted one or more times by —CN, -Hal, —OH, C1-C6-alkyl, C3-C6-cycloalkyl, C1-C6-hydroxyalkyl, C1-C6-alkoxyalkyl, —NR³R⁴, —CONR⁶R⁷, —(CO)—R⁶ or —COOR⁷ and/or by optionally mono- or poly-Hal-, C1-C6-alkoxy- or —(CO)—R⁶-substituted aryl or heteroaryl, where the substituents in the case of polysubstitution may be identical or different;

$R^3$ and $R^4$ are identical or different and are selected from the group consisting of j) —H, and jj) optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —NR⁶R⁷—, —CONR⁶R⁷—, —(CO)—R⁶— or —COOR⁷-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may comprise in the ring optionally one or more nitrogen, oxygen and/or sulfur atoms and/or one or more —(CO)— or —SO₂— groups and/or one or more double bonds, and where the substituents in the case of polysubstitution may be identical or different;

$R^3$ and $R^4$ in addition to the aforementioned definition may together form a C3-C6-heterocycloalkyl ring which comprises at least one nitrogen atom in the ring and may optionally comprise additionally in the ring one or more nitrogen, oxygen or sulfur atoms and/or one or more —(CO)— or —(SO₂)— groups and/or optionally one or more double bonds, where the ring formed by $R^3$ and $R^4$ may be optionally substituted one or more times by —CN, -Hal, —OH, C1-C6-alkyl, C3-C6-cycloalkyl, C1-C6-hydroxyalkyl, C1-C6-alkoxyalkyl, or by —NR⁶R⁷, —CONR⁶R⁷, —(CO)—R⁶ or —COOR⁷ and/or by optionally mono- or poly-Hal-, C1-C6-alkoxy- or —(CO)—R⁶-substituted aryl or heteroaryl, where the substituents in the case of polysubstitution may be identical or different;

$R^6$ and $R^7$ are identical or different and are selected from the group consisting of j) —H and jj) optionally mono- or poly-Hal-, —OH—, —CN-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may comprise in the ring optionally one or more nitrogen, oxygen and/or sulfur atoms and/or one or more —(CO)— or —SO₂— groups and/or one or more double bonds, and where the substituents in the case of polysubstitution may be identical or different, and the isomers, diastereomers, enantiomers and salts thereof.

2. The compound as claimed in claim 1, where $R^1$ and $R^2$ are identical or different and selected from the group consisting of j) —H and JJ) optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl, —(CO)—R⁶—, —NR³R⁴—, —NR³(O)-L- or —NR³(CO)R⁷— substituted C1-C6-alkyl, C1-C6-alkoxy, C2-C6-alkenyl, C2-C6-alkynyl, C3-C6-cycloalkyl, C3-C6-heterocycloalkyl, where the C3-C6-heterocycloalkyl may optionally comprise in the ring one or more nitrogen, oxygen and/or sulfur atoms and/or one or more —(CO)— or —SO₂— groups and/or one or more double bonds, where the substituents may in the case of polysubstitution be identical or different, and where $R^1$ and $R^2$ in addition or alternatively to the preceding definition may together form a C3-C6-heterocycloalkyl ring which comprises at least one nitrogen atom in the ring and may optionally additionally comprise in the ring one or more nitrogen, oxygen or sulfur atoms and/or one or more —(CO)— or (SO₂)— groups and/or optionally one or more double bonds, where the ring formed by $R^1$ and $R^2$ may be optionally substituted one or more times by —CN, -Hal, —OH, C1-C6-alkyl, C3-C6-cycloalkyl, C1-C6-hydroxyalkyl, C1-C6-alkoxyalkyl, —NR³R⁴, —OONR⁶R⁷, —(CO)—R⁶ or —COOR⁷ and/or by optionally mono- or poly-Hal-, C1-C6-alkoxy- or —(CO)—R⁶-substituted aryl or heteroaryl, where the substituents may in the case of polysubstitution be identical or different.

3. The compound as claimed in claim 1 or 2, wherein $R^1$ and $R^2$ are identical or different and selected from the group consisting of j) —H and JJ) optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryloxy-, —S—C1-C6-alkyl-, —(CO)—R⁶—, —NR³R⁴—, —NR³(O)-L- or —NR³COOR⁷-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —SO₂— groups and/or one or more double bonds, where the group aryl or heteroaryl defined in jj) may be substituted as long as alkyl is not involved, where the substituents may in the case of polysubstitution be identical or different, and where $R^1$ and $R^2$ in addition or alternatively to the preceding definition may together form a C3-C6-heterocycloalkyl ring which comprises at least one nitrogen atom in the ring and may optionally additionally comprise in the ring one or more nitrogen, oxygen or sulfur atoms and/or one or more —(CO)— or —(SO₂)— groups and/or optionally one or more double bonds, where the ring formed by $R^1$ and $R^2$ is optionally substituted one or more times by —CN, -Hal, —OH, C1-C6-alkyl, C3-C6-cycloalkyl, C1-C6-hydroxyalkyl, C1-C6-alkoxyalkyl, —NR³R⁴, —CONR⁶R⁷, —(CO)—R⁶ or —COOR⁷ and/or by optionally mono- or poly-Hal-, C1-C6-alkoxy- or —(CO)—R⁶-substituted aryl or heteroaryl, where the substituents may in the case of polysubstitution be identical or different.

4. The compound as claimed in claim 3, where Q is —OH—, -Hal-, —CN—, alkyl-, —OR⁶— or —NR³R⁴-substituted phenyl, pyridyl, pyrimidinyl, thiophenyl, furyl, imidazolyl, or pyrazolyl.

5. The compound as claimed in claim 4, where $R^1$ and $R^2$ are identical or different and selected from the group consisting of —H, NR³R⁴-substituted C1-C4-alkyl, optionally additionally substituted one or more times by -Hal, —OH, —CN, C1-C6-alkyl, C1-C6-alkoxy, C1-C6-hydroxyalkyl, C3-C6-cycloalkyl, C3-C6heterocycloalkyl, C2-C6-alkynyl, aryl, aryloxy, heteroaryl, —S—C1-C6-alkyl, —(CO)—R⁶, —NR³(CO)-L, or —NR³COOR⁷, where $R^3$ and $R^4$ may optionally, identically or differently, be C1-C6-alkyl, where $R^3$ and $R^4$ may together form a C3-C6-heterocycloalkyl ring which comprises at least one nitrogen atom in the ring and may optionally additionally comprise in the ring one or more nitrogen, oxygen or sulfur atoms and/or one or more —(CO)— or —(SO$_2$)— groups and/or optionally one or more double bonds, and where R6 and R7 is identically or differently —H, —OH, C1-C6-alkoxy, or C1-C3-alkyl.

6. The compound as claimed in any of claims 4, where $R^1$ is selected from the group consisting of —H and C1-C3-alkyl, where $R^2$ is selected from the group consisting of $NR^3R^4$-substituted C3-C4 alkyl, optionally additionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—R$^6$—, —NR$^3$(CO)-L- or —NR$^3$COOR$^7$-substituted, where $R^3$ and $R^4$ are identically or differently optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —NR$^6$R$^7$—, —CONR$^6$R$^7$—, —(CO)—R$^6$— or —COOR$^7$-substituted C1-C6-alkyl, where $R^3$ and $R^4$ may together form a C3-C6-heterocycloalkyl ring which comprises at least one nitrogen atom in the ring and may optionally additionally comprise in the ring one or more nitrogen, oxygen or sulfur atoms and/or one or more —(CO)— or —(SO$_2$)— groups and/or optionally one or more double bonds, and where R6 and R7 is identically or differently —H, —OH, C1-C6-alkoxy, or C1-C3 alkyl.

7. The compound as claimed in claim 1, namely:
(3-phenylimidazo[1,2-b]pyridazin-6-yl)-(3-pyrrolidin-1-yl-propyl)amine
(3-morpholin-4-ylpropyl)-(3-phenylimidazo[1,2-b]pyridazin-6-yl)amine
(3-(3-chlorophenyl)imidazo[1,2-b]pyridazin-6-yl)-(3-pyrrolidin-1-ylpropyl)amine
(3-(3-chlorophenyl)imidazo[1,2-b]pyridazin-6-yl)-(3-morpholin-4-ylpropyl)amine
[3-(1-methyl-1H-pyrazol-4-yl)imidazo[1,2-b]pyridazin-6-yl]pyridin-3-ylmethylamine
(3-phenylimidazo[1,2-b]pyridazin-6-yl)pyridin-3-ylmethylamine
(3-imidazol-1-ylpropyl)-(3-phenylimidazo[1,2-b]pyridazin-6-yl)amine
(4-fluorobenzyl)-(3-phenylimidazo[1,2-b]pyridazin-6-yl)amine
cyclohexylmethyl(3-phenylimidazo[1,2-b]pyridazin-6-yl)amine
(2,4-difluorobenzyl)-(3-phenylimidazo[1,2-b]pyridazin-6-yl)amine
[3-(5-methyl-1H-pyrazol-4-yl)propyl]-(3-phenylimidazo[1,2-b]pyridazin-6-yl)amine
1-[2-(3-phenylimidazo[1,2-b]pyridazin-6-ylamino)ethyl]imidazolidin-2-one
(2-morpholin-4-ylethyl))-(3-phenylimidazo[1,2-b]pyridazin-6-yl)amine
N*1,N*1-diethyl-N*4-(3-phenylimidazo[1,2-b]pyridazin-6-yl)pentane-1,4-diamine
N,N-diethyl-N'-(3-phenylimidazo[1,2-b]pyridazin-6-yl)propane-1,3-diamine
(3-phenyl imidazo[1,2-b]pyridazin-6-yl)-(2-pyrrolidin-1-yl-ethyl)amine
[3-(3-chlorophenyl)imidazo[1,2-b]pyridazin-6-yl]pyridin-3-ylmethylamine
[3-(3-chlorophenyl)imidazo[1,2-b]pyridazin-6-yl]-(3-imidazol-1-ylpropyl)amine
3-(3-chlorophenyl)imidazo[1,2-b]pyridazin-6-yl)-(4-fluorobenzyl)amine
3-(3-chlorophenyl)imidazo[1,2-b]pyridazin-6-yl)cyclohexylmethylamine
3-(3-chlorophenyl)imidazo[1,2-b]pyridazin-6-yl)-(2,4-difluorobenzyl)amine
1-{2-[3-(3-phenyl)imidazo[1,2-b]pyridazin-6-ylamino]ethyl}imidazolidin-2-one
N*4*-[3-(3-chlorophenyl)imidazo[1,2-b]pyridazin-6-yl] N*1*N*1-diethylpentane-1,4-diamine
N'-[3-(3-chlorophenyl)imidazo[1,2-b]pyridazin-6-yl]-N,N-diethylpropane-1,3-diamine
[3-(3-chlorophenyl)imidazo[1,2-b]pyridazin-6-yl]-(2-pyrrolidin-1-ylethyl)amine
(3-imidazol-1-ylpropyl)-[3-(1-methyl-1H-pyrazol-4-yl)imidazo[1,2-b]pyridazin-6-yl]amine
(4-fluorobenzyl)-[3-(1-methyl-1H-pyrazol-4-yl)imidazo[1,2-b]pyridazin-6-yl]amine
cyclohexylmethyl-[3-(1-methyl-1H-pyrazol-4-yl)imidazo[1,2-b]pyridazin-6-yl]amine
(2,4-difluorobenzyl)-[3-(1-methyl-1H-pyrazol-4-yl)imidazo[1,2-b]pyridazin-6-yl]amine
[3-(1-methyl-1H-pyrazol-4-yl)imidazo[1,2-b]pyridazin-6-yl]-[5-methyl-1H-pyrazol-4-yl)propyl]amine
1-{2-[3-(1-methyl-1H-pyrazol-4-yl)imidazo[1,2-b]pyridazin-6-ylamino]ethyl}imidazolidin-2-one
(3-(1-methyl-1H-pyrazol-4-yl)imidazo[1,2-b]pyridazin-6-yl)-(2-morpholin-4-ylethyl)amine
N*1,N*1*-diethyl-N*4-[3-(1-methyl-1H-pyrazol-4-yl)imidazo[1,2-b]pyridazin-6-yl]pentane-1,4-diamine
N,N-diethyl-N'-[3-(1-methyl-1H-pyrazol-4-yl)imidazo[1,2-b]pyridazin-6-yl]propane-1,3-diamine
[3-(1-methyl-1H-pyrazol-4-yl)imidazo[1,2-b]pyridazin-6-yl]-(2-pyrrolidin-1-ylethyl)amine
pyridin-3-ylmethyl-(3-thiophen-3-ylimidazo[1,2-b]pyridazin-6-yl)amine
(4-fluorobenzyl)-(3-thiophen-3-ylimidazo[1,2-b]pyridazin-6-yl)amine
cyclohexyl methyl-(3-thiophen-3-ylimidazo[1,2-b]pyridazin-6-yl)amine
(2,4-difluorobenzyl)-(3-thiophen-3-ylimidazo[1,2-b]pyridazin-6-yl)amine
[3-(5-methyl-1H-pyrazol-4-yl)propyl]-(3-thiophen-3-ylimidazo[1,2-b]pyridazin-6-yl)amine
1-[2-(3-thiophen-3-ylimidazo[1,2-b]pyridazin-1-ylamino)ethyl]imidazolidin-2-one
(2-morpholin-4-ylethyl)-(3-thiophen-3-ylimidazo[1,2-b]pyridazin-6-yl)amine
N*1,N*1*-diethyl-N*4-[3-thiophen-3-ylimidazo[1,2-b]pyridazin-6-yl]pentane-1,4-diamine
N,N-diethyl-N'-(3-thiophen-3-ylimidazo[1,2-b]pyridazin-6-yl)propane-1,3-diamine
(2-pyrrolidin-1-ylethyl)-(3-thiophen-3-ylimidazo[1,2-b]pyridazin-6-yl)amine 8. A method for preparing a compound as claimed in any of claims 1 to 7, with the following stages of the method:
A1) 3-amino-6-halopyrazine is reacted with chloractetaldehyde to give 6-haloimidazo[1,2-b]pyridazine,
A2) the product from stage A1 is reacted with N-bromosuccinimide to give a 3-bromo-6-haloimidazo[1,2-b]pyridazine,
A3) the product from stage A2 is converted by reaction with a compound NHR$^1$R$^2$ in a Buchwald-Hartwig cross-coupling reaction into a (3-bromoimidazo[1,2-b]pyridazin-6-yl)-(R$^1$)—(R$^2$)-amine,
A4) the product from stage A3 is reacted for example with a boronic acid which is optionally substituted by the radicals A and B to give the compound according to the general formula I, or B1) 3-amino-6-halopyrazine is reacted with chloractetaldehyde to give 6-haloimidazo[1,2-b]pyridazine, B2) the product from stage B1 is reacted with N-bromosuccinimide to give a 3-bromo-6-haloimidazo[1,2-b]pyridazine, B3) the product from stage B2 is reacted for example with a boronic acid which is optionally substituted by the radicals A and B to give the compound according to the general formula II, B4) the product from stage B3 is converted by reacting with a compound $NHR^1R^2$ in a Buchwald-Hartwig cross-coupling reaction into the compound according to the general formula I, or C1) 3-amino-6-halopyrazine is reacted with chloractetaldehyde to give 6-haloimidazo[1,2-b]pyridazine, C2) the product from stage C1 is converted by reacting with a compound $NHR^1R^2$ in a Buchwald-Hartwig cross-coupling reaction into an imidazo[1,2-b]pyridazin-6-yl)-$(R^1)$—$(R^2)$-amine, C3) the product from stage C2 is reacted with N-bromosuccinimide to give a (3-bromoimidazo[1,2-b]pyridazin-6-yl)-$(R^1)$—$(R^2)$-amine, C4) the product from stage C3 is reacted for example with a boronic acid which is optionally substituted by the radicals A and B to give the compound according to the general formula I.

9. The use of a compound as claimed in any of claims 1 to 7 for producing a pharmaceutical composition.

10. The use of a compound as claimed in any of claims 1 to 7 for inhibiting a cellular kinase, in particular a kinase from the group of the protein kinase C family such as, for example, PKC theta, delta, iota, alpha and zeta.

11. The use of a compound as claimed in any of claims 1 to 7 for producing a pharmaceutical composition for the treatment or for the prophylaxis of a disorder which is associated with overexpression or mutation of a cellular kinase, in particular a cellular kinase according to claim 10.

12. The use as claimed in claim 9, where the disorder is a disorder from the group consisting of "epidermal hyperproliferation such as psoriasis, Alzheimer's, autoinflammatory disorders, Crohn's disease, exaggerated immune response, contact dermatitis, atopic dermatitis, multiple sclerosis, ALS, diabetes, asthma".

13. The use as claimed in claim 9 for modulating, in particular reducing, an immune response, for example after a transplantation has taken place to avoid rejection of an organ.

14. A method for producing a pharmaceutical composition, where a physiologically effective dose of a compound as claimed in any of claims 1 to 7 is mixed with at least one pharmaceutical excipient, and a dosage form is manufactured.

15. A method for the treatment or prophylaxis of a disorder which is associated with overexpression or mutation of a cellular kinase, in particular a disorder according to claim 12, where a pharmaceutical composition comprising a physiologically effective dose of a compound as claimed in any of claims 1 to 7 is administered to a person suffering from or under threat of suffering from the disorder.

16. An intermediate according to formula IIa

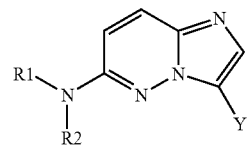

General formula IIa where

Y is replaced by —H or -Hal, $R^1$ and $R^2$ are identical or different and selected from the group consisting of j) —H and jj) optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —S—C1-C6-alkyl-, —(CO)—$R^6$—, —$NR^3R^4$—, —$NR^3$(CO)-L- or —$NR^3COOR^7$-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —$SO_2$— groups and/or one or more double bonds, and where the substituents in the case of polysubstitution may be identical or different;

$R^1$ and $R^2$ in addition or alternatively to the preceding definition may together form a C3-C6-heterocycloalkyl ring which comprises at least one nitrogen atom in the ring and may optionally additionally comprise in the ring one or more nitrogen, oxygen or sulfur atoms and/or one or more —(CO)— or —($SO_2$)— groups and/or optionally one or more double bonds, where the ring formed via $R^1$ and $R^2$ may be optionally substituted one or more times by —CN, -Hal, —OH, C1-C6-alkyl, C3-C6-cycloalkyl, C1-C6-hydroxyalkyl, C1-C6-alkoxyalkyl, —$NR^3R^4$, —$CONR^6R^7$, —(CO)—$R^6$ or —$COOR^7$ and/or by optionally mono- or poly-Hal-, C1-C6-alkoxy- or —(CO)—$R^6$-substituted aryl or heteroaryl, where the substituents in the case of polysubstitution may be identical or different;

$R^3$ and $R^4$ are identical or different and selected from the group consisting of j) —H and JJ) optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —$NR^6R^7$—, —$CONR^6R^7$—, —(CO)— or $R^6$— or —$COOR^7$-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —$SO_2$— groups and/or one or more double bonds, and where the substituents in the case of polysubstitution may be identical or different;

$R^3$ and $R^4$ in addition or alternatively to the preceding definition may together form a C3-C6-heterocycloalkyl ring which comprises at least one nitrogen atom in the ring and may optionally additionally comprise in the ring one or more nitrogen, oxygen or sulfur atoms and/or one or more —(CO)— or —($SO_2$)— groups and/or optionally one or more double bonds, where the ring formed by R3 and R4 may optionally be substituted one or more times by —CN, -Hal, —OH, C1-C6-alkyl, C3-C6-cycloalkyl, C1-C6-hydroxyalkyl, C1-C6-alkoxyalkyl or by —$NR^6R^7$, —OONR⁶R⁷, —(CO)—R⁶ or —COOR⁷ and/or by optionally mono- or poly-Hal-, C1-C6-alkoxy- or —(CO)—R6-substituted aryl or heteroaryl, where the substituents in the case of polysubstitution may be identical or different;

R⁶ and R⁷ are identical or different and selected from the group consisting of j) —H and jj) optionally mono- or poly-Hal-, —OH—, —CN-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —SO₂— groups and/or one or more double bonds, and where the substituents in the case of polysubstitution may be identical or different, and the isomers, diastereomers, enantiomers and salts thereof.

17. An intermediate according to general formula IIb

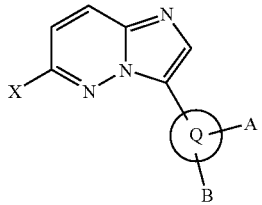

General formula IIb

Q is aryl or heteroaryl;

A and B are identical or different and selected from the group consisting of i) H, Hal, —OH, —NR³R⁴, —CN or —NO₂,
ii) optionally mono- or poly-Hal-, —OH—, C3-C6-heterocycloalkyl-, —NR³R⁴—, or —(CO)—NR³-L-substituted C1-C6-alkyl, C1-C6-alkoxy, C3-C6-cycloalkyl or C3-C6-heterocycloalkyl, where the C3-C6-heterocycloalkyl may optionally comprise in the ring one or more nitrogen, oxygen and/or sulfur atoms and/or one or more —(CO)— or —(SO₂)— groups and/or one or more double bonds, and
iii) —NR³(CO)-L, —NR³(CO)—NR³-L, —(CO)—R⁶, —O—(CH₂)ₚ—R⁶, —(CO)—(NR³)-L, —NR³(CS)—NR³R⁴, or —O—(CH₂)-aryl, where the substituents in the case of polysubstitution may be identical or different, A and B in addition or alternatively to the preceding definition together form a O-fused C5-C7-cycloalkyl or C5-C7-heterocycloalkyl ring, where the latter comprises at least one oxygen or nitrogen atom in the ring and may optionally additionally comprise in the ring one or more oxygen, nitrogen or sulfur atoms and/or one or more —(CO)— or —(SO₂)— groups and/or optionally one or more double bonds, p is 0 to 4, L is optionally mono- or poly-C1-C6-alkyl-, C1-C6-hydroxyalkoxy-, C1-C6-alkoxyalkoxy-, C3-C6-heterocycloalkyl- or —NR³R⁴-substituted C1-C6-alkyl or C3-C6-cycloalkyl or C3-C6-heterocycloalkyl, where the C3-C6 heterocycloalkyl may optionally comprise in the ring one or more nitrogen, oxygen and/or sulfur atoms and/or one or more —(CO)— or —(SO₂)— groups and/or one or more double bonds;

X is chlorine, bromine, O—SO₂—CF₃ or O—SO₂—C₄F₉;

R³ and R⁴ are identical or different and selected from the group consisting of j) —H, and jj) optionally mono- or poly-Hal-, —OH—, —CN—, C1-C6-alkyl-, C1-C6-alkoxy-, C1-C6-hydroxyalkyl-, C3-C6-cycloalkyl-, C3-C6 heterocycloalkyl-, C2-C6-alkynyl-, aryl-, aryloxy-, heteroaryl-, —NR⁶R⁷—, —CONR⁶R⁷—, —(CO)—R⁶— or —COOR⁷-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one more —(CO)— or —SO₂— groups and/or one or more double bonds, and where the substituents in the case of polysubstitution may be identical or different;

R³ and R⁴ may in addition or alternatively to the preceding definition together form a C3-C6-heterocycloalkyl ring which comprises at least one nitrogen atom in the ring and may optionally additionally comprise in the ring one or more nitrogen, oxygen or sulfur atoms and/or one or more —(CO)— or —(SO₂)— groups and/or optionally one or more double bonds, where the ring formed via R3 and R4 may optionally be substituted one or more times by —CN, -Hal, —OH, C1-C6-alkyl, C3-C6-cycloalkyl, C1-C6-hydroxyalkyl, C1-C6-alkoxyalkyl, or by —NR⁶R⁷, —CONR⁶R⁷, —(CO)—R⁶ or —COOR⁷ and/or by optionally mono- or poly-Hal-, C1-C6-alkoxy- or —(CO)—R⁶-substituted aryl or heteroaryl, where the substituents may in the case of polysubstitution be identical or different;

R⁶ and R⁷ are identical or different and selected from the group consisting of j) —H and jj) optionally mono- or poly-Hal-, —OH—, —CN-substituted C1-C6-alkyl, C1-C6-alkoxy, C2-C6-alkenyl, C2-C6-alkynyl, C3-C6-cycloalkyl, C3-C6-heterocycloalkyl, aryl or heteroaryl, where the C3-C6-heterocycloalkyl may optionally comprise in the ring one or more nitrogen, oxygen and/or sulfur atoms and/or one or more —(CO)— or —SO₂— groups and/or one or more double bonds, and where the substituents in the case of polysubstitution may be identical or different and the isomers, diastereomers, enantiomers and salts thereof.

The invention claimed is:

1. A compound selected from the group consisting of:
(3-phenylimidazo[1,2b]pyridazin-6-yl)-(3-pyrrolidin-1-ylpropyl)amine
(3-morpholin-4-ylpropyl)-(3-phenylimidazo[1,2b]pyridazin-6-yl)amine
(3-(3-chlorophenyl)imidazo[1,2-b]pyridazin-6-yl)-(3-pyrrolidin-1-ylpropyl)amine
(3-(3-chlorophenyl)imidazo[1,2-b]pyridazin-6-yl)-(3-morpholin-4-ylpropyl)amine
[3-(1-methyl-1H-pyrazol-4-yl)imidazo[1,2b]pyridazin-6-yl]pyridin-3-ylmethylamine
(3-phenylimidazo[1,2b]pyridazin-6-yl)pyridin-3-ylmethylamine
(3-imidazol-1-ylpropyl)-(3-phenylimidazo[1,2b]pyridazin-6-yl)amine
(4-fluorobenzyl)-(3-phenylimidazo[1,2b]pyridazin-6-yl)amine
cyclohexylmethyl-(3-phenylimidazo[1,2-b]pyridazin-6-yl)amine
(2,4-difluorobenzyl)-(3-phenylimidazo[1,2b]pyridazin-6-yl)amine
[3-(5-methyl-1H-pyrazol-4-yl)propyl]-(3-phenylimidazo[1,2-b]pyridazin-6-yl)amine
1-[2-(3-phenylimidazo[1,2-b]pyridazin-6-ylamino)ethyl]imidazolidin-2-one
(2-morpholin-4-ylethyl))-(3-phenylimidazo[1,2-b]pyridazin-6-yl)amine $N^1,N^1$-diethyl-$N^4$-(3-phenylimidazo[1,2-b]pyridazin-6-yl)pentane-1,4-diamine N,N-diethyl-N'-(3-phenylimidazo[1,2-b]pyridazin-6-yl)propane-1,3-diamine (3-phenylimidazo[1,2-b]pyridazin-6-yl)-(2-pyrrolidin-1-ylethyl)amine

[3-(3-chlorophenyl)imidazo[1,2-b]pyridazin-6-yl]pyridin-3ylmethylamine

[3-(3-chlorophenyl)imidazo[1,2-b]pyridazin-6-yl]-(3-imidazol-1-ylpropyl)amine 3-(3-chlorophenyl)imidazo[1,2-b]pyridazin-6-yl)-(4-fluorobenzyl)amine 3-(3-chlorophenyl)imidazo[1,2-b]pyridazin-6-yl)cyclohexylmethylamine 3-(3-chlorophenyl)imidazo[1,2-b]pyridazin-6-yl)-(2,4-difluorobenzyl)amine 1-{2-[3-(3-phenyl)imidazo[1,2-b]pyridazin-6-ylamino]ethyl}imidazolidin-2-one $N^4$-[3-(3-chlorophenyl)imidazo[1,2-b]pyridazin-6-yl]$N^1$,$N^1$-diethylpentane-1,4-diamine N'-[3-(3-chlorophenyl)imidazo[1,2-b]pyridazin-6-yl]-N,N-diethylpropane-1,3-diamine

[3-(3-chlorophenyl)imidazo[1,2b]pyridazin-6-yl]-(2-pyrrolidin-1-ylethyl)amine (3-imidazol-1-ylpropyl)-[3-(1-methyl-1H-pyrazol-4-yl)imidazo[1,2-b]pyridazin-6-yl]amine (4-fluorobenzyl)-[3-(1-methyl-1H-pyrazol-4-yl)imidazo[1,2-b]pyridazin-6-yl]amine cyclohexylmethyl-[3-(1-methyl-1H-pyrazol-4-yl)imidazo[1,2-b]pyridazin-6-yl]amine (2,4-difluorobenzyl)-[3-(1-methyl-1H-pyrazol-4-yl)imidazo[1,2-b]pyridazin-6-yl]amine

[3-(1-methyl-1H-pyrazol-4-yl)imidazo[1,2b]pyridazin-6-yl]-[5-methyl-1H-pyrazol-4-yl)propyl]amine 1-{2-[3-(1-methyl-1H-pyrazol-4-yl)imidazo[1,2-b]pyridazin-6-ylamino]ethyl}imidazolidin-2-one (3-(1-methyl-1H-pyrazol-4-yl)imidazo[1,2-b]pyridazin-6-yl)-(2-morpholin-4-ylethyl)amine $N^1,N^1$-diethyl-$N^4$-[3-(1-methyl-1H-pyrazol-4-yl)imidazo[1,2b]pyridazin-6-yl]pentane-1,4-diamine N,N-diethyl-N'-[3-(1-methyl-1H-1-pyrazol-4-yl)imidazo[1,2-b]pyridazin-6-yl]propane-1,3-diamine

[3-(1-methyl-1H-pyrazol-4-yl)imidazo [1,2-b]pyridazin-6-yl-(2-pyrrolidin-1-ylethyl)amine pyridin-3-ylmethyl-(3-thiophen-3-ylimidazo[1,2-b]pyridazin-6-yl)amine (4-fluorobenzyl)-(3-thiophen-3-ylimidazo[1,2-b]pyridazin-6-yl)amine cyclohexylmethyl-(3-thiophen-3-ylimidazo[1,2-b]pyridazin-6-yl)amine (2,4-difluorobenzyl)-(3-thiophen-3-ylimidazo[1,2-b]pyridazin-6-yl)amine

[3-(5-methyl-1H-pyrazol-4-yl)propyl]-(3-thiophen-3-ylimidazo[1,2-b]pyridazin-6-yl)amine 1-[2-(3-thiophen-3-ylimidazo[1,2-b]pyridazin-6-ylamino)ethyl]imidazolidin-2-one (2-morpholin-4-ylethyl)-(3-thiophen-3-ylimidazO[1,2-b]pyridazin-6-yl)amine $N^1,N^1$-diethyl-$N^4$-[3-thiophen-3-ylimidazo[1,2-b]pyridazin-6-yl]pentane-1,4-diamine N,N-diethyl-N'-(3-thiophen-3-ylimidazo[1,2-b]pyridazin-6-yl)propane-1,3-diamine and (2-pyrrolidin-1-ylethyl)-(3-thiophen-3-ylimidazo[1,2-b]pyridazin-6-yl)amine.

2. A pharmaceutical composition, comprising a compound as claimed in claim 1 and at least one pharmaceutical excipient.

\* \* \* \* \*

UNITED STATES PATENT AND TRADEMARK OFFICE
CERTIFICATE OF CORRECTION

PATENT NO. : 7,750,000 B2  
APPLICATION NO. : 11/514308  
DATED : July 6, 2010  
INVENTOR(S) : Prien et al.

Page 1 of 2

It is certified that error appears in the above-identified patent and that said Letters Patent is hereby corrected as shown below:

Column 270, line 50 reads "[3-(1-methyl-1H-pyrazol-4-yl)imidazo[1,2b]pyridazin-6-"
should read -- [3-(1-methyl-1H-pyrazol-4-yl)imidazo[1,2-b]pyridazin-6- --.

Column 270, line 52 reads "(3-phenylimidazo[1,2b]pyridazin-6-yl)pyridine-3-ylm-"
should read -- (3-phenylimidazo[1,2-b]pyridazin-6-yl)pyridine-3-ylm- --.

Column 270, line 54 reads "(3-imidazol-1-ylpropyl)-(3-phenylimidazo[1,2b]py-"
should read -- (3-imidazol-1-ylpropyl)-(3-phenylimidazo[1,2-b]py- --.

Column 270, line 56 reads "(4-fluorobenzyl)-(3-phenylimidazo[1,2b]pyridazin-6-yl)"
should read -- (4-fluorobenzyl)-(3-phenylimidazo[1,2-b]pyridazin-6-yl) --.

Column 270, line 60 reads "(2,4-difluorobenzyl)-(3-phenylimidazo[1,2b]pyridazin-6-"
should read --(2,4-difluorobenzyl)-(3-phenylimidazo[1,2-b]pyridazin-6- --.

Column 271, line 23 reads "[3-(3-chlorophenyl)imidazo[1,2b]pyridazin-6-yl]-(2-pyr-"
should read -- [3-(3-chlorophenyl)imidazo[1,2-b]pyridazin-6-yl]-(2-pyr- --.

Column 271, line 33 reads "[3-(1-methyl-1H-pyrazol-4-yl)imidazo[1,2b]pyridazin-6-"
should read -- [3-(1-methyl-1H-pyrazol-4-yl)imidazo[1,2-b]pyridazin-6- --.

Column 272, line 6 reads "[1,2b]pyridazin-6-yl]pentane-1,4-diamine" should
read -- [1,2-b]pyridazin-6-yl]pentane-1,4-diamine --.

Column 272, line 7 reads "N,N-diethyl-N'-[3-(1-methyl-1H-1-pyrazol-4-yl)imidazo"
should read -- N,N-diethyl-N'-[3-(1-methyl-1H-pyrazol-4-yl)imidazo --.

Column 272, line 10 reads "6-yl-(2-pyrrolidin-1-ylethyl)amine" should read
-- 6-yl]-(2-pyrrolidin-1-ylethyl)amine --.

Signed and Sealed this

Twenty-third Day of November, 2010

David J. Kappos  
*Director of the United States Patent and Trademark Office*

Column 272, line 19 reads "[3-(5-methyl-1H-pyrazol-4-yl)propyl)-(3-thiophen-3-"
should read -- [3-(5-methyl-1H-pyrazol-4-yl)propyl]-(3-thiophen-3- --.

Column 272, line 23 reads "(2-morpholin-4-ylethyl)-(3-thiophen-3-ylimidazO[1,2-b]"
should read -- (2-morpholin-4-ylethyl)-(3-thiophen-3-ylimidazo[1,2-b] --.